(12) United States Patent
Chang et al.

(10) Patent No.: US 6,183,751 B1
(45) Date of Patent: *Feb. 6, 2001

(54) UNIQUE ASSOCIATED KAPOSI'S SARCOMA VIRUS SEQUENCES AND USES THEREOF

(75) Inventors: Yuan Chang, New York, NY (US); Roy A. Bohenzky, Mountain View, CA (US); James J. Russo, New York, NY (US); Isidore S. Edelman, New York, NY (US); Patrick S. Moore, New York, NY (US)

(73) Assignee: The Trustees of Columbia University in the City of New York, New York, NY (US)

( * ) Notice: Under 35 U.S.C. 154(b), the term of this patent shall be extended for 0 days.

This patent is subject to a terminal disclaimer.

(21) Appl. No.: 08/757,669

(22) Filed: Nov. 29, 1996

Related U.S. Application Data

(63) Continuation-in-part of application No. 08/592,963, filed on Jan. 29, 1996, now abandoned, and a continuation-in-part of application No. PCT/US95/15138, filed on Nov. 21, 1995, and a continuation-in-part of application No. PCT/US95/10194, filed on Aug. 11, 1995, and a continuation-in-part of application No. 08/420,235, filed on Apr. 11, 1995, now Pat. No. 5,801,042, and a continuation-in-part of application No. 08/343,101, filed on Nov. 21, 1994, now Pat. No. 5,630,754, which is a continuation-in-part of application No. 08/292,365, filed on Aug. 18, 1994, now abandoned.

(51) Int. Cl.$^7$ .................. A61K 39/12; A61K 39/245; C07H 21/04
(52) U.S. Cl. .................. 424/199.1; 424/204.1; 424/186.1; 424/194.1; 424/229.1; 424/230.1; 435/235.1; 435/320.1; 435/70.1; 530/350; 530/300; 536/23.72
(58) Field of Search .................. 424/199.1, 194.1, 424/204.1, 186.1, 229.1, 230.1; 536/23.72; 435/70.1, 320.1, 235.1; 530/350, 300

(56) References Cited

U.S. PATENT DOCUMENTS 5,861,240 * 1/1999 Ganem et al. .................. 435/5

OTHER PUBLICATIONS

Baer et al (1984) DNA sequence and expression of the B95–8 Epstein–Barr virus genome, Nature 310, 207–211.
Mosca et al (1987) Herpes simplex virus type–1 can reactivate transcription of latent immunodeficiency virus, Nature 325, 67–70.
Delli Bovi et al (1987) Isolation of a rearranged human transforming gene following transfection of Kaposi sarcom DNA, Proc Natl Acad Sci USA 84, 5660–5664.
Gallo (1993) Aspects of the molecular pathogenesis of AIDS, J Cellular Biochem 17E, 5.
Gallo (1994) New approaches for interfering with human immunodeficiency virus replication and for Kaposi's sarcoma, J Cellular Biochem 18B, 108.

Chang et al (1994) Identification of herpesvirus–like DNA sequences in AIDS–associated Kaposi's sarcoma, Science 265, 1865–1869.
Cesarman et al (1995) Kaposi's sarcoma–associated herpesvirus–like DNA sequences are present in AIDS–related body cavity based lymphomas, The FASEB Journal 9, A973, Abstract 5650.
Gompels et al (1988) Conservation of glycoprotein H (gh) in herpes–viruses: nucleotide sequence of the gH gene from herpesvirus saimiri, J Gen Virol 69, 2819–2829.
Forrester et al (1991) Construction and properties of a mutant of herpes simplex virus type 1 with glycoprotein H coding sequences deleted, J Virol 66, 341–348.
Roop et al (1993) A mutant herpes simplex virus type 1 unable to express glycoprotein L cannot enter cells, and its particles lack glycoprotein L cannot enter cells, and its particles lack glycoprotein H, J Virol 67, 2285–2297.
Scott et al (1993) Identification and sequence analysis of the homologues of the herpes simplex virus type 1 glycoprotein H in Marek's disease virus and the herpesvirus of turkeys, J Gen Virol 74, 1185–1190.
Liu et al (1993) Human herpesvirus–6 glycoprotein H and L homologs are components of the gp100 complex and the gH external domain is the target for neutralizing monoclonal antibodies, Virology 197, 12–22.
Tewari et al (1994) Characterization of immune responses to baculovirus–expressed equine herpesvirus type 1 glycoproteins D and H in a murine model, J Gen Virol 75, 1735–1741.
McGowan et al (194) Expression and characterization of equine herpesvirus 1 glycoprotein H using a recombinant baculovirus, Arch Virol 137, 389–395.
Pulford et al (1994) Expression of the Epstein–Barr virus envelope fusion glycoprotein gp85 gene by a recombinant baculovirus, J Gen Virol 75, 3241–3248.
Farrell et al (1994) Vaccine potential of a herpes simplex virus type 1 mutant with an essential glycoprotein deletd, J Virol 68, 927–932.
Baranowski et al (1995) Synthesis and processing of bovine herpesvirus–1 glycoprotein H, Virology 206, 651–654.
Ambroziak and Blackbourn (1995) Herpes–like sequences in HIV–infected and uninfected Kaposi's sarcoma, Science 268, 582–583.

(List continued on next page.)

Primary Examiner—Ali Salimi
(74) Attorney, Agent, or Firm—John P. White; Cooper & Dunham LLP

(57) ABSTRACT

This invention provides an isolated nucleic acid molecule which encodes Kaposi's Sarcoma-Associated Herpesvirus (KSHV) polypeptides. This invention provides an isolated polypeptide molecule of KSHV. This invention provides an antibody specific to the polypeptide. Antisense and triplex oligonucleotide molecules are also provided. This invention provides a vaccine for Kaposi's Sarcoma (KS). This invention provides methods of vaccination, prophylaxis, diagnosis and treatment of a subject with KS and of detecting expression of a DNA virus associated with Kaposi's sarcoma in a cell.

15 Claims, 29 Drawing Sheets

OTHER PUBLICATIONS

Bassett et (1995) Cancer in the African population of Harare, Zimbabwe, 1990–1992, Int J Canc 63, 29–36.
Benelli et al (1996) Isolation of spindle–shaped cell populations from primary cultures of Kaposi's sarcoma of different stage, Cancer Lett 100, 125–132.
Boshoff et al (1995) Kaposi's sarcoam–associated herpesvirus infects endothelial and spindle cells, Nat Med 1, 1274–1278.
Brady et al (1995) Altered cytokine expression in T lymphocytes from human immunodeficiency virus tat–transgenic mice, J Virol 69, 7622–7629.
Braun et al (1995) Identification of target genes for the Ewing's sarcoma EWS/FLI fusion protein by representational difference analysis, Mol Cell Biol 15, 4623–4630.
Broder and Karp (1995) Progress against cancer, J Cancer Res 121, 633–647.
Cesarman et al (1995) Kaposi's sarcoma–associated herpesvirus–like DNA sequences are present in AIDS–related body cavity base lymphomas, Faseb J 9, A973.
Cesarman et al (1995) Kaposi's sarcoma–associated herpesvirus–like DNA sequences in AIDS–related body–cavity––based lymphomas, New Eng J Med 332, 1186–1191.
Cesarman (1995) Periorbital edema in Kaposi's sarcoma, New Eng J Med 333, 799.
Cesarman et al (1995) In virtro establishment and characterization of two acquired immunodeficiency syndrome–related lymphoma cell lines (BC–1 and BC–2) containing Kaposi's sarcoma–associated herpesvirus–like (KSHV) DNA sequences, Blood 86, 2708–2714.
Chang (1995) Letter to the editor, Science 267, 1079.
Chang et al (1995) Letter to the editor, Annal Oncol 6, 744–745.
Chang et al (1994) Identification of herpesvirus–like DNA sequences in AIDS–associated Kaposi's sarcoma, Science 266, 1856–1869.
Chee et al (1990) Human cytomegalovirus encodes three G protein–coupled receptor homologues, Nature 344, 744–777.
Cohen (1994) Is a new virus the cuase of KS?, Science 266,1803–1804.
Cohen (1995) Controversy: is KS really caused by new herpesvirus, Science 268, 1847–1848.
Coleman et al (1995) Generalized endemic Kaposi's sarcoma, Clin Exp 20, 471–473.
Collandre et al (1995) Kaposi's sarcoma and new herpesvirus, Lancet 345, 1043.
Costagliola et al (1995) Can antiviral agents decrease the occurence of Kaposi's sarcoma!, Lancet 346, 578.
Delellis et al (1995) Herpesvirus–like DNA sequences in non–AIDS Kaposi's sarcoma, J Infec Dis 172, 1605–1607.
Drew and Brindley (1995) Female–specific sequences isolated from Schistosoma mansoni by representational difference analysis, Mol Biochem Parasitology 71, 173–181.
Dupin (1995) Letter to the editor, New Eng J Med 333, 798.
Duvic (1995) Human immunodeficiency virus and the skin: selected controversies, J Inves Derm 10, S117–S120.
Ekman (1995) Herpes virus like (KSHV) DNA in various forms of Kaposi's sarcoma (KS) and malignant lymphoma (ML), National Canc Inst 11, S74.
Farid (1995) Letter to the editor, New Eng J Med 332, 1647.
Gallo (1995) Human retroviruses in the second decade: a personal perspective, Nat Med 1, 753–759.

Geddes et al (1995) Birthplace and classic Kaposi's sarcoma in Italy, J Nat Canc Inst 87, 1015–1017.
Glassman and Hale (1995) Cutaneous cryptococcosis and Kaposi's sarcoma occurring in the same lesions in a patient with the aquired immunodeficiency syndrome, Clin Exp Derm 20, 480–486.
Gluckman et al (1995) KS–associated herpesvirus–like DNA sequences after allogenic bone–marrow transplatation, Lancet 346, 1558–1559.
Gooding (1992) Virus proteins that counteract host immune defenses, Cell 71, 5–7.
Griffiths (1995) Progress in the clinical management of herpesvirus infections, Antiviral Chemistry Chemotherapy 6, 191–209.
Grau et al (1995) Association of Mycoplasma penetrans with human immunodeficiency virus infection, J Infec Dis 172, 672–681.
Horuk (1994) Molecular properties of the chemokine receptor family Trends Pharmacol Sci 15, 159–165.
Howard et al (1995) Association of hyman herpes virus with pulmonary Kaposi's sarcoma, Lanet 346, 712.
Hermans and Clumeck (1995) Kaposi's sarcoma in patients infected with human immunodeficiency virus (HIV): an overview, Cell Mol Biol 41, 357–364.
Ioachim (1995) Kaposi's sarcoma and KSHV, Lancet 346, 1360.
Jahan et al (1989) Analysis of human KS biopsies and cloned cell lines for cytomegalovirus, HIV–1, and other selected DNA virus sequences, Aids Research Human Retro 5, 225–231.
Jones et al (1995) AIDS–associated Kaposi's sarcoma, Science 267, 1078–1079.
Jung and Desrosiers (1995) Association of the viral oncoprotein STP–C–488 with cellular ras, Mol Cell Biol 15, 6506–6512.
Jung et al (1995) Downregulation of lck–mediated signal transduction by tip of Herpesvirus saimiri, J Virol 69, 7814–7822.
Kaplan et al (1995) USPHS/IDSA guidelines for the prevention of opportunistic infections in persons infected with human immunodeficiency virus: introduction, Clin Inf Dis 21, S1–S11.
Karcher and Alkan (1995) Herpes–like DNA sequences, AIDS–related tumors, and Castleman's disease, New Eng J Med 333, 797–798.
Karp and Broder (1995) Molecular foundations of cancer: new targets for intervention, Nat Med 1, 309–320.
Kempf et al (1995) Human herpesvirus type 6 and cytomegalovirus in AIDS–associated Kaposi's sarcoma, Human Pathol 26, 914–919 (Exhibit.
Klauke et al (1995) Sex hormones as a cofactor in the pathgenesis of epidemic Kaposi's sarcoma, Aids 9, 1295–1296.
Lebbe et al (1995) Kaposi's sarcoma and a new herpesvirus, Lancet 345, 1180.
Levy (1995) A new human herpesvirus: KSHV or HHV8?, Lancet 346.
Levine (1995) Viral–associated neoplasms in humans: additional clues, J Nat Canc Inst 87, 947–949.
Lin et al (1995) Is Kaposi's–sarcoma–associated herpesvirus detectable in semen of HIV–infected homosexual men? Lancet 346, 1601–1602.

Lisitsyn (1995) Representational difference analysis: finding the difference between genomes, Trends Genetics 11, 303–307.
Murphy (1994) The molecular biology of leukocyte chemoattractant receptors, Annu Rev Immunol. 12, 593–633.
Macasaet et al (1995) Kaposi's sarcoma presenting as a vulvar mass, Obstet Gyn 86, 695–697.
Mallery et al (1995) Cultured AIDS–related Kaposi's sarcoma (AIDS–KS) cells demonstrate impaired bioenergetic adaption to oxidant challenge.
McGrath et al (1995) Identification of a clonal form of HIV in early Kaposi's sarcoma: evidence for a novel model of oncogenesis, "sequential neoplasia" J Acq Immun Def 8, 379–385.
implication for oxidant stress in AIDS–KS pathogenesis, J Cell Biol 59, 317–328.
Marmor et al (1995) Evidence for an effect of human leukocyte antigens on susceptibility to Kaposi's sarcoma related to charge and peptide–properties of class I molecule, Aids9, 1194–1195.
Memar and Tyring (1995) Cutaneous viral infections, J Am Acad Derm 33, 279–287.
Memar et al (1995) Human herpesvirus–8: detection of novel herpesvirus–like DNA sequences in Kaposi's sarcoma and other lesions, J Mol Med 73, 603–609.
Moore et al (1995) Bacillary angiomatosis in patients with AIDS: multiorgan imaging findings 1, Radiology 197, 67–72.
Moore and Chang (1995) Detection of herpes–like DNA sequences in Kaposi's sarcoma in patients with and those without HIV infection, New Eng J Med 332, 1181–1185.
Morris et al (1995) Viral infection and cancer, Lancet 346, 754–758.
Maier et al (1996) Over–expression of hepatocyte growth factor in human Kaposi's sarcoma, Int J Cancer 65, 168–172.
Nador et al (1995) Herpes–like DNA sequences in a body––cavity–based lymphoma in an HIV–negative patient, New Eng J Med 333, 943.
Newton et al (1995) Cancer and HIV infection in Rwanda, Lancet 345, 1378–1379.
Noel (1995) Kaposi's sarcoma and KSHV, Lancet 346, 1359.
Pastore et al (1995) Distribution of Kaposi's sarcoma herpesvirus sequences among lymphoid malignancies in Italy and Spain, Br J Haem 91, 919–920.
Rady et al (1995) Herpesvirus–like DNA sequences in non–Kaposi's sarcoma skin lesions of transplant patients, Lancet 345, 1339–1340.
Rady et al (1995) Herpesvirus–like DNA sequences in classic Kaposi's sarcomas, J Med Virol 47, 179–183.
Relman (1995) Has trench fever returned, New Eng J Med 332, 463–464.
Roizman (1995) New viral footprints in Kaposi's sarcoma, New Eng J Med 332, 1227–1228.
Roulston et al (1995) Regulation of human immunodeficiency virus type 1 and cytokine gene expression in myelid cells by NF–kB/Rel transcription factors, Microbiol Res 59, 481–505.
Rubin (1995) Letter to the editor, Science 267, 157–158.
Saiag et al (1995) Local treatments of AIDS associated Kaposi's sarcoma, Ann Der Ven 122, 551–557.

Schalling et al (1995) A role for a new herpes virus (KSHV) in different forms of Kaposi's sarcoma, Nat Med 1, 707–708.
Schulz and Weiss (1995) A finger on the culprit, Nature 373, 17.
Schutte et al (1995) Identification by representational difference analysis of a homozygous deletion in pancreatic carcinoma that lies within the BRCA2 region, Proc Natl Acad Sci USA 92, 5950–5954.
Serraino et al (1995) HIV transmission and Kaposi's sarcoma among European women, Aids 9, 971–973.
Soulier et al (1995) Kaposi's sarcoma–associated herpesvirus–like DNA sequences in multicentric Castleman's disease, Blood 86, 1276–1280.
Stewart et al (1995) Herpesvirus infections in persons infected with human immunodeficiency virus, Clin Inf Dis 21, S114–S120.
Su et al (1996) Detection and sequence analysis of a new herpesvirus–like agent in AIDS and non–AIDS Kaposi's sarcoma in Taiwan, J Formosan Med 95, 13–18.
Telford et al (1995) The DNA sequence of equine herpesvirus 2, J Mol Biol 249, 520–528.
Wang et al (1995) Acquired immunodeficiency syndrome–related Kaposi's sarcoma, Mayo Clin Proc 70, 869–879.
Whitby et al (1995) Detection of Kaposi's sarcoma associated herpesvirus in peripheral blood of HIV–infected individuals and progression to Kaposi's, Lancet 346, 799–802.
Winston and Klotman (1996) Are we missing an epidemic of HIV–associated nephropathy? An Soc Nephrol 7, 1–7.
Ziegler and Katongole–Mbidde (1996) Kaposi's sarcoma in childhood: an analysis of 100 cases from Uganda and relationship to HIV infection, Int J Canc 65, 200–203.
Ansari et al (1996) Primary body cavity–based AIDS–related lymphomas, Am J Clin Pathol 105, 221–229 (Exhibit 2).
Armenian et al (1996) Risk factors for non–Hodgkin's lymphoma in acquired immunodeficiency syndrome (AIDS), Am J Epidemiol 143, 374–379 (Exhibit 3).
Arvanitakis et al (1996) Human herpesvirus KSHV encodes a constitutively active G–protein–coupled receptor linked to cell proliferation, Nature 385, 347–350 (Exhibit 4).
Biggar and Melbye (1996) Marital status in relation to Kaposi's sarcoma, non–hodgkin's lymphoma, and anal cancer in the pre–AIDS era, J Acq Immun Def Syn Hum Retroviral 11, 178–182 (Exhibit 5).
Biogoni te al (1996) Human herpesvirus 8 is present in the lymphoid system of healthy persons and can reactivate in the course of AIDS, J Infect Dis 173, 542–549 (Exhibit 6).
Corey (1996) Commentary: lack of detection of HSV DNA in PBMCs and lymph nodes of HIV–infected persons, J Med virol 48, 47 (Exhibit 7).
DiAlberti et al (1996) Kaposis's sarcoma herpesvirus in oral Kaposi's sarcoma, Oral Oncol 328, 68–69 (Exhibit 8).
Foreman et al (1996) Cultured Kaposi's sarcoma tumor cells fail to stimulate T cell proliferation, Clin Immunol Immunopathol 78, 172–179 (Exhibit 9).
Gyulai et al (1996) Herpesvirus–like DNA sequence in angiosarcoma in a patient without HIV infection, N Eng J Med 334, 540–541 (Exhibit 10).
Heredia et al (1996) Detection of herpesvirus type 8 (HIV–8) sequences in patients with Kaposi's sarcoma in Spain, J Acq Immun Def Syn Hum Retroviral 11, 310–311 (Exhibit 11).

Jaffe (1996) Primary body cavity–based AIDS–related lymphomas, evolution of a new disease entity, Am J Clin Pathol 105, 141–143 (Exhibit 12).

Jin et al (1996) Detection of Kaposi's sarcoma–associated herpesvirus–like DNA sequence in vascular lesions, a reliable diagnostic marker for Kaposi's sarcoma, Am J Clin Pathol 105, 360–363 (Exhibit 13).

Kemeny et al (1996) Herpesvirus–like nucleic acid sequences in patients with western European sporadic Kaposi's sarcoma, J Invest Derm 106, 381 (Exhibit 14).

Kiaris et al (1996) Detection of herpesvirus–like DNA sequences in Mediterranean Kaposi's sarcoma, Oncol Rep 3, 355–356 (Exhibit 15).

Renne et al (1996) Lytic growth of Kaposi's sarcoma–associated herpesvirus (human herpesvirus 8) in culture, Nat Med 2, 342–346 (Exhibit 16).

Retting et al (1996) Kaposi's sarcoma–associated herpesvirus infection of bone marrow dendritic cells from multiple myeloma patients, Science 276, 1851–1854 (Exhibit 17).

Sable and Mandel (1996) The role of molecular techniques in the unstanding of emerging infections, Molec Med Today 2, 120–128 (Exhibit 18).

Sosa et al (1996) Herpesvirus–like DNA in AIDS Kaposi's sarcoma in Argentina, J Acq Immun Def Syn Hum Retroviral 11, 308 (Exhibit 19).

Tompkins (1996) Bartonella species infections, including cat–scratch disease, trench fever, and bacillary angiomatosis: what molecular techniques have revealed, Western J. Med 164, 39–41 (Exhibit 20).

Tur (1996) Treatment of Kaposi's sarcoma, Arch Dermatol 132, 327–331 (Exhibit 21).

Tyring (1996) HHV8 and skin cancers in immunosuppressed patients, Lancet 347, 338–339 (Exhibit 22).

Weiss (1996) Human herpesvirus 8 in lymphoma and Kaposi's sarcoma: now the virus can be propagated, Nat Med 2, 277–278 (Exhibit 23); and.

Zalla (1996) Kaposi's sarcoma: an update, Dermatol Surg 22, 274–287 (Exhibit 24).

Carbone et al (Sep. 1, 1996) Kaposi's sarcoma–associated herpesvirus DNA sequences in AIDS–related and AIDS–unrelated lymphomatous effusions, Br J Haematol 94, 533–543 (Exhibit 2).

Cesarman et al (Jul. 1996) Kaposi's sarcoma–associated herpesvirus in non–AIDS related lymphomas occurring in body cavities, Am J Pathol 149, 53–57 (Exhibit 3).

Chang et al (Jan. 22, 1996) Kaposi's sarcoma–associated herpesvirus and Kaposi's sarcoma in Africa, Arch Intern Med 156, 202–204 (Exhibit 4).

Corbellino et al (May 20, 1996) Restricted tissue distribution of extralesional Kaposi's sarcoma–associated herpesvirus–like DNA sequences in AIDS patients with Kaposi's sarcoma, AIDS Res Hum Retroviruses 12, 651–657 (Exhibit 5).

Decker et al (Jul. 1, 1996) The Kaposi sarcoma–associated herpesvirus (KSHV) is present as an intact latent genome in KS tissue but replicates in the peripheral blood mononuclear cells of KS patients, J Exp Med 184, 283–288 (Exhibit 6).

Dictor et al (Jun. 1996) Human herpesvirus 8 (Kaposi's sarcoma–associated herpesvirus) DNA in Kaposi's sarcoma lesions, AIDS Kaposi's sarcoma cell lines, endothelial Kaposi's sarcoma simulators, and the skin of immunosupressed patients, Am J Pathol 148, 2009–2016 (Exhibit 7).

Enwonwu (Jul. 1996) Pathogenesis of oral Kaposi's sarcoma in HIV–fection: relevance of endogenous glucocorticoid excess in blood and saliva, (Eur J Cancer B) Oral Oncol 32B, 271–274 (Exhibit 8).

Gaidano et al (Jul 1996) Establishment of AIDS–related lymphoma cell lines from lymphomatous effusions, Leukemia 10, 1237–1240 (Exhibit 9).

Humphrey et al (Jul. 1, 1996) Kaposi's sarcoma (KS)–associated herpesvirus–like DNA sequences in peripheral blood mononuclear cells: association with KS and persistence in patients receiving anti–herpesvirus drugs, Blood 88, 297–301 (Exhibit 10).

Luppi et al (May 16, 1996) Frequency and distribution of herpesvirus–like DNA sequences (KSHV) in different stages of classic Kaposi's sarcoma and in normal tissues from an Italian population, Int J Cancer 66, 427–431 (Exhibit 11).

Mesri et al (May 1, 1996) Human herpesvirus–8/Kaposi's sarcoma–associated herpesvirus is a new transmissible virus that infects B cells, J Exp Med 183, 2385–2390 (Exhibit 12).

Miller et al (May 16, 1996) Antibodies to butyrate–inducible antigens of Kaposi's sarcoma–associated herpesvirus in patients with HIV–1 infection, N Eng J Med 334, 1292–1297 (Exhibit 13).

Monini et al (May 2, 1996) Kaposi's sarcoma–associated herpesvirus DNA sequences in prostate tissue and human semen, N Engl J Med 334, 1168–1172 (Exhibit 14).

Nador et al (Jul 15, 1996) Primary effusion lymphoma: a distinct clinicopathologic entity associated with the Kaposi's sarcoma–associated herpes virus, Blood 88, 645–656 (Exhibit 15).

Offerman et al (Sep. 1996) Antioxidant–sensitive regulation of inflammatory–response genes in Kaposi's sarcoma cells, J Aquir Immune Defic Syndr Hum Retroviral 13, 1–11 (Exhibit 16).

O'Neil et al (Apr. 1996) Herpes virus–like sequences are specifically found in Kaposi sarcoma lesions, J Clin Pathol 49, 306–308 (Exhibit 17).

Otsuki et al (Aug. 1996) Detection of HHV–8/KSHV DNA sequences in AIDS–associated extranodal lymphoid malignancies, Leukemia 10, 1358–1362 (Exhibit 18).

Rudlinger (Feb. 1996) Das enigma Kaposi–sarkom, Der Hautrartz 47, 91–95 (Exhibit 19).

Said et al (Jun. 15, 1996) Kaposi's sarcoma–associated herpesvirus (KSHV or HHV8) in primary effusion lymphoma: ultrastructural demonstration of herpesvirus in lymphoma cells, Blood 87, 4937–4943 (Exhibit 20).

Su et al (Jan. 1996) Detection and sequence analysis of a new herpesvirus–like agent in AIDS and non–AIDS Kaposi's sarcoma in Taiwan, J Formos Med Assoc 95, 13–18 (Exhibit 21).

Tomita et al (Mar. 28, 1996) Absence of Kaposi's–sarcoma–associated herpesvirus–like DNA sequences (KSHV) in angiosarcomas developing in body––cavity and other sites, Int J Cancer 66, 141–142 (Exhibit 22).

Zhong et al (Jun. 25, 1996) Restricted expression of Kaposi sarcoma–associated herpesvirus (human herpesvirus 8) genes in Kaposi sarcoma, Proc Natl Acad Sci 93, 6641–6646 (Exhibit 23); and.

Ziegler et al (Jan. 17, 1996) Kaposi's sarcoma in childhood: an analysis of 100 cases from Uganda and relationship to HIV infection, Intl J Cancer 65, 200–203 (Exhibit 24).

Albrecht et al, 1992, J. of Virology, vol.66 (8), pp. 5047–5058, 1992.*

* cited by examiner

FIGURE 2A

```
1    CGTGAACACC CCGCGCCCCG CGCCCCCCAC ACCGCGCCGC CCCTCCCCCT CCCCCCGCTC
61   GCCTCCCGGC GCTGCCGCCA GGCCCCGGCC GGAGCCGGCC GCCCGGGGGG GGCAGGGCGC
121  GCCCGGCGGC TCCCTCGCGG GGCGGGGGAC GGGGGAGGgg ggcgccggc  CCCCGCGCGC
181  CGCGGCAGCG GAGCGCGAGc gccccgccg  gccgccgcGCG GCGGCGCAGG CCCCGGGGCC
241  CCGAGCCCCG AGCCCCGCCG GGGTACGGGG CTAGgccacg cctactttt  tttcgggcg
301  gccccccgac cctctctcgg ccccccggTC CCCGGgCCC GCGGCGCCC  CCCCGGGGG
361  GTAAACAGG GGGGGGGGA  TGCGGCCCCG GCGGCGCCCG CGGCGGCGGC GGCGCTTGCt
421  ttcgttttct cccgcggccc cccgggcgcg agccgcgcgg cgcgcggg  cgccccctcc
481  cccgggggc  tcggcggggg gccCCCTGTC CCgcgcgcgg cccgcgccc  ccGGCGCCGG
541  cggcccccga TCCCGCGGGC GCCCCCCGCC CCTGCCGGGG ACGCCGGCGG GCCTGCGGCG
601  CCTCCCGCCC GGGCATGGGg ccgcgcgccg cctcaggggcc cggcgcggcc ggcgcctggt
661  ccccgccccc gccgcggggg gacccccggc AGCGAGGGAA GGGGGCGCCC TCTCTCTACT
721  GTGCGAGGAG TCTGGGCTGC TGTGTGTGAG CCTGTTTGGG GGAGCCTCCT CAGTGCTTGC
781  TACGTGGAGC CCTGGACACT A
```

FIGURE 3A

```
                     10            20            30
vMIP-I     MAPVHVLCCV SVLLATFYLT PTESAGSLVS
vMIP-II    M-DTKGILEV XVLTALLCLQ XGDTLG-ABW
huMIP-1α   M-QVSTAAL- AVLLCTMALC NQVLSAPLAA
huMIP-1β   M-KLCVTVL- SLMLVAAFC SPALSAPMGS
huRANTES   M-KVSAARL- AVILIATALC APASASPYGS 40            50            60
vMIP-I     YTPNSCCYGF QQHPPPVQIL KEWYPTSPAC
vMIP-II    HRPDKCCLGY QKRPLPQVLL SSWYPTSQLC
huMIP-1α   DTPTACCFSY TSRQIPQNFI ADYFETSSQC
huMIP-1β   DPPTACCFSY TARKLPRNFV VDYYETSSLC
huRANTES   DT-TPCCFAY IARPLPRAHI KEYFYTSGKC 70            80            90
vMIP-I     PKPGVILLTK RGRQICADPS KNWVRQLMQR
vMIP-II    SKPGVIFLTK RGRQVCADKS KDWVKKLMQQ
huMIP-1α   SKPSVIFLTK RGRQVCADPS EEWVQKYVSD
huMIP-1β   SQPAVVFQTK RSKQVCADPS ESWVQEYVYD
huRANTES   SNPAVVFVTR KNRQVCANPE KKWVREYINS 95
vMIP-I     LPAIA-
vMIP-II    LPVTAR
huMIP-1α   LELSA-
huMIP-1β   LELN--
huRANTES   LEMS--
```

FIGURE 3B

```
                    10              20              30
vIL6   MCWFKLWSLL  LV----GSLL  VSGTRGKLPD
huIL6  MNSFSTSAFG  PVAFSLGLLL  VLPAAFPAPV 40              50              60
vIL6   AP-EFEKDL-  --LIQRLNWM  LWV-----I
huIL6  PPGEDSKDVA  APHROPLTSS  ERIDKQIRYI 70              80              90
vIL6   DECFRDL---  -CYRTGICKG  ILEPAAIFHL
huIL6  LDGISALRKE  TCNKSNMCES  SKEALAENNL 100             110             120
vIL6   KLPAINDTDH  CGLIGFNETS  CLKKLADGFF
huIL6  NLPKMAEKDG  CFQSGFNEET  CLVKIITGLL 130             140             150
vIL6   EFEVLFKFLT  TEFGKSVINV  DVMELLTKTL
huIL6  EFEVYLEYLQ  NRFESSEEQA  RAVQMSTKVL 160             170             180
vIL6   GWDIQEELNK  LTKTHYSPPK  FDRGLLGRLQ
huIL6  IQFLQKKAKN  LDAITTPDPT  TNASLLTKLQ 190             200             210
vIL6   GLKYWVRHFA  SFYVLSAMEK  FAGQAVRVLD
huIL6  AQNQWLQDMT  THLILRSFKE  FLQSSLRAL- 220
vIL6   SIPDVTPDVH  DK
huIL6  --------R   QM
```

FIGURE 3C-1-A

```
                            10                  20                  30
vIRF       MDPGQRPNPF  GAPGAIPKKP  CLSQGSPGTS
huISGF3γ
huICSBP 40                  50                  60
vIRF       GSGAPCDEPS  RSESPGEGPS  GTGGSAAAGD
huISGF3
huICSBP 70                  80                  90
vIRF       ITRQAVVAAI  TEWSRTRQLR  ISTGASEGKA
huISGF3                                         MASGRARCTR
huICSBP                                         MCDRNGGGR 100                 110                 120
vIRF       SIKDWIVCQV  NSGKFPGVEW  EDEERTRFRI
huISGF3    KLRNWVEQV   ESGQFPGVCW  DDTAKTMFRI
huICSBP    -LRQWLIEQI  DSSMYPGLIW  ENEEKSMFRI 130                 140                 150
vIRF       PVTPLADPCF  EWRRDGELGV  VYIRERGNMP
huISGF3    PWKHAGKQDE  REDQDAAFFK  AWAIFKGKYK
huICSBP    PWKHAGKQDY  NQEVDASIFK  AWAVFKGKFK 160                 170                 180
vIRF       VDASFKGTRG  RRRMLAALRR  TRGLQEIG-K
huISGF3    EGDTGGPAVW  KTRLRCALNK  SSEFKEVPER
huICSBP    EGDKAEPATW  KTRLRCALNK  SPDFEEVTDR 190                 200                 210
vIRF       GISQDGHHFL  VFRVRKPEEE  QCVECGVVAG
huISGF3    GRMDVAEPYK  VYQLLPGIV   SGQPGTQKVP
huICSBP    SQLDISEPYK  VYRIVPEEDQ  KCKLGVATAG
```

FIGURE 3C-1-B

```
                     220              230                240
vIRF      A V H D F N N M A - - R L L Q E G F F S - - - - P G Q C L
huISGF3   S K R Q H S S V S S  E R K E E E D A M Q  N C T L S P S V L Q
huICSBP   C V N E V T E M E C  G R S E I D E L I K - - - - E P S V D D 250              260                270
vIRF      P G E I V T P V P S  C T T A E G Q E A V  I D W G - - - - -
huISGF3   D S L N N E E E G A  S G G A V H S D I G  S S S S S S P E P
huICSBP   Y M G M I K R S P S  P P D A C R S Q L L  P D W A H E P S T 270              280                300
vIRF      - - - - - - - - - -  - - - - - - - - - - - - - - - R L
huISGF3   Q E V T D T T E A P  F Q G D Q R S L E F  L L P P E P D Y S L
huICSBP   G R R L V T G Y T T  Y D A H H S A F S - - - - - - - Q M
```

FIGURE 3C-2-A

```
                        310                  320                  330
vIRF      F I R M Y Y N G E Q   V H E L L T T S Q S   G C R I S S A L R R
huISGF3   L L T F I Y N G R V   V G E A Q V Q S L D   - C R L V A E - - -
huICSBP   V I S F Y Y G G K L   V G Q A T T T C P E   G C R L S L S Q P G 340                  350                  360
vIRF      D P A V H Y C A V G   S P G Q V W L P - N   V P N L A C E I A K
huISGF3   - P - - S G S - E S   S M E Q V L F P K P   G P L E P T - - Q R
huICSBP   L P G T K L Y G P E   G L E L V R F P - P   A D T I P S E R Q R 370                  380                  390
vIRF      R E L C D T L D A C   A K G I L L T S S C   N G I F C V C Y H N
huISGF3   - - - - - - L L S Q L E R G I L V A S N P   R G L F V Q R L C P
huICSBP   Q V T R K L F G H L   E R G V L H S S R -   Q G V F V K R L C Q 400                  410                  420
vIRF      G P V H F I G N T V   P P D S G P L L L P   Q G K P T R I F N P
huISGF3   I P I S W N A P Q A   P P G P G P H L L P   S N E C V E L F R T
huICSBP   G R V F C V V V V V   V C K G R P N K L E   R D E V V Q V F D T
```

FIGURE 3C-2-B

```
                    430                    440                   450
vIRF       N T F L V G L A N - - - S - - P L P A P  S H V T C P L V K L
huISGF3    A Y F C R D L V R Y  F Q G L G P P P K F  Q V T L N F W E E S
huICSBP    S Q F F R E L Q Q F  Y N S Q G R L P D G  R V L C F G E E F 460                    470                   480
vIRF       W L G K P V A V G K  L E P H A P S P - -  R D F A A R C S N F
huISGF3    H G S S H T P Q N L  I T V K M E Q A F A  R Y L L E Q T P E Q
huICSBP    P D M A P L R S K L  I L V Q I E Q L Y V  R Q L A E E A G K S 490                    500                   510
vIRF       S D A C V L E I M   P K P L W D A M Q -   - - - - - - - - -
huISGF3    Q A A I L S L V - -  - - - - - - - - -   - - - - - - - - -
huICSBP    C G A G S V M Q A P  E E P P P D Q V F R  M F P D I C A S H Q 520
vIRF       - - - - - - - - -   - -
huISGF3    - - - - - - - - -   - -
huICSBP    R S F F R E N Q Q I  T V
```

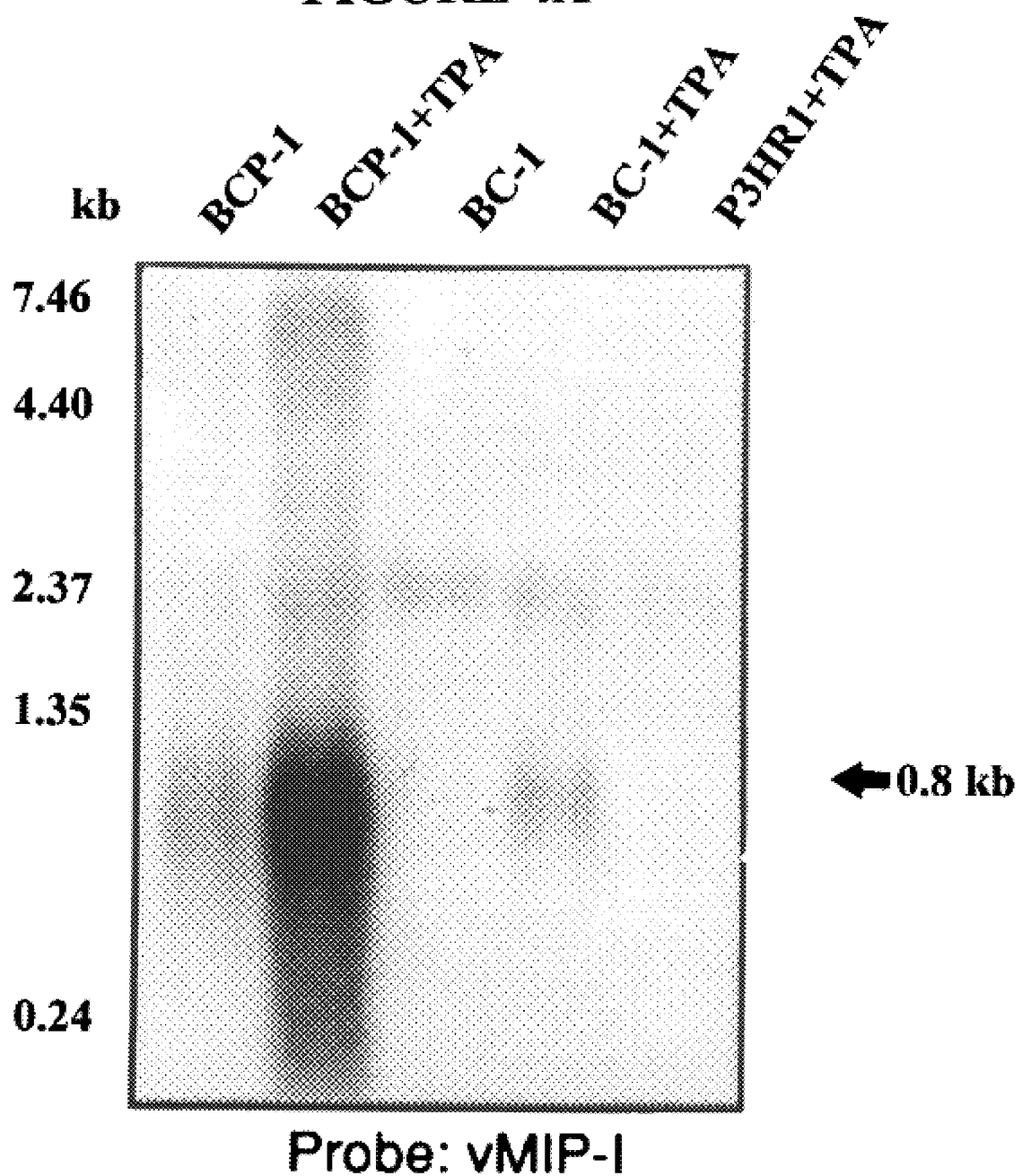

Probe: β-actin

Probe: β-actin

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH:  337 amino acids
      (B) TYPE: amino acid
      (D) TOPOLOGY: linear (ii) MOLECULE TYPE: protein (xi) SEQUENCE DESCRIPTION: SEQ ID NO:1:

```
Met Phe Pro Phe Val Pro Leu Ser Leu Tyr Val Ala Lys Lys Leu Phe
 1               5                  10                  15

Arg Ala Arg Gly Phe Arg Phe Cys Gln Lys Pro Gly Val Leu Ala Leu
                20                  25                  30

Ala Pro Glu Val Asp Pro Cys Ser Ile Gln His Glu Val Thr Gly Ala
            35                  40                  45

Glu Thr Pro His Glu Glu Leu Gln Tyr Leu Arg Gln Leu Arg Glu Ile
        50                  55                  60

Leu Cys Arg Gly Ser Asp Arg Leu Asp Arg Thr Gly Ile Gly Thr Leu
65                  70                  75                  80

Ser Leu Phe Gly Met Gln Ala Arg Tyr Ser Leu Arg Asp His Phe Pro
                85                  90                  95

Leu Leu Thr Thr Lys Arg Val Phe Trp Arg Gly Val Val Gln Glu Leu
                100                 105                 110

Leu Trp Phe Leu Lys Gly Ser Thr Asp Ser Arg Glu Leu Ser Arg Thr
```

-continued

```
                  115                 120                 125
Gly Val Lys Ile Trp Asp Lys Asn Gly Ser Arg Glu Phe Leu Ala Gly
    130                 135                 140

Arg Gly Leu Ala His Arg Arg Glu Gly Asp Leu Gly Pro Val Tyr Gly
145                 150                 155                 160

Phe Gln Trp Arg His Phe Gly Ala Ala Tyr Val Asp Ala Asp Ala Asp
                165                 170                 175

Tyr Thr Gly Gln Gly Phe Asp Gln Leu Ser Tyr Ile Val Asp Leu Ile
                180                 185                 190

Lys Asn Asn Pro His Asp Arg Arg Ile Ile Met Cys Ala Trp Asn Pro
                195                 200                 205

Ala Asp Leu Ser Leu Met Ala Leu Pro Pro Cys His Leu Leu Cys Gln
        210                 215                 220

Phe Tyr Val Ala Asp Gly Glu Leu Ser Cys Gln Leu Tyr Gln Arg Ser
225                 230                 235                 240

Gly Asp Met Gly Leu Gly Val Pro Phe Asn Ile Ala Ser Tyr Ser Leu
                245                 250                 255

Leu Thr Tyr Met Leu Ala His Val Thr Gly Leu Arg Pro Gly Glu Phe
                260                 265                 270

Ile His Thr Leu Gly Asp Ala His Ile Tyr Lys Thr His Ile Glu Pro
        275                 280                 285

Leu Arg Leu Gln Leu Thr Arg Thr Pro Arg Pro Phe Pro Arg Leu Glu
290                 295                 300

Ile Leu Arg Ser Val Ser Ser Met Glu Glu Phe Thr Pro Asp Asp Phe
305                 310                 315                 320

Arg Leu Val Asp Tyr Cys Pro His Pro Thr Ile Arg Met Glu Met Ala
                325                 330                 335

Val
```

(2) INFORMATION FOR SEQ ID NO:2:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:2:

```
Thr His Tyr Ser Pro Pro Lys Phe Asp Arg
1               5                   10
```

(2) INFORMATION FOR SEQ ID NO:3:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:3:

```
Pro Asp Val Thr Pro Asp Val His Asp Arg
1               5                   10
```

(2) INFORMATION FOR SEQ ID NO:4:

(i) SEQUENCE CHARACTERISTICS:
        (A) LENGTH: 24 base pairs
        (B) TYPE: nucleic acid (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:4:

AGCATATAAG GAACTCGGCG TTAC                                              24

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:5:

GGTAGATAAA TCCCCCCCCT TTG                                               23

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:6:

TGCATCAGCT TCTTCACCCA G                                                 21

(2) INFORMATION FOR SEQ ID NO:7:

(i) SEQUENCE CHARACTERISTICS:
        (A) LENGTH:23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO: 7:

TGCTGTCTCG GTTACCAGAA AAG                                               23

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:8:

TCACGTCGCT CTTTACTTAT CGTG                            24

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:9:

CGCCCTTCAG TGAGACTTCG TAAC                            24

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:10:

CTTGCGATGA ACCATCCAGG                                 20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:11:

ACAACACCCA ATTCCCCGTC                                 20

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:12:

TCACGTCGCT CTTTACTTAT CGTG                                                  24

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:13:

CGCCCTTCAG TGAGACTTCG TAAC                                                  24

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:14:

AGCATATAAG GAACTCGGCG TTAC                                                  24

(2) INFORMATION FOR SEQ ID NO:15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:15:

GGTAGATAAA CTCCCCCCCT TTG                                                   23

(2) INFORMATION FOR SEQ ID NO:16:

(i) SEQUENCE CHARACTERISTICS:
        (A) LENGTH: 801 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:16:

```
CGTGAACACC CCGCGCCCCG CGCCCCCCAC ACCGCGCCGC CCCTCCCCCT CCCCCCGCTC        60
GCCTCCCGGC GCTGCCGCCA GGCCCCGGCC GGAGCCGGCC GCCCGCGGGG GGCAGGGCGC       120
GCCCGGCGGC TCCCTCGCGG GGCGGGGGAC GGGGGAGGGG GGCGCCGGGC CCCCGCGCGC       180
CGCGGCAGCG GAGCGCGAGG GCCCCCGCCG GCCGCCAGCG GCGGCGCAGG CCCCGGGGGC       240
CCGAGCCCCG AGCGGGGCCG GGGTACGGGG CTAGGCCACG AATAATTTTT TTTTCGGGCG       300
GCCCCCCGAA CCTCTCTCGG CCCCCCGGTC CCCGCGGCCC GCGCGCGCCC CCCCGGGGGG       360
GTAAAACAGG GGGGGGGGGA TGCGGCCGCG GCGGCGCCCG CGGCGGCGGC GGCGCTTGCT       420
TTCGTTTTCT CCCGCGGCCC CCCGGGCGCG AGCCGCGCGG CGGCGGCGGG CGCCCCCTCC       480
CCCGGGGGGC TCGGCGGGGG GCCCCCTGTC CCCGCGCGGG CCCGCGACCC CCGGCGCCGC       540
CGCGCCCCGA TCCCGCGGGC GCCCCGCCCC CCTGCCGGGG ACGCCGCCGG GCCTGCGGCG       600
CCTCCCGCCC GGGCATGGGG CCGCGCGCCG CCTCAGGGCC CGGCGCGGCC GGCGCCTGGT       660
CCCCGCCCCC GCCCGCGGGG GAACCCGGGC AGCGAGGGAA GGGGGCGCCC TCTCTCTACT       720
GTGCGAGGAG TCTGGGCTGC TGTGTGTGAG CCTGTTTGGG GGAGCCTCCT CAGTGCTTGC       780
TACGTGGAGC CCTGGACACT A                                                801
```

(2) INFORMATION FOR SEQ ID NO:17:

(i) SEQUENCE CHARACTERISTICS:
        (A) LENGTH: 35100 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:17:

```
TACTAATTTT CAAAGGCGGG GTTCTGCCAG GCATAGTCTT TTTTTCTGGC GGCCCTTGTG        60
TAAACCTGTC TTTCAGACCT TGTTGGACAT CCTGTACAAT CAAGATGTTC CTGTATGTTG       120
TCTGCAGTCT GGCGGTTTGC TTTCGAGGAC TATTAAGCCT TTCTCTGCTA TCGTCTCCAA       180
ATTTGTGCCC TGGAGTGATT TCAACGCCTT ACACGTTGAC CTGTCTGTCT AATGCATCCT       240
TGCCAATATC CTGGTATTGC AACAATACTC GGCTTTTGCG ACTGACGGAG AGAAGAGTCA       300
TTCTTGACAC CATTGCCTGC AATTTTACTT GTGTGGAACA ATCTGGGCAT CGACAGAGCA       360
TTTGGATTAC ATGGCGTGCA CAACCTGTCT TACAAACCTT GTGTGCACAG CCATCAAACA       420
CAGTCACTTG TGGTCAGCAT GTTACTTTGT ATTGTTCTAC CTCTGGAAAT AATGTTACCG       480
TTTGGCATCT ACCAAACGGA CGAAATGAAA CCGTGTCACA AACTAAATAC TATAATTTTA       540
CGCTGATGAG CCAAACTGAG GGGTGTTATA CTTGTTCTAA CGGGCTGTCG TCTCGCCTGT       600
CAAATCGTAT ATGTTTTTGG GCGCGTTGTG CCAATATAAC TCCAGAAACT CATACTGTAT       660
CTGTCAGCAG TACTACAGGC TTTAGAACAT TGAGTACTAA TAGCTTAGTG AAGATAATCC       720
ATGCAACCAC ACGTGATGTA GTTGTAGTGA AAGAAGCAAA ATCTACACAT TTCATATTG        780
AAGTGCATTT TCTTGTATTT ATGACACTCG TAGCTCTGAT AGGAACCATG TGTGGTATCT       840
TAGGAACTAT TATCTTTGCC CATTGTCAAA AACAACGTGA CTCAAACAAA ACAGTGCCAC       900
AACAATTGCA GGATTATTAT TCCCTACACG ATTTGTGCAC GGAAGACTAT ACGCAACCAG       960
TGGATTGGTA CTGACATTCA GGTAAGATAA TCTAAATATT CTCTATAACA TAATTGTAAT      1020
GTGTTTTATG TTTATAGCTA CAAATGTTTT ATGCAAAATA CATTTATGA GGTCGGATAC       1080
```

```
TTATTAAAAG CATTGTCTTA AGTACATTAA AAGGACATTG TATAACCGTG CTACTTACAG    1140

CATGGCCTTT TTAAGACAAA CACTGTGGAT TTTATGGACA TTTACCATGG TTATTGGCCA    1200

GGACAATGAA AAGTGTTCCC AAAAAACCTT AATTGGATAT AGACTAAAAA TGTCTCGTGA    1260

CGGTGACATT GCAGTTGGAG AAACAGTGGA ATTACGTTGT AGATCTGGAT ACACTACTTA    1320

TGCCCGCAAT ATAACAGCAA CATGTTTACA AGGTGGGACG TGGTCTGAAC CAACGGCAAC    1380

ATGTAACAAA AAGTCCTGTC CAAACCCAGG TGAAATACAA AATGGAAAGG TTATATTTCA    1440

TGGTGGACAA GATGCCTTAA AATATGGGGC AAACATTTCA TATGTTTGTA ATGAAGGATA    1500

TTTTTTGGTT GGTCGAGAAT ACGTGCGATA TTGTATGATT GGAGCATCTG GCCAAATGGC    1560

GTGGTCATCT TCTCCTCCTT TTTGTGAAAA AGAAAAGTGT CACAGACCGA AAATCAAAAA    1620

TGGAGATTTT AAGCCTGATA AGATTATTA TGAGTATAAT GATGCAGTTC ATTTTGAATG    1680

TAATGAAGGA TATACTCTAG TTGGACCACA TTCCATTGCA TGTGCAGTTA ATAACACGTG    1740

GACATCTAAC ATGCCAACCT GTGAACTCGC AGGCTGTAAA TTTCCATCGG TGACTCATGG    1800

TTATCCAATC CAAGGTTTTT CTCTTACTTA TAAACATAAG CAAAGTGTTA CTTTTGCATG    1860

CAATGATGGA TTTGTTCTCA GAGGATCCCC CACAATTACG TGTAACGTTA CTGAATGGGA    1920

CCCACCACTT CCTAAGTGTG TTTTGGAAGA TATAGATGAT CCAAACAATT CAAATCCTGG    1980

ACGTTTGCAT CCAACACCCA ATGAAAAACC AAATGGTAAT GTCTTTCAAC GCTCAAACTA    2040

TACAGAACCT CCAACAAAGC TGAAGCACAC CCATACAGCA GCTACTTGTG ATACCAACTG    2100

TGAACAGCCA CCTAAAATCC TGCCAACATC CGAAGGTTTT AATGAGACTA CCACATCTAA    2160

TACAATTACA AAACAATTAG AGGATGAGAA AACTATATCC CAGCCAAATA CACATATTAC    2220

ATCTGCCTTA ACATCCATGA AAGCGAAAGG TAACTTTACC AACAAGACCA ATAACTCTAC    2280

TGATCTACAT ATAGCGTCTA CACCCACTTC CCAAGATGAT GCTACGCCTT CAATACCTAG    2340

TGTACAGACA CCCAATTATA ATACTAACGC ACCGACACGT ACACTAACGT CTCTCCATAT    2400

TGAAGAAGGC CCATCCAATT CTACTACTTC AGAAAAGGCC ACTTCCTCTA CTCTCTCACA    2460

CAACTCACAC AAAAATGACA CCGGAGGCAT ATACACAACA TTAAACAAAA CAACACAGTT    2520

GCCATCCACT AATAAACCTA CAAACAGTCA AGCCAAGAGT TCCACTAAGC CACGCGTTGA    2580

GACACACAAT AAAACAACCA GTAATCCTGC CATTTCTTTA ACAGATTCTG CAGATGTGCC    2640

TCAGAGACCG CGAGAACCAA CACTCCCTCC CATTTTCAGG CCACCGGCGT CTAAAAATCG    2700

CTATCTGGAA AAGCAACTAG TTATTGGACT ACTAACCGCT GTCGCCCTAA CGTGTGGACT    2760

GATTACCTTA TTTCACTATC TGTTCTTTCG TTAGCCTAGA ACTTGCTCCA GTGTTAGACA    2820

GGGCTATGAT TGCTTCTCCA CGCTGTCCAC CTTAACACTT CCCAATAACA AATCCGGTAT    2880

GCAGCAGCGT GACACTACTA ATGTAACCTA AAAAATGTGC ATGTGGTATG TATTGTACTA    2940

AAGATACCGA CCAATACAAG ACAACTAATA TTAACCATAG TGTGCGTTTC TTTGTATAAA    3000

ATACGCGTGT GGGAAAGCGA CAGAAGGGGG CGGCGTTTCC ATATGAGGCC AAGTGCATTG    3060

GCTATTTTAG GGGCGGTGAC CACGCACTAT AGTGCGCGGT GTGGCAGAAA ATTCACACCG    3120

TATATAAACA AGGAAAGGGG ACTCTGCGCG CTTAAGCGCC AAGCCATTAT ACACACGGGT    3180

TTTTTGTTGT CTTGGCCAAT CGTGTCTCCA TGGCGCTAAA GGGACCACAA ACCCTCGAGG    3240

AAAATATTGG GTCTGCGGCC CCCACTGGTC CCTGCGGGTA CCTCTATGCC TATCTGACAC    3300

ACAACTTCCC CATAGGGGAA GCCTCCCTGC TGGGCAATGG CTACCGGAG GCAAAAGTAT    3360

TTTCACTACC TCTTTTGCAC GGGCTCACAG TGGAATCCGA TTTCCCCTTA AACGTAAAGG    3420

CGGTGCACAA GAAAATCGAT GCAACCACAG CTTCTGTGAA ATTAACTTCA TACCACAGGG    3480
```

```
AGGCCATCGT CTTTCATAAT ACTCACTTAT TTCAGCCAAT CTTTCAAGGA AAGGGACTGG    3540

AAAAGTTATG TCGAGAGAGC CGAGAGCTGT TTGGATTTTC AACGTTTGTT GAGCAACAAC    3600

ACAAAGGGAC GCTCTGGAGC CCAGAGGCAT GCCCTCAGCT ACCCTGCGCG AATGAGATTT    3660

TTATGGCGGT CATAGTTACA GAGGGATTCA AGGAGAGACT GTACGGCGGC AAACTGGTGC    3720

CCGTGCCCTC TCAGACAACG CCCGTACACA TTGGGGAACA CCAGGCGTTC AAGATACCCT    3780

TGTATGACGA GGATCTGTTT GGTCCAAGTC GCGCCCAAGA ACTATGTAGG TTTTACAACC    3840

CCGATATCAG TAGATACCTA CATGACTCCA TATTCACTGG AATAGCACAG GCTCTAAGGG    3900

TAAAGGACGT TAGCACGGTC ATCCAAGCCT CAGAAAGGCA ATTTGTGCAC GACCAATACA    3960

AGATACCAAA GCTGGTCCAA GCCAAGGACT TCCCCCAGTG TGCTTCCAGG GGAACCGACG    4020

GGTCTACCCT AATGGTGATA GACAGTCTGG TGGCTGAACT TGGTATGAGT TATGGTCTGT    4080

CCTTTATTGA GGGACCCCAG GATAGCTGCG AGGTTCTAAA TTATGACACG TGGCCCATCT    4140

TTGAAAACTG CGAGACGCCA GATGCCCGCC TTCGTGCACT AGAAGTTTGG CACGCAGAGC    4200

AGGCCTTGCA TATTGGCGCC CAGCTGTTTG CGGCCAACTC TGTGCTCTAC CTGACCAGAG    4260

TGGCAAAGCT GCCTCAGAAG AATCAGAGAG GAGACGCCAA CATGTACAAC TCATTCTACC    4320

TACAGCATGG CCTGGGATAC CTCTCAGAGG CAACAGTAAA GGAAAATGGA GCCTCTGCCT    4380

TCAAGGGCGT GCCAGTGTCT GCACTGGATG GGTCATCTTA CACCCTCCAG CACCTGGCCT    4440

ACGCGTCCTC TTTCTCCCCA CATCTCCTGG CAAGGATGTG TTACTATCTG CAGTTCTTGC    4500

CCCACCATAA AAACACCAAC AGTCAGTCAT ACAATGTGGT GGACTACGTG GGCACCGCGG    4560

CACCTAGTCA AATGTGTGAC CTGTGTCAGG GCAATGTCC AGCTGTATGC ATCAACACGC    4620

TGTTTTACAG GATGAAGGAC AGGTTCCCAC CTGTTCTGTC AAACGTTAAG AGAGACCCAT    4680

ATGTGATCAC GGGCACAGCG GGAACGTACA ATGACCTAGA GATTCTCGGA AACTTTGCCA    4740

CCTTCAGGGA GAGAGAGGAG GAGGGGAATC CTGTGGAAGA TGCTCCAAAG TATACATATT    4800

GGCAACTATG CCAGAATATA ACCGAGAAGC TAGCGTCCAT GGGCATCTCG GAGGGCGGCG    4860

ATGCCCTAAG AACCCTCATT GTGGACATCC CCAGCTTCGT CAAAGTGTTC AAGGGGATAG    4920

ACAGCACGGT AGAGGCAGAG CTCCTAAAGT TTATTAACTG CATGATCAAA AACAATTACA    4980

ACTTCAGAGA GAACATCAAA TCCGTCCATC ACATCCTTCA GTTTGCATGC AACGTATACT    5040

GGCAGGCGCC GTGCCCGGTT TTTCTGACCC TTTACTACAA GTCACTGCTG ACGGTCATAC    5100

AGGACATATG TCTGACGTCA TGTATGATGT ACGAGCAGGA CAACCCGGCC GTGGGAATTG    5160

TACCATCCGA GTGGCTTAAA ATGCACTTTC AGACAATGTG GACCAACTTC AAGGGTGCCT    5220

GCTTCGACAA AGGAGCAATC ACGGGCGGGG AACTAAAAAT AGTCCACCAG TCCATGTTCT    5280

GTGACCTCTT TGACACCGAC GCTGCCATAG GAGGGATGTT TGCACCCGCT CGGATGCAGG    5340

TCAGGATAGC CAGAGCAATG CTCATGGTTC CAAAAACCAT AAAAATAAAA AACAGGATCA    5400

TCTTTTCCAA CTCCACCGGA GCAGAGTCGA TCCAGGCAGG TTTTATGAAG CCGGCCAGCC    5460

AAAGGGATTC ATACATCGTC GGAGGACCCT ACATGAAATT CCTAAACGCC CTGCACAAAA    5520

CACTTTTTCC TTCCACAAAA ACTTCTGCCC TGTACTTGTG GCATAAGATT GGCCAGACCA    5580

CAAAAAATCC CATACTACCA GGTGTCTCGG GGAACACCT AACGGAGTTA TGTAATTATG    5640

TAAAGGCAAG TAGCCAGGCT TTCGAAGAGA TAAATGTTTT GGACCTTGTG CCAGACACCC    5700

TGACATCATA TGCGAAAATA AAACTAAACA GTTCCATTCT CCGGGCTTGC GGACAGACAC    5760

AGTTTTATGC AACTACTCTC TCTTGCCTTT CGCCAGTGAC TCAGCTGGTT CCGGCCGAGG    5820
```

-continued

```
AGTACCCCCA CGTACTGGGG CCAGTGGGGT TGTCATCTCC AGATGAATAC AGGGCAAAAG    5880

TCGCCGGCAG GTCTGTAACC ATTGTACAGT CAACACTGAA GCAAGCTGTT TCCACCAACG    5940

GACGACTCCG GCCTATCATT ACCGTGCCAC TGGTGGTCAA CAAATATACA GGGAGCAACG    6000

GGAACACAAA CGTCTTTCAC TGTGCAAACC TGGGATACTT CTCGGGGAGA GGGGTGGACA    6060

GAAATCTCAG GCCAGAAAGC GTCCCCTTTA AAAGAATAA TGTCAGCTCT ATGCTAAGAA    6120

AACGCCACGT GATTATGACC CCCCTGGTAG ACAGGCTGGT AAAGAGAATA GTTGGCATCA    6180

ACTCTGGGGA ATTCGAGGCA GAAGCGGTTA AGAGAAGTGT GCAGAATGTC CTGGAAGACA    6240

GAGATAACCC AAACCTGCCG AAGACAGTTG TATTAGAGTT GGTTAAGCCA CCTCGGTGGA    6300

GCTCCTGTGC AAGTCTCACA GAGGAGGACG TGATTTACTA CCTGGGCCCT TATGCCGTAC    6360

TTGGGGACGA GGTCCTGTCA TTACTGAGCA CAGTGGGCCA GGCGGGGGTG CCATGGACGG    6420

CCGAGGGTGT GGCCTCGGTC ATCCAGGACA TAATAGATGA TTGCGAGTTA CAGTTTGTGG    6480

GCCCAGAAGA GCCTTGCCTT ATCCAAGGAC AGTCGGTAGT GGAGGAGCTT TTTCCGTCCC    6540

CGGGCGTCCC AAGCCTGACA GTGGGTAAAA ACGAAAAAT CGCATCCCTG CTCTCTGACC    6600

TGGATTTGTA GTTGTGTACC CGTAACGATG GCAAAGGAAC TGGCGGCGGT CTATGCCGAT    6660

GTGTCAGCCC TAGCCATGGA CCTCTGTCTT CTTAGTTACG CAGACCCGGC AACACTGGAC    6720

ACTAAAAGTC TGGCCCTCAC TACAGGGAAG TTTCAGAGCC TTCACGGCAC ACTACTCCCC    6780

CTCCTCAGAC GACAAAACGC ACACGAATGC TCAGGTCTGT CACTAGAATT GGAGCACTTT    6840

TGGAAAACGT GGCTGATGCT CTGGCCACGT TGGGAGTGTG CACTAGCAGA AAACTGTCTC    6900

CAGAAGAGCA TTTTTCCCTC CTGCATTTGG ACACAACATG CAACAAGCAA CCGGAGCGTT    6960

AGGTTTAATT TTTACGGAAA TTGGGCCTTG GAGTTAAAGC TGTCACTAAT AAACGACGTT    7020

GAAATTTTCT TTAAACGTCT TAGTAGCGTT TTTTATTGTA TAGGATCGGG CAGTGCTCTG    7080

GAGGGTTTAG GGGAGGTATT GCGTTTCGTT GGGAAGCTGA GGGGTATCTC ACCCGTACCT    7140

GGGCCGGACC TATATGTCTC AAATCTGCCC TGCCTAGAAT GCCTTCAGGA AGTGTGTCTG    7200

ACTCCCAACC AGGGCACCAG TCTGCAGGCC ATGCTCCCAG ACACGGCCTG CAGTCACATA    7260

TGTACCCCCG CATGCGGTGA GCCTGTCCGG GGCCTCTTTG AGAACGAGCT AAAACAGCTC    7320

GGGCTTCAAA CCCCTGAGTC CATACCTACT ACCCCCTGTC AGTCCCGGGT AAGGCAAGAT    7380

GATGAAATCA GACAGAGCTC TCTAATGGCG GTAGGAGATC ACCACATTTT CGGAGAGGTG    7440

ACCAGATCTG TCCTGGAAAT CTCAAACCTG ATCTATTGGA GCTCTGGCCA CTCGGATGCC    7500

ACCTGCGACG GAGACAGAGA CTGCTCTCAC CTGGCCTCGC TGTTTACTCA CGAGGCTGAC    7560

ATGCATAAAA GGCGCGTCGA CCTGGCCGGA TGCTTGGGCG AACGCGGCAC GCCCAAACAC    7620

TTTTTTGACT GCTTTCGCCC AGACTCCCTA GAAACCCTTT TCTGTGGTGG TCTTTTTAGC    7680

TCCGTGGAGG ACACCATAGA AAGTCTCCAA AAGGACTGCT CTTCTGCCTT CTACCAACAG    7740

GTAAACTACA CTACTGCACT GCAAAAACAG AACGAGTTTT ACGTCCGACT CAGCAAACTG    7800

CTGGCAGCTG GTCAGCTAAA TTTGGGCAAA TGTTCCACTG AAAGTTGCCA ATCCGAGGCC    7860

CGTAGGCAGC TGGTAGGTGG GGGCAAACCA GAGGAAGTGC TGAGGGATGC AAAACACCGG    7920

CAAGAACTAT ACCTTCAGAA AGTGGCACGC GACGGTTTTA AAAAACTCTC TGATTGTATA    7980

AGACACCAGG GCCACATCCT GTCTCAGACC CTGGGTCTAA GACTGTGGGG GTCTGTCATC    8040

TACAACGAGG CATCTGCCCT ACAAAACCAC TTTTTACACA GAGCACAGTT CATATCCCTC    8100

CCCTGGCAGG ACCTGACGGT CGACTGTCCA ACGCGGTTTG AAAATTCTAA ATATATCAAA    8160

AATTCTCTGT ACTGCCAGCG TCTGGGGCGG GAACACGTAG AGATCCTGAC ACTGGAGTTC    8220
```

```
TACAAACTTA TCACGGGCCC GCTGTCAAAG CGACATACTT TATTTCCCAG TCCTCCAAAT    8280
GTGACGCTGG CTCAGTGCTT CGAGGCTGCG GGCATGCTTC CCCATCAAAA GATGATGGTA    8340
TCAGAGATGA TCTGGCCCAG CATAGAGCCG AAGGACTGGA TAGAGCCCAA CTTCAACCAG    8400
TTCTATAGCT TTGAGAATCA AGACATAAAC CATCTGCAAA AGAGAGCTTG GAATATATC     8460
AGAGAGCTGG TATTATCGGT TTCTCTGTAC AACAGAACTT GGGAGAGGGA GCTAAAAATA    8520
CTTCTCACGC CTCAGGGCTC ACCGGGGTTT GAGGAACCGA AACCCGCAGG ACTCACAACG    8580
GGGCTGTACC TAACATTTGA GACATCTGCG CCCTTGGTGT TGGTGGATAA AAAATATGGC    8640
TGGATATTTA AAGACCTGTA CGCCCTTCTG TACCACCACC TGCAACTGAG CAACCACAAT    8700
GACTCCCAGG TCTAGATTGG CCACCCTGGG GACTGTCATC CTGTTGGTCT GCTTTTGCGC    8760
AGGCGCGGCG CACTCGAGGG GTGACACCTT TCAGACGTCC AGTTCCCCCA CACCCCCAGG    8820
ATCTTCCTCT AAGGCCCCCA CCAAACCTGG TGAGGAAGCA TCTGGTCCTA AGAGTGTGGA    8880
CTTTTACCAG TTCAGAGTGT GTAGTGCATC GATCACCGGG GAGCTTTTTC GGTTCAACCT    8940
GGAGCAGACG TGCCCAGACA CCAAAGACAA GTACCACCAA GAAGGAATTT TACTGGTGTA    9000
CAAAAAAAAC ATAGTGCCTC ATATCTTTAA GGTGCGGCGC TATAGGAAAA TTGCCACCTC    9060
TGTCACGGTC TACAGGGGCT TGACAGAGTC CGCCATCACC AACAAGTATG AACTCCCGAG    9120
ACCCGTGCCA CTCTATGAGA TAAGCCACAT GGACAGCACC TATCAGTGCT TTAGTTCCAT    9180
GAAGGTAAAT GTCAACGGGG TAGAAAACAC ATTTACTGAC AGAGACGATG TTAACACCAC    9240
AGTATTCCTC CAACCAGTAG AGGGGCTTAC GGATAACATT CAAAGGTACT TAGCCAGCC     9300
GGTCATCTAC GCGGAACCCG GCTGGTTTCC CGGCATATAC AGAGTTAGGA CCACTGTCAA    9360
TTGCGAGATA GTGGACATGA TAGCCAGGTC TGCTGAACCA TACAATTACT TTGTCACGTC    9420
ACTGGGTGAC ACGGTGGAAG TCTCCCCTTT TTGCTATAAC GAATCCTCAT GCAGCACAAC    9480
CCCCAGCAAC AAAAATGGCC TTAGCGTCCA AGTAGTTCTC AACCACACTG TGGTCACGTA    9540
CTCTGACAGA GGAACCAGTC CCACTCCCCA AAACAGGATC TTTGTGGAAA CGGGAGCGTA    9600
CACGCTTTCG TGGGCCTCCG AGAGCAAGAC CACGGCCGTG TGTCCGCTGG CACTGTGGAA    9660
AACCTTCCCG CGCTCCATCC AGACTACCCA CGAGGACAGC TTCCACTTTG TGGCCAACGA    9720
GATCACGGCC ACCTTCACGG CTCCTCTAAC GCCAGTGGCC AACTTTACCG ACACGTACTC    9780
TTGTCTGACC TCGGATATCA ACACCACGCT AAACGCCAGC AAGGCCAAAC TGGCGAGCAC    9840
TCACGTCCCT AACGGGACGG TCCAGTACTT CCACACAACA GGCGGACTCT ATTTGGTCTG    9900
GCAGCCCATG TCCGCGATTA ACCTGACTCA CGCTCAGGGC GACAGCGGGA ACCCCACGTC    9960
ATCGCCGCCC CCCTCCGCAT CCCCCATGAC CACCTCTGCC AGCCGCAGAA AGAGACGGTC    10020
AGCCAGTACC GCTGCTGCCG GCGGCGGGGG GTCCACGGAC AACCTGTCTT ACACGCAGCT    10080
GCAGTTTGCC TACGACAAAC TGCGGGATGG CATTAATCAG GTGTTAGAAG AACTCTCCAG    10140
GGCATGGTGT CGCGAGCAGG TCAGGGACAA CCTAATGTGG TACGAGCTCA GTAAAATCAA    10200
CCCCACCAGC GTTATGACAG CCATCTACGG TCGACCTGTA TCCGCCAAGT TCGTAGGAGA    10260
CGCCATTTCC GTGACCGAGT GCATTAACGT GGACCAGAGC TCCGTAAACA TCCACAAGAG    10320
CCTCAGAACC AATAGTAAGG ACGTGTGTTA CGCGCGCCCC CTGGTGACGT TTAAGTTTTT    10380
GAACAGTTCC AACCTATTCA CCGGCCAGCT GGGCGCGCGC AATGAGATAA TACTGACCAA    10440
CAACCAGGTG GAAACCTGCA AAGACACCTG CGAACACTAC TTCATCACCC GCAACGAGAC    10500
TCTGGTGTAT AAGGACTACG CGTACCTGCG CACTATAAAC ACCACTGACA TATCCACCCT    10560
```

```
GAACACTTTT ATCGCCCTGA ATCTATCCTT TATTCAAAAC ATAGACTTCA AGGCCATCGA    10620

GCTGTACAGC AGTGCAGAGA AACGACTCGC GAGTAGCGTG TTTGACCTGG AGACGATGTT    10680

CAGGGAGTAC AACTACTACA CACATCGTCT CGCGGGTTTG CGCGAGGATC TGGACAACAC    10740

CATAGATATG AACAAGGAGC GCTTCGTAAG GGACTTGTCG GAGATAGTGG CGGACCTGGG    10800

TGGCATCGGA AAAACGGTGG TGAACGTGGC CAGCAGCGTG GTCACTCTAT GTGGCTCATT    10860

GGTTACCGGA TTCATAAATT TTATTAAACA CCCCCTAGGT GGCATGCTGA TGATCATTAT    10920

CGTTATAGCA ATCATCCTGA TCATTTTTAT GCTCAGTCGC CGCACCAATA CCATAGCCCA    10980

GGCGCCGGTG AAGATGATCT ACCCCGACGT AGATCGCAGG GCACCTCCTA GCGGCGGAGC    11040

CCCAACACGG GAGGAAATCA AAACATCCT GCTGGGAATG CACCAGCTAC AACAAGAGGA    11100

GAGGCAGAAG GCGGATGATC TGAAAAAAAG TACACCCTCG GTGTTTCAGC GTACCGCAAA    11160

CGGCCTTCGT CAGCGTCTGA GAGGATATAA ACCTCTGACT CAATCGCTAG ACATCAGTCC    11220

GGAAACGGGG GAGTGACAGT GGATTCGAGG TTATTGTTTG ATGTAAATTT AGGAAACACG    11280

GCCCGCCTCT GAAGCACCAC ATACAGACTG CAGTTATCAA CCCTACTCGT TGCACACAGA    11340

CACAAATTAC CGTCCGCAGA TCATGGATTT TTTCAATCCA TTTATCGACC CAACTCGCGG    11400

AGGCCCGAGA AACACTGTGA GGCAACCCAC GCCGTCACAG TCGCCAACTG TCCCCTCGGA    11460

GACAAGAGTA TGCAGGCTTA TACCGGCCTG TTTCCAAACC CCGGGCGAC CCGGCGTGGT     11520

TGCCGTGGAC ACCACATTTC CACCCACCTA CTTCCAGGGC CCCAAGCGGG GAGAAGTATT    11580

CGCGGGAGAG ACTGGGTCTA TCTGGAAAAC AAGGCGCGGA CAGGCACGCA ATGCTCCTAT    11640

GTCGCACCTC ATATTCCACG TATACGACAT CGTGGAGACC ACCTACACGG CCGACCGCTG    11700

CGAGGACGTG CCATTTAGCT TCCAGACTGA TATCATTCCC AGCGGCACCG TCCTCAAGCT    11760

GCTCGGCAGA ACACTAGATG GCGCCAGTGT CTGCGTGAAC GTTTTCAGGC AGCGCTGCTA    11820

CTTCTACACA CTAGCACCCC AGGGGTAAA CCTGACCCAC GTCCTCCAGC AGGCCCTCCA     11880

GGCTGGCTTC GGTCGCGCAT CCTGCGGCTT CTCCACCGAG CCGGTCAGAA AAAAAATCTT    11940

GCGCGCGTAC GACACACAAC AATATGCTGT GCAAAAAATA ACCCTGTCAT CCAGTCCGAT    12000

GATGCGAACG CTTAGCGACC GCCTAACAAC CTGTGGGTGC GAGGTGTTTG AGTCCAATGT    12060

GGACGCCATT AGGCGCTTCG TGCTGGACCA CGGGTTCTCG ACATTCGGGT GGTACGAGTG    12120

CAGCAATCCG GCCCCCCGCA CCCAGGCCAG AGACTCTTGG ACGGAACTGG AGTTTGACTG    12180

CAGCTGGGAG GACCTAAAGT TTATCCCGGA GAGGACGGAG TGGCCCCCAT ACTCAATCCT    12240

ATCCTTTGAT ATAGAATGTA TGGGCGAGAA GGGTTTTCCC AACGCGACTC AAGACGAGGA    12300

CATGATTATA CAAATCTCGT GTGTTTTACA CACAGTCGGC AACGATAAAC CGTACACCCG    12360

CATGCTACTG GGCCTGGGGA CATGCGACCC CCTTCCTGGG GTGGAGGTCT TGAGTTTCC     12420

TTCGGAGTAC GACATGCTGG CCGCCTTCCT CAGCATGCTC CGCGATTACA ATGTGGAGTT    12480

TATAACGGGG TACAACATAG CAAACTTTGA CCTTCCATAC ATCATAGCCC GGGCAACTCA    12540

GGTGTACGAC TTCAAGCTGC AGGACTTCAC CAAAATAAAA ACTGGGTCCG TGTTTGAGGT    12600

CCACCAACCC AGAGGCGGTT CCGATGGGGG CAACTTCATG AGGTCCCAGT CAAAGGTCAA    12660

AATATCGGGG ATCGTCCCCA TAGACATGTA CCAGGTTTGC AGGGAAAAGC TGAGTCTGTC    12720

AGACTACAAG CTGGACACAG TGGCTAAGCA ATGCCTCGGT CGACAAAAAG ATGACATCTC    12780

ATACAAGGAC ATACCCCCGC TTTTTAAATC TGGGCCTGAT GGTCGCGCAA AGGTGGGAAA    12840

CTACTGTGTT ATTGACTCGG TCCTGGTTAT GGATCTTCTG CTACGGTTTC AGACCCATGT    12900

TGAGATCTCG GAAATAGCCA AGCTGGCCAA GATCCCCACC CGTAGGGTAC TGACGGACGG    12960
```

```
CCAACAGATC AGGGTATTTT CCTGCCTCTT GGAGGCTGCT GCCACGGAAG GTTACATTCT   13020

CCCCGTCCCA AAAGGAGACG CGGTTAGCGG GTATCAGGGG GCCACTGTAA TAAGCCCCTC   13080

TCCGGGATTC TATGACGACC CCGTACTCGT GGTGGATTTT GCCAGCTTGT ACCCCAGTAT   13140

CATCCAAGCG CACAACTTGT GCTACTCCAC ACTGATACCC GGCGATTCGC TCCACCTGCA   13200

CCCACACCTC TCCCCGGACG ACTACGAAAC CTTTGTCCTC AGCGGAGGTC CGGTCCACTT   13260

TGTAAAAAAA CACAAAAGGG AGTCCCTTCT TGCCAAGCTT CTGACGGTAT GGCTCGCGAA   13320

GAGAAAAGAA ATAAGAAAGA CCCTGGCATC ATGCACGGAC CCCGCACTGA AAACTATTCT   13380

AGACAAACAA CAACTGGCCA TCAAGGTTAC CTGCAACGCC GTTTACGGCT TCACGGGCGT   13440

TGCCTCTGGC ATACTGCCTT GCCTAAACAT AGCGGAGACC GTGACACTAC AAGGGCGAAA   13500

GATGCTGGAG AGATCTCAGG CCTTTGTAGA GGCCATCTCG CCGGAACGCC TAGCGGGTCT   13560

CCTGCGGAGG CCAATAGACG TCTCACCCGA CGCCCGATTC AAGGTCATAT ACGGCGACAC   13620

TGACTCTCTT TTCATATGCT GCATGGGTTT CAACATGGAC AGCGTGTCAG ACTTCGCGGA   13680

GGAGCTAGCG TCAATCACCA CCAACACGCT GTTTCGTAGC CCCATCAAGC TGGAGGCTGA   13740

AAAGATCTTC AAGTGCCTTC TGCTCCTGAC TAAAAAGAGA TACGTGGGGG TACTCAGTGA   13800

CGACAAGGTT CTGATGAAGG GCGTAGACCT CATTAGGAAA ACAGCCTGTC GTTTTGTCCA   13860

GGAAAAGAGC AGTCAGGTCC TGGACCTCAT ACTGCGGGAG CCGAGCGTCA AGGCCGCGGC   13920

CAAGCTTATT TCGGGCAGG CGACAGACTG GGTGTACAGG GAAGGGCTCC CAGAGGGGTT   13980

CGTCAAGATA ATTCAAGTGC TCAACGCGAG CCACCGGGAA CTGTGCGAAC GCAGCGTACC   14040

AGTAGACAAA CTGACGTTTA CCACCGAGCT AAGCCGCCCG CTGGCGGACT ACAAGACGCA   14100

AAACCTCCCG CACCTGACCG TGTACCAAAA GCTACAAGCT AGACAGGAGG AGCTTCCACA   14160

GATACACGAC AGAATCCCCT ACGTGTTCGT CGACGCCCCA GGTAGCCTGC GCTCCGAGCT   14220

GGCAGAGCAC CCCGAGTACG TTAAGCAGCA CGGACTGCGC GTGGCGGTGG ACCTGTACTT   14280

CGACAAGCTG GTACACGCGG TAGCAACAT CATCCAATGC CTCTTCCAGA ACAACACGTC   14340

GGCAACCGTA GCTATGTTGT ATAACTTTTT AGACATTCCC GTGACTTTTC CCACGCCCTA   14400

GTGACTCAGA CGCGGAAACA GCGCCTAGAA AGTTTCCTCT TGCGCTATGT GGGACAACTA   14460

GAGTCCAACC TGGCAAGCAG TGGAGCAAGA CGCCAGACAG CCGATCTCGA AAAAAATAAT   14520

GCAGACAGAG GCAACGTTCA TCCTAGGTGA CTGGGAGATA ACGGTGTCTA ACTGCCGGTT   14580

TACTTGCAGC AGCCTAACAT GTGGCCCCCT TTACAGATCT AGCGGCGACT ACACGCGGCT   14640

AAGAATCCCC TTCTCTCTGG ATCGACTAAT ACGTGACCAT GCCATCTTTG GGCTAGTGCC   14700

AAATATTGAG GATCTGTTAA CCCATGGGTC ATGCGTCGCC GTAGTGGCCG ACGCAAACGC   14760

CACAGGCGGC AACGCGCGAC GCATCGTCGC GCCTGGCGTG ATAAACAATT TTTCAGAACC   14820

CATCGGCATT TGGGTACGCG GCCCTCCGCC GCAAACGCGC AAGGAAGCTA TTAAGTTCTG   14880

CATATTTTTT GTCAGTCCCC TGCCCCCGCG GGAGATGACC ACATATGTGT CAAGGGCGG   14940

CGATTTGCCT CCCGGAGCAG AGGAACCCGA AACACTACAC TCCGCCGAGG CACCCCTACC   15000

GTCGCGCGAG ACGCTGGTAA CTGGACAGCT GCGATCCACC TCGCCGCGAA CGTATACGGG   15060

ATACTTTCAC AGTCCTGTCC CGCTCTCTTT TTTGGACCTC CTGACATTCG AGTCCATTGG   15120

GTGTGACAAC GTGGAAGGTG ACCCCGAGCA ATTGACACCC AAGTACTTGA CGTTCACGCA   15180

GACGGGAGAA AGACTTTGCA AAGTAACCGT TTACAACACC CATTCGACAG CATGCAAGAA   15240

GGCCCGTGTT CGTTTCGTCT ACAGACCGAC GCCGTCCGCC CGTCAGCTTG TCATGGGTCA   15300
```

```
GGCTTCACCC CTCATAACAA CCCCTCTGGG AGCCAGGGTA TTCGCAGTCT ATCCAGACTG   15360

TGAGAAAACT ATCCCACCTC AGGAAACCAC CACCCTGAGG ATTCAATTGC TGTTCGAGCA   15420

GCATGGTGCC AACGCCGGAG ACTGCGCCTT TGTCATCATG GGGCTCGCCC GTGAAACAAA   15480

GTTTGTCTCA TTTCCCGCAG TACTCCTTCC GGGCAAGCAC GAACACCTTA TTGTATTCAA   15540

CCCACAGACA CATCCTCTGA CCATTCAACG GGACACAATA GTGGGCGTGG CAATGGCTTG   15600

CTATATCCAC CCCGGTAAGG CAGCCAGCCA GGCACCATAC AGCTTCTACG ACTGCAAGGA   15660

AGAGAGCTGG CACGTGGGGC TCTTCCAGAT CAAACGCGGA CCGGGAGGGG TCTGTACACC   15720

ACCTTGCCAC GTAGCGATTA GGGCCGACCG CCACGAGGAA CCCATGCAAT CGTGACTGTC   15780

CGAGCACATA TGGCGCAGGA GTCAGAGCAG TGCTCCCGTG CGTTTGCAGT GTGCAGTAGT   15840

AAACGACAGC TCGGGCGCGG CGAGCCCGTG TGGGATTCCG TCATTCACCC GAGCCACATC   15900

GTCATCTCTA ATCGAGTACC CCTCTTACTA AGAGAACAGC ACATATGTCT CCCTTCGTGC   15960

CCCAGCGTCG GCCAGATCCT CCACAGAGCC TACCCCAACT TTACATTTGA CAACACGCAC   16020

CGCAAGCAGC AAACGGAGAC CTACACTGCA TTCTACGCTT TGGGGACCA AAATAACAAG   16080

GTTAGGATCT TGCCCACTGT TGTGGAAAGC TCCTCGAGCG TGCTGATTTT TAGACTGCGT   16140

GCATCGGTCT CTGCGAACAT CGCCGTGGGA GGGCTCAAAA TAATAATACT TGCTCTCACC   16200

CTGGTGCATG CCCAAGGAGT GTACCTGCGT TGCGGTAAGG ACCTTTCTAC ACCACACTGC   16260

GCACCGGCTA TTGTTCAGCG TGAGGTGCTG AGCAGCGGGT TTGAGCCGCA GTTTACCGTA   16320

ACTGGCATTC CAGTGACATC CTCGAACTTA AACCAATGCT ACTTTCTGGT AAGAAAGCCA   16380

AAAAGCCGGC TGGCAAAGCC GTTTGCACGC CTGTCCGCGG AGACGACTGA GGAGTGTCGC   16440

GTCAGGTCTA TCCGCCTTGG GAAGACACAC CTGCGGATAT CGGTGACTGC GCCTGCGCAG   16500

GAAACGCCCG TCTGGGGGCT CGTGACCACG AGCTTCAGCC TTACCCCCAC CGCACCGCTG   16560

GCCTTTGATC GTAACCCGTA CAATCACGAG ACATTTGCCT GTAATGCCAA GCACTACATC   16620

CCAGTCATCT ACAGCGGACC AAAAATTACG CTGGCCCCGC GCGGCCGCCA GGTAGTCTGG   16680

CACAACAACA GCTACACGTC CTCCCTGCCA TGCAAAGTCA CAGCCATCGT GTCAAACCAC   16740

TGCTGTAACT GTGACATATT TTTAGAGGAC TCGGAATGGC GCCCAAACAA GCCAGCACCC   16800

CTGAAACTGG TGAACACGAG TGATCATCCC GTCATATTGG AGCCGGACAC ACACATTGGA   16860

AACGCCCTCT TCATCATCGC ACCCAAGGCC CGAGGTTTAC GCAGACTGAC TCGCTTAACC   16920

ACAAAAACCA TTGAACTTCC TGGCGGGGTA AAGATAGACA GCAGGAAATT ACAAACATTC   16980

AGAAAAATGT ATGTTGCCAC CGGACGCAGT TAGGTGTCCG GTTCCCACCC ACACATTTGT   17040

CTTTATTGCT TTCAAATAAA ACGGTGTTCT GTCAACCTCC TCCGGGCTCA CTAGTATTGT   17100

GTTCCCATAC GCGCCTGTCG CCCCAGGATC AACACTTCGT CCCCTATCCA CCCTAATACA   17160

TAACACACAC AAAGACATAG TGACTGTAGA CAGTTAATCT TTATTGTCTA GACACGCAAA   17220

GTATATTAGT GTTATAAGAA ATTTTATGTC ACGTCGCTCT TTACTTATCG TGGACGTCAG   17280

GAGTCACGTC TGGGATAGAG TCCAAAACAC GCACCGCTTG ACCTGCAAAC TTTTCCATTG   17340

CACTCAGAAC ATAAAACGAA GCAAAGTGTC TCACCCAATA CTTAAGTCCC TGAAGCCTCC   17400

CTAATAGACC GCGGTCAAAT TTGGGTGGAC TGTAGTGCGT CTTAGTCAGC TTATTGAGCT   17460

CTTCCTGTAT GTCCCATCCT AAGGTCTTCG TCAGAAGCTC CATGACGTCC ACGTTTATCA   17520

CTGATTTTCC AAACTCCGTC GTTAAAAACT TAAACAACAC CTCGAATTCA AAAAAGCCAT   17580

CGGCGAGCTT TTTAAGGCAG CTAGTCTCAT TAAATCCTAT TAACCCGCAG TGATCAGTAT   17640

CGTTGATGGC TGGTAGTTTC AGATGAAAAA TAGCAGCGGG CTCTAGAATA CCCTTGCAGA   17700
```

```
TGCCGGTACG GTAACAGAGG TCGCGGAAGC ATTCATCGAT CACCCATAGC ATCCAATTGA    17760

GTCTCTGAAT GAGAAGATCC TTTTCAAACT CGGGGGCGTC CGGCAACTTG CCCCGCGTTC    17820

CAGATACCAG CAGTGAACCG ACCAGCAAGA GAGACCACAA CTTGAACCAG CACATGGCTG    17880

CTAACGCGGC ATACACTAGC CGGTGGTGCC CGAGCGGGAG TTACGAAGTC TCACTGAAGG    17940

GCGGGGTCGC GGGTCGGGGC CGCTCCAAAT CAGGCAACGC CGTATCCGAA CTCTGAGTCA    18000

CTTTTATGTA GGTCTCAAAC ATGTAAAAGA TACCACGTTC TTGAAAAACC CTCTCTTGCT    18060

CGCCAGGCTT GGGGTTCACG CGGGCATACG CAGCCAAGCT ATCATGCGAG AGAAACACGT    18120

CACACGCAAA GTCATGTAAA ACCCGGGTTA AAAATAGCCT AACTGGCCAG GGGCCAGTGA    18180

GCGCCTCCCG GTACAAGTCC CCACCCCCGA TGACCCAAAC CTTGTCAATT TGCTGTGCTA    18240

GCTCTGGGCT TCTCGCCAAC CCAAGCGCGG CATCGAGCGA ACTCGCCAAA AGTGAGCAC    18300

CAGGGGGCGG GGTTTCTAAC GTGCGACTTA GAACCACATT GATTCTACCC GCCAATGGTC    18360

GACAGCCCGC GGGAATCGAA AGCCATGTGC GCCGCCCCAT AACAACCATG TTTTGTTTTC    18420

CAGGGGCACA GTCGGTAGTC AGCTGTCGAA AACGCCTCAT GTCTCCCCGC AATGCAGGCC    18480

ACGGGAGACA TCTGTTTTTT CCGATCCCGA GTTTGGTATC AACCGCAACT ACACAGTAAA    18540

GTGTAGGATC CATGCCGCGA GGGTATAGGT AAACACCACC AACCACACAG TGTGCTCTTA    18600

TATACTTTTA ATGAAACATA AGGGCAGACG AAACAGCCGA ACGTTTCCTA ATCACGCCCA    18660

TGGAACCATA GCCACCCCCA GGCAAACCCT GTGGAAGGAT ATCAACTAGA GAGGAGGGTC    18720

CAGCCTTATT ATGGCAGGAG ACACTATAAG CCCCATCGCC CGACTGGGCA CCAACATAAC    18780

CGCCACAGTA AGTGGCCCTA TACCGCTCAG CGCCCAAGTT GTTACAGTCA CACCCAACCG    18840

CGGTTGGCTC TACATTGTCA TCACGTCCAT CATTATGTGT TGGTTCTCCC GCTTCCTTGT    18900

ACCCTGCAGC TTCATCCACG GATTCTTCTG AGTCGCGATG CACAGGAGCG CCATCCGCGG    18960

GGCCATCTTG GTCGCCTGGA GCTGCCCCCG CGGGGCCATT TTGGTCGCCT GGAGCTGCCC    19020

CCGCGGGCCC CTCCTCGTCC TGGTTATCCC CACGGGGAAG AATTTCCTGA AGCTCGATCT    19080

CCTCTACTGC ACACTCTGGT GATGTCGGCC GAGGTCTATA TGGAAACACT TCAACCCGCG    19140

TGTTTACAGC AGCGTATGCC CGCCCCACGT GGCGCATCAT GTGGAAAAAC GCACCCAACC    19200

CAAAAACGAC AAACAATTGG TAAAACACGA AAAAAACGTA GTACGCGGCT GCAGCGACGT    19260

GATCTATCTC TGGGTCATGA CCGCCCACTA TATATAGCCA AACCCACGTC GCAGCGGCAA    19320

GGCCAGCGGC CCCCAATGTC ATAATGAAAA TAAAAACAAT CAGTTCCAGA CCCTCCTGGT    19380

AAGTCAGCCG AGGCAATAGC GTCATTTCGC GCAAGGGTCG CCAGACCACG CGCGTGTTGT    19440

ATACGACGCC ACATATCTGA CAGGCCGTGT TTCTAGAGAT AGTGAGCCAG GTGCTTAAAC    19500

AACTTCTATG GACGTTCTCG AGCTCTCCTG TGCATCCACA GGCTCTAAAT CTCTCATTTC    19560

CGAGCTCCTC GTTGCAAATC CAGCAGACAG GAACATCCTC ATCTTCCATA TCCTGAGAGA    19620

GAACCCACAA TAAAACATGG CATTAACCCC TGCAACAAGT GACCGTACCA GGGCACGCGT    19680

CCAGGCAACC GGGGTCCCCC TCGTTGGTCT ATACAATTCC ATGACTACCT ACTGGTAATG    19740

CTACAGCCAC TCACTGTACA AGCCGGTTAA CTGGGAGGCG ACGCTGGCGT GGTATCGGCC    19800

AACTGAAACA CACCACTCCA CTCCAAACAC TTATGTACTT TGTGGCTCGG CTTTATTGTA    19860

ACAGCCAAGA GGGGCGTTTG TGGCTCAGCT TTATTGTAAC AGCCAAGAGG GACGTATGTG    19920

GCTATCTCAC AAAAAGTCAC CGATTCATGT AGACAACCCG CTCCCACGAA TTCGGTTTTT    19980

AAAAAGCCCT CACGTATACA GACGGGCCAC TAAATACGCA CATGAGCGGG CATCCTGTTT    20040
```

-continued

```
CCGCCTTGAC GCCCACCACT CTGACCGCAC GCTAAACATC GCCCTACCTG CTATACTGCC      20100
ATTTCCATAC GAATGGTAGG ATGCGGGCAG TAGTCCACCA GTCTAAAATC ATCAGGTGTA      20160
AACTCTTCCA TGGAAGAAAC AGACCGGAGT ATCTCCAGGC GCGGAAAGGG ACGTGGAGTG      20220
CGCGTCAGCT GCAGCCGTAG TGGCTCTATA TGCGTTTTGT AGATGTGGGC ATCTCCCAAC      20280
GTGTGAATAA ACTCCCCGGG TCTAAGACCA GTAACATGAG CAAGCATATA AGTTAAGAGG      20340
GAATAGCTGG CAATGTTAAA AGGAACTCCC AAACCCATGT CTCCCGACCT CTGATACAGC      20400
TGACAGGAAA GCTCACCGTC AGCTACATAA AATTGACATA ACAAGTGACA GGGCGGAAGC      20460
GCCATCAACG ACAAGTCCGC CGGGTTCCAC GCACACATAA TGATTCTTCT ATCGTGCGGA      20520
TTATTTTTTA TTAAATCCAC AATGTACGAC AATTGGTCAA ACCCCTGGCC TGTATAGTCA      20580
GCATCCGCGT CCACGTACGC CGCCCCAAAG TGCCTCCACT GGAAACCGTA AACAGGTCCC      20640
AAATCCCCCT CCCTTCTGTG CGCCAGGCCG CGCCCGGCCA GGAACTCCCT GGAGCCATTT      20700
TTGTCCCATA TCTTGACTCC TGTTCTTGAA AGCTCCCTGG AGTCAGTACT CCCCTTCAGA      20760
AACCAAAGCA GCTCTTGCAC TACGCCTCGC CAAAACACCC GCTTTGTGGT TAGTAAGGGA      20820
AAGTGGTCCC GCAGACTATA CCTGGCCTGC ATGCCAAATA GAGAGAGGGT GCCTATGCCG      20880
GTGCGGTCGA GTCGATCGCT GCCACGGCAC AAAATTTCCC TCAACTGCCT GAGATACTGA      20940
AGTTCCTCGT GGGGCGTCTC AGCCCCAGTT ACCTCATGCT GAATCGAACA AGGGTCAACC      21000
TCGGGGCCA AAGCCAAGAC GCCAGGCTTT TGACAGAAGC GAAACCCCCT GGCACGGAAT      21060
AACTTTTTGG CGACATACAA GCTTAAAGGT ACAAACGGAA ACATGATAGA TCCTGGAAGT      21120
TTGTGAAGCC CTGTGCCCGG AGAGACACCC CTCAACTCGC AGTGCTCGGA GACCTACATG      21180
TATACTCAGG CTCTTCTATA AACCCTCCCC AAAAGTTTAT AAAACACCGT ACGTAATACA      21240
CATTACTCAC AGTTCCCACG GTGACGCCCA AACCCATGCA CACGGGCGTG ATCGATACCA      21300
GAAAACATCA AAGAACAAA AAGTGTGTGT CTGACATTCA CATTTATTTT TACAAGACAA      21360
TTTTGTGCAG TAGAGTTGTG CCTTCCGACA CCCCGCGCCG TTCGCTGTTC TCCTGTAATT      21420
GGGAGATCCC ACTCCTTGGC AGGCACGTTT CACGAAACGC TCTTGTCTCG CTGGCCTTAG      21480
ACTTGTGGAC CCAACATGGG TATCGTTAGA GATCCGTCGC GTAAATGCGC AGCTGGCAAA      21540
GCATTCTTCA GCGAGCAGTG ACTGGTAATT GCTGCATCAG CTTCTTCACC CAGTCTTTCG      21600
ATTTGTCGGC ACACACCTGG CGACCACGCT TTGTCAAAAA TATCACACCC GGCTTGCTGC      21660
ACAGTTGGGA GGTGGGGTAC CAGCTGGACA GAAGCACCTG TGGTAATGGT CTTTTCTGGT      21720
AACCGAGACA GCACTTGTCC GGTCTATGCC AGGACGCTCC CAGCGTGTCC CCAGATTGCA      21780
AACAAAGCAA GGCAGTCAGC ACAGCGACGA GCAGGATGCC CTTGGTGTCC ATAACTCCCC      21840
TCGTGTGTCC TCGTGTAAAT GCGAAACGGC GATGTTAGGT CAGGCGCGGT AAACAGCTCA      21900
ACTCGGTTCA AAACACGTAC GTGATGTAGT GCTGGTTCTA CGACGCCTAC CTGTAAACTC      21960
CAGGATCCTG GCTTTTATT ACGAAGGCCA ACACCCCAAA AAATCCACGC CCCCGTGACC      22020
GCAGGGCGG TTACTAACGA CGGTTACAGG TCCCTCCCGA GCCACGCACC TGCCATGTAA      22080
CCTGCAAGGT AACCAGACAA ACATCTAGGA AGCGTAAATA TCCCCAGGTA GGAGAAGTAT      22140
TGCATATGTC ACAGACTCAA CACACACGGG CCGTTACGCA ACGGCTAGGG GCATAACCCT      22200
TTACCGGCGC GAAGCGCTAC GCGCTTCGCG AGAGGTATCT CCGTGTGCTT CTCCATCAGA      22260
AGACGCGTGC GCCGCTTCGC AGGCGACCCG CATACTTTCC GCCCCGAGTG CGTTACAAAA      22320
ATGACTGCCT TCTGGCGACA ATACACGGTG GACGTCCAGT ACCACCCGCA TATCAGCTTA      22380
TCCGGTGGCA ATCTGGCACT GGACAGGGAA TTCTCGCAAC AATCCGAGGC CATGATGGTG      22440
```

-continued

```
GCAGGACCGC TGGCCGCACA TAGCTCAATC ACGGCCACCC AGAAGAGCAG CCCCAAATGT   22500

GCGCGCAACA CCCAGCACAT GCTCCACATA CAGTTCTGGC GCCACAACGA TGATGCGCAA   22560

AGGGGTGCAT TACCCTAAAT CCCAGCCTAG TTATAAATTA TTGAAGCCCA GGCGACCAGG   22620

GGTCGCCGCG CTTTTCCTCC CCAAACGCGA CGATAAAGAC CAGCGTTGCC AAATGTAACT   22680

TATGTATAAC CCAAAATATT GCGCATCGAT AAGGTTTGCC AAAACACCCG AAAGTACACA   22740

CACAAAAAAA CAGCAACAAG ACGCTCACTA GACATTCACC CCTTCCCCCA CCCCCGAAAA   22800

CAAAACAACT TGACACAGGG GAAACACCAG GGGCGGCGGA GGTTGTCAAT AGTGTCCAGT   22860

ATTTCGTTAG ACGCGGGTTC TTGGACCCGA TGTCCCAGGT CATTAAAGTC TCAAATGGGA   22920

TTAAAGGATC ATAGTTCCCA GGTTTAATAC TCCAAGCTAT CCCAGAACAG GACCCCGGCA   22980

GAACCCCGCT TAACAGCACC AAATCCACTT GCGGTCCCAG AAAAGGTCGC CGAGGTGGCA   23040

AGGTGACTGA AAAGGTCATA GAGAGGACAC CGGTCCCATT TCCCACGGTC CAAAAATCCA   23100

GCGCGCCCCA CCGGCTTTCC GAGAACTTCG GCAAAGCTAA TTTGCATGCG CTAATCCTTT   23160

TATGTGCATA AATTATGTAG ATGAGGAGTC GCGCATGCGC AGAAAAATTC AGAGCGCCCG   23220

GGTGCACGGG GTCACCTCCA GGTCACGCCG CTAGGTGGGA CCGTGAGCGA CTCGAAAAAT   23280

TATAATTTTT GGCCATTTCA TGGGCGCCGC CATCTTGAAT TTGCTAATCC CCCATAATCC   23340

TCTGCCCCGC TCCCATTGGT CCGCCGGCCC GTCAATCAAA GTTTTCCGAG CCGCCATTGG   23400

CCCATCCGGC CGACCAATCC CGTTCGAGCT AGGCGACCGC GCCATTCCAT TGGACGCCCC   23460

AGCCGTCAAT CAAATTCGGA GGCCTCCCAT TGGCCCCTAT CCCTAGAACT CCCAAGCTGA   23520

TTGGCCCAGA GCGGGAACCA ATCAGCGATT AGAGTTTTGT TTTGATTTTT CCTATATATA   23580

TATATATAAT CCTTTAATCC TAGCGCAGCT GAGTCATCGC AGCCCTATT CCAGTAGGTA   23640

TACCCAGCTG GGTAATCCAG TAGGTATACC CAGGTGGGTG AACCCAGCTG GGTATACCCA   23700

GCTGCAATTC TATAATTAAA CAAGGTAGAA ACCAACGGGG TCCTCAGGTG GTATTTCCGG   23760

AAGCATTACC AAATAAGGCA ACCTCAGCTG GGAATACCAG CGGACTACCC CCAACTGTAT   23820

TCAACCCTCC TTTGTTTTCC GGAAGTATAT CCATTTATGG AAATCAGCTG GGTCACTCTA   23880

CTGGGTTATT CTTTATAATA GGGCCCGATG AGTCATGGGG TTGGGATTTT TCTACTAGGT   23940

CGTTTCGGTG GATGGGTGCC AGGATTATAG GGGCCCTGTC CACGGGGTTG TTCGGTGGCG   24000

GGGGGGGGGC TAGTGAGTCA CGGGCCTGGA ATCTCGCCTC TGGGTGGTTT CGGTAGATGG   24060

GGGCCGGGAG GATGGGCCC CGCCCACCGC TGGCGCGCCC CAGAACATGG GTGGCTAACG   24120

CCTACATGGG CAGCTTGTCC TACGGTTACG CCCATTTGAG ACGGGTTAAC CAACTGTTAC   24180

ACCCCTTCGC CGGGAACGCT ATAAAAACGA GGGACAGCAG CCCCCCCTCG CGCACTGCGC   24240

GCGCGGCGGC ACGTGGGACG GATCTCTTGG ATTTACCCGT AACGAGGAGC CCCGGCAGCA   24300

CCCCAGGAGC CCCGGCAGCA CCCCAGGAGC CCCGGCAGCA CCCCAGGAGC CCCGGCAGCA   24360

CCCCAGGAGC CCCGGCAGCA CCCCAGGAGC CCCGGCAGCA CCCCAGGAGC CCCGGCAGCA   24420

CCCCAGGAGC CCCGGCAGCA CCCCAGGAGC CCCGGCAGCA CCCCAGGAGC CCCGGCAGCA   24480

CCCCAGGAGC CCCGGCAGCA CCCCAGGAGC CCCGGCAGCA CCCCAGGAGC CCCGGCAGCA   24540

CCCCAGGAGC CCCGGCAGCA CCCCAGGAGC CCCGGCAGCA CCCCAGGAGC CCCGGCAGCA   24600

CCCCAGGAGC CCCGGCGCGC CACCCTCCCC GGAGGGGGAT CCCGGCGCGC CACCCTCCCC   24660

GGAGGGGGAT CCCGGCGCGC CACCCTCCCC GGAGGGGGAT CCCGGCGCGC CACCCTCCCC   24720

GGAGGGGGAT CCCGGCGCGC CACCCTCCCC GGAGGGGGAT CCCGGCGCGC CACCCTCCCC   24780
```

```
GGAGGGGGAT CCCGGCGCGC CACCCTCCCC GGAGGGGGAT CCCGGCGCGC CACCCTCCCC    24840
GGAGGGGGAT CCCGGCGCGC CACCCTCCCC GGAGGGGGAT CCCGGCGCGC CACCCTCCCC    24900
GGCAACAACC TGTTGCCATG TATGGCGATT TGTATCAGTC ACAAGCACAC AACCCCTGCT    24960
AGTATTAATG GTGTTTAAAA CGTTCTACAC GTACGGCGGA CCGCATCCGT CGCAAGCACG    25020
CGCATATAAC CCCCAAATGC ACCATGATGA GAAGCACAGC CACGCGTCAA AAAACTTTAA    25080
AAACATCGTT ATCCAATATC ATTAAAAACC ACACCGAAAT TTACACAGGT AGCACGTCAC    25140
CGTGTTAGTG TCACCCACTG TACACAAGGC GTGTCGTATA TGTAGTATAG GTATTTGATG    25200
AGGCGGAAGC ATATCCCGCT TCCAGCGAAC GGAAATAAGA ATCATCCGTT CCAGCATTTA    25260
TTCAAAGAGG GCACAGAGGA TTCACATTGT TTAGAGAGAT TTTTTCTTAG TCACCATTCC    25320
ATACTTGGGC AGTATTGGCC TACGATTTGG GCGACGTTTC AGGCTGGTCT ATTCTCCGTC    25380
CACTTTTCCC CGGCTATTCT GTCCCAGCAT AGGCTCTTGA AATAAACAAT GTTTACCGAG    25440
TAAAAGGTTC CACTCACCCT CATTTGTCGT TGCACCCATC CCCCCTTTGC TTAATCACCC    25500
GAAAACTAGA GGACACGGAT GGAAAACATA TCGCACGCGG GTTGTTTGAA AGTCAACAGC    25560
TACTTGTTTT TAATGAGGAC AGATTTGGGC ACAGGCCAGA GGGTAAAGCC CTACGTGTGC    25620
GCGGGGGGGG GGGTGTATAC GCTGCGAAAA CCTGCACGGT GCATAACACC CAGGGCGTCA    25680
CGTCACATAT CTCTGTGCAC CCAAGTGGTT GTTCAACCGT TGTTTTTTGG ATGATTTTTC    25740
CGCACCGGCT TTTTTGTGGG CGCGCATAGG TCGGTACGCG CTGTCCCCCT AAGTCCCGCA    25800
CGGTCGTTCG GGCCCCCGTC CGGCTCGTCT CCGGATGAAC CGTCACGTTC TTTGTCTCCA    25860
GAGGCGACGT CTCCTTCAGA TGACTCGTCC GTGGGCTCCT CGTCCGTCCC GCCCGCGGGT    25920
CCGACAAGGA CCGTCAATTC GATGTTATCT TCGTTCGCGG TTGGCCGGCG CGGCCGTCGG    25980
TATGGCAGTA CGGTCACCCG GGTGTTATTT GCCGCGTATA ATGCCCTCAC AGTGCCACTT    26040
ACGCGGCATA TGCCGCCAAA TGCAAACACA ATAAATATTT GGTAAAACCC AAAGAAGCAG    26100
AGAAAACCGA GCACGGCCCC GGGGGAGAAT GTTCCCGCAG GAGCAGTTAG GATGACCAGG    26160
AGCGTCCAGG TGCACAACGC CACGCCGACA AGCCCAGCCA CCACCACAGA CATCAGCAGA    26220
AACAGTTCAA AAATTTCTTG GCGCTCCATC TCCGGCCACA GGTTAAGGCG ACTACGCCAC    26280
TGCGTGCGCG TGCGGTATAT AACGCGACAC ATTTGACAGG CCGTGTTTCG AGACACTGTT    26340
AGCCAAGTGC TTAAACACTG CGGGTGGACG ACATCCAGCT CTCCGGTACA GGCGCAGGGG    26400
TGTATGCCCT CGTTCCCCAC CTCTTCCCTA CATATCCAGC AGATGGGTCC CTCTACACCC    26460
TCTTCTACGT CCTTAGACGC CATCTCTGCA GCTGGGGTGG AAGTCTGAAA AAGGGAAAGG    26520
GGAGGTGAGC AGAGTGCCCA GTTAGTCTCC GACCCGCCGT CCGCCCTACT GTCGCTATCC    26580
CGCCTTGACA GATGTCTAAC GTATTCACGG ACGCCACATG TGTGTCTATT TCCTACATC    26640
CAGGCTTTCC CTGGAAAACT GTCACAACCC ACCCTGCTTT AGCTCTACAT CTGTATTTTT    26700
GTTTACGCAC AGGATCAACG CTTCGTGCCC GTCCACCCCC GCGCTCTCCG CCTGTGTTTG    26760
GAGGTTTTAT GAGTGGTTAG TTCTAGGCAG CTCCGGACAA GTTGTCCAAA ACACGGCGCG    26820
CCCCGCCCTT CCTTCCCTCC GGATCCGCCC ACACCGGACC TATGAAATAA GGGACACGCG    26880
TCATCACTAG TTATGAGAGA AAAACCACAA CAGCTTTATT GGAAAACACC TGAGTGGATC    26940
CCCCACCCCC CGCGTACGAC AGGCGTTTCT GTGGTGCGCT TCTGGGAAAA ACGTTTTTCC    27000
CCCATTTCTT CCTCGACAGG TCTTCTAAGG TAGATAAATC CCCCCCCTTT GCGCGTCTCC    27060
TAGAATGGCC TAGGCGCACG ATGGCGTTGT CGCCTCGAGC AGTTGGGCCG CAGTGATATC    27120
TTCAACTTTC GACCGTCTAA GCTATGGCAG GCAGCCGCTG CATCAGCTGC CTAACCCAGT    27180
```

```
TTTTGGAAGG GTCTGCGCAG ATCTGACGCC CTCGCTTGGT CAGCAAAATA ACTCCGGGTT   27240

TTGGGCACGC TGGGGACGTG GGATACCACT CTTTTAGAAT TTGGACGGGC GGTGGGTGCT   27300

GCTGGAACCC GTAGCAGCAG CTATTAGGCG TGTACGACAC GAGTGACCCC GCGCTTTCTG   27360

TGGGCGTCAG GTAAAACGTG GCAAGCAGTA CGCTAACGCA GCATAAAACG TGGACGGGGG   27420

CCATCTGGAG GTGCCAAGTT CGCAACAGTC TAAAGAAAAC CGTAAAGGCT ATTTGGGGTT   27480

TCTGTTCTGT CAGATGTAAC GCCGAGTTCC TTATATGCTT ACCTGATTCT GGTCTCACCT   27540

GTTTATTTAT AGTGGCGTAT GCTAACCGCC AGCTTACATG CGGGATAAGT TGGCCTAACT   27600

CACCAAAAAC GGGTTGCAGA CAAAAGTGAT TGTTGGGGCG CTTACTTAGA AGGTGTGAGG   27660

GTTTCTAAGA AACCCCGCCA ACGCCCGGAA ACCGCATGCG TTCCAGTCGG TGCGGCCTGC   27720

GCCGGCGTCG CTGTGGCGCC TTTGTGGGCT TTGAGTTCTG TCATTAAGCC AGGTTTCCAT   27780

TGCCACCCGG GCGAAAACAA GCCGGGTAGT TTCAGGGGTC ATCGGCGAT CAGTGTACCA   27840

TATTCCCACG ACCCATCAAC ACCGCTGCTT GAGGCGTGTC TCTGTATGTG TCACCGGAGA   27900

CTGCATGTAT CGTGCATATC TGTATTGTGC GCTTGCGCGG AGACAACATA CCGACGACCA   27960

AGTCAGGGGT CACCTCCAGT GCACGCCGCT AGGTGGGACC GTGGGCGAGC CGAAATAATT   28020

ATATATTTTT TTGGCACGGT TGTGAGCAAC GCCATCGTGA GTTGGTTAAT ACCCTCTAAA   28080

CGCATAGTCT TTTTTATTT GTCAACCAAC CAGTCAATCA CCTGTCATCG CCGCTCAGAA   28140

GCACACGTCT TCGCCAATG CCGTGTTGGC GGGTTTGACC ACGGTTACTG ATAGGTAGAC   28200

GAGTCCGACA ATCACACACG TCCGCCAGCG ATTTGCAGCG CAGCTAAAAT CGCGTGGCCG   28260

GGTTGGTAGA AGCAAATTAT CCAATGGTCG TGTTTGGGTT TGTTTTGGGG TTATCTACAT   28320

ATTATATTCC TTATCCCGAC TGGTTGCGGA AGTATTCGCA GCTTGGCTAC TCTGCTCGAT   28380

TACCCCGTGA ATAACTGGGC GGGGGGTGAC CCAACATAGT GATTCGGTAG ATTTGGGGA   28440

CTGGATGAAC ATTAATGAAA GTTATTAAT GTTCATCCGT ATTGTGTATA TGTAATTTGG   28500

TTTCCATATT TGGTAGGAGT ATGGAGTTTT CTTATGGATT ATTAAGGGTC AGCTTGAAGG   28560

ATGATGTTAA TGACATAAAG GGGCGTGGCT TCCAAAAATG GGTGGCTAAC CTGTCCAAAA   28620

TATGGGAACA CTGGAGATAA AAGGGGCCAG CTTGAGTCAG TTTAGCACTG GGACTGCCCA   28680

GTCACCTTGG CTGCCGCTTC ACCTATGGAT TTTGTGCTCG CTGCTTGCCT TCTTGCCGCT   28740

TCTGGTTTTC ATTGGTGCCG CCGATTGTGG GTTGATTGCG TCGCTTTTGG CAATATACCC   28800

ATCCTGGCTT TCGGCTAGGT TTTCCGTCCT ACTTTTCCCA CATTGGCCTG AGAGCTGTAG   28860

TACAAAAAAC ACCGCGCGGT CTGGAGCTCT CCATAAGCCC GCAGAACAAA AGCTGCGATT   28920

TGCCCAAAAA CCTTGCCATG GCAACTATAC AGTCACCCCT TGCGGGTTAT TGCATTGGAT   28980

TCAATCTCCA GGCCAGTTGT AGCCCCCTTT TATGATATGC GAGGATACTT AACGTGTCTG   29040

AATGTGGAAT ATAATGTGAA AGGAAAGCAG CGCCCACTGG TGTATCAGAA CAGTGGTGCA   29100

CTACCTATCT GCTCATTCGT TGTTTCGGTT CTGTGTTTGT CTGATTCTTA GATAGTGTTG   29160

AGGTAATTCT AGAAAGCGGA TTGAGTGTAA ATCGGGCCAC TTTGCCCTAA ATGTGACAAT   29220

CTGGATGTGT ATCTTATTGG TGCGTTGTGA AGCATTTTAA AATGCGTTTT AGATTGTATC   29280

AGGCTAGTGC TGTAATGGTG TGTTTATTTT CCAGTGTAA GCAAGTCGAT TTGAATGACA   29340

TAGGCGACAA AGTGAGGTGG CATTTGTCAG AAGTTTCAAA GTCGTGTAAG AACATTGGAC   29400

TAAAGTGGTG TGCGGCAGCT GGGAGCGCTC TTTCAATGTT AATGTTTTAA TGTGTATGTT   29460

GTGTTGGAAG TTCCAGGCTA ATATTTGATG TTTTGCTAGG TTGACTAACG ATGTTTTCTT   29520
```

```
GTAGGTGAAA GCGTTGTGTA ACAATGATAA CGGTGTTTTG GCTGGGTTTT TCCTTGTTCG  29580

CACCGGACAC CTCCAGTGAC CAGACGGCAA GGTTTTTATC CCAGTGTATA TTGGAAAAAC  29640

ATGTTATACT TTTGACAATT TAACGTGCCT AGAGCTCAAA TTAAACTAAT ACCATAACGT  29700

AATGCAACTT ACAACATAAA TAAAGGTCAA TGTTTAATCC ATATTTCCTG ACTTGTGTCT  29760

TGACTTGCGT CGATTGGGAT GGGGTGTGG GATGGGGTG TGGGATGGGG GTGTGGGATG  29820

GGGGTGTGGG ATGGGGTGT GGGATGGGG TGTGGGATGG GGTGTGGGA TGGGGTGTG  29880

GGATGGGGGT GTGGGATGGG GGTGTGGGAT GGGGTGTGG GATGGGGTG TGGGATGGGG  29940

GTAAATGACA ATGGGGGTAA ATGACAATGG GGCGCTTGGT GACACATTTG CCCCACCGTC  30000

GCCTGCCCGG AACCAGCTTG GTGATGTGCT GTCTGGCTCT CAGGTGCACT TTATGCAAAG  30060

CAGTTGAGGC GCATTAGATA TATAAAACTT GGGTACACAC CCTTGGTGCT GTGCGCGTGC  30120

TATGTGCCCT GGTGACCGTC CACAATGGAC GAGGACGTTT TGCCTGGAGA GGTGTTGGCC  30180

ATTGAAGGGA TATTCATGGC CTGTGGATTA AACGAACCTG AGTACCTGTA CCATCCTTTG  30240

CTCAGCCCTA TTAAGCTATA CATCACAGGC TTAATGCGAG ACAAGGAGTC TTTATTCGAG  30300

GCCATGTTGG CTAATGTGAG ATTTCACAGC ACCACCGGTA TAAACCAGCT TGGGTTGAGC  30360

ATGCTGCAGG TTAGCGGCGA TGGAAACATG AACTGGGGGC GAGCCCTGGC TATACTGACC  30420

TTTGGCAGTT TTGTGGCCCA GAAGTTATCC AACGAACCTC ACCTGCGAGA CTTTGCTTTG  30480

GCCGTTTTAC CTGTATATGC GTATGAAGCA ATCGGACCCC AGTGGTTTCG CGCTCGCGGA  30540

GGCTGGCGAG GCCTGAAGGC GTATTGTACA CAGGTGCTTA CCAGAAGAAG GGGACGGAGA  30600

ATGACAGCGC TATTGGGAAG CATTGCATTA TTGGCCACTA TATTGGCAGC GGTCGCGATG  30660

AGCAGGAGAT AACGCGTAAT TCGAGGTCCC CGGAAGAGTA GAGGGTTGCA TGTTATACAA  30720

ACAACATAAA CATTAAATGA ACATTGTTCA AAACGTATGT TTATTTTTTT TCAAACAGGG  30780

GAGTAGGGTA GGAAGGGTAC GTCTAATACG TAACTGTTCG CTACTGCTTG TTCAGGAGCT  30840

CCTCGCAGAA CATCTTGCGA ATTTTAGATT TTGGACTAGA GCGACTGCTG GCTTCAACGC  30900

GGTTCGATGT AGGGTTCGGC GTAGGAGCGT CTTTCTCCAC CGCCGCGCAT GGTGTATGCG  30960

TGGTCTCCGG TGCCTGTTGT TGGATGCTCT GCGTGCTGGA GGCGGGGGTG GGTTCAGCGG  31020

GTGGTGCGCC AACTACCGCG AGTCCTGTAG AGACTGGCGG GTGGCTCACA TGTGGCTGAG  31080

CAAAAAGGAT GGGCGCCGCT TGCTGGAACT GACCGTGTGG CGCCTGCACG TAAATGGGTG  31140

GGTGTACGTA GGTTCCTCCG TGCTCCTTCA TTGTCGGGAA TTGACACGGG ACCGCTGAAT  31200

TGGCGTGGGG CCTGTAGTGT GGATCTACTG CGGCTGCTGC TGCAGAGGAG GACGGCGGTG  31260

GCCCTGCGTG CCAACCGTTC AGTTTCATCT CTTTGAGTTC AGACTGTATT TCCGCTATGT  31320

TCTTTGACAT GGACAAGATA TCCTTGTGAT ACGCCGGCTC CTCTCCTGGA AAGAGGTGTC  31380

CTTCGTCGTC CTCTGCGCCG CGCTTGCGCT TCCCCGTCCT ATATCCAGGC AGCTGTGGCG  31440

AGTAATACCA TGGATCGTAT GGGTTCTTGT AAGCGTAGCC GTATGGTGGC GCTGGGTTTG  31500

AAACATACGA AGGTAGGTGA TGGTCGGTGG GGAACATCTG GCCCCACAC CCCATTAGGC  31560

CTGGCCCTGA AAGTGTATGT GACATTTTTG CCGCTGTGGT CTTCATTCCA TCGATGCTGC  31620

TTTGTAGCAT GCTCAGGAAG GCGGATTTGG GGATGGATAT GATATCCTCT TGACCAGAGC  31680

TGTTCATGGC TGGTCTGGGT GGTGTGACGG CTTGGATGCC GACCGGGAAT TGGCTGGCCT  31740

TTAAATACGC CGGGCTCAAT ATGCTGGCCA CACCTCTGTC AGTTTTCAAT AGGTCGAGGC  31800

GGTCCCGTAT GAAGCTGGCA TCTATAGCTT TTGCCATTAA GGTCTCCAGG GGACTGACGA  31860

AATTTGGTGT GGAAAGGTCC TCCAGCCTGC AGCTACTTAC GTGCTGGAGG ATGTGGGCGC  31920
```

```
GCTCCGACTT AGATACTGAT GAGAATCTGG AAACCACCCA CTCGGCGTCG TGTCCGTACA    31980

CGGCCACTGT GCCGCGTCGG CGCCCCAGGG CGCATAGTGA TACGTGTTGA AACACGGGAC    32040

CGCTGGGAGT CTGGGATAAC TCGCGGGGAT GTATAGACGA TAAAGACAGC CCCGGGAGCC    32100

ACGTGTGGAG TATCTCCAAC AGTGGTTCCT TAGGGAGATT TTTCACGGGG CTCTGGCCA     32160

CGTGGGAGGT GTCCGCCAGC CTGGATGCCA GCTCTAGGAA GGCTGGCGAC GTGATGGCTC    32220

CGGTGCAGAA ATACCGTGGG GACACTTGAA ATAGACCCAG TGTCCAGCCC ACTTCTGTCT    32280

CTGGTAGGTG TTCGATTGTT ATTGGAAGGG GTTCTGTGAC TGGGAGATAA TCCGTCACCT    32340

GATCCGGATC GAGATAGAGC TCTTGCTCCA GCTTGGGGCA GGACACAACA TCTACAAACC    32400

CTCCGACGTA CAGGCCCTGT GCCATGCTCG GAAAATACGT GTGTGAGACC GAGCCGCTGA    32460

GCCCGGGGCT TAGGAGGCTC ATGTGGCGCT TTTTGCAAAA TAAGAATTTA AATACATTCC    32520

ACGCCCAAGA GCTGCGTTTT ATTCATTTGG TTCTCTGCAG GATGTACAAT TTCGGTCTAA    32580

ATGTGTACCT GTTAAGGGAG GCTACTGCCA ATGCCGGGAC CTACGACGAG GTGGTCCTGG    32640

GACGCAAGGT TCCTGCGGAG GTGTGGAAGC TCGTGTACGA TGGGCTCGAG GAGATGGGCG    32700

TGTCAAGTGA GATGCTGCTG TGTGAGGCAT ACCGGGACAG CCTCTGGATG CACTTGAACG    32760

ATAAGGTGGG GCTCTTGAGG GGCCTGGCGA ATTATCTGTT TCACCGGCTA GGGGTCACCC    32820

ACGACGTTCG CATCGCCCCG GAAAACCTGG TGGACGGAAA CTTTTTGTTT AATCTGGGAA    32880

GTGTGCTCCC CTGCAGGCTG CTCCTTGCGG CGGGCTACTG CCTCGCCTTT TGGGCAGCG     32940

ATGAACACGA ACGCTGGGTG CGCTTCTTCG CCCAGAAGCT TTTCATTTGC TACCTGATAG    33000

TCTCCGGGCG TCTTATGCCA CAGAGGTCTC TGCTAGTTTG GGCCAGCGAA ACGGGCTATC    33060

CCGGTCCGGT GGAGGCAGTC TGTCGCGACA TCCGCTCCAT GTACGGCATA CGAACGTATG    33120

CGGTCTCGGG TTATCTTCCG GCTCCGTCCG AAGCGCAGCT GGCCTACCTT GGTGCGTTTA    33180

ACAACAACGC GGTTTAAACG ACCGCGAGGA CCACCGGCAG GCAGCCAAGA ACCATAAAGT    33240

ACGCTCTATC GTAGTCATCG CCGCCGCCAA ACTGGGACTT GATAATCTCC TGGAGAAGGG    33300

TGGGTGGGA TGGGTGTGAA AGCAGGACGT CCAGGCCCTC TTCTGTTGCC AGGCGGAGGG     33360

CTGTTCTCGC CTGGAGCAGC GCCAGTGGAT CTCGGAATGT AAGCTGCTGG TTCAGGATTT    33420

CGAATATCTC ATTAAACCTA CTGCCTGTCA GATTTACAAA TGGTCCGGGT TGTTTGTGGG    33480

ACACGGTCGA TCGCGCCTCG AGGGCGGCCA GTATTATGCC AGGGAAGATG AAGGACACGG    33540

GGGCGTTTGG ATTAGCCTGC AGTGTGGGGA TTATGTAGTG CTCCGATATG AACGAAAATA    33600

GCTGGCCCCT TTTCAGCATG GGGGCGTTTG GATCCGGTAG GGCACCGGGC TGAAATTTGG    33660

GTCCCAGCAG GGATACCAGG TTCAAGCGGC GGTTTGGGTG CCCTCGCGCG ACTTGCCCAA    33720

ACTCCAGCAA TCCATACGCG AGGATAAACA CCTCCAGCGC AACAATCCCC GCTCGCAGGT    33780

TCCACTGGTA TGCGGAAAAT GGTGGTATAT CGGACCCAAA CATGGCGCTC GTAATGGCGA    33840

ATACCAAGTC CATGGCGGGC GCTGTCCCTG GCGCGCCCGT ACCCTTGTTG TGGGGAAATA    33900

ATCCAGCCTT AGCCATCATT GCGTGAAGCT TGTGGCGCTG GAAGAAGGCT GTCGGATAGC    33960

GGCTCTCCTT ATTGAGAGGC GCCAGCGAGG CGCGCTCCTG GGGGTTTGAG TATGTGAAGC    34020

TGAAGTCCCC AGGACCGCTT TCCTGTTTTA GCTGAGTGAT TAGCAGGTCT AGCTTTTGAG    34080

GCAGGTCTGC TAACAGGTCA TCGGGAGTAG CGGGCAGTTG CCTGGATGTC TTTTGACAAA    34140

AGTACGCGTT GACGAGGCAA AGCGCGGCCT GGGTGTCCGT GAGATGCCTG GCGTCGGCGA    34200

AAAAGTCAGC GGTGGTCGAG GCGACCGTCG TCAGGGTGTG AGAGATGAGT TTGAGCGATG    34260
```

-continued

```
TGGAATTCTG AAAGTTAACA GTCCCCTTTA GTTCTTTAGG GAAGACGCGC CGCTGCATGG    34320

CGTTGTCCGT GAGGCTGATG AACCACGGCC CAAAGGATGG CAACCACTGA TTCTGGTTCA    34380

TGTACAGGGT GGGCATGAGC TCGCCGCGCA GGTCCCTGTC AACGGAGAAG TGAGGGTCCC    34440

CGGGGACGAT CGCCACGGTG AAGTTACGGT GGCTGGCCTG CGGGGGGGAT GTCACTAAGG    34500

GAGGCTCATG GGAACGGCTT TGGGGCATGT CTATGTTGTC AGACCATGTC ATGTTGCCTA    34560

TCATCTGTTT CACCGCGTCG ATATCTGCGT TAATGACGCG GACGCGTGAG TCATGGACCT    34620

GAACAAGCCG GTCCAGCTCT AGGGAAAGCA GGTGTGCCTT TGTCTTTCGT TCTCGATTTC    34680

GCACGAGTTG GCTGCGCAGT CCAAGGGCGA CCCTTCTTGT TTCTTCCATG GTGGGCTTGT    34740

GAATAAACAG CACGTTTTCC GGGTGTGGGG CCCAGAATCT TCCCGCCTCT GTCCATCTTC    34800

GGTTTTTTGG GTACCTTAGA TAGGACCTTT CTGATGTCAG CATTTTCTCT AGCAGTGAGA    34860

AAGGCGCACA ATTTTCCTTC GGTGGTGTGC ACCGGCGTGG GAAACGCCCC GGGTGATTCA    34920

GAGTATACTG TCTTTAGTGT TTTCTGATTC TTAAATATCA GCAGGGCGT GATAGTCCAC     34980

GCCTCGGTAC CCGGAGGGGC CGAGTGAGCG ATGTAATGGA TCGAGTCGGA GAGTTGGCAC    35040

AGGCCTTGAG CTCGCTGTGA CGTTCTCACG GTGTTGGTTG GGATCAGCTG GTGACTCAGA    35100

(2) INFORMATION FOR SEQ ID NO:18:

(i) SEQUENCE CHARACTERISTICS:
        (A) LENGTH: 35100 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:18:

CAAGTCTTGA GCTCTACAAC GTAACATACG GGCTGATGCC CACCCGATAC CAGAATTACG       60

CAGTCGGCAA TTCTGTGCCC TAGAGTCACC TCAAAGAATA ATCTGTGGTG TCCAAGGGGA      120

GGGTTCTGGG GCCGGCTACT TAGAAACCGC CATAGATCGG GCAGGGTGGA GTACTTGAGG      180

AGCCGGCGGT AGGTGGCCAG GTGGGCCCGG TTACCTGCTC TTTTGCGTGC TGCTGGAAGC      240

CTGCTCAGGG ATTTCTTAAC CTCGGCCTCG GTTGGACGTA CCATGGCAGA AGGCGGTTTT      300

GGAGCGGACT CGGTGGGGCG CGGCGGAGAA AAGGCCTCTG TGACTAGGGG AGGCAGGTGG      360

GACTTGGGGA GCTCGGACGA CGAATCAAGC ACCTCCACAA CCAGCACGGA TATGGACGAC      420

CTCCCTGAGG AGAGGAAACC ACTAACGGGA AAGTCTGTAA AAACCTCGTA CATATACGAC      480

GTGCCCACCG TCCCGACTAG CAAGCCGTGG CATTTAATGC ACGACAACTC CCTCTACGCA      540

ACGCCTAGGT TTCCGCCCAG ACCTCTCATA CGGCACCCTT CCGAAAAAGG CAGCATTTTT      600

GCCAGTCGGT TGTCAGCGAC TGACGACGAC TCGGGAGACT ACGCGCCAAT GGATCGCTTC      660

GCCTTCCAGA GCCCCAGGGT GTGTGGTCGC CCTCCCCTTC CGCCTCCAAA TCACCCACCT      720

CCGGCAACTA GGCCGGCAGA CGCGTCAATG GGGGACGTGG GCTGGGCGGA TCTGCAGGGA      780

CTCAAGAGGA CCCCAAAGGG ATTTTTAAAA ACATCTACCA AGGGGGGCAG TCTCAAAGCC      840

CGTGGACGCG ATGTAGGTGA CCGTCTCAGG GACGGCGGCT TTGCCTTTAG TCCTAGGGGC      900

GTGAAATCTG CCATAGGGCA AAACATTAAA TCATGGTTGG GGATCGGAGA ATCATCGGCG      960

ACTGCTGTCC CCGTCACCAC GCAGCTTATG GTACCGGTGC ACCTCATTAG AACGCCTGTG     1020

ACCGTGGACT ACAGGAATGT TTATTTGCTT TACTTAGAGG GGGTAATGGG TGTGGGCAAA     1080

TCAACGCTGG TCAACGCCGT GTGCGGGATC TTGCCCCAGG AGAGAGTGAC AAGTTTTCCC     1140
```

```
GAGCCCATGG TGTACTGGAC GAGGGCATTT ACAGATTGTT ACAAGGAAAT TTCCCACCTG   1200

ATGAAGTCTG GTAAGGCGGG AGACCCGCTG ACGTCTGCCA AAATATACTC ATGCCAAAAC   1260

AAGTTTTCGC TCCCCTTCCG GACGAACGCC ACCGCTATCC TGCGAATGAT GCAGCCCTGG   1320

AACGTTGGGG GTGGGTCTGG GAGGGCACT CACTGGTGCG TCTTTGATAG GCATCTCCTC    1380

TCCCCAGCAG TGGTGTTCCC TCTCATGCAC CTGAAGCACG GCCGCCTATC TTTTGATCAC   1440

TTCTTTCAAT TACTTTCCAT CTTTAGAGCC ACAGAAGGCG ACGTGGTCGC CATTCTCACC   1500

CTCTCCAGCG CCGAGTCGTT GCGGCGGGTC AGGGCGAGGG GAAGAAAGAA CGACGGGACG   1560

GTGGAGCAAA ACTACATCAG AGAATTGGCG TGGGCTTATC ACGCCGTGTA CTGTTCATGG   1620

ATCATGTTGC AGTACATCAC TGTGGAGCAG ATGGTACAAC TATGCGTACA AACCACAAAT   1680

ATTCCGGAAA TCTGCTTCCG CAGCGTGCGC CTGGCACACA AGGAGGAAAC TTTGAAAAAC   1740

CTTCACGAGC AGAGCATGCT ACCTATGATC ACCGGTGTAC TGGATCCCGT GAGACATCAT   1800

CCCGTCGTGA TCGAGCTTTG CTTTTGTTTC TTCACAGAGC TGAGAAAATT ACAATTTATC   1860

GTAGCCGACG CGGATAAGTT CCACGACGAC GTATGCGGCC TGTGGACCGA AATCTACAGG   1920

CAGATCCTGT CCAATCCGGC TATTAAACCC AGGGCCATCA ACTGGCCAGC ATTAGAGAGC   1980

CAGTCTAAAG CAGTTAATCA CCTAGAGGAG ACATGCAGGG TCTAGCCTTC TTGGCGGCCC   2040

TTGCATGCTG GCGATGCATA TCGTTGACAT GTGGAGCCAC TGGCGCGTTG CCGACAACGG   2100

CGACGACAAT AACCCGCTCC GCCACGCAGC TCATCAATGG GAGAACCAAC CTCTCCATAG   2160

AACTGGAATT CAACGGCACT AGTTTTTTTC TAAATTGGCA AAATCTGTTG AATGTGATCA   2220

CGGAGCCGGC CCTGACAGAG TTGTGGACCT CCGCCGAAGT CGCCGAGGAC CTCAGGGTAA   2280

CTCTGAAAAA GAGGCAAAGT CTTTTTTTCC CCAACAAGAC AGTTGTGATC TCTGGAGACG   2340

GCCATCGCTA TACGTGCGAG GTGCCGACGT CGTCGCAAAC TTATAACATC ACCAAGGGCT   2400

TTAACTATAG CGCTCTGCCC GGGCACCTTG GCGGATTTGG GATCAACGCG CGTCTGGTAC   2460

TGGGTGATAT CTTCGCATCA AAATGGTCGC TATTCGCGAG GGACACCCCA GAGTATCGGG   2520

TGTTTTACCC AATGATTGTC ATGGCCGTCA AGTTTTCCAT ATCCATTGGC AACAACGAGT   2580

CCGGCGTAGC GCTCTATGGA GTGGTGTCGG AAGATTTCGT GGTCGTCACG CTCCACAACA   2640

GGTCCAAAGA GGCTAACGAG ACGGCGTCCC ATCTTCTGTT CGGTCTCCCG GATTCACTGC   2700

CATCTCTGAA GGGCCATGCC ACCTATGATG AACTCACGTT CGCCCGAAAC GCAAAATATG   2760

CGCTAGTGGC GATCCTGCCT AAAGATTCTT ACCAGACACT CCTTACAGAG AATTACACTC   2820

GCATATTTCT GAACATGACG GAGTCGACGC CCCTCGAGTT CACGCGGACG ATCCAGACTA   2880

GGATCGTATC AATCGAGGCC AGGCGCGCCT GCGCAGCTCA AGAGGCGGCG CCGGACATAT   2940

TCTTGGTGTT GTTTCAGATG TTGGTGGCAC ACTTTCTTGT TGCGCGGGGC ATTACCGAGC   3000

ACCGATTTGT GGAGGTGGAC TGCGTGTGTC GGCAGTATGC GGAACTGTAT TTTCTCCGCC   3060

GCATCTCGCG TCTGTGCATG CCCACGTTCA CCACTGTCGG GTATAACCAC ACCACCCTTG   3120

GCGCTGTGGC CGCCACACAA ATAGCTCGCG TGTCCGCCAC GAAGTTGGCC AGTTTGCCCC   3180

GCTCTTCCCA GGAAACAGTG CTGGCCATGG TCCAGCTTGG CGCCCGTGAT GGCGCCGTCC   3240

CTTCCTCCAT TCTGGAGGGC ATTGCTATGG TCGTCGAACA TATGTATACC GCCTACACTT   3300

ATGTGTACAC ACTCGGCGAT ACTGAAAGAA AATTAATGTT GGACATACAC ACGGTCCTCA   3360

CCGACAGCTG CCCGCCCAAA GACTCCGGAG TATCAGAAAA GCTACTGAGA ACATATTTGA   3420

TGTTCACATC AATGTGTACC AACATAGAGC TGGGCGAAAT GATCGCCCGC TTTTCCAAAC   3480

CGGACAGCCT TAACATCTAT AGGGCATTCT CCCCCTGCTT TCTAGGACTA AGGTACGATT   3540
```

-continued

```
TGCATCCAGC CAAGTTGCGC GCCGAGGCGC CGCAGTCGTC CGCTCTGACG CGGACTGCCG    3600

TTGCCAGAGG AACATCGGGA TTCGCAGAAT TGCTCCACGC GCTGCACCTC GATAGCTTAA    3660

ATTTAATTCC GGCGATTAAC TGTTCAAAGA TTACAGCCGA CAAGATAATA GCTACGGTAC    3720

CCTTGCCTCA CGTCACGTAT ATCATCAGTT CCGAAGCACT CTCGAACGCT GTTGTCTACG    3780

AGGTGTCGGA GATCTTCCTC AAGAGTGCCA TGTTTATATC TGCTATCAAA CCCGATTGCT    3840

CCGGCTTTAA CTTTTCTCAG ATTGATAGGC ACATTCCCAT AGTCTACAAC ATCAGCACAC    3900

CAAGAAGAGG TTGCCCCCTT TGTGACTCTG TAATCATGAG CTACGATGAG AGCGATGGCC    3960

TGCAGTCTCT CATGTATGTC ACTAATGAAA GGGTGCAGAC CAACCTCTTT TTAGATAAGT    4020

CACCTTTCTT TGATAATAAC AACCTACACA TTCATTATTT GTGGCTGAGG GACAACGGGA    4080

CCGTAGTGGA GATAAGGGGC ATGTATAGAA GACGCGCAGC CAGTGCTTTG TTTCTAATTC    4140

TCTCTTTTAT TGGGTTCTCG GGGGTTATCT ACTTTCTTTA CAGACTGTTT TCCATCCTTT    4200

ATTAGACGGT CAATAAAGCG TAGATTTTTA AAAGGTTTCC TGTGCATTCT TTTTGTATGG    4260

GCATATACTT GGCAAGAAAT CCGAGCACCT CAGAAAGTGG ATTGCCGTCA CATATCAGTT    4320

CGACCACCCC TGCACCTAGC CATGCGGCGC TTTGACGGTC TTTGGGGCTA CACATCATAA    4380

AGTACTTTTC CATGGCTTCT ATAAGCACCT TGGAACAATC TGGGGGTTGG CGAATGGGTT    4440

CCCTAAACGG GAAATCCTCT ATGGTATTCA GGCAGAAGAC CGCGTCCTCC ACCCGACGTT    4500

TGAGTCTTTC TAGCAGAGCG CCGAAGAACT CCCGCTCGTG TGTTTTCGCA GGGGCAAGTT    4560

CTGCGCCGTA CAGCGATGAG AAACACGACA CGATGTTTTC CAGCCCCATG CTGCGCAGCA    4620

ACACGTGCTT CAGGAACAGG TGTTGTAGCC GGTTCAGTTT TAGCTTGGGT AGAAAAGTTA    4680

TCGAGTTGTT AGCACGCTCC ATGATGGTAA CGGTGTTGAA GTCACAGACC GGGCTTTCTC    4740

CGAGTCTCGG CCGCCTGAGT CCAATCATGT AGAACATAGA CGCGGCCTCG TTGTCTGTGT    4800

TAAGTGACAC GATATCCCGT TCGCAAACCT GTGCGATGTT GTGTTTCAGT ATAGATCTGG    4860

TCTGACCGGC ACGGGGTGTT ATGGGGTGAC GCGGTAAAGG CGACTCTGGG TCAAACACCT    4920

TTATGCGGTT GGCGGCCTCG TCGATGACGA CACGCTTGTT CGCGGCGTGT ATGGGACGC    4980

GACGGCATCC CGCTGGCAGA TCTATAATCT TAAAGTTGGT ATAAGACTGG TCGCTCGTTA    5040

TGGCCAGCCG GCACTCCGGT AGTATCTGCG TGTCCTCGAA TTCGTGGCCG CGTACGACTG    5100

GCTTGGAGTG CAGGTAAACG CCAAGAGATG CGGTCTCTTC GCCTACGCAC AAGTGGCTTC    5160

TTAACGCGTA GGGGTGCGGT GAGAGCATGA TCCGTAGCAA CGATAGTTCC GGGTGCCTAG    5220

CCGCGTAGAG TGGCAGGGTA GACGAGTCCG GAGTCCCAAA CTTTTCGAAC AACAGTGGCA    5280

TCGGGACTTC AGGATTAGAG ACTCCCACCA TGGCCGCCAC CGCCGGAGAG GTCAAGACGT    5340

GAAACACGCG CTCGCCTGTC GACAGGCGCG CCGCGCCCTC TACTAGACTA GCCTTCACGT    5400

CCGGAACTCG TAACATAGCT TAGACCAGCG GACGGACGCA ACGTACGTGG GGATCGGCTG    5460

GCGGTGTCTG CTCGTTGGAC GCGGCCGTTC GGTGGCGCCA GTGCAGGCCT AGTTTGCGAA    5520

TGGCGTGACG GACAATTTGT GGCTTTAGAG CGGCGAACCG ATGACCCGTG GTGGCGACGA    5580

ACGAAATGAA GTTTGCATTG CGGCCCAACT CGTCTAGCCT GGTCTTCTTG TTTCGGGCAT    5640

AGATTTTCGG GATTAGGTTA CACTTTTTAT ATCCCAGTAC TGCGCACTCG TGTTTGCTTT    5700

TAGTGTGACT GATTATCTTC TTTGAGAAGT CAAACAGGCC CCGGGCGGCG GCTCGCCTAA    5760

TGCAAGCCAC GTCAAGCCTG AGAAACGAAC AGCATTCCAC CAGACACTCC AGGAACCTTT    5820

TGTGTAGCGT CTGTATTTGG GAACGGTTTC TGTGCTCAAG TAGGGAGAAT ATTCTATTTT    5880
```

-continued

```
TGTTTCCGTC GATGCGCGCG TGCTGGTCCG TGAGAATGGG CGCCAGCTCG TGGCGAATCT    5940
GTTCCACAAG AGGCTGCCCG TACACTTTAG AAATCGTGGC TGTCGCGGCC TTAAACCAGG    6000
ACACGTTTAG CCCATCCTTG CTGGAGACCA CAGATGGAAA GTTTGTGGTC CAAAATACGT    6060
TTTTTCGCCC CATTCTCACC ATGTACTGGT TTTCCAGTCC GTGCAGGTCC AACGTGGAGT    6120
TCCAATTTGC TATCGATACA GGAAATATGT GCCTGATTGG CAGAAAGCAT TTCAGCGTAC    6180
CCATTGCGAA GAGAAAGTGC AGCATGTCCC CACTGATGTT GATGTTATT GCGGTGCCTT     6240
GACACATGTT GTCGGAAAAA AACACGCTTA TGGTAAAAGA AGGTTCCTTT ACGGAGTACT    6300
TTCGTATAAC AAAATTGTTG GTCAATCTGG GGATGTTTAA AATAGTCTTT TGCAGGGTGT    6360
TAGGAACGTG GCAGCTTATC TTAGTGTTAA TCACCATGTT GGTGTTGAAT ATGGTGATCT    6420
TGAAGTTTTC CAAACTGACG TGTTTTGTGG GTTCCAGCAT GTCTGACACT GTAGAGCTGC    6480
CCAGAGTCCG CGCGTCCGTG GCCGCGTATC GTTGGAAGCA CGCCTGCAAA TTTCCTTTCA    6540
TGGCTGCTCG CCGGTCTTTC GGCGCGTACC GGATTCTTGA AAGCGTCGCC GCCAGGAGAC    6600
GCGGTGTCTC GTGGGTGCCT AAAAAGTTTG CGCAGGGGTG CAGTCCGCTG CACGAGTGGC    6660
CGATGCAGTC TGCCACTGCC ATACACATGA CGAGTCTGTA GATGGCCGGT GTGCCCGGAT    6720
ACACTAGATA GTAGGTACAA TCTGGGGTAC TGACGACCAC CCTGTATGGC TTTGGTCCGG    6780
GGTCCTTGCG TTGGATTTTT ACGTGCAGAC GGGACACGAG CTGGTTTAGA GCCAGCTGAA    6840
AGCCCACCAG ATCCCGTCCG TTAACCTTGA CGTCCTGGTG CTTACTCTGT TTCGACAGGT    6900
TCTTCAGCAC GGTGGGCAGT CGCTCTACGT TGTGAGCGAT GGCACGGCGC AGCGAGACCA    6960
GCTCTCCGTG CCACCCCCAC GTGGCCATGA AGCTGCTGAT GTTAAACTTT AAAAAATGTA    7020
GCTGTGCGTC TGGGGATGCG GGTGGCATTA TTGAAAACGA GAGATGCTTC AGGCTCTCCA    7080
GGAGTGCAAA ATAATTTTGA TAGATTGTGG GTTGTAGACT ATGGGCAAC ACCGCCAGAA     7140
ACGCATGAAA ACACTGTTCG AACTCCCAGA ACTCCAGGTA CCTGCACACT ATCCTGAACA    7200
TGGCTTTGTA ACATATGGTG CACGTTAGTA GCGCGGGAAG ATACAGCGAG CGTAGCTCCC    7260
TGAATTCGCA GGGTTTATCA CAATCATCGG TAAGTTCCCA TGATCCCACC GCAGGTAGGT    7320
AGTTGTCGGT GTCTATCTGT CCGCGCGTAA ACACTCCACC ACCGTCAATT ATTAAACCTT    7380
CGCCGCTGTA CCGTCGACCC ACTTTTCCCA AAAGAGTCCC TTCTTGATGT ATAAAAGGGT    7440
GGAGGCGTTC CCCCAGGAGT AGTCTGCGTA TCGCTCTGCA GGCGAAAAAG GTGGGCTCGG    7500
GCTGCATCAT CTTATCAAGA CCTTCTAAGG TCAGCTCTGC CTGCAGGTGC GAGTTGGTGG    7560
CCAGACAGCA GAATATTTCC AGCTGTGATT CCCAAGTCGC TTGATAACAC GTGGTCTGCG    7620
GACTCGTCGT CAGGGAGGCG CTCGGTGGCA GTAGTAGGGG GCCCTCGAGC GCTGCCATGG    7680
AGGCGACCTT GGAGCAACGA CCTTTCCCGT ACCTCGCCAC GGAGGCCAAC CTCCTAACGC    7740
AGATTAAGGA GTCGGCTGCC GACGGACTCT TCAAGAGCTT TCAGCTATTG CTCGGCAAGG    7800
ACGCCAGAGA AGGCAGTGTC CGTTTCGAAG CGCTACTGGG CGTATATACC AATGTGGTGG    7860
AGTTTGTTAA GTTTCTGGAG ACCGCCCTCG CCGCCGCTTG CGTCAATACC GAGTTCAAGG    7920
ACCTGCGGAG AATGATAGAT GGAAAAATAC AGTTTAAAAT TTCAATGCCC ACTATTGCCC    7980
ACGGAGACGG GAGGAGGCCC AACAAGCAGA GACAGTATAT CGTCATGAAG GCTTGCAATA    8040
AGCACCACAT CGGTGCGGAG ATTGAGCTTG CGGCCGCAGA CATCGAGCTT CTCTTCGCCG    8100
AGAAAGAGAC GCCCTTGGAC TTCACAGAGT ACGCGGGTGC CATCAAGACG ATTACGTCGG    8160
CTTTGCAGTT TGGTATGGAC GCCCTAGAAC GGGGGTTAGT GGACACGGTT CTCGCAGTTA    8220
AACTTCGGCA CGCTCCACCC GTCTTTATTT TAAAGACGCT GGGCGATCCC GTCTACTCTG    8280
```

```
AGAGGGGCCT CAAAAAGGCC GTCAAGTCTG ACATGGTATC CATGTTCAAG GCACACCTCA    8340

TAGAACATTC ATTTTTTCTA GATAAGGCCG AGCTCATGAC AAGGGGGAAG CAGTATGTCC    8400

TAACCATGCT CTCCGACATG CTGGCCGCGG TGTGCGAGGA TACCGTCTTT AAGGGTGTCA    8460

GCACGTACAC CACGGCCTCT GGGCAGCAGG TGGCCGGCGT CCTGGAGACG ACGGACAGCG    8520

TCATGAGACG GCTGATGAAC CTGCTGGGGC AAGTGGAAAG TGCCATGTCC GGGCCCGCGG    8580

CCTACGCCAG CTACGTTGTC AGGGGTGCCA ACCTCGTCAC CGCCGTTAGC TACGGAAGGG    8640

CGATGAGAAA CTTTGAACAG TTTATGGCAC GCATAGTGGA CCATCCCAAC GCTCTGCCGT    8700

CTGTGGAAGG TGACAAGGCC GCTCTGGCGG ACGGACACGA CGAGATTCAG GAACCCGCA    8760

TCGCCGCCTC TCTCGTCAAG ATAGGGGATA AGTTTGTGGC CATTGAAAGT TTGCAGCGCA    8820

TGTACAACGA GACTCAGTTT CCCTGCCCAC TGAACCGGCG CATCCAGTAC ACCTATTTCT    8880

TCCCTGTTGG CCTTCACCTT CCCGTGCCCC GCTACTCGAC ATCCGTCTCA GTCAGGGGCG    8940

TAGAATCCCC GGCCATCCAG TCGACCGAGA CGTGGGTGGT TAATAAAAAC AACGTGCCTC    9000

TTTGCTTCGG TTACCAAAAC GCCCTCAAAA GCATATGCCA CCCTCGAATG CACAACCCCA    9060

CCCAGTCAGC CCAGGCACTA AACCAAGCTT TTCCCGATCC CGACGGGGGA CATGGGTACG    9120

GTCTCAGGTA TGAGCAGACG CCAAACATGA ACCTATTCAG AACGTTCCAC CAGTATTACA    9180

TGGGGAAAAA CGTGGCATTT GTTCCCGATG TGGCCCAAAA AGCGCTCGTA ACCACGGAGG    9240

ATCTACTGCA CCCAACCTCT CACCGTCTCC TCAGATTGGA GGTCCACCCC TTCTTTGATT    9300

TTTTTGTGCA CCCCTGTCCT GGAGCGAGAG GATCGTACCG CGCCACCCAC AGAACAATGG    9360

TTGGAAATAT ACCACAACCG CTCGCTCCAA GGGAGTTTCA GGAAAGTAGA GGGGCGCAGT    9420

TCGACGCTGT GACGAATATG ACACACGTCA TAGACCAGCT AACTATTGAC GTCATACAGG    9480

AGACGGCATT TGACCCCGCG TATCCCCTGT TCTGCTATGT AATCGAAGCA ATGATTCACG    9540

GACAGGAAGA AAAATTCGTG ATGAACATGC CCTCATTGC CCTGGTCATT CAAACCTACT    9600

GGGTCAACTC GGGAAAACTG GCGTTTGTGA ACAGTTATCA CATGGTTAGA TTCATCTGTA    9660

CGCATATGGG GAATGGAAGC ATCCCTAAGG AGGCGCACGG CCACTACCGG AAAATCTTAG    9720

GCGAGCTCAT CGCCCTTGAG CAGGCGCTTC TCAAGCTCGC GGGACACGAG ACGGTGGGTC    9780

GGACGCCGAT CACACATCTG GTTTCGGCTC TCCTCGACCC GCATCTGCTG CCTCCCTTTG    9840

CCTACCACGA TGTCTTTACG GATCTTATGC AGAAGTCATC CAGACAACCC ATAATCAAGA    9900

TCGGGATCA AAACTACGAC AACCCTCAAA ATAGGGCGAC ATTCATCAAC CTCAGGGGTC    9960

GCATGGAGGA CCTAGTCAAT AACCTTGTTA ACATTTACCA GACAAGGGTC AATGAGGACC    10020

ATGACGAGAG ACACGTCCTG GACGTGGCGC CCCTGGACGA GAATGACTAC AACCCGGTCC    10080

TCGAGAAGCT ATTCTACTAT GTTTTAATGC CGGTGTGCAG TAACGGCCAC ATGTGCGGTA    10140

TGGGGGTCGA CTATCAAAAC GTGGCCCTGA CGCTGACTTA CAACGGCCCC GTCTTTGCGG    10200

ACGTCGTGAA CGCACAGGAT GATATTCTAC TGCACCTGGA GAACGGAACC TTGAAGGACA    10260

TTCTGCAGGC AGGCGACATA CGCCCGACGG TGGACATGAT CAGGGTGCTG TGCACCTCGT    10320

TTCTGACGTG CCCTTTCGTC ACCCAGGCCG CTCGCGTGAT CACAAAGCGG GACCCGGCCC    10380

AGAGTTTTGC CACGCACGAA TACGGAAGG ATGTGGCGCA GACCGTGCTT GTTAATGGCT    10440

TTGGTGCGTT CGCGGTGGCG GACCGCTCTC GCGAGGCGGC GGAGACTATG TTTTATCCGG    10500

TACCCTTTAA CAAGCTCTAC GCTGACCCGT TGGTGGCTGC CACACTGCAT CCGCTCCTGG    10560

CAAACTATGT CACCAGGCTC CCCAACCAGA GAAACGCGGT GGTCTTTAAC GTGCCATCCA    10620
```

-continued

```
ATCTCATGGC AGAATATGAG GAATGGCACA AGTCGCCCGT CGCGGCGTAT GCCGCGTCTT   10680
GTCAGGCCAC CCCGGGCGCC ATTAGCGCCA TGGTGAGCAT GCACCAAAAA CTATCTGCCC   10740
CCAGTTTCAT TTGCCAGGCA AAACACCGCA TGCACCCTGG TTTTGCCATG ACAGTCGTCA   10800
GGACGGACGA GGTTCTAGCA GAGCACATCC TATACTGCTC CAGGGCGTCG ACATCCATGT   10860
TTGTGGGCTT GCCTTCGGTG GTACGGCGCG AGGTACGTTC GGACGCGGTG ACTTTTGAAA   10920
TTACCCACGA GATCGCTTCC CTGCACACCG CACTTGGCTA CTCATCAGTC ATCGCCCCGG   10980
CCCACGTGGC CGCCATAACT ACAGACATGG GAGTACATTG TCAGGACCTC TTTATGATTT   11040
TCCCAGGGGA CGCGTATCAG GACCGCCAGC TGCATGACTA TATCAAAATG AAAGCGGGCG   11100
TGCAAACCGG CTCACCGGGA AACAGAATGG ATCACGTGGG ATACACTGCT GGGGTTCCTC   11160
GCTGCGAGAA CCTGCCCGGT TTGAGTCATG GTCAGCTGGC AACCTGCGAG ATAATTCCCA   11220
CGCCGGTCAC ATCTGACGTT GCCTATTTCC AGACCCCCAG CAACCCCCGG GGGCGTGCGG   11280
CGTGCGTGGT GTCGTGTGAT GCTTACAGTA ACGAAAGCGC AGAGCGTTTG CTCTACGACC   11340
ATTCAATACC AGACCCCGCG TACGAATGCC GGTCCACCAA CAACCCGTGG GCTTCGCAGC   11400
GTGGCTCCCT CGGCGACGTG CTATACAATA TCACCTTTCG CCAGACTGCG CTGCCGGGCA   11460
TGTACAGTCC TTGTCGGCAG TTCTTCCACA AGGAAGACAT TATGCGGTAC AATAGGGGGT   11520
TGTACACTTT GGTTAATGAG TATTCTGCCA GGCTTGCTGG GGCCCCCGCC ACCAGCACTA   11580
CAGACCTCCA GTACGTCGTG GTCAACGGTA CAGACGTGTT TTTGGACCAG CCTTGCCATA   11640
TGCTGCAGGA GGCCTATCCC ACGCTCGCCG CCAGCCACAG AGTTATGCTT GACGAGTACA   11700
TGTCAAACAA GCAGACACAC GCCCCAGTAC ACATGGGCCA GTATCTCATT GAAGAGGTGG   11760
CGCCGATGAA GAGACTATTA AAGCTCGGAA ACAAGGTGG GTATTAGCTA ACCCTTCTAG   11820
CGTTGGCTAG TCATGGCACT CGACAAGAGT ATAGTGGTTA ACTTCACCTC CAGACTCTTC   11880
GCTGATGAAC TGGCCGCCCT TCAGTCAAAA ATAGGGAGCG TACTGCCGCT CGGAGATTGC   11940
CACCGTTTAC AAAATATACA GGCATTGGGC CTGGGGTGCG TATGCTCACG TGAGACATCT   12000
CCGGACTACA TCCAAATTAT GCAGTATCTA TCCAAGTGCA CACTCGCTGT CCTGGAGGAG   12060
GTTCGCCCGG ACAGCCTGCG CCTAACGCGG ATGGATCCCT CTGACAACCT TCAGATAAAA   12120
AACGTATATG CCCCCTTTTT TCAGTGGGAC AGCAACACCC AGCTAGCAGT GCTACCCCCA   12180
TTTTTTAGCC GAAAGGATTC CACCATTGTG CTCGAATCCA ACGGATTTGA CCTCGTGTTC   12240
CCCATGGTCG TGCCGCAGCA ACTGGGGCAC GCTATTCTGC AGCAGCTGTT GGTGTACCAC   12300
ATCTACTCCA AAATATCGGC CGGGGCCCCG GATGATGTAA ATATGGCGGA ACTTGATCTA   12360
TATACCACCA ATGTGTCATT TATGGGGCGC ACATATCGTC TGGACGTAGA CAACACGGAT   12420
CCACGTACTG CCCTGCGAGT GCTTGACGAT CTGTCCATGT ACCTTTGTAT CCTATCAGCC   12480
TTGGTTCCCA GGGGGTGTCT CCGTCTGCTC ACGGCGCTCG TGCGGCACGA CAGGCATCCT   12540
CTGACAGAGG TGTTTGAGGG GGTGGTGCCA GATGAGGTGA CCAGGATAGA TCTCGACCAG   12600
TTGAGCGTCC CAGATGACAT CACCAGGATG CGCGTCATGT TCTCCTATCT TCAGAGTCTC   12660
AGTTCTATAT TTAATCTTGG CCCCAGACTG CACGTGTATG CCTACTCGGC AGAGACTTTG   12720
GCGGCCTCCT GTTGGTATTC CCCACGCTAA CGATTTGAAG CGGGGGGGGG GTATGGCGTC   12780
ATCTGATATT CTGTCGGTTG CAAGGACGGA TGACGGCTCC GTCTGTGAAG TCTCCCTGCG   12840
TGGAGGTAGG AAAAAAACTA CCGTCTACCT GCCGGACACT GAACCCTGGG TGGTAGAGAC   12900
CGACGCCATC AAAGACGCCT TCCTCAGCGA CGGGATCGTG GATATGGCTC GAAAGCTTCA   12960
TCGTGGTGCC CTGCCCTCAA ATTCTCACAA CGGCTTGAGG ATGGTGCTTT TTTGTTATTG   13020
```

```
TTACTTGCAA AATTGTGTGT ACCTAGCCCT GTTTCTGTGC CCCCTTAATC CTTACTTGGT   13080

AACTCCCTCA AGCATTGAGT TTGCCGAGCC CGTTGTGGCA CCTGAGGTGC TCTTCCCACA   13140

CCCGGCTGAG ATGTCTCGCG GTTGCGATGA CGCGATTTTC TGTAAACTGC CCTATACCGT   13200

GCCTATAATC AACACCACGT TTGGACGCAT TTACCCGAAC TCTACACGCG AGCCGGACGG   13260

CAGGCCTACG GATTACTCCA TGGCCCTTAG AAGGGCTTTT GCAGTTATGG TTAACACGTC   13320

ATGTGCAGGA GTGACATTGT GCCGCGGAGA AACTCAGACC GCATCCCGTA ACCACACTGA   13380

GTGGGAAAAT CTGCTGGCTA TGTTTTCTGT GATTATCTAT GCCTTAGATC ACAACTGTCA   13440

CCCGGAAGCA CTGTCTATCG CGAGCGGCAT CTTTGACGAG CGTGACTATG GATTATTCAT   13500

CTCTCAGCCC CGGAGCGTGC CCTCGCCTAC CCCTTGCGAC GTGTCGTGGG AAGATATCTA   13560

CAACGGGACT TACCTAGCTC GGCCTGGAAA CTGTGACCCC TGGCCCAATC TATCCACCCC   13620

TCCCTTGATT CTAAATTTTA AATAAAGGTG TGTCACTGGT TACACCACGA TTAAAAACCA   13680

CTCACTGAGA TGTCTTTTTA ACCGCTAAGG GATTATACCG GGATTTAAAA CCGCCCACTG   13740

ATTTTTTTAC GCTAAGAGTT GGGTGCTTGG GGGGTTTTGC ATTGCTCTGT TGTAAACTAT   13800

ATATAAGTTA AACCAAAATT CGCAGGGAGA CAAGGTGACG GTGGTGAGAA CTCAGTTGAG   13860

AGTCAGAGAA TACAGTGCTA ATCAGGGTAG ATGAGCATGA CTTCCCCGTC TCCAGTCACC   13920

GGAGGAATGG TGGACGGCTC CGTCCTGGTG CGAATGGCCA CCAAGCCTCC CGTGATTGGT   13980

CTTATAACAG TGCTCTTCCT CCTAGTCATA GGCGCCTGCG TCTACTGCTG CATTCGCGTG   14040

TTCCTGGCGG CTCGACTGTG GCGCGCCACC CCACTAGGCA GGGCCACCGT GGCGTATCAG   14100

GTCCTTCGCA CCCTGGGACC GCAGGCCGGG TCACATGCAC CGCCGACGGT GGGCATAGCT   14160

ACCCAGGAGC CCTACCGTAC AATATACATG CCAGATTAGA ACGGGTGTG TGCTATAATG   14220

GATGGCTATG GGGGGGCTGT AGATAATTGA GCGCTGTGCT TTTATTGTGG GGATATGGGC   14280

TTGTACATGT GTCTATCATC GGTAGCCATA AAATGGGCCA TGACAACTGC CACAAGTAAG   14340

TCGTCCGACA TGTGCTTTTG CTTGGCGCTG TATGACTGCC CTCCATCCCT AAGCGGGACG   14400

CACTTGATCG CGCGGACCTG TTCTACCAGG TAGGTCACCG GGTCAAATGA TATTTTGATG   14460

GTGTTGGACA CCACCGTCTG GCTGGCGCTC AGGGTGCCGG AGTTCAGAGC GTAGATGAAT   14520

GTCTCAAACG CGGAGGATTT CTCGCCTCCC AACATGTAAA TTGGCCACTG CAGGGCGCTG   14580

CTCTTGTCAG TATAGTGTAG AAAATGTATG GGGAGCGGGC ATATTTCGTT AAGGACGGTT   14640

GCAATGGCCA CCCCAGAATC TTGGCTGCTG TTGCCTTCGA CCGCCGCGTT CACGCGCTCA   14700

ATTGTGGGGT GGAGCACAGC GATCGCCTTA ATCATCGTGC ATGCGCAGGA CGCTATCTCG   14760

TAAGCAGCTG CGCCAGTGAG GTCGCGCAGG AAGAAATGCT CCATGCCCAA TATGAGGCTT   14820

CTGGTGGGAG TCTGAGTACT CGTGACAACG GCGCCCACGC CAGTACCGGA CGCCTCCGTG   14880

TTGTTCGTAT ACGCGGGGTC GATGTAAACA AACAGCTGTT TTCCAAGGCA CTTCTGAACC   14940

TGCTGGGCGG TGGTGTCTAC CCGACACATG TCAAACTGTG TCAGCGCTGC GTCACCCACC   15000

ACGCGGTAAA GCGTAGCATT TGACGACGCT GCTCCCTCGC CCATTAGTTC GGTGTCGAAT   15060

GCCCCCTCCA TAAAGAGGTT GGTGGTGGTT TTGATGGATT CGTCGATGGT GATGTACGTC   15120

GGAATGTGCA GTCTGTAACA AGGACAGGAC ACTAGTGCGT CTTGCAGGTG GAAATCTTCG   15180

CGGTGGTCCG CACACACGTA ACTGACCACA TTCAGCATCT TTTCCTGGGC GTTCCTGAGG   15240

TTAAGCAGGA AACTCGTGGA GCGGTCTGAC GAGTTCACGG ATGATATAAA TATAAGCTTG   15300

GCGTCTTTCT GAAGCATGAA ACCCAGAATA GCCGGCAGTG CATCCTTTTT AATAAAATTC   15360
```

-continued

```
GCCTCGTCTA CGTAGAGCAG GTTAAAGGTC TGTCCCCGAA TGCTCTGCAG ACACGGAAAG    15420

ACACAAAAGA GGGGCTCATA AGCGGCTAAC AGTAAAGGAG AGGAGGCGAA CAGTGCGTGG    15480

CTCTTGTTCT TGGGAATAAA AGGGGGCGTG TGTGCCGATC GTATGGGTGA GCCAGTGGAT    15540

CCTGGACATG TGGTGAATGA GAAAGATTTT GAGGAGTGTG AACAATTTTT CAGTCAACCC    15600

CTTAGGGAGC AAGTGGTCGC GGGGGTCAGG GCACTGACG GCCTCGGTCT CGCTGACTCT     15660

CTATGTCACA AAACAGAAAG ACTCTGCCTG CTGATGGACC TGGTGGGCAC GGAGTGCTTT    15720

GCGAGGGTGT GCCGCCTAGA CACCGGTGCG AAATGAAGAG TGTGGCGAGT CCCTTATGTC    15780

AGTTCCACGG CGTGTTTTGC CTGTACCAGT GTCGCCAGTG CCTGGCATAC CACGTGTGTG    15840

ATGGGGCGC CGAATGCGTT CTCCTGCATA CGCCGGAGAG CGTCATCTGC GAACTAACGG     15900

GTAACTGCAT GCTCGGCAAC ATTCAAGAGG GCCAGTTTTT AGGGCCGGTA CCGTATCGGA    15960

CTTTGGATAA CCAGGTTGAC AGGGACGCAT ATCACGGGAT GCTAGCGTGT CTGAAACGGG    16020

ACATTGTGCG GTATTTGCAG ACATGGCCGG ACACCACCGT AATCGTGCAG GAAATAGCCC    16080

TGGGGGACGG CGTCACCGAC ACCATCTCGG CCATTATAGA TGAAACATTC GGTGAGTGTC    16140

TTCCCGTACT GGGGGAGGCC CAAGGCGGGT ACGCCATGGT CTGTAGCATG TATCTGCACG    16200

TTATCGTCTC CATCTATTCG ACAAAAACGG TGTACAACAG TATGCTATTT AAATGCACAA    16260

AGAATAAAAA GTACGACTGC ATTGCCAAGC GGGTGCGGAC AAAATGGATG CGCATGCTAT    16320

CAACGAAAGA TACGTAGGTC CTCGCTGCCA CCGTTTGGCC CACGTGGTGC TGCCTAGGAC    16380

CTTTCTGCTG CATCACGCCA TACCCCTGGA GCCCGAGATC ATCTTTTCCA CCTACACCCG    16440

GTTCAGCCGG TCGCCAGGGT CATCCCGCCG GTTGGTGGTG TGTGGGAAAC GTGTCCTGCC    16500

AGGGGAGGAA AACCAACTTG CGTCTTCACC TTCTGGCTTG GCGCTTAGCC TGCCTCTGTT    16560

TTCCACGAT GGGAACTTTC ATCCATTTGA CATCTCGGTA CTGCGCATTT CCTGCCCTGG     16620

TTCTAATCTT AGTCTTACTG TCAGATTTCT CTATCTATCT CTGGTGGTGG CTATGGGGGC    16680

GGGACGGAAT AATGCGCGGA GTCCGACCGT TGACGGGGTA TCGCCGCCAG AGGGCGCCGT    16740

AGCCCACCCT TTGGAGGAAC TGCAGAGGCT GGCGCGTGCT ACGCCGGACC CGGCACTCAC    16800

CCGTGGACCG TTGCAGGTCC TGACCGGCCT TCTCCGCGCA GGGTCAGACG GAGACCGCGC    16860

CACTCACCAC ATGGCGCTCG AGGCTCCGGG AACCGTGCGT GGAGAAAGCC TAGACCCGCC    16920

TGTTTCACAG AAGGGGCCAG CGCGCACACG CCACAGGCCA CCCCCCGTGC GACTGAGCTT    16980

CAACCCCGTC AATGCCGATG TACCCGCTAC CTGGCGAGAC GCCACTAACG TGTACTCGGG    17040

TGCTCCCTAC TATGTGTGTG TTTACGAACG CGGTGGCCGT CAGGAAGACG ACTGGCTGCC    17100

GATACCACTG AGCTTCCCAG AAGAGCCCGT GCCCCCGCCA CCGGGCTTAG TGTTCATGGA    17160

CGACTTGTTC ATTAACACGA AGCAGTGCGA CTTTGTGGAC ACGCTAGAGG CCGCCTGTCG    17220

CACGCAAGGC TACACGTTGA GACAGCGCGT GCCTGTCGCC ATTCCTCGCG ACGCGGAAAT    17280

CGCAGACGCA GTTAAATCGC ACTTTTTAGA GGCGTGCCTA GTGTTACGGG GGCTGGCTTC    17340

GGAGGCTAGT GCCTGGATAA GAGCTGCCAC GTCCCCGCCC CTTGGCCGCC ACGCCTGCTG    17400

GATGGACGTG TTAGGATTAT GGGAAAGCCG CCCCCACACT CTAGGTTTGG AGTTACGCGG    17460

CGTAAACTGT GGCGGCACGG ACGGTGACTG GTTAGAGATT TTAAAACAGC CGATGTGCA     17520

AAAGACAGTC AGCGGGAGTC TTGTGGCATG CGTGATCGTC ACACCCGCAT GGAAGCCTG     17580

GCTTGTGTTA CCTGGGGGTT TTGCTATTAA AGGCCGCTAT AGGGCGTCGA AGGAGGATCT    17640

GGTGTTCATT CGAGGCCGCT ATGGCTAGCC GGAGGCGCAA ACTTCGGAAT TCCTAAACA     17700

AGGAATGCAT ATGGACTGTT AACCCAATGT CAGGGGACCA TATCAAGGTC TTTAACGCCT    17760
```

```
GCACCTCTAT CTCGCCGGTG TATGACCCTG AGCTGGTAAC CAGCTACGCA CTGAGCGTGC  17820

CTGCTTACAA TGTGTCTGTG GCTATCTTGC TGCATAAAGT CATGGGACCG TGTGTGGCTG  17880

TGGGAATTAA CGGAGAAATG ATCATGTACG TCGTAAGCCA GTGTGTTTCT GTGCGGCCCG  17940

TCCCGGGGCG CGATGGTATG GCGCTCATCT ACTTTGGACA GTTTCTGGAG GAAGCATCCG  18000

GACTGAGATT TCCCTACATT GCTCCGCCGC CGTCGCGCGA ACACGTACCT GACCTGACCA  18060

GACAAGAATT AGTTCATACC TCCCAGGTGG TGCGCCGCGG CGACCTGACC AATTGCACTA  18120

TGGGTCTCGA ATTCAGGAAT GTGAACCCTT TTGTTTGGCT CGGGGGCGGA TCGGTGTGGC  18180

TGCTGTTCTT GGGCGTGGAC TACATGGCGT TCTGTCCGGG TGTCGACGGA ATGCCGTCGT  18240

TGGCAAGAGT GGCCGCCCTG CTTACCAGGT GCGACCACCC AGACTGTGTC CACTGCCATG  18300

GACTCCGTGG ACACGTTAAT GTATTTCGTG GGTACTGTTC TGCGCAGTCG CCGGGTCTAT  18360

CTAACATCTG TCCCTGTATC AAATCATGTG GGACCGGGAA TGGAGTGACT AGGGTCACTG  18420

GAAACAGAAA TTTTCTGGGT CTTCTGTTCG ATCCCATTGT CCAGAGCAGG GTAACAGCTC  18480

TGAAGATAAC TAGCCACCCA ACCCCCACGC ACGTCGAGAA TGTGCTAACA GGAGTGCTCG  18540

ACGACGGCAC CTTGGTGCCG TCCGTCCAAG GCACCCTGGG TCCTCTTACG AATGTCTGAC  18600

TACTTCAGCC GCTTGCTGAT ATATGAGTGT AAAAAACTTA AGGCCCTGGG CTTACGTTCT  18660

TATTGAAGCA TGTTGCGCAC ATCAGCGAGC TGGACCGTCC TCCGGGTCGC GTGTAGATTA  18720

TGGTTCCGTT CTCCTTCTTG ATGTTTAAAT TTTGGGGGG GAACCACCGA CAAAGCGTCT  18780

TTATGATTTC CGCGAACACG GAGTTGGCTA CGTGCTTTTG GTGGGCTACG TACCCAATGT  18840

TAATGTTCTC TACGGATGCC AGTAGCATGC TGATGATCGC CACCACTATC CATGTCTTTC  18900

CGTGTCTCCT TGGTATTAGG AATACGCTTG CCTTTTGCTT AAACGTCTGT AAAACACTGT  18960

TTGGAGTTTC AAATAAACCG AAGTACTGCT TAAACAATCC AAACAACTGG TGCGTCTTTT  19020

GTGGGGCCTT GATTGAAACC AAAAAGAAAA AGTGTGCAT TACTAGCTGC TGTTGGAAGG  19080

GCTCCAGCCA GTGCACCCCG GGAACGTAAC AGCCGTTCAG AAAGGACGAA AGGTTAACCA  19140

GAAAAGCCTG AAGTTCGCGG TAGACAGAGC AGGCGTGCAG GGAGTCGTGT GTTTTTCTGG  19200

CCGCCTGGTA CTCGACCAGT TGATCGGCCG TGGAGACGTG CGCGTCCTCG CGCACACACC  19260

GCATCTGCAA GTATGTTGAT AGGGACTCCA ATAGGCGCGG CTTTGCGGGG ACGTTGTCCT  19320

CGGACGGTCT GGGGGTTCCC ACGTCGGGAT TTGCTGACGT GGGCGTGGCG GGATGGTGCC  19380

GTGTGCAGTA TGTTTCCAGG ACCGAACTGT ATGAGTTTAT TCTGTGCACC ACGCCAATAA  19440

AAGGGTGCGC CATCCGTGCC GTTTTGGGAC AGTGTCGCGT GAATGTCGGG GCACTCAGTT  19500

CCCACCTCTC TCCGGCGTCT TTGGCGGTCT CCTGCAGGTT GGCGGCAAGG CGCTCCCTGT  19560

GACGGCTGAG CAGCATGTTT GCTTTGAGCT CGCTCGTGTC CGAGGGTGAC CCGGAGGTGA  19620

CCAGTAGGTA CGTCAAGGGC GTACAACTTG CCCTGGACCT TAGCGAGAAC ACACCTGGAC  19680

AATTTAAGTT GATAGAAACT CCCCTGAACA GCTTCCTCTT GGTTTCCAAC GTGATGCCCG  19740

AGGTCCAGCC AATCTGCAGT GGCCGGCCGG CCTTGCGGCC AGACTTTAGT AATCTCCACT  19800

TGCCTAGACT GGAGAAGCTC CAGAGAGTCC TCGGGCAGGG TTTCGGGGCG GCGGGTGAGG  19860

AAATCGCACT GGACCCGTCT CACGTAGAAA CACGCGAAA GGGCCAGGTG TTCTACAACC  19920

ACTATGCTAC CGAGGAGTGG ACGTGGGCTT TGACTCTGAA TAAGGATGCG CTCCTTCGGG  19980

AGGCTGTAGA TGGCCTGTGT GACCCCGGAA CTTGGAAGGG TCTTCTTCCT GACGACCCCC  20040

TTCCGTTGCT ATGGCTGCTG TTCAACGGAC CCGCCTCTTT TTGTCGGGCC GACTGTTGCC  20100
```

```
TGTACAAGCA GCACTGCGGT TACCCGGGCC CGGTGCTACT TCCAGGTCAC ATGTACGCTC   20160

CCAAACGGGA TCTTTTGTCG TTCGTTAATC ATGCCCTGAA GTACACCAAG TTTCTATACG   20220

GAGATTTTTC CGGGACATGG GCGGCGGCTT GCCGCCCGCC ATTCGCTACT CTCGGATAC    20280

AAAGGGTAGT GAGTCAGATG AAAATCATAG ATGCTTCCGA CACTTACATT TCCCACACCT   20340

GCCTCTTGTG TCACATATAT CAGCAAAATA GCATAATTGC GGGTCAGGGG ACCCACGTGG   20400

GTGGAATCCT ACTGTTGAGT GGAAAAGGGA CCCAGTATAT AACAGGCAAT GTTCAGACCC   20460

AAAGGTGTCC AACTACGGGC GACTATCTAA TCATCCCATC GTATGACATA CCGGCGATCA   20520

TCACCATGAT CAAGGAGAAT GGACTCAACC AACTCTAAAA GAGAGTTTAT TAAGTCGGCT   20580

CTGGAGGCCA ACATCAACAG GAGGGCAGCT GTATCGCTAT TTGATCGTTT TGGGGGTAGC   20640

AGCGCCGTGT TTGAGAAGCA GTTTCAGGAC GCACAGCATG CCGTCAGGGC CCACGGTGCA   20700

CTGAAGCGCG AAGCCGAGCT CGGGACTCTG GTACGCAAGG CGGGCCAGAG GTTTGAGGCG   20760

CTGAAAAGGG AACGGTCAAT TTTGCGCCAG CCGCGCGACC TCCCACGGGT CGCCGACATT   20820

GACGCCCTGG TCGACGCCGT CGCGGACCTC AAAGAAGAGG TGGCCGTGCG CCTAGATGCG   20880

CTGGAAGAGA ATGGAGAGGA GACCCCCACT CACTCCTCTT CGGAGATCAA GGACACAATC   20940

GTCAGGTGGA GGCTTGACGA TTTGCCCCCG GTGTGCCCTG AAACTCCCTA AGGCTACCCG   21000

GATTTCAGAG AGACCCTGGG CGTCCACATG GCAGCTGAAT CAGCATATAC AGGTGTCCAA   21060

GACTAAAAAG GCCACCGCGT ATCTTAAAGC GCCCCGTGAA TGGGGCAGT  GCACGCACCA   21120

GGATCCAGAC TGGTCCAAGC GTCTGGGTCG TGGCGCCTTT GGCATAATCG TCCCTATCTC   21180

CGAGGATCTG TGTGTGAAGC AGTTTGATAG CCGCCGGGAG TTTTTCTACG AGGCAATTGC   21240

CAACGACCTG ATGCAGGCCA CCCGAGAGAG GTACCCCATG CATTCTGGTG GATCTAGACT   21300

GCTAGGATTC GTGCAGCCTT GCATACCCTG TAGATCGATT GTGTATCCTA GAATGAAGTG   21360

CAACCTGCTG CAGCTGGACT GGAGTCAGGT CAACCTGAGT GTCATGGCGG CGGAGTTCAC   21420

CGGCCTAATG GCGGCGGTGT CCTTTCTAAA CAGATACTGT GGCATGGTGC ACTGCGACGT   21480

TAGTCCAGAC AATATTTTGG CCACAGGAGA CCTAACGCCC ATGAACCCCG GGAGGCTGGT   21540

CCTTACCGAT TTCGGTTCCG TTGCGCTACA CTCTGGGAGC AAGTGGACTA ACCTTGTGGT   21600

GACCTCTAAC CTGGGGTTTA AGCAACACTG CTACGACTTC AGGGTGCCAC CCAAACTCAT   21660

TTGTAAGCAT CTCTATAAGC CGTCTTGCGT CCTCTTCCAG TGTTACCTAT CCAGTCTCGG   21720

TAAGATGCAC GCGCAGGTAT TGGACCAACC GTACCCTATC AGCCCTAACA TGGGACTGAC   21780

CATCGACATG TCCTCGTTGG GCTACACTCT GCTGACATGC CTGGAACTCT ATCTCGATCT   21840

GCCGCTAAAC AACCCTCTGA AGTTCTTGGG TTCAGCCACC AGAGACGGAC GCCCCGAACC   21900

CATGTACTAC TTGGGCTTCA TGATTCCCAG GGTGGTGATG ACTCAGATCC TGTCCGCTGT   21960

GTGGACCATG ACGCTTGACC TGGGACTAGA TTGCACCGGC AAAGCCCAGG CGATTCCCAT   22020

GCGACAGGAG CACCAGCTGG CGTTTCAGAA GCAGTGCTAT TTATATAAAG CCAACCAAAA   22080

GGCAGAGTCG TTAGCGAACT GCTCCGATAA GCTAAACTGC CCCATGTTAA AGTCTCTCGT   22140

TAGAAAGCTA CTAGAGCGAG ACTTTTTCAA CCATGGAGGC CACCCCACA  CCCGCGGACT   22200

TGTTTTCTGA AGACTATCTG GTTGACACCC TGGATGGGTT AACAGTGGAT GACCAACAGG   22260

CTGTCCTCGC AAGCTTGAGC TTTTCAAAGT TTCTAAAGCA CGCCAAGGTT CGAGACTGGT   22320

GCGCACAGGC CAAGATCCAA CCCAGCATGC CTGCGCTGCG CATGGCTTAC AACTATTTCC   22380

TTTTTTCAAA AGTGGGCGAG TTTATTGGTA GTGAGGATGT GTGTAACTTT TCGTGGACC    22440

GTGTGTTTGG TGGTGTCAGG TTACTGGACG TGGCCAGCGT GTACGCCGCC TGTTCGCAAA   22500
```

-continued

```
TGAACGCACA TCAGCGGCAC CACATCTGCT GTCTAGTGGA GAGGGCCACT AGTAGTCAGA    22560

GTCTGAACCC CGTGTGGGAC GCCCTGCGAG ACGGAATTAT ATCTTCATCC AAGTTTCACT    22620

GGGCAGTTAA ACAACAGAAC ACTTCAAAAA AGATATTCAG CCCATGGCCT ATAACGAACA    22680

ACCACTTTGT CGCGGGCCCG CTTGCCTTTG GGCTGCGGTG CGAGGAGGTG GTGAAAACGT    22740

TGCTGGCCAC CCTTTTGCAC CCGGACGAGA CAAATTGTCT CGATTATGGG TTTATGCAGA    22800

GTCCGCAAAA TGGAATATTT GGCGTGTCGC TGGATTTCGC GGCGAACGTC AAAACTGACA    22860

CCGAGGGTCG TCTACAGTTT GACCCTAACT GTAAAGTGTA TGAAATAAAA TGCAGGTTCA    22920

AGTACACCTT TGCGAAAATG GAGTGTGACC CCATATACGC CGCGTATCAG CGGCTGTACG    22980

AGGCACCCGG AAAGCTGGCA CTGAAGGACT TCTTCTATAG CATTTCCAAG CCTGCGGTTG    23040

AGTACGTGGG ACTTGGAAAA CTGCCCAGTG AATCTGATTA CTTGGTGGCT TATGATCAGG    23100

AATGGGAGGC GTGTCCTCGC AAAAAGAGGA AATTAACGCC CCTTCACAAT CTTATTAGGG    23160

AGTGTATTTT GCACAACTCG ACCACGGAGT CTGACGTCTA CGTACTTACT GATCCTCAAG    23220

ATACTCGGGG TCAAATCAGT ATTAAAGCCC GCTTCAAAGC CAACCTCTTC GTGAACGTCC    23280

GTCACAGCTA CTTTTATCAG GTATTGCTGC AGAGTTCGAT CGTCGAGGAG TACATTGGCC    23340

TAGATAGCGG CATTCCTCGC CTCGGATCAC CGAAATACTA CATCGCCACC GGCTTCTTCA    23400

GAAAGCGGGG CTATCAGGAT CCTGTCAACT GTACCATCGG TGGCGATGCT TTAGACCCGC    23460

ACGTGGAGAT TCCTACGCTG CTAATCGTAA CCCCCGTCTA CTTTCCCCGA GGCGCAAAGC    23520

ATCGTCTGCT TCACCAAGCT GCCAACTTTT GGTCAAGAAG TGCGAAGGAC ACCTTTCCAT    23580

ATATCAAATG GGATTTCTCC TATCTATCTG CAAACGTCCC TCACAGCCCG TAGACGTGGA    23640

CGGGGAACCG CTCGACGTAG TCGTGGACTA TGACCCCATT CGCGTTTCAG AAAAGGGCAT    23700

GTTGCTTGAG CAATCGCAAT CCCCATATCC CGCATTAAAA AAGAAGAAAA AAAATAAAGA    23760

AGCAATTTAT TAAGCAAACA GTATGGTTTT CTGTACGTAT TTTATTCCGT GGTGGGTGAA    23820

AAATAACGGG GGATGGAGGA AGAGGGATGG GTTTATAATG CCAATATATC AGCTAAATGA    23880

ATATCATTTG CGTTTCGTCG ATTTCACTGT CACTTTCATG GTCGGACTGG TATTGGGTCC    23940

TCGGGGCGGG CGTCGATATG TCCTTCACTT TGGCGCGGGC TCTGGTCTTT GCTGGGAGGG    24000

GCGGCGGTTT CTGGTGAACA GTCGGAGTTC TATCGACCGT CGGCGCCGAC GTCGCCAGAG    24060

GCATGTATGC CGCACTCGGC GTACAGAGTC CCCAGTCGCT CCTTATAACG CGTATAACGA    24120

TGGCTAGGAT GCACAGTATA GGGATACAGG AGATATTGAT AGCCACTATG TAGTGGAGAT    24180

TAGCCTGCAC GAACGCGTTT TCATACCTGA TGACAGGCAG CAGTAGAATC AGATAACCCA    24240

CCAATACTCC CACGTAAAAG CCTACCTGCC GTCTCATAAA CTTACCAGG AAAAATTCCG    24300

TGTTTATGTA CCACACGACC GTCAAGGCTA GGAACATGTT CACCGCACCA AAAATGGCGT    24360

CTGACACGAG CACGTAAAAG CTGTTGCCAA CGGCCATCAT GGTGCTCAAT GAAAACAGCA    24420

GCATTTCCAA GGCGGTTGTT GATAGGTACA GGTTGACGCA GACCGGTTTC CACCGAGTCA    24480

GCAGTGACTC CATCATGGTA TTATCAGGTA CGTGCTGTTC CAGGAGAGGT ATTTCCCACT    24540

GGGCGGAGTT ACATGTTATC AGTGACTGGA TGTGGGCAAA GGATATGCAA AAATGAATGC    24600

AGTAGACAAA GGCTGCCATA AGTACGTGTT TATATGACAG AACATGGATA AACAGTTGCA    24660

TGCTCCACAT CCTTAAGATG GCGACATAAA GCACGCTATG TGATCCAAGT AGCGCTATCC    24720

AGGATTGCAT GCTCATCATG GTAGTGGCGT GAACATGCTT GGCCCGATAT ACGGCCACCG    24780

CCGCGAGACA GTAGTATACT ATGGCAATGC CGTCCACGAT AAAAGTCCAA AATATGTACA    24840
```

-continued

```
CCAGCATCTC TGGTTTCTCT AAAAACAGGG TCGGGGTGAG GTGCTTCGCT GAGTTGCGCA    24900
CCGTGAGGTT TAGCGCGCTG TAGTTTACCA GATTGTTGAA GTAGCAGGGG AAACCAAGGC    24960
CCTCGTACGT GGCGGCCATG GGCACGACTG CAGAGCAAAT GTACATAATT ACAGCCACAA    25020
ACAACAGCTT GACCCAGGAG GACATGAGAA AACGGTCGCT CTTTGAAGCG CGCATGTTTC    25080
TCGGTCTTTT TAACTTTCGC CAGGCGGCGC TGCGGCGGGA GAGCCAATCT GATGCCACTG    25140
CCTATCGCGG TTGACTTTTA AATACGCGCC CCGGGCAGAA GCCAGAGGTA GTCGACTCAT    25200
TGACTCAATG GCAACGAGCG AAGAAACGGC GGCCGGTTAT GTCATCGGTG TCTACTTTCA    25260
CAGCGTTCAC GTCCACTGCC GCATTATTGT CTGGCAGGTT AATTTTCTAC CCCTGGACCC    25320
AAACGACGGG GAGACTGAAT GCTACTTTGT GGTGGACACG CTGACGAAAG AGGCGATGGA    25380
GCGCATGCCC GAAATCCAGG AATGCGTCCC GTCTATTACT GAACACGCCC GTGACCTGGC    25440
GATCTGGGAG TTGGCGCTGC GACTGCAGAA TCAGACGATC GTCAAGGCCG TCCGACAGC    25500
GTCGCTTCCG GTGGTTCTAA TTATGACTGT GGGTCGCATA GTGAATGATG TGATTCCCTG    25560
CCCCAACGTC AGAACACCCA GACCACTAGC CTGTGCTTAC CTACACTGTG AGGCGACGGT    25620
GACCTTTGAG GTCCCACTAA CCGGGCCCGC GGCGTCCACC GGAACGTGGC ACAGCTCTAT    25680
CTATAGGGAA TGTGCGATCT CGGCTATCGA GATATGCTTG AAGACCAGTC GAGGCATATA    25740
CTCCTGCCAG TCGAACGAGG CCCCTGAGGC CAAGAGGGAA AAGCGAGGTT TAGACATATC    25800
AGATGTGTTT GTCTGTCTCA CGTATGATAT CCCTATCGCA GGGCGGGTCC TTTCTCTGCT    25860
GGTGCCCCAC GCGCCCGCTT TTCACGTCTT ATGGATCAAT GAGGACAGCA AGTGGAACGG    25920
GGCAGCCGTC GAATTTTTCA GAGCCCTACA CCATAAGCTG TTCAGTGAAC GCAATGGTAT    25980
ACCCCCTCTG TGGTTGTACG TGTTCCCGGG AGCTGTGGAA GAGGGCACAG CCTTTGCGCC    26040
ATTACTTCCC GCATTCCCTT GCATACCTTT GCGGTATGGG TCGCCTACCT CTCTGGACAG    26100
GGCGTCCGTG CAGTGGGACC TATTTGAACC GCACATCCTG ACCCACTTTG ACGGGATAAA    26160
GCGAACTTCT TTGGCAGATA CAGTGTTTGG GTACGACTCC CTGGCCATTT CAAGGGAATG    26220
TGAAGATCAG TATGTGTGGC CCACGCCTGT CACTGACATT AATATTAATT TGTGCACGGA    26280
TAGTGACACT ATGGCCATCG TTAGAGAACC ATCCGGTCTG GTGGCCGTGA ATCTAGAAGC    26340
CCTGTTGCGC ACCGACTCCG TATTATCGCG GGTCTCGTCC ATTGTCTCAC TCGATACGCT    26400
CTTGGACCTT TCCACCCCGG AGTGCCGTAG GAGCGTGGAG CTTAGATACA ACTCACTTTT    26460
GTCGACTGTA TTATCATGGT CCACCTCTAG GGGTCACAAA TGGGCCGCAA TCGTGAAGTG    26520
GAAGTTATTT TTCCTCGTCC AAGCTTTGGA GCCTGAGGTG AGACCTACTG TCCCTGCTTG    26580
AAGCGGAGAG GGGGTGGTGC GAGTTGGCAG TTGACGGGTT TGTGATAGCT GGAGTGCTGA    26640
CCACGGCACA GGACCCATTA ACTTTCCTAT GTGTTTATTT TTAGCAATGG TCTCCAGAAT    26700
TCAAGGATCT CAAAAGGGCC TGCCAGATGG CCGGGTTTAC TCTGAAGGGG GGACTTCGG    26760
GGGATCTTGT ATTCTCATCG CATGCGAACT TGCTCTTTTC AACCTCGATG GGATATTTCC    26820
TCCATGCAGG CAGTCCAAGG TCGACAGCGG GGACGGGGG TGAGCCTAAC CCACGTCACA    26880
TCACCGGACC AGACACTGAG GGAAATGGGG AACACAGAAA CTCCCCCAAC CTCTGCGGCT    26940
TTGTTACCTG GCTGCAAAGC TTAACCACAT GCATTGAACG AGCCCTAAAC ATGCCTCCCG    27000
ACACTTCCTG GCTGCAGCTG ATAGAGGAAG TGATACCCCT GTATTTTCAT AGGCGAAGAC    27060
AAACATCATT CTGGCTCATC CCCCTATCGC ACTGTGAAGG GATCCCAGTA TGCCCCCCTT    27120
TACCATTTGA CTGCCTAGCA CCAAGGCTGT TTATAGTAAC AAAGTCCGGA CCCATGTGTT    27180
ACCGGGCAGG CTTTTCGCTT CCTGTGGATG TTAATTACCT GTTCTATTTA GAGCAGACTC    27240
```

-continued

```
TGAAAGCTGT CCGGCAAGTT AGCCCACAGG AACACAACCC CCAAGACGCA AAGGAAATGA  27300

CTCTACAGCT AGAGGCCTGG ACCAGGCTTT TATCTTTATT TTGAAAAAAG GGAAACAATG  27360

GGGGGTTTGA AAAGGGTGCA CATTTTCAGA TATTTTAAAA CTTCATTGTT CTCCAGGTGC  27420

TTGGTAAAGA TGGTATCACA ATAAAAAATG TTTACTGGGT CCGCGCAGGT TTGTTTGTCA  27480

TCTTCATTCT CTCCACTAGA CTCCAGTTTA AAAGACTCTA GATAAATGGG TTTCATTAGT  27540

CCCCCCATGG GGGTTGAAGC GTCGCCTATC GCCTTATGAA GCTTAAACAT AACGAGTGGG  27600

GTGGCCCTGA AATGATCGTC CACGGACAGC TCGTAAACAA AGGCGGCCGT GGCAGTCAAC  27660

GTCTCTATAC CGTGCATGAC GAAGGCCGCG TCCATCCCCG GCGTCCTCTC ATGTGTCTTT  27720

CTGGCGCGAC AAATAATAGA TCTCAAAAAC GTTGGTGACA TGTCTCGACA GTTCTCGAGC  27780

ATCGATAACA GGCAGCAGAG CTCGGTTATG CCGGGAGATG TAGGTCTAAG GAGGCACACT  27840

CGCTCTTGGA ACACGTGAGG GTGTAGGTCT ATGTGGGTCA CCATGTCTTC GTGCTCCACC  27900

AGGCACACCA CCGTAAATCC CACAAAGTTG GGCGAGGACA GGCGAGATTT CACGTGCTCC  27960

CTGAGACACG CTATATCTAA GTGGCCCATC ACGGACATTT TGGGGTATT GCTTCCAACC  28020

AGTGCGTTGT TTTTCCTATG CACTTCCAGG ACAAGGCGGG GCACCACAGG GTGGGGGTAT  28080

ACGGGACAGG CCTCTTCTGA CTCGCGAGTC TTCGGGGCAT GAGTACTCAT TGGCACTCCA  28140

GTCAGTCTCG CCAGGGCCCT TTCCAGGGAC ATTCTCGAAG GGTGGTGTAA CTAGACAGTA  28200

TTTCTGTCCC ACGTCGGTTA TATACACAAA GAGTCTGCTA GTCTGATATA AATAGGCCGC  28260

GATGTCCTGC AAGCTGGAGG ATACGAAGGA GTGACTAATG AGCTCCATCT GAAGCAGGTC  28320

CGCGATCACA TACGTGAATG GACCAAGCAG GATGGATATG GTGTCCTGAG AATAGGTGAC  28380

GCTGAGCCGC TGCCCTTGGT TGTCAACAAC GGGAGCCAGC TTGTAGGTTT GAAACATCTC  28440

GCTTTCCCAC AGGTTCGTGA GATCTTTCAT GCTTTCTCTC ACTGGGGGTA TGTAAGAAGA  28500

GAAAAAGCTA TTTAGCACGG CACTGCCCGA TGGGATATGG GAAGACGTTA GCTGCAGAGA  28560

GGGGTCCTGT AAACGTCCCA GAGATTGAAA TGTGTTGGCG GTCAGCAGAT TCACACTCCC  28620

GGGACCCTTT GCGTCACCGG GCTGTTGGTG TGACAGCTGT GTCTCAATAC ATTTTAGCCT  28680

CTTCATGCAG AGCTCCCTCT CCTTTTCAAG TTGAGTTATT GTGTCAAATT GTTCGTTTAT  28740

CTGGTTGGTG AGACACTTGA AAACGCTGTT GGACACCTGG CGCCTGAGCC CCTGAGTGGT  28800

CGTCTCTTGG CCTGTGCCGA ATAGTTTATT CTTGTCTACT ATGTTTTGGG ACACGTCGGT  28860

GACAAAGTCC TCCACGACGT CGGTGACACC GCTCACTGTC TTGTTTTCTG CCAGTTTCAT  28920

GAGCAGGTTG AGGAGCTCTC GCTTGGGGTC TGTTCTCTGA GAGGCCTGCT CCAGGTGGGT  28980

CATGATGTCT TTGTACACAT TGTTACAGGC GCTTCCAACG AGGGCCTTGG TGGGGCTGT  29040

GTTCAGGAGC TGGCAAAGTT TTGCGTGCTC TGCCGTCCGG TGACAGCTCA TAATGCTGGT  29100

ATACATCCTC TGAATGGGGC TGTCAAAGAT CACCCGCCCA GCCAAGATGG CGGGCATAGT  29160

AATCACCTCC ACATGAACCC TTTTCTGCTT ATACAATCCC ACGAAAGTGT TTTTAACACA  29220

GTCATAGTCT ATGCTCACCT CTGAGTAGCC CGGAATATAG AGGGCGCTTA AACTAGACAC  29280

CAGGTTGCTA ATCTCCTGAG TCACGCTGGT GAGTATCCGG CCTATGGTTT TTTCACCAGA  29340

GGCCAGACGC TGGCAATCTT TCATCAGCTG TTCCTGGATA GAGTTAACCA GCTTGTGGTC  29400

GGGTGTGTGC TTGACGACTG GTACCATTCC TACCGTGACC ACCCAGTCTA CGTATCTCTC  29460

ATACGAGAGC TGTGTCTTGG CGTAGAGGAC CCGGTTGATG GCATTGAGAA GCAGGTGGTC  29520

TAATGTCATG CGCATAGTCT GGGCCCAGGA GTCGAAGGTT GACCTTCTGT AAGACCCCCA  29580
```

```
CTGTGCTTCC TTTTCTGGCC ACCTGGTTTT TGCTGAGGAC TCGTATGTCC TCCAGTCGGA    29640
CAAGACGTGG TCGTAGCTAC AGTTGGCCAA TGCATTCTTG TACAGGTGGA TAAATAGCTG    29700
TCTGAAAAAA ACACCCGGGT TTCGCAGGCT GCAGTGTAGA GTCTGACCTC TGACATAAGA    29760
ATACTTGCCT TGCAGGATCT CAAAGAGGGA GATGGACAGC TCGGAAGGGT GCACTGATAT    29820
GGACGAGCCC AGCCCCGGGT TCATCCTCAA CATGACATCG GATGCCAAAG TCAGGAGCGT    29880
AGTGGAACAG ATTGACAGGT TGTCAAATAT CACTACCTCG CCCCCGGAGA TGGGCTGGTA    29940
TGACCTAGAG TTCGATCCAC TGGAAGACGA AGGCCCCTTT CTGCCGTTTT CGGCATACGT    30000
AATAACGGGG ACTGCAGGAG CGGGGAAAAG CACCAGCGTA TCCGCCCTAC ATCAGAATCT    30060
CAACTGCCTA ATTACGGGGG CTACAGTGGT AGCGGCACAG AATCTTTCCA GGGCTTTAAA    30120
GTCCTACTGT CCCACTATAT ACCACGCCTT CGGATTCAAG AGCAGACACA TTAATATCTG    30180
CCAGAGGAAA GTGCCCAAGG TAACTCAGTC CTCCATCGAG CAACTCCAGA GATACGAGCT    30240
GGCTAGGTAC TGGCCAACTG TCACCGATAT TATTCGAGAA TTTATGCGCA AGAAACAAAA    30300
GGGGCAGTAT AGCTCCCTCT CTCAAAGCGC TTTCAGACTC CTTTGCCGTA TGGGTGGAGC    30360
CAATTTGTGG ACGAGTAACA TTATCGTGAT AGACGAAGCT GGAACCCTCT CGTCCCATAT    30420
TTTGACGGCC GTGGTGTTCT TCTATTGGTT TTACAACAGT TGGCTGGACA CCCCGCTATA    30480
CAGAAATGGT GCCGTGCCTT GCATAGTCTG CGTGGGGTCT CCCACCCAGA CGGACGCCTT    30540
TCAGTCGGTC TTCAACCACA CGCAGCAGAG AAACGAGATA TCTGCCTGTG ATAATGTGCT    30600
CACCTTCCTA TTGGGAAAAC GTGAGGTTGC AGATTATATT AGGCTGGACG AGAATTGGGC    30660
CCTATTTATA AACAATAAGC GCTGTACGGA TCCCCAGTTT GGTCACTTGC TGAAGACCTT    30720
AGAATATAAT CTAGACATAT CACCAGAGTT AATGGACTAT ATAGATAGGT TTGTGGTTCC    30780
GAAGAGTAAG ATTCTGGACC CGCTCGAGTA TGCAGGGTGG ACAAGACTCT TCATCTCACA    30840
CCAGGAGGTG AAGTCTTTTC TGGCAACGCT GCACACCTGC CTGTCGAGTA ATAAGGATGC    30900
TGTGTCCACA AAGCTTTTCA CCTGCCCAGT GGTCTGTGAG GTGTTTACAG AGCCATTTGA    30960
GGAGTACAAA CGGGCGGTAG GCCTCACACA CATGACTCCC ATAGAATGGG TAACAAAAAA    31020
TCTTTTCAGG CTAAGTAACT ACTCGCAGTT TGCTGATCAG GACATGGCTG TGGTTGGGAC    31080
CTATATCACA GACGCGTCCA CACAGATCAC CTTCGCCACT AAATTTGTCA AAACAGCTA    31140
TGCTACCCTT ACTGGAAAGA CCAAAAAATG TATATGCGGG TTTCACGGGT CATACCAAAG    31200
ATTCAAGTCC ATCCTAGACG GGGAGCTATT TATCGAAAGT CATTCGCACG ATAACCCCGC    31260
TTATGTGTAC AGTTTCCTTA GTACCCTGCT ATATAATGCC ATGTACTCAT TTTACGCGCA    31320
CGGGGTGAAG CAGGGGCATG AAGAATTCCT CAGGGACCTC AGGGAACTGC CGGTGTCTCA    31380
AGAGCTGATC TCTGAGATGA GCTCCGAGGA CGTTCTGGGG CAGGAGGGGG ACACAGATGC    31440
CTTCTACCTC ACCGCCAGCC TCCCACCATC CCCCACCCAC GCGGCTCTTC AACACTGGT    31500
GGCCTATTAC TCCGGGGCCA AGGAACTATT CTGCAACAGG CTGGCCCTGG CACGCCGACA    31560
CTTTGGTGAC GAGTTCCTCC ACTCCGATTT TTCAACGTTT ACGGTGAACA TCGTGGTGCG    31620
AGATGGCGTG GACTTTGTGT CCACTTCCCC CGGGCTCCAC GGTCTAGTGG CATACGCATC    31680
CACTATAGAC ACCTATATAA TCCAGGGATA TACGTTCCTC CCAGTGAGAT TCGGCCGTCC    31740
AGGAGGACAG CGCCTCAGCG AGGACCTGCG CAGAAAGATG CCCTCCATAG TTGTCCAGGA    31800
CTCATCGGGG TTCATTGCCT GCCTGGAAAA TAACGTCACC AAGATGACAG AGACCCTCGA    31860
AGGTGGCGAC GTGTTTAACA TATGTTGTGC AGGGGACTAC GGTATCAGTT CTAATCTGGC    31920
TATGACCATA GTGAAGGCAC AGGGGGTTTC ACTAAGTAGG GTGGCCATAT CGTTCGGCAA    31980
```

```
CCACCGCAAT ATCAGAGCCA GTCTAGTGTA TGTGGGTGTA TCCAGGGCCA TCGACGCTCG    32040

TTACCTGGTA ATGGACAGTA ATCCCCTTAA GCTAATGGAC CGCGGTGACG CCCAGTCCCC    32100

ATCCTCAAAG TACATCATCA AAGCCCTATG CAACCCCAAG ACTACTCTGA TCTACTGACC    32160

CGTACCCCTC TCTTAGGACA CTGATGTGTT TGGGAATAAA GCATGAGACT TGACACCTAT    32220

AATGGTCTGT ATTGACACCA TTCTTTTATT TATCAGTCCA GCCACGGCCA GTTATATGCA    32280

CCGTTTCCAC ACAGGGGTGG CGTGGAGGCC AGGATGCGGG TTGGGTCGCT GCACCTGGAC    32340

CCCGCGGTAG TTGTGCTTCC TGATGAAATC GAGTGGGCGG AAGTACTGGG AGATTGGGTT    32400

GGGAGGTGAC CCTTTGTGCT CGACGGAGAC ACGATCACGC TCACGGCGGA CGAGGGCTCC    32460

TCGTCTGTGT CACTCCCCGA GGATATAATT ATCACGGACG CCACTGCTTT GCGGCTTAAG    32520

TTTGGTTGTC TCTGGCAGCG CACCACATCC TCGCTACCAG AGGAGGCGGT AGACTGCCTT    32580

TTGCGCTTCT GGCCCACGTC CATGAGCCCG ATTCTCTGAC TCAATACTTC CCCTTGGTCT    32640

TCTCCGTCCT CCTCGGACGA GGGTGGCTGG TGGGAAAAAT GGCGCGCGTC GGTAAACGCG    32700

GCCTCATTGT TCACGTCCGG AGAGTTGGAA CTGTCATCGC TATCAGAGTC CGATGTCAGG    32760

TCGACGATCG CGGTGGGTGC GGCGCGCAGG GGGCGCCACG AGGGCCCTTC ATCAGGGTCG    32820

CTGTATGGTG AACTTTGTGT TCCAGGTACA CTATTTCTGG AAGCAGGTGA AAGTCCGTAT    32880

GCCCCGGTCC CAGTGTATGC CGCCATCGGT TCCAGGATAG CAACCCCCTC GTCGTCTGAA    32940

GGTGAGAGCC CAGCAGGGGA AAATCCGTCA TCCTGACTAA CCCATCCCAT GGACGCCTCG    33000

GACTCCGCCG TGTCCGTTGA ACTGCGCACG CGGCCCGCTA CCACTGCTAC CGGTTTGGGC    33060

GTATGGGCCC GTCTGGCCAG AGGCCTCGGG CGCAAGTGAG ATAAAGGTTG AAAAAAGTCT    33120

GCAGGGTACC CCTCTGGCTC GTCTTCCTCC TGAACATCGT CATTTTCTTC TTCATCTTCA    33180

TCTTCCTCAT CCTCGTCATA TTCAGATTCG CCGCTCGACT GATCCGGGGA TATCTGTAGA    33240

TCCAGAGGGG TTGCTGGCGG CGATGGCGTG TCCTCGGCGA AGACGTCGTC TGGGGCAGAC    33300

ATATCTATCA CCGTGGGTCC AGCATAGCCG CGCGGCCTGC CAAATCCTGG AAGTGATGAA    33360

AGAGGTGGAG GTGGGAATAT GAACTTCACG GGGGGTCGTC TGCGAGGCGC TCCTTCAATT    33420

GGAAGCATTC TCTCTTCATC GTGTGTGCTA GACGAGGTCC TCACAAACAT CGCCATGGCC    33480

TTGTACGGGG TTGACCGCTA GGGGCGGAAA TTTACAAAGC ACACGAGTTA TTGCCTTTAC    33540

TGCTCCAACA GGCCCCAGTC CACAGTCTCA CGCCGGTGGC GAGTCAAATA GTCGTTGGCT    33600

AGGTTAAAGT GATTACAGCC CTGGAACCGA GGCCATCGCG AGTGTCGGCC ACCAAGAGAG    33660

GCCAGCGGAG ATGGATGCTG GGCCGTAAGC ACCAGGTGTT TCTGTGCGTT TATGAGCGGA    33720

GTTCTGTCAA TGGCCTTGCG CCCCCACAGG AGAAAAACGC AATGTTCTAA CTTTGAGGAT    33780

ATGCTACTGA TGATGAAACT CGTGAACCAA TCCCAGCCAA GTCCCTCGTG TGAGCCGGCC    33840

CTCCCCTTCT CCACCGTCAA AACTGTGTTT AGTAGCAACA CACCCTGGCG AGCCCAGCTG    33900

TCGAGGCACC CGTGGGAAGG AGTACTGAAA TTGGGACGG AAGCCTCTAG CTCTCTAAAG     33960

ATGCTTCTCA AACTGGGTGG AACCTGACAT TGCCGATCCA CACTAAACGC CAGGCCAGTA    34020

GCTTGGCCCT TGTGGTACGG GTCCTGGCCT AAGATCACCA CTTTAATATC CTCTGGATCG    34080

CAGCAGTGGG ACCACCACAT CAGCTTGTCC TGTGGGGAT ACACTGTGGT GGTTAGCCTA     34140

AGTTCCCGAA TCTGTCTGAG CAGCGAGAGC AGTTTCTGTT TCAGAAATGA TGAGAGGCTC    34200

AGAAAGGAAA TCCACTTAGG TGCCAGTAAC AGATCCCGGT CGTCCACCCC CTGACTGATG    34260

GATAGGGTGC CCCTAAAGAC CGTCTGTTGC AACCATGCGT CCATGTTGAA CTTATTTTCC    34320
```

```
CTTTTGACCT GCGTGCGCTC TCCGGCTGCT GCTTTTAGCC CGAGTCTGAC TTCCGCTAAC   34380

AGAACCTGTC CGGTTCATGG CCTTTCCCAC GCTTATTATA ATTATGTTTA CGTTGTGAAT   34440

AGAGCTATCT GCAGTGGTCG CGTTAAAACC TACAGTATAG GCCGTCAAAC TTCGTTGTAA   34500

ATACCACAAC AACCTCAGGT TTTCCTGCGA CGCCCAGGAC CCCAATCTTC GAACGACCGC   34560

GACTAAAAAT GACCTCAGAT TAAACCCATT CACGCATGTT TCCACGGTAA TGTCGCCTGT   34620

TTTGCTTCGC AGCTTGGCTA TACAGACCCC GTTGCAGTGA TTCGGATCGG CGAAGTGGAT   34680

AGAGTGGACC GCAAAGAACA ACGGCAGGGT AGAGGCTGCC GATGCCTGAA TTGCGCAACA   34740

TGGTAAGGCG ACGTATGCGT GAGATGTGAC CAATAGGGTG GTCCACAGGA CGGCAAATAG   34800

CGCAAAGATC CCCATGGGGC AAATCCGGGT TTCACCCTTG TGTTGCCTGG TTCGGTGCTC   34860

CCCAGGGAGC CCCCTTCCGT AATATCTGTT TTATATAGTG AGGGTTCACG CATGCGCGAG   34920

TCCCGACTAA TGAGGACAAT TACTGAAATT GACCTTTTCG CGACACGGGG GTGAGGTCTA   34980

TTTCCCACGA CATACTTCCG CGGAAAAATA CCCACGCTCC TTAATTTCCG TGGGAAGACG   35040

ATGGGGGAAA TGTGGCATTA CCTGACACGG TTTCAATCAT ACTCATCGTC GGAGCTGTCA   35100
```

(2) INFORMATION FOR SEQ ID NO:19:

(i) SEQUENCE CHARACTERISTICS:
        (A) LENGTH: 35100 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:19:

```
CACGTCTGGC TGAGATTTTC TAAAAAGTCA TCCAATGAAT CATCGGAATC ATCAGCACAC     60

TCTAGAACTA CTCCATATGC CGGGGTGCGC GGGGGTCCCG AGTAGTGCAC GTCGCCATCG    120

GGAGACACAG ATGATGGGTT TGAAATGTCC ATACGGGCCG TGTGCACAAG GGTCACGTCC    180

CCATCCCCAA CACAAGGACC TTTAGATACC CTCTCCCGGC ATGTGCGCGT ATCCGGGCAA    240

GCAAGCTGGT GTTCTGGATT CCAAACGTGC CCAGCGGTAC CCAAAATCGC CAGGGCGTGT    300

TTTATTATTT CCACAGGAAC CGGTTTCTCT AATTGCATCA CCAGGGTATC CAAAAGCCGG    360

GCTTCCACGT TGATCCGGCT TACCGACAGT TCTTTCCAGG GTTTCCTGGT GGGGCGCGGC    420

AGCTGACTCA AAAAGGTCAC TGCCTCTGCC CATGGGCGGG TGGGTGACAG TCCGCCATAC    480

TCTTCCAGGA CACTGGCCAT GCATGACTCC AACCGTCTCA CGTCCGAGGT AATGTGCTCT    540

ATGAAGATGT GGTAGAGCCA GCAGACGTTC AAACACGATG AAATCAAGCT AAGCTCCCGC    600

CGGAACTCCA CATCCACAAA GGGGTATTGC TCCGGTGTCT GTATTAGGTC TGGAATAGAA    660

AACTCAGAAA AAGACACTGA CCCACCAAGG AGAACCTGGC GTCTTGCAAA GTTGATGAGC    720

CCCGCAGAAA GAATGTGTCT CCCGTGGGAC AAAGAGCTTG GGGGGGCAGA GATGGCGCTA    780

CAGTGGGTGA TTTCTTCTAC CACGGTCATA CATTGGTGGC ACCCACAGGC CTGTTCCAGT    840

ATCAGCATAA ATCTATCTTT GCAGTCATCC CAGATCAAAG TCATGTCAGA TGCTGTTGCC    900

TGGCATTTTG CCCGCATGTA CATTTCCTGT CCCACATATT TTAACATCTG TAATACTGGA    960

AGTAGATTCA GTCTGGTGTT GAGCCCCCCC GGGGAAGCCA GCGTATGCTT CAGGACCACC   1020

AGGGACGCTA AGAACCCCGG GTGTCCGCGC TCCGGAAACA GACCTCTGAG AATACGCTCG   1080

GTCTTGACGA AACCCGATGT GGTACCGAAT GCCACAATCT GTGCCCTCCA GCTCTCACAA   1140

TTTTCATCTC CAATACCCGG AATTGGGATA CACACCTCCA TGTTCAGTCA CATGTACGCT   1200
```

-continued

```
AGGGTCTCCC CACCCAACCC CCATAGGACC CAGCTACAGC TTATCCTCCA CTAAATACCA    1260
GGCAGCTACC GGCGACTCAT TAAGCCCCGC CCAGAAACCA GTAGCTGGGT GGCAATGACA    1320
CGTCCCCTTT AAAAAGTCAA CCTTACTCCG CAAGGGGTAG TCTGTTGTGA GAATACTGTC    1380
CAGGCAGCCA CAAAAATGGC GCAAGATGAC AAGGTAAAGA TCGACCTTTT TATTGTATAC    1440
TGAACAATGC GTGTTTACAA TGGTGTAGGT GGGAGCAGAG TTCGCCAAGC TCTACGTCCG    1500
AACAGTCGGG TGTCAGGGCT CTTATTAAGT GTTCGGTGTA CTTGACCAAA GCCGCGGAAC    1560
CTAGGTTGGG TCTGTACAGG TCGTACCAGG CAAAAAAGGA TCGGGCGGTG CTTTTCAGGA    1620
GAGTTAGGGA CGTGCTGATT ATGTGGACAA GCTTCTGCTC GTAAATGCAC CGCTGGTACA    1680
TCTGAACGAC AGCTGTCCAA AAAAACAAA GGTTCAGCTG CACGTTAAAA TCTGTATCCT    1740
GAAAGTCCTC GTAAATGACA GTTTCTACCA AGAAAAACTT TTTTACCACG CTGGCCATCC    1800
ACTGAAAGGA GGGAGCACAC GTCCCGTTGT GCGTTGTTAG GATATCCCTA ACTTCGGAGC    1860
GGAGACGGCC GGACGCTCCC ACAAAATGGG AGAGGCACCA CTCTGTGCAG TCCGCGGTCT    1920
GGGGTTCTGA TTCCAGGGGC GCCGTGTGGG GGTATTGGAG AGTCAAAACT CTGGGCAGTC    1980
CCTTAATGAG CTCTCTCTCA AAACCTATGC AGCCAGCGTC CACTAGTGGC AGCATGCCGT    2040
TAATAACACC CCTTATCTTG TCGTTGCCAA GTTTGTACAA CTGCTGCAGG GAATAAGCCA    2100
AATTCGCCCT AGCCGCGGGA ACCAGGTACG GCTCGCTTTG TCGGTGCTGG ACCAATATCT    2160
GAATGGTCTT TGCAAGGTAT AGGGTCTTCT CAACGTTTAG AGCGGGTACG TGGCAGTCTG    2220
GATTGAGGGT GGCGACGGAC AGGGTATCTA ACTCCTGAAG TATCTGATCC CAGGACGGGT    2280
AATGATACCT AAACAGATGG TTGAACAGGT GATCTTTAAG GGGCCTTCTC GATGTCATTG    2340
TAAAAACTAT GACACGCCAC TCTCTCCTTA GGGTAAGAAG CTTCGGCGGT CCTGTGTGGA    2400
AAGCTTCGTC GGCCTCTCGG ACGAACTGAA GGCCCAACTC TACCAGTGTG TGCTCCTTAT    2460
AAATGACGCA TACGAAACAA TCTACGATCC CAGTGACCTA AATAGAGTGG TGGAAGATGT    2520
GTGCATTCGG ATTATGAAAG AATGTTCCAA GCTTGGTGCG CTATGTGGTC TGTTTACAGA    2580
CATTAACATG TTTAACCTTT TCTGCTTTTT TCGTGCCTCT CGAATGAGGA CCAAAGGCGC    2640
GGCCGGGTAC AACGTGCCAT GCGCAGAGGC ATCCCAAGGC ATTATTCGGA TCCTCACGGA    2700
GAGGATCTTA TTCTGCACAG AAAAGGCATT TCTGACAGCC GCATGCAGCG GGGTGAGCCT    2760
GCCTCCAGCC ATATGTAAGC TACTACACGA AATATACACT GAAATGAAGG CCAAATGCCT    2820
GGGGCCTGG AGGCGACTCG TCTGCAATCG GAGGCCCATT ATGATATTAA CCTCTTCCCT    2880
ACTGAAGCTC TACAACACGT ACGATACCGC CGGGCTGCTC TCTGAGCAGT CCAGGGCCCT    2940
CTGCCTTTTG GTTTTCCAAC CGGTCTACCT TCCGAGGATT ATGGCGCCGC TGGAGATCAT    3000
GACCAAGGGT CAGCTCGCCC CTGAAAACTT TTACAGCATC ACCGGTTCTG CTGAGAAACG    3060
CCGGCCAATT ACCACCGGCA AGGTCACTGG ACTGTCCTAT CCAGGAAGCG GTCTCATGCC    3120
AGAATCTTTA ATTTTGCCAA TCCTGGAGCC AGGACTGTTG CCGGCTTCCA TGGTAGACCT    3180
CAGCGATGTG CTGGCAAAAC CCGCCGTTAT TCTGAGCGCC CCTGCCCTGA GCCAGTTTGT    3240
CATTAGCAAA CCCCATCCCA ACATGCCGCA CACCGTCAGC ATCATCCCCT TTAACCCATC    3300
GGGTACAGAC CCGGCGTTTA TTAGTACGTG GCAGGCCGCG TCACAGAATA TGGTGTACAA    3360
CACATCCACC GCGCCCTTAA AACCGGCCAC CGGTAGTTCA CAGACGGTGT CAGTCAAGGC    3420
GGTTGCTCAA GGGGCCGTGA TTACTGCGAC AACGGTGCCG CAGGCAATGC CAGCGCGGGG    3480
TACCGGAGGG GAGTTGCCTG TAATGTCAGC GTCCACTCCT GCAAGAGATC AGGTCGCTGC    3540
ATGTTTTGTC GCAGAGAACA CCGGAGATTC TCCCGACAAC CCGAGCTCTT TCCTGACGTC    3600
```

```
ATGTCACCCT TGCGATCCGA ACACGGTTAT AGTGGCCCAG CAATTTCAAC CACCGCAATG    3660

CGTTACGTTG TTGCAGGTTA CCTGTGCCCC CTCTTCGACA CCACCCCCCG ATTCAACAGT    3720

CCGGGCCCCG GTGGTGCAGT TGCCAACAGT AGTCCCTCTG CCGGCCAGCG CGTTCCTCCC    3780

GGCGCTCGCC CAACCAGAAG CCTCGGGCGA AGAGCTTCCG GGCGGTCATG ACGGAGACCA    3840

AGGTGTGCCG TGTAGAGATT CAACGGCGGC GGCTACGGCG GCAGAGGCGA CAACACCCAA    3900

ACGAAAGCAG AGAAGCAAAG AGAGGAGCTC AAAGAAGCGT AAGGCTTTGA CCGTGCCAGA    3960

AGCCGACACC ACGCCATCGA CCACGACACC TGGTACCTCT TTGGGATCAA TTACCACCCC    4020

CCAGGATGTG CACGCCACGG ATGTCGCCAC GTCTGAGGGA CCATCGGAGG CACAACCCCC    4080

GCTACTGTCG TTACCCCCGC CACTGGACGT AGATCAGAGT CTATTCGCCC TGTTAGACGA    4140

AGCGGGCCCT GAAACATGGG ATGTCGGGTC GCCTCTCTCC CCCACTGACG ACGCGCTGTT    4200

GTCCAGTATT CTGCAAGGAC TGTACCAGCT GGACACGCCA CCGCCTCTGC GGTCACCCTC    4260

CCCCGCTTCC TTCGGCCCGG AGTCTCCGGC GGATATACCG TCACCTTCTG GTGGAGAGTA    4320

TACGCAACTG CAACCGGTCA GGGCGACCTC GGCGACGCCC GCTAACGAGG TACAGGAGTC    4380

CGGCACACTG TACCAGCTGC ACCAATGGCG TAATTACTTC CGAGACTGAA GTGTTCGCAA    4440

GGGCGTCTGT GCCTGCGTTA ACTTCCCAGG CAGTTTATTT TTAACAGTTT GGTGCAAAGT    4500

GGAGTTAACC TACAGATTCT ACTTAAAATA GCTCATTTTC TCACGAATCT GGTTGATTGT    4560

GACTATTTGT GAAACAATAA TGATTAAAGG GGGTGGTATT TCCTCCGTTG TCGACTATAA    4620

CCTGGCGTGT AAACGTGTAA CCCTGCCAAA TGCCCAGAAT GAAGGACATA CCTACTAAGA    4680

GTTCCCCGGG AACGGACAAT TCTGAGAAAG ATGAAGCTGT CATTGAGGAA GATCTAAGCC    4740

TCAACGGGCA ACCATTTTTT ACGGACAATA CTGACGGTGG GGAAAACGAA GTCTCTTGGA    4800

CAAGCTCGCT GTTGTCAACC TACGTAGGTT GCCAGCCCCC GGCCATACCG GTCTGTGAAA    4860

CGGTCATTGA CCTTACAGCG CCTTCCCAAA GTGGCGCGCC CGGTGACGAA CATCTGCCAT    4920

GCTCACTGAA TGCAGAAACT AAATTCCACA TCCCCGATCC TTCCTGGACG CTCTCTCACA    4980

CACCACCAAG AGGACCACAC ATTTCGCAAC AGCTTCCAAC TCGCAGATCC AAGAGGCGAC    5040

TACATAGAAA GTTTGAAGAG GAACGCTTAT GCACTAAGGC CAAACAGGGC GCAGGTCGCC    5100

CCGTGCCTGC GTCTGTAGTT AAGGTAGGGA ACATCACCCC CCATTATGGG GAAGAACTGA    5160

CAAGGGGTGA CGCCGTCCCA GCCGCCCCTA TAACACCCCC CTCCCCGCGC GTTCAACGCC    5220

CAGCACAGCC CACACATGTC CTGTTTTCTC CTGTTTTTGT CTCTTTAAAG GCCGAAGTAT    5280

GTGATCAGTC ACATTCTCCC ACGCGAAAGC AAGGCAGATA CGGCCGCGTG TCATCGAAAG    5340

CATACACAAG ACAGCTGCAG CAGGTATAGA CGGGAAACAG GTGTCTATCT TGGCCGGCTG    5400

GTTACTCAAA TGGGAACAAT GGCGCCACCT TGCTGTCTTT GTAGGCATTA GAAGAAAAGG    5460

ATGCACAACT ATGTTTCCTA GCGGCGAGAT TGGAGGCACA TAAGGAACAG ATTATTTTCC    5520

TTCGCGACAT GCTGATGCGA ATGTGCCAGC AGCCAGCGTC GCCAACGGAC GCGCCACTCC    5580

CACCATGTTG AAGCTTGGTT GTGCCGTCGT CCGGGAGAAC CATGCCAGAC TTTGTGTGGT    5640

AAGAAGGAAT TGTTATCCGG CAGCAATATT AAAGGGACCC AAGTTAATCC CTTAATCCTC    5700

TGGGATTAAT AACCATGAGT TCCACACAGA TTCGCACAGA AATCCCTGTG GCGCTCCTAA    5760

TCCTATGCCT TTGTCTGGTG GCGTGCCATG CCAATTGTCC CACGTATCGT TCGCATTTGG    5820

GATTCTGGCA AGAGGGTTGG AGTGGACAGG TTTATCAGGA CTGGCTAGGC AGGATGAACT    5880

GTTCCTACGA GAATATGACG GCCCTAGAGG CCGTCTCCCT AAACGGGACC AGACTAGCAG    5940
```

```
CTGGATCTCC GTCGAGTGAG TATCCAAATG TCTCCGTATC TGTTGAAGAT ACGTCTGCCT    6000

CTGGGTCTGG AGAAGATGCA ATAGATGAAT CGGGGTCGGG GGAGGAAGAG CGTCCCGTGA    6060

CCTCCCACGT GACTTTTATG ACACAAAGCG TCCAGGCCAC CACAGAACTG ACCGATGCCT    6120

TAATATCAGC CTTTTCAGGT GTATTACACG TTTCAACTGT AATCCCTCGC AATTGGGTAA    6180

ACCGTCGGTG TGTAGGGATA AAGCGTAACC TTACGTTCTG TCTCATCTAC AGGATCATAT    6240

TCATCTGGGG AACCATCCAG GACCACGCGA ATTCGCGTAT CACCGGTCGC AGAAAACGGC    6300

AGAAATAGTG GTGCTAGTAA CCGTGTGCCA TTTTCTGCCA CCACTACAAC GACTAGAGGA    6360

AGAGACGCGC ACTACAATGC AGAAATACGG ACCCATCTTT ACATACTATG GGCTGTGGGT    6420

TTATTGCTGG GACTTGTCCT TATACTTTAC CTGTGCGTTC CACGATGCCG GCGTAAGAAA    6480

CCCTACATAG TGTAACACAA AACCATAAAA GTAAATAAAC GTGTTTATTG TTCACATGAT    6540

AAAGAGTGGT ACTCTTTACT GGTTTGGGGG TTGGGTTGTG GCGTGGTGGC TGGTCCGCGG    6600

TTCAGTCATC AACCCCCGCC CGTGTTGTCG AGGCTCCTCT TCGTCGCCTG TTATTGGCAC    6660

CAGGAGGCGG TTTAGCGGTG CCCCCGTCTG ACATGCAGAC GTCGATTCTA AGCGAAAGTC    6720

CCTTCAGGGC ATCGTCCACT TGCTTTTGTG TTACAACCTT GCTGAATATT GTCCTGACCC    6780

TGGCTTCGAT TTTCTTAGCG GCCGCCGCAC TCAGTGCACC CACAGTAGCG GTAAGCTGCG    6840

CTTCCTTCTC GGTGGCCGTC AGAGGCCGAT CTCTCGGATC GGCAGTGGAT CCCAGTGCTT    6900

TCCGAAGCTC CCGATTCTCC ACAGTCAATT GGCTTATCTT TGCGGTTAGG TCTTCCATCG    6960

TAAGGTCCTT TTTGGGTCTG CCCCTGGGCG CGGCCATGTC AGGTACGCGT AGATGTACGT    7020

GTTGGTGATG CTCACAACAA AAGCCCAAAT CCCTCCTTTA TACCCAGCTT TAAATACTTT    7080

ATTGAAAAAC CATAGCTTTC GTCAGCGCTT GTGCGAGTAA TCACATGCCA GTCTATGCAT    7140

GGACCACCTC GTCCACAAAC TTGAAAAAAC AAAGATATAC CAGATAGAAA AATGTGGCCA    7200

CGACGACTAG TAACGCGTTA ATCAAGGCCC AGACGCTAGA AAAGCTAGAA AGGGAGGGGC    7260

TAAAACTATC CGCGGAACAA GCAACGTCAT AGAATCCTGG GGTAGTGACT GATGTGGGAC    7320

CGGGCGAAGG CCTGGCGCTG AGCCCAGCCG TACTGGGACT AGAACGCTCT GTAGATGATG    7380

CGACACCTGT CGAGTTGGCC GTAACCCAGC AGTGACCTAG TATCGAGGCC ACAAATAAAG    7440

CCAGGGCCAC CGTGGACGCT GTCATTATGA ACAACCGCCG AGGCTCCAAG CCGTCTATCC    7500

AACGTTCCGC GTTCGCCTCT TATATACACT CTGCAATGCA GTCCGACTCT GCCCCTCTAC    7560

CCAGGGTGGA ATATGTGTTC GAAACAAGCA AATTTAGAAT GACGTCGAGA GCAAATGAAG    7620

CCAGACTCAG ACTGACAAAT GAGTGTCCGA TACTGGTGAG ACCCCACGAG CCGTTCATCA    7680

TGCCCACCGG AATACACTTC ACGCGAACCC CTAGCTGCGC TTTCATCCTG ACCGGAGAGA    7740

CCGACAAGGA TGTATTTTGC CACACGGGCC TAATCGACGG AGGCTACCGC GGGGAGATAC    7800

AGGTTATTTT ACTCAACAAG AGGAAGTACC CTGTGACGCT GTATCGCGGG GAGCTCAACA    7860

TCTGCCTGTC TGCTTTCAAT TACGTGCTAC CTCCGTTGAG GGACGTATCA TTCTTAACCC    7920

CCCCTATGTA TGCAAACGAC GCCGGATTTG ACGTGATGGT GATGCACTCT ATGGTTATCC    7980

CTCCTACTAC TGACCAACCG TTCATGATAT ATCTAGGAGT GGAGACCCCA GGCCCCCTG    8040

AACCCCACGT GGCTCTAGCA TTGGGGCGAT CCGGTCTAGC ATCTAGGGGT ATAGTTATAG    8100

ACGTTAGTGA GTGGGACCG CGAGGATTGC AGCTGAAGTT TTATAACTAC TCGGGCAGC    8160

CGTGGCTGGC GCAGCCCGGT AGCCGCATAT GCCAGATTGT GTTTGTGGAA CGCAGACACA    8220

TCCTCAAGGG CTTCAAAAAG TGCTTGCGCC ATAGGAAGCT AGCTCCTGGC GTCCGTTTCC    8280

GGGAGGCTCG AGTGCATTTT CGCGAGGATA CAAATAGCGT CCGAAAACAT ACCCACGAAG    8340
```

-continued

```
ACAACCCCGT CCACGAACCC AACGTAGCCA CCGCTTCCGC TGACATTCGT GGAACCAAGG   8400

GGCTGGGGTC GTCTGGGTTT TAGAGCCGCC GCCAAATGCG GCCAGTTTAT TAGGGCGATT   8460

CGATCCCGCA ACCCACAGCA TCCCCCAAAT AAAAAAACGA GTGTACACAG CCAATGTTTT   8520

TATTATTGTT CGATTCATTA CTGGTACCAG AGAATAAAGC CAACCTATGT CGAACCTATC   8580

GCGCTTTCTG TCGTCTCTTC CAGGGTTGAC GAAGGCCGGG GAGGGATTGA CGAATGCATC   8640

GCGGAAACGG ACGGGTCTTC GGTGGGTGGC TTGGGTAAAG TTGCCTCCGG CTGGCGCGTA   8700

ACGGCAGGCG TGAGAGGCAA TACAGAAGTG GGTTCCGACA AGGAGTGGCT GATCTCAGAG   8760

GCCCATATTA CCGAGTCGTC TGACGCCATA GCAGTCGCCA GTTTTCCAT CTCCATGAGC    8820

GAAACGCATT CCCCGGCCCT TTTGTTTAAG AGGGACTGGA GCGCACTGTC GTCCACGGTA   8880

ATCTCGCCGA CCGCCAAGGC CAGCATTGTG TTCCACACGA CGTTCTGAAT AGACTGCAGT   8940

TTTTTCACCT GGGTTTTCAC GGTCTCCTGG CAGCCCGCCG GAATTTTAGC CACGTCAAAA   9000

CGCTTCAGGT AGTCTGTGAT CTTGTTTGAC TGTACAGCCA GAAGGTAGGT CTGGTGCAGC   9060

GCCGTCGTGC CAAGGTTCGA CTGGACAACG TCACCCAGAC ACACTCCGGG GGGGAGGCCC   9120

AAATCTATCT CTTGCCGCCA GCGCTCTGGA CAGCCTTCCA GAGGGTCACC GAGGCGCTTG   9180

TAAGCGTGGT TGCCGCGTCC AAAAAGGTTT ATACCGCAAC ACGTCCAGGT GTACCATGGA   9240

GACGACATAC CGCCGCGAGG CGCTGACAGT AAGGGTTATT TTTTGTACGA GTGGCGACAG   9300

CGCCGAGACG ATCGCCGACG TCCTTACGGG GGCCCCAACG TCAGCGTCCT TCTTTTCTGT   9360

ACTCCACGAC CTTTTTTATT CCCAGATACT CGCCCCCAGG GTAACCCTAA AATTGTGCCT   9420

CCCCGCACGG CGTCCTGGCA ACGGCACAAG GTGTTCGCCC GTGTTGGTCC TACGTACTGA   9480

CGCATCAGTG GCCTCGGGGT TCCTTGGCGG CCGGCCACTG GAGGCGTCCG ACATTAAATA   9540

TATGCTGCTC AGCGACCAGA CCGCGGGGTT GTTCAAGCCG CTGTTGGAGA TAATCGGTGG   9600

CGCGCGCGCA CCACCAAATC AGGACGCGTG CACTTTCCAG AGCCAGGTGG CCTGGCTCAG   9660

AACGAAATTT GTTACCGCAT TGAGAAAACT TTACAAGATG ACTCCCTCAC CCTACTGGAT   9720

GCTGTCTGCA TTTGGCGCTC AGGAAGCCCA GTTCGTCCTG ACCAGCTCAT TCTATTTTTT   9780

TGAACACACT GTGGTCTGTA CCACAGAGAC AGTTTCTCAC CTGTCTAGAC TGTTTTCGCC   9840

TCAACAGGGA CAGACGCTGG TTTCCGTTAC CAGCCACGAG GAGCTGGGGC AGCTATACGG   9900

CACTTCCCCT TTCAGGCGGC GCGTCCCCGC GTTCGTCGCT TATGTAAAAG AGAAATTAGC   9960

GAGAGACAGT CTGGAGACGG AGGCCATCGA CCGCACCATA GACCAGATCA GGGCAAACT   10020

CATGCTGTCT AACCAGGACC TGGTCCATTT CATATATATC TCCTTTTATC AGTGCCTCAA   10080

CAAACGGGCG TTCCTGCGCT ACTCTAGACA GACGTCCTCT TCAAGTGCTC TAAGGGAGCT   10140

GGGGGAAGAC CCTCAATTGT GTGGCGCCCT ACACGGGGAG TTTCGTGACC ACGTCCAGTC   10200

CTACTACCAC AAAAAAACCT ACCTATCCAC TTACATAGAC ATTCGGTACG TGGGTGGCGT   10260

ATTACCAGAC GGCTATTTTG GCGGGAGTCT TGTAGGCGAG CGGTGCGTTT ATTGGTGCGG   10320

GCAGTCAAAG GACACGGCCA GCCTGTTGGC CACCATTAGC CAACAGGTGC CGCACCTGAG   10380

GTTGCAAAAC GAGTTCGCTG GCATGCTAGA CGTGGCCGCA CTGCGAGGTT CCGATGACGG   10440

TCAGTTTAAA GAGGGCCTTT TCTCCCACAG TCAAGCCCTA CCCCTGTACA GGTGCGAGTT   10500

TCTGGGCAAG CAGTTTTTCA CAATGCTTCA GGAAGACGGC CTAGAGCGAT ACTGGGAGCA   10560

AAGTGTGATA TTTCCAGGCG ACCAGGACTG GGATATGTTA TCTGACAAAG ACCTCACCTA   10620

CCGAATTTTT TACCATGACC TCAGCCTATC GCTGCCAACA CTGAAGGAAC AGCTCCTTGT   10680
```

```
TTCAAGACAC GAATACTTCA ACCCTCGCTT GCCAGTGTAT AGATGGGTAT TAGACTTTGA    10740

CCTGCCCGTC TGCCGCGACA TTGACAGGAC ATTCGAGGAG GTGCACTCTC TCTGTTGTTC    10800

CCTGCGTGAG GCCATACTCG ACATCATTCA ACTCCTTGGA CCAGTGGATC CTCGAACACA    10860

CCCAGTATAT TTTTTCAAAT CAGCCTGTCC ACCGGACGAG TGGCGCGGCG AAGACGTCGC    10920

CAGCACCAGC TTCTGTCGGT GTCATGACAA ACTGGGTATG CGTATTATCG TCCCGTTCCC    10980

AGAAGGAGTA TGCGTCGTTG GGTCGGAGCC CATGGTGGCA CTCACTGGCA TTCTAAACAG    11040

GACGATAAAG CTTGATCCGG AGCTGGTCCA CAGATTCCCG TCAATACAAA AAAAGGGGGG    11100

CCCTTTCGAC TGTGGCATAT ACGGCCGAGG ACGAAGCGTC CGGCTTCCCC ACTGTTACAA    11160

GGTGGGCTTA GTGGGGAAC TCTGCCGCCT ACTGAAGATA CTAGTCTGTC ACCCCGCCCC    11220

CAACGGCAAG GCGCAGTACG TGCGGCGCGC CTTTACGCTT CGCGAACTGC TCCATCACTC    11280

CCCGGGCCAC AGCGCCGGTC ATGTCGGCCG AATCATCTAT AGCATCATGG ATCGCAATGA    11340

GAATTTTTTA GAAAACAAGA CCATTAGCTA TCTGCCGGCC AAAATACCTC ACATCTTTCA    11400

GCGGATAGAG ACCCTATCCG GTCGTTCAAT AGAGGACTGG CTACACTCGG CCGTTTGGGA    11460

TAAAGCATAC GACACTATAT GTAAATTTTT CCCAGATGAA AAAGCACAAC AGTTTTCTCA    11520

CGTTGCATTT ACGCAACAAG GGGAAAACAT CATCCAGTTA AGACCCCGTC AGGGAAGACA    11580

CTTCCTCTGC ATCAACCATA ATCATAAAAA CAAGTCAAAA ACAGTCCGTG TATTCCTTAC    11640

CCTTCATTCC ATTAGGGTGA GCGAAGTCAC GGTAACACTT ATGAGTCAGT GTTTTGCCAG    11700

CAAGTGTAAC AATAATGTTC CCACGGCCCA TTTTTCGTTT GTGGTACCAG TGGGACTGGC    11760

CAGTTAATCC CACTATATAA CCTGGCTGCC AGGTTCCCAA AATAGCCCGC GGCATACGGC    11820

TCACTTCCCC CCACATTCCC CCCGTGCACA ATATAAGAAC CAAAGGACAT GGTACAAGCA    11880

ATGATAGACA TGGACATTAT GAAGGGCATC CTAGAGGGTA AGTCCTCGTC TACAACAGAC    11940

TTTTCCCATT TCTAACGTAT CGTGCTATCT TCGTCGCCCG GCGGACCATC CCCCCACCCC    12000

TCATTTATCG CGTTTGATAT TACAGACTCT GTGTCCTCCT CTGAGTTTGA CGAATCGAGG    12060

GACGACGAGA CGGACGCACC GACACTGGAA GACGAGCAAT TGTCCGAACC CGCCGAGCCT    12120

CCGGCAGACG AGCGCATCCG TGGTACCCAG TCGGCCCAGG GAATCCCACC CCCCCTGGGC    12180

CGCATCCCAA AAAAATCTCA AGGTCGTTCT CAACTGCGCA GTGAGATCCA GTTTTGCTCC    12240

CCACTGTCTC GACCCAGGTC CCCCTCACCA GTAAACAGGT ACGGTAAAAA AATCAAGTTT    12300

GGAACCGCCG GTCAAAACAC ACGTCCTCCC CCTGAAAAGC GTCCTCGGCG CAGACCACGC    12360

GACCGCCTAC AATACGGCAG AACAACACGG GGCGGACAGT GTCGCGCTGC ACCGAAGCGA    12420

GCGACCCGCC GTCCGCAGGT CAATTGCCAG CGGCAGGATG ACGACGTCAG ACAGGGTGTG    12480

TCTGACGCCG TAAAGAAACT CAGACTCCCT GCGAGCATGA TAATTGACGG TGAGAGCCCC    12540

CGCTTCGACG ACTCGATCAT CCCCCGCCAC CATGGCGCAT GTTTCAATGT CTTCATTCCC    12600

GCCCCACCAT CCCACGTCCC GGAGGTGTTT ACGGACAGGG ATATCACCGC TCTCATAAGA    12660

GCAGGGGCA AAGACGACGA ACTCATAAAC AAAAAAATCA GCGCAAAAAA GATTGACCAC    12720

CTCCACAGAC AGATGCTGTC TTTTGTGACC AGCCGCCATA ATCAAGCGTA CTGGGTGAGT    12780

TGCCGTCAG AAACCGCAGC CGCCGGAGGC CTGCAAACGC TTGGGGCTTT CGTGGAGGAA    12840

CAAATGACGT GGGCCCAGAC GGTTGTGCGC CACGGGGGT GGTTTGATGA GAAGGACATA    12900

GATATAATTT TGGACACCGC AATATTTGTC TGCAATGCGT TTGTTACCAG ATTTAGATTA    12960

CTTCATCTTT CCTGCGTTTT TGACAAGCAG AGCGAGCTAG CACTGATCAA ACAGGTGGCA    13020

TATTTGGTAG CGATGGGAAA CCGCTTAGTA GAGGCATGTA ACCTTCTTGG CGAGGTCAAG    13080
```

```
CTTAACTTCA GGGGAGGGCT GCTCTTGGCC TTTGTCCTAA CTATCCCAGG CATGCAGAGT    13140

CGCAGAAGTA TTTCTGCGCG CGGACAGGAG CTGTTTAGAA CACTTCTGGA ATACTACAGG    13200

CCAGGGGATG TGATGGGGCT ACTAAACGTG ATAGTAATGG AACATCACAG CTTGTGCAGA    13260

AACAGTGAAT GTGCAGCGGC AACCCGGGCC GCAATGGGGT CGGCCAAATT TAACAAGGGT    13320

TTATTCTTTT ATCCACTTTC TTAAGGATTG CCAAACCCCA TGGCAGAGTG TCTCCCGTAT    13380

TCCATGTAAC TCACGTAGCC TTTCTCTAAT AAACAAGCTA CCTGCAAACT ATACACAAAT    13440

GAAATGAGTC AGGCGTGGTC TCTTCTCTAC CGTGAATCGC ACCTTAAACA CAACACCAGA    13500

CCGCCACCAG GTGGCACCCA ACATCCATTA TGGAAAAACC CCGCGCCACC TTCCGCCACG    13560

TGGAGCCAAC AAACAAGACA CACCCGCCAA TGTTTTGGTC TCTTTATTGA TATGATATAC    13620

TCCCTCCCAT AACAATACGG TGTAGGCATT TTGTATTATT TATTGCATGG CATCCCATAA    13680

CGGCTTCGGC ATTATTTCGA GTACGACGCA GGCGTCTGAG AAATTACTGC ACCTCGCCGC    13740

AAAGTCTCGC GGGGACGGGG CGTGGGGCTC TAACTTGCCA ACCGCCACCG GTTTCCCCAG    13800

CCACAGCTTC ACCAAAGGAC ACGTCACGTG AGAGGGTGCT GGTAACGGTG AATTTGCCAA    13860

CCCCACCAGA AATGTATTCG GGTTAAATAT CCTCGTCGGT TTTCCCTGGG GCAGCAAGAG    13920

GGGGCCGGAG TCAGGCGGAA CGGTATTTCC AATAAAGTGC ACGGGCCCGT TATGATAACA    13980

TACGCAAAAT ATGCCATTAC AAGAGCTAGT CAGCAGAATG CCTTTTGCAC ATGCGTCCAG    14040

CGTATCGCAT AGCTCCCGCT TGGCTATCTC GCAGGCCAGG TTTGGCACAT TGGGTAGCCA    14100

TACCTGGCCC GGAGACCCCA CTGCACAGTA ATGAACTGCG GGGTCCCTAC GCAAGGCCGA    14160

TGAGATTCGA CAGCCCGACT GGCTTGTCGT CAGTAACTCA TGAACCTGTT CGCCATTATA    14220

ATACATCCTG ATAAACAACC GACCCAGTC AATGACGGCC TCCTGACCCT CTGCCGTCGT    14280

ACAAGATGGC ACGGGCGTTA CAATCTCGCC TGGCAAGCAC TGCCCCGGGG AAAAAAATCC    14340

CTCTTGCAAG AGACGTGCCA TATTGTTAAA ATCGTGGACG GCTCCGGCCA CGACTCCACA    14400

TTCCACGCAT TGTTCTTCCT CCGGTTTACG TACTCTAAAG ACCAGAAAAT GGTGTCCATC    14460

CTGAGAAATG CCTTTGCCAA TCTCTTGTAA ACCCCGCGTC CTGCGTAGCG CGGCAAGCAT    14520

TCGCCTGCGC CCCCTGGTGC CTTTAAACGA GGCGTCCACG GGCATGTTAC CCCTTTCGCG    14580

GATATACACA ACACCCAATT CCCCGTCTCT GCGCCATTCA AAACAGGGGT CCGCGAGGGG    14640

CGTAACTGGT ATACGGAAGC GGGTGCGCTC TTCGTCTTCC CACTCTACTC CGGGAAATTT    14700

TCCACTGTTG ACTTGACATA CTATCCAATC CTTGATTGAC GCTTTCCCCT CACTGGCACC    14760

GGTAGATATT CTTAGTTGTC GTGTCCGGCT CCACTCCGTT ATCGCAGCCA CCACAGCCTG    14820

CCGTGTAATA TCGCCTGCGG CTGCAGAACC CCCGGTCCCG GAGGGTCCTT CTCCCGGTGA    14880

CTCCGACCTG GATGGTTCAT CGCAAGGAGC CCCGGAGCCA GATGTTCCCG GTGACCCTTG    14940

TGACAAACAA GGTTTTTTGG GTATCGCCCC AGGCGCCCCA AAAGGGTTCG GTCTTTGGCC    15000

TGGGTCCATT GTCCCGCAAC CAGACTAGCT CGCGCCGCAA TGTCCAGTGG TAAGCACAGC    15060

TATGCCGGGG AGCCACCGGC CATCAGATAT AGAGAGGCGA CAGGCTCTCT ATATATCACG    15120

GCTAGGTGGC TGACATATTA GTGGGCCTAG CCGCAGAATT GCCTGGGTAG TCAAAAACCA    15180

GCGTTTCTCA AATTAACCGA AACTACATTT TTCTATTTTA AGTACGGGAT ACAAAGCAGG    15240

GTCTGAGGCA ATCTGCCGCC CTCCACCCCC ACCCACCATA CCCAAAAAAG ATATGTCAGA    15300

AAGAGCACTC TACCTATTAA CTCGTGGAGA AACATCTAC AAAATCTGTA CATTATTTTT    15360

AATACTTTAA TTTGTGCAGG TTTCTTCACC CCACACCTGC TTTTTGTCTG GTACAAAAAA    15420
```

-continued

```
CCACTGCAGG GTCCCGCCTA TAGCCAACTC CTAAGCGGGT TTTTTGCTAA AGCACTTTTT     15480

TAGACTGTCC CAGAAACCAC ATAGCTTCCT TTTCACTCAT TTGAAAAACA GCCCCGCCCA     15540

ACTGCCTGGA GAATTTTCCA CCCCCTCTAC CATTTCGCGC CTTTACCGCT GGTGCGAAAT     15600

CTAGCCATCC TATCACCGCG GATCCGCTGG ACCAATATAC CACGCCCACT TTTCGTAATC     15660

AGCAACCCTC TACGCCTACA CCCCTATGAC TGAATATAAC CCCCAACAAG GCTATGAAAT     15720

CATGAATGGT AACTGTCTGG ACACCAATCT TCCGCGGGGT GGCGGCAGTG CGACGCAAGT     15780

ATCCACAATA AATGGTGCAA TAATTGGCGA AATGTCGTGT CTGGTTTATT TGGACTACAA     15840

GATTACATCC GGTTTTATAA TTCACATATA TGATCAATGT AGACTATCCC AAATGGAGCC     15900

TATAAAAATT TTAACAGTCA AGGGTACATT TTGGAAATTT TCTGTAGATG CCGGGGATGC     15960

GCCGAAAAAT ACCGTCCCGC ACGTCACTGG GTTGACGCTC AGCGGTGTCT GTGGGATTGC     16020

GGCTGTGGTT GCCAGGTATC GCGCGGTGTT GAACAGCTGC TGCGGAACTC TGGGGCTAAA     16080

GCTTCGGAGG ATGCGTTCAT AGCGGGAATT TGGATTACCA AACCACCAGC CTTCCACTTG     16140

AGTGGCGTTT CTGGAGTATA TTCCAGACAT CGAGCAAAAT ATTGGGAATC CGTGGCCAAG     16200

GCCTTCAAAA ACTCGGTTCA AAATCTCCAT TTGCTCGGGT GAGGGGACTG TAAGACGCGG     16260

TATGCGAAGC AGTTCTGGTA CGAAACTCTG ACATAGGTGC CCCAACGTAT CCCCAACAGG     16320

CCAGCTACAT AACATTGCCT CGCCCGCGTC ACCTTCGCGT CTCAGAGTTC CACGAAGGTT     16380

CCCATACACA AAGATTTCCA CAACAAAAGA CACCCGCTGA CTATCAGGGG GATCAAAAAA     16440

CATCTTTGAA GGTGGCTTTT CGGGACCGGA GTGGCTAACG GGCGTACGCC GCCCGTGCGG     16500

GGACCTGGAC CTCGGGCGCC GCCTATCCGT GGCCTGTCTG GTTGAGGAGC TCGGTTCCTC     16560

CTGCAGCTCA GACAAAATGT TACCCAACCC TTCTTCCCAC GTACATATAT CCTCTCCTTG     16620

AAGGTTCGAG AGCGTAAGAG GGAGACCCAA AGGCGGCGGC ACTAAAGATT GTTCTGGTCC     16680

ATAACCCCCC ACTGCATATC TATCTCCAGC ATATGTACTA CAAGTGGAA CTCTGGGCCT     16740

TTCGCCACTA CCCGGGCACA CACACTCCCG CCGCTCCAGC TCTGTCGGTA AATGCGAAAC     16800

CTCGGGGTTC ACAGCGGGCT CCGGTGCAGA ATAAAGCACC GTAGGTTGGA AAACGCGCGG     16860

CCCACTGACA GGTAGGGGCG TGGATGCTAC AGTGGTAGAT GGGGTATCGG AATCCCCAGT     16920

GAGGTCAATA ATCTCCACTT CGAGGGCACC AGAACTAGTT GTCACGCGTC TGTATCCAGT     16980

CGCCATGTTG TCCCCCTGGC AGACGTACGG TATTCCAGAC GAGGATGGCT CCTGTCGCTC     17040

TGCCACCTCT GGGGTGGGTG GTGCGCCGGC GGAGGGCGTG GCCGACGCGC CACCCTGCGT     17100

GTGGGAAAGA CCCTGGTTTG GAGCGCCTCC ACTAGACCAC GGAATCCAAA GCGGTGTGCG     17160

AACTTCCGGC ACCACGGCGT GACCAACTGG TGGGTGCCAA ACAGGCGCGC GTATGGGTCG     17220

CGTAGCTGGC GGTTCTGCCA ATGGACTCCA ATTGTAACAT GATGGTTTCG CATACCCGGG     17280

CGCGGGGCGC CTGGGCGGTT GAGGTTCGAA GGGATACACC CGCTCACTCG CAGCACCCTG     17340

AGGAGCCCGG CCTTCTGTAG ATGCCCCGCA AGCGCCTTCG GCACCGGTTT CCCGGCGGGG     17400

AAGCCACGCG CGAGCACATT GGCCGCTTTG GGGGAGCAAT CCCTGTGGCG CCAGAGGTGC     17460

ACCCTGGCTG AACTCACCGA CAAATGTTCC CGCTTGGGCG TGCGGCGGAA TCCAACTGGG     17520

GGCAGCAGGA TTCAGCTGGC TGCTAGGAAT CCCCGTATAT GTCCAACGGG GGGAAAGGGG     17580

ATCAAATTGG CCCGTGGTTG GCGGATGCAC TTTCTCCGGG AGACCAGACG CGCCCTGAGG     17640

CCACCATCCC GTGACAGGAA GATCTCCCCA TGGAAAACAC GCAGGTATCC ACGGGGACGT     17700

AGATGGCAGC CTAGACCCAT CGCGCATGGG AGGGGCTAGT TGCCCCGTAT CCCCCGGCGT     17760

CTGTGCGACG CCGGAGACCC CTGACACAGT ACCGGCAAGC CGTGTTTCGT GCTGCGGCTT     17820
```

```
GGGCGGCGCC GTGCCCGGTA GGCCTGCACC AGATGAGTGA GGGTCTGAAG GGCCGGTCAG   17880

CGTTGATGGA GCAGGCGGAT CTCCGGGAAC CCGCCACGTA AAGGACGAGG CCTGCGTAAC   17940

TTGTCGCGTC CCAGAGGACC CCATACCTGA GGTAGATGCG CCCTCATTCA CTGGTATCCA   18000

CACGGAGCAG GCAGCCTTCT GTTCAGTCGT TATATCGCCA ACATTGTAAT AGCGGTTCGA   18060

TTTCCGAGGG CGACCCCTCA GCCCCGATGG CGCCTTAGGG GGAGCAGGTG CTGCAGCCCC   18120

TGCCTCCTCG TAGCTTTGTT CTCTAAGTAA AAGGCACGAG AGTTAACGTG GTTAGGGTAC   18180

CTAAAGTATT TCCCGCCGAC ACCAACGCAT CAAACCTCAC ACCCCCTTCC CCGAGTTACA   18240

TACCTAGTGT CACTGCGTCG CGTAGCCGTG GTTTGCATTG GGGGGGACAA CAGACACTGA   18300

ATAAATCGCT GCAGTTTTTC AGGACCATAC GCGGCCCCAT AGCAATACGT ACAGTTTTTA   18360

AACGGCGTTC GCACCAACTG CCATACTACG TAGCTACCAC CAAATGTGTC GCTGTACCGT   18420

AAATCGTTCC GCACGACGGC CCTCCTGGTT CCACGCAACA GTCTCCCAAA ACGTCCATAC   18480

ACCGTCTGTC CCACGACAGG CGATGGTCCG TAGACTCTAT CACACTCCTC ATCAAATGCA   18540

TGGTACACCG AATACCAGCC AGGCGGGATA TCGCTGCCGG CAGGCAGGGG CGCGGGGCT   18600

GCAAAAAGAA GGTTGTTCCT ATCAAACCAG GAAAAATAGG GAAACTTATT GTTTTCAAGG   18660

GCATCAATAA TCCATAACGT GGCCCATTCT GAGCCACCGG CTTTAGGCAT GGTCCGACAC   18720

AGAAACCGAT CGGCGTTCGT CTTTGAGGCA CAGTCCCGAC TGAGCCTTAT AGTGCCCCCC   18780

TTCTTGCTAT GAAAAAAACC CACGACCGTT ACGCAAATTT GAGGAGCTAC TCACCTAAAA   18840

GTAGCTCCTT TGACAAATGT CCTGGTTTTA TACCAATTGT TCACAATGAC ATATTGTGCT   18900

GGCGGAAACA GGTGTCCCGA TGTATCCTCG GCAAGTAAGC ACCATTACCA TGTGCCATCA   18960

TATTGTGTGG CACAAAAAAA GCAACTTTTC ACGCACGCAG CATAAGACCC GAGCCAGTCG   19020

CGCCCTCCAT CGCGCCTGCG AATTTTCCCA CCACCCAATA TTGTGGCAGA TCTTTCTTAT   19080

GTATATGTGG TTACAAACAC CACGCCCCTT AAGCTGTCCT CTCTCCCAAG GGGACTAGAT   19140

TATAACAGTG ACATACGAAA CCGAGACGCT CTCAAATGCT TTCTATTTTA TTTATCGATT   19200

CCGGGTTAAC ATAATCACAG GTAGCTATAA AATCCCCATC CTCTTGACCT GGTAACCCTG   19260

GCTTGAGGTT TCCTCTGTTA TCAAACAAAC CTGACCACAA CTGTACAGAG AAAAGTGGGT   19320

GAAATGTAGT GTTTATTTTA TCCTCACACT TTCACTTAAC CACAGCCCGT CAAACCACAG   19380

GGACCCTGTT GGCTGACTAT TAGTCATCAC ATGTAACTGA ACGCAATCTG AGCTTGATGA   19440

CGAGGGGGAC CATATCGAAC TGTTCTGCCG ACGTTGGGTC ACCTCCGATG AACACAGTTG   19500

TTTTTTTAAT GTGCTCATGT CCCTGTATGC GATATTGTGC CACATTAAAA ACATCCAGAA   19560

CAGCCCTAGA TGACAGTCCG CAGATCACAC CAAACTTCTT TGGAGGATTA TTTCCATGAT   19620

ATAATACGGT AGACTTGCAC AAATTCTTAA CATAAATGCC AGATCGGAGA GAAACTATCA   19680

CAAGACCCGA AGCAAACGAG CGCAGCACGG CCGCCAGCAG GTTAACGTCT CCTGGCCCTG   19740

TGTTATTGTC GTCAGGTTTG GGCAACAAAA CTCTTAACCC TTTGCGCGAA TGCAAGCAAG   19800

AGTGGCTAAT GTCTGCCAGT GGGTTCTGGG AACATAGAAT AAACACCTTT CGTTCCACTT   19860

CCAAAGACAT TGCAGGGCGG CCAAAATAAA ACACTTCCAC ACCAAGCCTA TCGGTTATCA   19920

TTACTGGCGG CCGTGCCACT CTATAATATG CGGATCTAAG CTTCCTGTGG CGAATGCGCC   19980

TCGTGGTAGG CCTCTCGTGT CTCCGTGGCC CATCATCCCA TAAAAATTCG CCAACAACTG   20040

GCCGGCGTCT GGACGCCGGC GGCAGTCCAG CACCATCATC GACTTCTTCG TCACTTATCT   20100

CCAACACATA TTCCCCTGCT ACATTCTGGG CCTCGAGTGC CCCAGCTAAG TACACATCCT   20160
```

-continued

```
CTACACCCGC CCCGACAGCC GAGGCGGCGA TTGAGCCCTC TGTTACCACG CCGCTTGCAT    20220
CCGTGTCGCC TCCGGGCTGT GATGTTGCGA TAACATCCTC TGGGATGCCA AGCAGATCAA    20280
AGAGGTCTTC ATCGCACATC GCCCTCATTA GCATGTCCAT CTCCTGTCCC ACGTGGTACA    20340
TCAATGCACA TGCAGATTCT TTATCAAGCA GTGTGAGGTC ATCTTCAACG TTGTCTGTGT    20400
GCACCGTTGT TTCATCGGCC GGGGGGGGCT GCGAGTCGCT ATGACGCGTC GAGGGTCCTT    20460
CGTCTCCAGA GCCAGGAGAG TCGGCATTGG CATCATCAAC TGGCTGAACC CCAGACGCAC    20520
TATGGCGCGT CGATGGTCCC TCGTCTCCAG AGTCCTCAGA TTCCGCGCCC GTCTGCGTGA    20580
CCGGCACATC GCAAAAGGCT GGGTGATCCT CCTCACTGGA ATCCGAGTTT CACCCACAA     20640
ATGGCCTACA GAAAAAAAAA CAAATATGTC AACCGGACTA GGGTGGCCAA ACCATTTGCC    20700
CCACCCCTCC CCACTCTTTC CCCAGGGGAC ACATCTTACC TTGGTCTTCT CCGATGCTTC    20760
TCGAGCCGTA CACTGTGTTG ATACAAAATT TCCCATAGTG ATGACCCACT GTGTAGGTGA    20820
GTCCTGGCAT GAACGCACCA CCAGCATTCC TTTACCTCGG CACACAGGAG GCGCCACCTT    20880
CTACAATTAA TTCCCTGTAC GACCTCGTAC TCTTCACCTG GCAAGCGTCT AAGGCGCCGC    20940
GACGTGGTAC ATATTTTCCC AAAAGCCGTA ATCGGCGAGC CCAGTAAATC TCTGGGATGC    21000
AGGCCCTTCG ATAGGCATTC CCTCTTAAAA TCAATGAAAA ACTGTAGGCT ATCCAGAGGA    21060
ATTACGTCAT TACGGGCAGC CGGAGCAAGA AATGTTCCAG TAGATCTATC TAGCCACTTG    21120
ACCAAAGGAT ATTTATCAGA GTCCAAAGCA CCTACAATAA ACTCAGAAAT CCAGGTAAGC    21180
CTGCGTCCCG CCATGTTGAC CTGTCAGAAT GGTCTGCCTC CGAGCATTAC CCCACCTCAA    21240
CAGAAGTAAT CTACTACGCA AACCACAACA TGCTTCCTGC AGCTTTAACC TTCAGTCACG    21300
GGTCAAAAAG CATTGCCTGT ATTAGACACA TGTGTTTCTC ACTATGAATC GTGCTCTCCA    21360
GCGCTGGCAA GAACATCTGG GGTGATGCTG CCCCGGACCA GCTTTGAAAC AGGGTATTGC    21420
ATGCATAATG AAGCCCACAT GTTTGTCTTA CTTTACTAAC CTCATTACCT TGCATTGCAG    21480
GGGACACCCC CTTGCCTTGG CAGCTGAGTG AATCCCAACC GCCTAGGAAA AAAATAACCA    21540
CTCAGACTTT ATTTTGCAGC CACACGGTGG CGCTAACCTT TAATGATGTC CCACTCAGTG    21600
AGTTTGGCCA CTCCCAAGCC CACATGGGCC TACTATAACA GGAAACATAG AAGTTGCGGA    21660
TAGAGCCTGG TTTCTAACGG CAATGATATT TATAGTGCAA AACGGAGGGC GGTAAGACAA    21720
AGGGAGGTAC CCGGACAGAG TGACAAGAAG ACTTGTCAAA ATTTTAGTCT CTGTGGTAAA    21780
ATGGGCAAG GTAAATGTGC AAAATGACTG GATAGTGATC CGAGTCATAT TCAGGCGACG     21840
GCCGGCGGCC CAGAAACAGG GACGCGTACC GGGACCCTTC AGGTTCTCGA TTATGTCGCT    21900
CCACGTCAAA AGCTTGTTGG ATCTCGTGGC GGTGGGACAG GGGCCTACAT TGCCTATTC     21960
TTCTTCGCGA TGCATTTCCA ACAAAGTATG CTGGGTATTC AATAATCCC TTCAGAAAAA     22020
TGCCCATGTT TGTACCGATG CCACAACTC CCATGGAAAA CCTGTCCAGC GTCTGTTCCA     22080
AAGTTCGGTT TGCGTCCACA CTACAGTGGG CCGTTCTGGG AAGTAAGCAT TTATACGGGG    22140
GTACCGTCTG ACATATGTGT TCAGGGGAGG CCTCTGGGAC TTGGGAGCAA ATAACGATGC    22200
CCCCCGTTAA ATCAAAGTGG GTCTTCACCT TTTCTCCGAA ATAATACACT TCCACCACTA    22260
GGGGCACAAG CTTGTCACCC ACTTTGTAAA TAGCCTGTTT CTTACTCAGG TATGCTGCCA    22320
CGGATTGGGT GGCGGTTAAG ACCTTGGGCC TCATGTCGCT TCCATACCAG TAAAATGTCT    22380
GGTCAGCTTT CTCTTGGTCC TCGACGTCCC GGTCATCACG ACACAACGGT GGAATACAAT    22440
CAATAAAATC ATCCACATTG TCGGAAGCTT GGAAAGATGA ACCCATGACA GAGGCCCCAG    22500
GTGCCGAACT CTCAAGGGGA TGCGTGGCGG GAAGTACTGA GACACTCTCC GTGGACCCCT    22560
```

```
CCTCACCTCC CTCCGACTGC ATCGGGCCCT GAGGGCTCGC AGTTTCACAC AGAAGTTCAC  22620

TCAGGTCGCC TAAGTCAGGA AGCTCCTGGC CTGAACCCAT GACAGAGGCC CCAGGTGCCG  22680

AACTCTCAAG GGGATGCGTG GCGGGAAGTA CTGAGACACT CTCCGTGGAC CCCTCCTCAC  22740

CTCCCTCCGA CTGCATCGGG CCCTGAGGGC TCGCAGTTTC ACACAGAAGT TCACCCAGGT  22800

CGCCTAAGTC AGGAAGCTCC TGGCCAACAT CTGACAAGAG ATCTAACAAA CACCCCTCAA  22860

TGTGATCCAC CATCGGTAGG CAATCATCCA GCCCACTGAC ATGACTGGGG ACGGGGCCTT  22920

CTGGGGAAAA TGGGGTTTGC GACTGTCCAG CAGGCGGCGC TAATAAGCCT TGTGTCTCAT  22980

GTGGAAAAAT AACAGGAGAA GGTAAACCCC CCGTTGGCAA ACATAGATCC GTCGGGGTGT  23040

GCACGTGTAA TGGGCCCTGC ACCTGGCTCG TGGAGGGACG CGGGGAATCC GGAGCTAATA  23100

AGCTCGATGA CTGACCAGAT GACCCAAACC CCGACGGTTC TGGCTCTTCA AAAAACAAAC  23160

TGTGCATATC CCTCCCTACA AAACCCTGAG CCCCCACCCA AAGTTCGTTT TCGCTGTCAC  23220

TCGATTCCGT ATCTTCGCTC TGTGACCGTG ATGAAACTTC AGCTGCGGAG GATGTTGTGG  23280

GCGTGGCGAC TGCCGCCGCC TGTTTCCTGG CGGCCTCCCT AAACAAAAGT TAATTACACA  23340

AAGGTAAGTC TGAGTGACAT CTCCAATTTC CCGTGATGCC CGCTGCACGT ACATCCCGCC  23400

GCCCACACAA CCCACCGCCC AGTACATCAA CCATCCTACC TCTGGGCTTT TTTTCTAAGG  23460

CTCCTTCTAA GTGCCTTTTC TCTGTGTTTG TCATCATGGG GATAGATCCC AAACAATGCT  23520

TTTAGCATGT TTTTCATGGC TGGTTCCTGC GTCAAGTACA CAAGACATCC TTCACATCCC  23580

TTGTATGGCC TAGGTGTCAT AATCCAGCGG TTGAGTTTCA TTTTTCCCTT ATAGATGGTA  23640

AAGGGCCTCT CCTGTCTGGC TCGATTGGCG GTCCTTAATA GCCGTCCAAA GCAGCCCAGG  23700

CCAGTCTCAG TCTCCGGGAT TTCTGGCAGC CCGTGCCTAC GTCGCTCCTC CAAAAATGCC  23760

TCATAGAAGT CATCGAAGCC TTCTGGCATT CTCTCCCGCC GGTTTCGACC CGGCACGGTG  23820

AATATTCTCT TTTGTTCATC CAACCACCCT ACCCCCAGA AGCGTCCACT GTCTAAAGCA  23880

TCTATAATAA AGTCCGTGAG CCATTCCGAC TCCGTGTAGC GAGGCATCTT TTTAGGCAAA  23940

AGCCACGACA CAAAACACCT TTTCCGTGGG CGACTTTCTC GCCACAACTA GCTGGACCCC  24000

AACCCCACTG GCACGTAGAC TCTGTGCCAT CTAACAACAA AACTCAATAT ATGCAGCTCA  24060

ACACCGCCCC CCCCAGCCGG TTGTCGGGCT GCGGAAACTT GTGGTTAGAA CTCACTACGG  24120

AAAAGGGAAC CAATGCAGTT GAACTACTGG CACACACCCA TAACCCGGGA CAGCACCCAG  24180

GCACTGTCCA CCCTCTAATA CAAGCGGCCT TTGGACGCGA GGGAGGGGTG TCATGGTCAA  24240

CAAACCAAGA AAAACACATG TATTATTCAA TTAGCCAACA ACTTTATTTA TTACCGACAG  24300

GAGACATGAG ATACATAAAT TTCCAACCGT GCATAGGGCC AATACCATCT GTGGAGCGTT  24360

AAGTGCCCTG TGGAGTTTTC GCCTAATTAG CTGAATCTCG ACCCCATTG CGGCCAGCAT  24420

GCTCACGAGG AATAGGCAGC AGAGGCAGGA CCTAACTAGG AGCATATCCG GACCTGATCC  24480

AAGTATGTGC ACCAAGGTGA GCAACACTGC CGCCAAAGGC AGGAGAACAA ATAGCGCTCG  24540

TCGGGAGGCG ACGGATACGC CCACGCATGA CAGTAACCCA ACATAAAATA GCGTCATATA  24600

CTTATCCAGG CCAATCAGGA CCGGAGTCAG CAGGCCGATC GAGGCCGTCG ATATCAGGGT  24660

GGCCAGCAGT AAGGTCACAA ACACGACAAC CTCGCGCCTA CAGTAGGCCC AGGCCTGGAA  24720

CACTGAATAG GTGATGTACT TCCCGGGCAT GATGAATATG GCCCTCCTCC TTTGCATTCC  24780

GGCCCTGATG TACACATGCT GTTCCAGGTG CCTAAATGCC AAAAGTCCCC CGACCAAGAA  24840

GACAATGAAG GGCAGCCAGA AAACGCCGGA CACAAAGACC TTCTTAAACA ACAGAAGGTA  24900
```

```
GTACACCATA AATGCTCCGC AGAAGCCCAG CTCATAGTAC CTGTGTACTA TTGGCGGCGC   24960

CTGATACACC GCCGTTGCGG TGGCTAGCGG ATAAGGTAAC AGCAGTAAAC AGTTAAGTAC   25020

GCACAGACCC GGTATGAAGG GCACACGAGA AAATGTAAAC CCAGAAAAGG CCGCGCAAAC   25080

TACAGCAGCA AACACTGCTG ACGCGCAGAT CCATTCCAGC CTCCGGTCCA GCTGTTTTTG   25140

CGCCGCAGGG CACAGACACA TGCATATCAG GGCCAAGTGC GTGACTGGCA GCGACCAGAA   25200

AAACACGGCC GTGATCTCTG TGGTAAAGAG TGTGAACGAG TACAGGGCCT TGAAGATAAA   25260

ACACCACAGA AAGGGGGTCG CCGCCAACGT CCCGCTCAGA TAACTGAAGA GCGACAGAGC   25320

GCGCTCACTG TCCAGGCGGC ACATGGTGTC AAATCAGGGG GTTAAATGTG GTTTTGGGCA   25380

CCTTCCCACG ATCCCTGGAC TGGCTCGAGT CTGAGCGCCT CTTGTGAGGC CTCTTTGTGC   25440

TGTCCTTAGT TGGCGCCGCT GGGGGGCAGC TGGTGACAGA GGCAGCGTCC TCAGAGGCGT   25500

CCTCCAGCGG CCCAAAGGGA CCAACTGGTG TGAGAGGGGG AGAATCCGGA GACTCCAATT   25560

CCGGCTGCCT CCTGGAGTCC GGTATAGAAT CGGGAACCTT TTGCGAAGAC TCGCCTCCCT   25620

CGGCAGACAC AGATCGGTTT ACCTCTAAAA GTAGGACACT TAACTTTACG TCACCTGATT   25680

GGCAGCCAGT GGGCACACCT TCCACTTCTA ATATTTCGTT GGAGTGCCAA ATCAGCCCGG   25740

GGGTAAACCA ACCCGGGACT TTACACAGTC TCAGGGCGGC GATTAAGGAC TCCAGGCTAA   25800

CCCGGCTCAG GGCGTCGGTG TGCACCACGC CCACATCCAC CGACTTCTTC CCCTTCAGAC   25860

CATCCCAGCC AGAAACGGGT TTGGTTTCTG GCTTGAAATC AATGATCTTG CTCACGCCAC   25920

CAAGAGAAAA TGTCACGATC GACAGCGTCT CGCTGACAGA CACAGTCACC GTTTGGTCCT   25980

CTTTTGTTTT TTGCTGCCTT AGCCACTTAA GTAGGAATGC ACCCGTTTTG CCACAGAGGA   26040

GAAGCCTGGT GGTCCTACCA CCGGCTTCCA TCCGATCGTG GAAAGGTAGG ATACCCTTTT   26100

GGTCCACCAC GCTTTTGTGC ACGGTGGAGG TGAGGTTGTC CCCGTAGGAA ATGGTGGTCC   26160

TGACGAACTG CGGTTGGGCC CCCGTATCGC ATGCCTCCCC CTTTCGATAA AAGGCTATGC   26220

CAGCGTCGAG TACATTCGCA CCGAATAGCT CACGCGTGTG CGTGAAGCCG CTACCGACGG   26280

ACGTATTCCT GAAGCTGAAG CTAACGTCTC CACTGCCTTC CGTGTGTCCC ACCAGGGGCG   26340

TAAGGGCATT CTTTATTCTT AACCCCAGAA CGCCAGCTGT CCCCACGCTG ACAGCACAC   26400

TGAGGGTTGG CGTGCAAGCC GATCCGTGCA CTTGCACTAC TCCGGTTTTA GTGGCACTCT   26460

TAATGTGTTC ATTGACCCTC CTGATTTTAG ACAGGAGGGT CACGTCCACC CTGACCCCAT   26520

AGTGAAAATC CACAGGCATG ATTGCGGCCG TAGACGCACA GAGAAATCAC AGGAAAGCTG   26580

CGCGCACACT GGGTGATCTG GAGACGATAG ACTGCCTTAA ATAGAACTTT TAGGGGAGGT   26640

GGAAGTGTGC GACATGGACA GGTTAACCTT CACAAATCGT CAGTCACACA CGTGGTGTAA   26700

TCAGAATTGT CTCGCTCAAA AAAATTCACA GCCTTGAAAC TGCCGGTGTA TGAGAGGGGG   26760

CACGCTTCTG GCGGAGGCGT GCCAAATATG GGAGGAACGA AAATATCACG CAGAATCCTG   26820

TCAGCGGTGG CTTCCAGGAA CCTCCGGATG TCCACCACGT TAACAAGCGT CACCCCGGCC   26880

GCCTTGGCCT GGATAAACCG AATCTCAATA TTCACTGCCT CCCTGAACAG CGCCTGGACC   26940

TCTGCGTGAC TGGGTTTTTC CTGTATCTCC ACCATAGTGT TGTACAACAT ACTGGCGGCC   27000

TTGGTGTGCA GCAGCTCGTC CCTGGAAATG TAATCGTTGG CAAGGCACAC CCCGGGCATG   27060

ATGCCTCGCA CCCTGCACAA ACTGATAGAG TAGAAGGAGC TAATAAAGTA TATCCCCTCC   27120

ACAATCAAAA ACATCAGAAT CTTCTGAGCT TTGGTGGTCG CCTTACGCAC CCTGGAGTGA   27180

AGCCACTCCA GCTTCTCGCA AAGGGCGGGG TCCAAAATGA TCTTGGCAGC ATATGCTAGA   27240

AGTTCGCCTC GACTGTTGTT GAAAAATATC TTCAAGATAT TGGCATACAC GACACCGTGG   27300
```

-continued

```
ATATTCTCCA TGGCAACCTG TTCGGCATAA TAGTGGGCCA CGTCGTGGCT GTTAAAATTT   27360

GTGACAAGGT CCTCAATGTT AAAGTTAACT AGGCGTTCGG CCATTCCCAA AAACGTAAAC   27420

AAAAATCTAT AAAAGTCCTT GTCGGCATCG CTGAGCTGGT GCACGTGGGA AACATCAAGG   27480

TGCAGGGGTA TCTGGCTAGG AAACCATCGG TTCTGCCAAG TCTCGCGCGT TAGCGCCAAA   27540

AATCCGTCGT GATCGCTTGT ATACAGAAAT CGATCAACTG AATCCATTGG CCTCACCCGG   27600

CTTGCAGAGA CCTACCTACT GACAGACCAG GCACTCGGGG TCTGCCGCGC AGGACTCCTC   27660

CTCCGGGTTT TTAGGTCCGG GTAACCACGC CCCATCTTGT TTCATCCCAG AGTGAGGCGG   27720

TGACCCTGGA TCTGCCAGGC ACTGAAGAGC CGTCAGACTA GATTGCTTCT GAACCCTACA   27780

GTAGTACATG AGGGTTTTTA GACCAAGCCT GTATCCATGT AGCAGCAGGT CCCTAAGATA   27840

GCTCGCATTC CTGACTCTGT CCTCCTTGAG GAAGAAGCTC ATGGACTGGC TCTGGTCTAC   27900

AAACGGCGCC CTGGCACGAG CCCTGTCCAG TAGCTTAAAT GGACAGTAAT CAAAGGCTGT   27960

TAGGAATACC CTATATCTTT CCCTGTGATG CTTGGGAAC GTGGAAACGT CCCCACCATA    28020

CTGTCTAACC ACCCGAAGGT CGTCGGGGAG AACCTTCTTA AAAAAAGTCA CATTGGGCCT   28080

CAACACCTCT TCTTTATTGG TGACCTTGGA AGATATATTA GCAAAAAAGG GGTACACAGA   28140

CTCGGCATAG CCAGTTACTT GCGAGGTCCC AGCCGTCGGC ATCACCGCCA GAAACTGAGA   28200

ATTGAATATG CCATGCTCGG CAATGCTCTT TCCCAACGCG TCCCAGCGAT GGCGTGGTAC   28260

AAACGAAGCA TCCTCCCCCT CCCATGTTTG CCAATGAAAC CTGCCCTTGG CGAAGTTACT   28320

GACCTCCCAG CCATGAAATG GGACACCCTG TCCCTCCAAA ACAAGGTTGT GACTAGTCTC   28380

CACCGCGGTG TAGTACATAG ACTGGAATAT ATTCTTGTCT AACTCAGCGC TCTCAGCATC   28440

GAGGTACCCG TACCCCAATT CCGCAAACAC ATCCGCCAAC CCTGAACAC CAATCCCCAT     28500

AGACCTCTCC TTTTGACCTC GCTCGACCCC CGGTGTTGGA TGGGAACCAC CCAGAATGCA   28560

GGCGTTGATG ACGAGGACTG CCACCCTTAC TGCGTCGCCC AAGGCCTCAA AACAAAAAAA   28620

CGGCCTGTTG GCGTCCGTGG TGCCAACCCT CGCGCTTTCA ACAGTTCTCA GACACTTTGG   28680

AAGGCAGATA TTTGCCAGGT TGCACACCGA AGTGTTTCTT CCTGGCAGTT GGACTATCTC   28740

TGCACACAAG TTTGAGCAGT TAATGGCCAT GCCCTGAGTG TCGGTCCAGT GGTGTTCATT   28800

GAGCGCTTCT TTTAAAAGCA CGTACGGTGA GCCTGTCTTT ATGATGGTGT GGATAAGAGT   28860

GAACATCATA GACTTCAACG GCATGCAACT AACGTACTTT CCAGCCCGCA CCAGGCGCTC   28920

GTATTCGTTA TCGAACGCAG CACCGTATAG CTTAATCAAA TTGGGGCGG TGGCTGGATC     28980

GAACAAATAC CATAACTTGG ATGGGTCCTT TTCATACATC CTGAAAAACA ATGTTGGGAT   29040

GCACACGCCC TGAAAGAGAC TGTGACATCT GTCGGGATTC TCCGGTAGTT TGGCGTTCAA   29100

AAAATCACAG ATTTGACTGT GCCAGAGTTC CATGTATGCG CTCGCGCCAA CGGGCCTGAT   29160

GTTATTGTCA TTGAAATAAT GAACCTGGGC ATCCACCAGT TTGAGGCAAC TGGCTATGTT   29220

CTTTTGGTGG GAGAATGACG TAACATCCAG ACCCACGCCT GACTTACTGG CCAGCAACGG   29280

ACTCATATCG TGGTACAGGG CGTCCAAAGT ACCCGACTCA TTCATCATGG AGGGCTGCAG   29340

AATAAAACAG CTGGCGAGTT GTCCGCCTTC GACTCCAGCT GAGCGCAGTA TTGGCGTGGC   29400

GCAGCACACG TGCTGCGCAG CGAGGTAGCC AAAAACGTAC TCCACTATAG CCATCTCAGA   29460

TACAGACTTA GCGTCCTCAA TAAGGTCCCG CGCCAACCAA TACAGGCATT CATGCTCTAA   29520

GCACTGACAG GCAACAAACA CGGAAACCCT CATAAACATT TGCGCCACGC TTTCATAGAC   29580

AGGCTCTGTC CCCATGGTCC TTAGGACGTA AGTATCATAC AACCTCACGG CCGATAGGTA   29640
```

```
GCCACAGTTA AGTGTGTCCT CGTAAGCTTT GGACCGTCTG TAGGCGCACA ACATATCTTC    29700

CAAGGCATCA ATGTTCTTTT GAATAAACGA TTCCACCCGA TGTCCCAACA CGCCTCGAAA    29760

AATCCCAAGA TACTGCTTGA GAGTCGCTGG GCACCTAGCC TCCATAATTT GGTGCCACAG    29820

CCGCCCCGCC ATGGCATTGG CCCGCACGTC CCACCCGACC CTAACCTTTA GAAAGTCTAT    29880

GAGAGATTGG GCACACATAT CAAAATCCGA CAATTGTCCC GCAGACACCT GAGACCCGCG    29940

TCGCTCTGGT GGGACAGCTC CCAAGTGAAC CTGACAAAAT GTCCGGACAG ACATGACCTT    30000

ACAGAAACAC AGTCCAGGGG CCACACGCGG CCTCAAAGTT CGCAAACACC AGTACAGGCA    30060

AGGACGTGCC CTTCACGTTC AGACTTTGGT GCACCGGATG AGAATCAAAG GGAACTGTGC    30120

CCAGCGTACA AACCGCCCCA AAAACAAGCC GATTTATATA CAGCTCGTGC CTCAGCTGAA    30180

TATACTTGGT CCGGATTACA TCCGTAAAGT GATCCTTTAT CATGGCCACA ACCTCCGCAA    30240

AGCCCTTCCC AGACTGGAAA AACGTCAGCG CCATAGATGG TCTCTGGTTC ACACGGAGAT    30300

AAACCAACGA GGCATAAATA GTAACGTTTA GGCCTGCCGG TTCCCGGCGC TGGACCATGG    30360

GACATGACTC ATCCAAATCA ACTAGCATAT CACAAGGGAG GGTCAAGCCT ACGTGTGCAC    30420

GGGGCTCGTC CCGGGCCAAC CCAACTCCCT TCATGGCGGA GGTGACCTTG GTCACGAAGG    30480

TACTGTGGAC ACTCTGGACC ATTGGACCTA CTGGGGTAAG GAGGGTATGA AACTCCCCAG    30540

TGTCCATGAG TTCACTCAAG TTAGGGATGA AATCCGCCAG GCCGGATCCA CTTCCGTACC    30600

ACACACCGGC CACTTTGTGA GTCTGTGGCG CTTTTGCCGC TTCCATTCCA GAGAGCATAA    30660

ACAGGGACGT GGGTGTTAGC AGCATATCCA TAGACGAGCC GTTGTCCTCC TGCTTGAATG    30720

AAAATAAAAA GGTTCCCAGA GGCTCCTGGG GACTAAAGGT CTGTGAATAC ACGAGGAAAT    30780

CTCCATAGGT CGGCTGCCTA AACGGCGCCT GCCGCAAGGC CTCATGCAGC GAGCCAACCG    30840

TGGGTCGTGT GGACGCCGCA TATTTAGAGA GTAAATCCCG CACCCCCTG GCAAACTCCG     30900

GTCCTCTAGT GAGGGATACC CGGTGAGTTG GTGGAGGTAA AGACCCAAC ACTTGCCTAC     30960

CCAGGCGAGC CGCATTTTCA GCCTGCACCT TCATATCCAC GCCGGCAATG GACGGCACAG    31020

ACGCTCTTGA AAAGCTTACC AAAGGCCTGA GTGGGGAGG CGGGAGCCTT CACCAGACAA     31080

AGCTGTTGAT GGAATTTCAA CTCCGAGGAC TGCCGGTGCC TGCCCTCTTA AACAGCAGCA    31140

CAACAGAGCA GTTTTTAAAT ACTGTTGCCC AACTGCCGAC GGACCTATCA AAATTTATAC    31200

GCGACTATCG CGTGTTCGCA CTGGTTCGCG CGGCGTATTT TTTAGAACCC CCTTCTAGCA    31260

TCGACCCCCT TGAGGCAGCG CGCGCTCTTG GACGCCTGGT TGATATATTA TCATCACAAC    31320

CACCGCAGAA CACCGCACCG GCGCAGCCAC CCACCTCCGA CGACACCCTG AATAACTGTA    31380

CATTGCTCAA ACTACTAGCC CACTACGCGG ATCAGATAGC AGGTTTCAAA ACCCCCGCTC    31440

TCCCTCCCGT GCCACCTGGA ATCATCGGCC TGTTCACATG CGTGGAACAG ATGTACCACG    31500

CATGTTTTCA GAAATACTGG GCAGCTGCAC TACCCCCAAT GTGGATACTG ACATACGACC    31560

CTCCCACTTC TCCGTTACAG GACTGGCTTA TAGTCGCCTA TGGTAACAAG GAAGGACTGC    31620

TACTCCCCTC TGGCATACCC TCGGAGGAGG TGTTAGCCAA AACATTAGTA ACAGAACACC    31680

ACGAGTTGTT CGTATCGCGG TCGAATTCGA CCGAGACCGC CGTCACCATG CCCGTATCCA    31740

AAGAACGCGC CCTCGCCATC TACCGGGTGT TCGCCAAGGG TGAGGTGGTG GCGGAAAATA    31800

CTCCCATTCT TGCCTTCACC GACGTGGAAC TATCCACACT CAAACCCCAC TATCTGTTCA    31860

TCTATGATTT TATCATAGAG GCATTATGCA AGAGCTACAC ATACTCATGC ACCCAGGCCC    31920

GCCTGGAATC CTTTTTGAGC CGAGGTATAG ACTTCATGAC TGACCTAGGT CAGTACCTAG    31980

ATACCGCTAC TAGCGGCAAG CAGCAGCTGA CGCACAGCCA AATAAAGGAA ATCAAATACA    32040
```

-continued

```
GGCTGCTAAG CTGCGGTCTC TCGGCTTCCG CGTGTGATGT TTTCAGAACT GTGATCATGA    32100

CCCTCCCATA TCGACCGACC CCCAACCTCG CTAACCTGTC CACGTTTATG GGATGGTTC     32160

ACCAACTGAC CATGTTCGGA CACTATTTCT ACCGGTGCCT GGGCAGCTAC AGTCCCACCG    32220

GCTTGGCCTT CACAGAATTG CAAAAGATAC TGACACGCGC CAGCGCGGAG CAAACGGAAC    32280

GTAACCCGTG GAGACATCCG GGTATCTCGG ACATTCCACT GCGTTGGAAA ATATCGCGTG    32340

CTCTAGCATT CTTCGTCCCT CCGGCCCCCA TAAACACTTT GCAGCGCGTG TACGCCGCGC    32400

TGCCCTCGCA ACTCATGCGG GCCATCTTCG AGATCTCGGT CAAGACCACA TGGGGAGGCG    32460

CCGTACCGGC AAACCTGGCG CGCGACATTG ACACAGGACC GAACACACAA CATATCTCCT    32520

CCACACCACC GCCCACCCTC AAGGATGTTG AGACATACTG TCAAGGTCTG CGGGTGGGAG    32580

ACACGGAGTA CGATGAGGAC ATTGTGAGAA GCCCGCTCTT TGCAGACGCG TTTACCAAGA    32640

GTCACTTGTT GCCTATACTG CGCGAGGTTC TGGAAAACCG CCTGCAGAAA AACAGAGCTC    32700

TGTTTCAGAT AAGATGGCTG ATAATATTTG CTGCCGAGGC GGCAACCGGG CTCATCCCTG    32760

CCAGGCGCCC GCTAGCCAGA GCCTACTTCC ACATCATGGA CATTCTGGAG GAGAGACATT    32820

CCCAAGACGC CCTATACAAC CTTTTGGACT GTATCCAGGA GCTCTTCACC CACATCAGGC    32880

AGGCTGTTCC AGACGCACAG TGTCCGCACG CCTTTCTACA GTCCCTGTTC GTCTTTCAAT    32940

TCCGCCCTTT CGTACTCAAA CACCAGCAGG GTGTAACCTT GTTTCTAGAT GGCTTGCAGA    33000

CATCCCTCCC CCCGGTGATA AGTCTGGCCA ACCTTGGAGA CAAGCTGTGT CGTCTCGAGT    33060

TCGAGTACGA CAGCGAGGGC GACTTCGTGC GCGTGCCAGT TGCACCGCCA GAACAACCAC    33120

CGCACGTACA TCTGTCGCAT TTCAAGAAGA CAATACAGAC CATCGAACAG GCCACCAGGG    33180

AGGCCACCGT AGCCATGACA ACAATCGCAA AGCCAATATA CCCCGCCTAC ATCCGGTTAC    33240

TGCAGCGGCT AGAATATCTT AACAGACTCA ACCACCACAT TCTCAGGATT CCCTTCCCAC    33300

AGGACGCCCT TTCTGAACTC CAGGAAACCT ACCTGGCGGC GTTTGCACGG TTGACAAAAT    33360

TGGCAGCGGA CGCAGCAAAC ACTTGTAGCT ACTCCCTCAC CAAGTACTTT GGAGTTTTAT    33420

TCCAACACCA GCTGGTCCCC ACGGCCATCG TTAAAAAACT GCTACATTTC GACGAGGCTA    33480

AAGATACCAC AGAAGCCTTT TTACAGAGCC TGGCACAACC CGTAGTGCAG GGACAACGGC    33540

AGGGGGCGGC TGGCGGGTCG GGTGTCCTGA CGCAGAAAGA ACTTGAGCTC TTGAACAAAA    33600

TAAACCCACA GTTTACAGAC GCTCAGGCTA ACATTCCTCC ATCTATTAAA CGTTCATATT    33660

CAAATAAATA TGACGTCCCT GAGGTCTCAG TCGACTGGGA AACGTACTCC CGGTCTGCCT    33720

TCGAGGCACC GGACGACGAA CTCCGTTTTG TCCCACTGAC GCTGGCAGGC CTCCGGAAAC    33780

TGTTTGTCGA ATAGAGGCCA TGGCAGCCCA GCCTCTGTAC ATGGAGGGAA TGGCCTCCAC    33840

CCACCAAGCT AACTGTATAT TCGGAGAACA TGCTGGATCC CAGTGCCTCA GCAACTGCGT    33900

CATGTACCTG GCGTCCAGCT ATTATAACAG CGAAACCCCC CTCGTCGACA GAGCCAGCCT    33960

GGACGATGTA CTTGAACAGG GCATGAGGCT GGACCTCCTC CTACGAAAAT CTGGCATGCT    34020

GGGATTTAGA CAATATGCCC AACTTCATCA CATCCCCGGA TTCCTCCGCA CAGACGACTG    34080

GGCCACCAAG ATCTTCCAGT CTCCAGAGTT TTATGGGCTC ATCGGACAGG ACGCGGCCAT    34140

CCGCGAGCCA TTCATCGAGT CCTTGAGGTC GGTTTTGAGT CGAAACTACG CGGGCACGGT    34200

ACAGTACCTG ATCATTATCT GCCAGTCCAA AGCCGGAGCA ATCGTCGTCA AGGACAAAAC    34260

GTATTACATG TTTGACCCCC ACTGCATACC AAACATCCCC AACAGTCCTG CACACGTCAT    34320

AAAGACTAAC GACGTTGGCG TTTTATTACC GTACATAGCC ACACATGACA CTGAATACAC    34380
```

```
CGGGTGCTTC CTTTACTTTA TCCCACATGA CTACATCAGC CCAGAGCACT ACATCGCAAA      34440

CCACTACCGC ACCATTGTGT TCGAAGAACT CCACGGGCCC AGAATGGATA TCTCCCGCGG      34500

GGTGGAATCA TGCTCCATCA CCGAAATCAC GTCCCCTTCT GTATCCCCCG CGCCTAGTGA      34560

GGCACCATTG CGCAGGGACT CCACCCAATC ACAAGACGAA ACGCGCCCGC GCAGACCTCG      34620

CGTCGTCATT CCTCCTTACG ATCCGACAGA CCGCCCACGA CCGCCTCACC AAGACCGCCC      34680

GCCAGAGCAG GCAGCGGGAT ACGGTGGAAA CAAAGGACGC GGCGGTAACA AAGGACGCGG      34740

CGGAAAGACG GGACGTGGCG GAAATGAAGG ACGCGGTGGC CACCAGCCAC CAGACGAGCA      34800

CCAGCCCCCA CACATCACCG CGGAACACAT GGACCAGTCC GACGGACAAG GCGCCGATGG      34860

AGACATGGAT AGTACACCCG CAAATGGTGA GACATCCGTT ACGGAAACCC CGGGCCCCGA      34920

ACCCAATCCC CCAGCACGGC CTGACAGAGA GCCACCGCCC ACTCCCCGG CGACCCCAGG       34980

CGCCACAGCG CTGCTCTCTG ACCTAACTGC CACAAGAGGG CAGAAACGCA AATTTTCCTC      35040

GCTTAAAGAA TCTTATCCCA TCGACAGCCC ACCCTCTGAC GACGATGATG TGTCCCAGCC      35100

(2) INFORMATION FOR SEQ ID NO:20:

(i) SEQUENCE CHARACTERISTICS:
        (A) LENGTH: 32207 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:20:

CTCCCAACAA ACGGCTCCGG ATACTGAAGA TATTTGGATT GACGACCCAC TCACACCCTT        60

GTACCCACTA ACGGATACAC CATCTTTCGA CATAACGGCG GACGTCACAC CCGACAACAC       120

CCACCCCGAG AAAGCAGCGG ACGGGGACTT TACCAACAAG ACCACAAGCA CGGATGCGGA       180

CAGGTATGCC AGCGCCAGTC AGGAATCGCT GGGCACCCTG GTCTCGCCAT ACGATTTTAC       240

AAACTTGGAT ACACTGCTGG CAGAGCTGGG CCGGTTGGGA ACGGCACAGC CTATCCCTGT       300

AATCGTGGAC AGACTAACAT CGCGACCTTT TCGAGAAGCC AGCGCTCTAC AGGCTATGGA       360

TAGGATACTA ACACACGTGG TCCTAGAATA CGGTCTGGTT TCGGGTTACA GCACAGCTGC       420

CCCATCCAAA TGCACCCACG TCCTCCAGTT TTTCATTTTG TGGGGCGAAA AACTCGGCAT       480

ACCAACGGAG GACGCAAAGA CGCTCCTGGA AAGCGCACTG GAGATCCCCG CAATGTGCGA       540

GATCGTCCAA CAGGGCCGGT TGAAGGAGCC CACGTTCTCC CGCCACATTA TAAGCAAGCT       600

AAACCCCTGC TTGGAATCCC TACACGCCAC TAGTCGTCAG GACTTCAAGT CCCTGATACA       660

GGCATTCAAC GCCGAAGGGA TTAGGATCGC CTCGCGTGAG AGGGAGACGT CCATGGCCGA       720

ACTGATAGAA ACGATAACCG CCCGCCTTAA ACCAAATTTT AACATTGTCT GTGCCCGCCA       780

GGACGCACAA ACCATTCAAG ACGGCGTCGG TCTCCTCAGG GCCGAGGTTA ACAAGAGAAA       840

CGCACAGATA GCCCAGGAGG CTGCGTATTT TGAGAATATA ATCACGGCCC TCTCCACATT       900

CCAACCACCT CCCCAATCGC AACAGACGTT CGAAGTGCTG CCGGACCTCA AACTGCGCAC       960

GCTCGTGGAG CACCTGACCC TGGTTGAGGC GCAGGTGACA ACGCAAACGG TGGAAAGTCT      1020

ACAGGCATAC CTACAGAGCG CTGCCACTGC TGAGCATCAC CTTACCAACG TGCCCAACGT      1080

CCACAGTATA CTGTCTAACA TATCCAACAC TCTAAAAGTT ATAGATTATG TAATTCCAAA      1140

ATTTATAATA AACACCGATA CACTGGCCCC ATATAAACAG CAGTTTTCAT ATCTGGGGGG      1200

TGAACTGGCA TCTATGTTCT CCCTTGACTG GCCTCACGCA CCTGCAGAGG CGGTAGAGCC      1260
```

-continued

```
ACTACCCGTG CTGACTTCTC TGCGAGGTAA AATCGCAGAG GCGCTGACGC GTCAAGAAAA    1320

CAAAAACGCT GTAGATCAAA TTCTAACCGA CGCCGAAGGC CTCCTTAAGA ACATTACCGA    1380

TCCAAACGGC GCACACTTCC ACGCCCAGGC CGTATCAATT CCAGTGTTAG AAAACTACGT    1440

ACATAACGCG GGGGTCCTTC TCAAGGGCGA AAAGAGCGAG AGGTTCTCCC GGCTGAAGAC    1500

CGCCATCCAA AACCTGGTAT CCTCCGAATC ATTTATCACC GTGACCCTAC ACAGTACAAA    1560

CCTTGGAAAC CTAGTTACCA ACGTACCAAA ACTTGGTGAG GCGTTCACCG GGGCCCGCA    1620

CCTCCTGACA AGCCCGTCCG TGAGACAGTC CCTTTCCACC CTGTGCACAA CCCTGCTGCG    1680

AGATGCCCTG GACGCCCTGG AAAAAAAGGA TCCGGCCCTT CTTGGTGAGG GGACCACGTT    1740

GGCGCTGGAG ACACTCCTAG GATACGGGTC GGTGCAGGAC TACAAGGAGA CGGTACAGAT    1800

AATATCCAGC CTTGTGGGCA TCCAAAAATT AGTCAGGGAC CAGGGCGCGG ACAAGTGGGC    1860

CACTGCCGTG ACAAGGCTAA CTGACCTCAA ATCAACTCTG GCCACGACCG CCATCGAGAC    1920

GGCTACGAAA CGGAAACTAT ACAGATTGAT CCAAAGGGAC CTCAAGAGG CTCAAAAACA    1980

CGAGACCAAT CGGGCCATGG AGGAATGAA GCAGAAAGTA CTGGCTCTTG ACAATGCGTC    2040

TCCGGAACGT GTCGCCACCC TCCTGCAACA GGCTCCCACC GCGAAGGCTA GAGAGTTTGC    2100

AGAGAAGCAC TTCAAAATAC TACTCCCCGT ACCCGCGGAC GCCCCCGTCC AAGCGTCTCC    2160

AACGCCGATG GAATACAGCG CCAGCCCCCT CCCGGACCCA AAGGATATAG ACAGAGCTAC    2220

ATCCATCCAC GGGGAACAGG CGTGGAAGAA GATACAGCAG GCGTTCAAGG ATTTCAACTT    2280

CGCCGTCCTG CGGCCCGCTG ACTGGGATGC CCTGGCAGCG GAGTACCAAC GCCGTGGTTC    2340

GCCCCTTCCG GCGGCCGTGG GTCCAGCGCT CTCAGGGTTC CTGGAGACGA TCCTAGGGAC    2400

GCTGAACGAC ATCTACATGG ATAAGCTCCG CTCCTTTCTG CCCGACGCGC AGCCTTTTCA    2460

GGCGCCGCCC TTCGACTGGC TAACGCCGTA TCAGGACCAA GTCAGCTTTT TCTTGCGCAC    2520

CATAGGGCTG CCGCTGGTGC GAGCGCTGGC CGACAAGATC AGCGTGCAGG CACTGAGGCT    2580

TAGCCACGCG CTCCAGTCCG GCGATTTGCA GCAGGCCACG GTGGGCACGC CCTGGAGCT    2640

CCCTGCCACA GAGTACGCGC GCATCGCCTC CAACATGAAG TCCGTGTTCA ACGACCACGG    2700

ACTTCAGGTG CGATCAGAGG TCGCGGATTA TGTGGAGGCC CAACGAGCCG ACGCACACAC    2760

GCCACACGTC CCACGTCCAA AGATACAGGC ACCAAAGACT CTGATTCCAC ATCCGGACGC    2820

AATCGTCGCG GACGGACTAC CCGCCTTTCT TAAGACGTCC CTACTGCAGC AAGAGGCCAA    2880

ACTTCTGGCG CTACAGCGGG CGGACTTCGA GTCGCTCGAG AGCGACATGC GCCGCAGA     2940

GGCCCAGAGA AAAGCATCGC GCGAGGAAAC CCAGCGCAAA ATGGCACACG CCATCACTCA    3000

GCTCTTACAG CAGGCACCCA GTGCGATCTC GGGGCGCCCG CTATCCTTAC AGGACCCGGT    3060

GGGCTTCCTC GAGGGCATCA TATACGACAA GGTCCTGGAG CGCGAATCCT ACGAGACGGG    3120

TCTCGAGGGA CTGTCCTGGC TCGAGCGACA CATCAAGTCC ATCACCGTAT ACGCTCCCGT    3180

AGAGGAGAAG CAAAGAATGC ACGTGCTGCT GGACGAGGTG AAAAAGCAGC GAGCAAACAC    3240

TGAGACCGCT CTCGAGCTAG AGGCCGCGGC TACGCACGGC GACGACGCTA GACTCCTGCA    3300

GCGAGCGGTC GATGAGCTGT CACCGTTGCG CGTTAAGGGG GGGAAGGCCG CGGTGGAATC    3360

CTGGCGGCAG AAAATCCAAA CCCTGAAATC CCTGGTACAG GAAGCGGAGC AGGCCGGCCT    3420

CCTGTTGGCC ACCATAGACA CGGTGGCCGG CCAGGCCCAG GAGACCATAT CACCATCCAC    3480

ACTCCAGGGA CTGTACCAAC AGGGACAGGA GGCCATGGCG GCCATTAAGC GGTTTAGGGA    3540

CTCGCCCCAG CTAGCTGGCC TGCAGGAAAA GCTGGCCGAG CTACAGCAGT ACGTCAAGTA    3600

CAAGAAGCAG TATCTGGAAC ACTTTGAGGC CACCCAAAGC GTAGTGTTTA CAGCCTTTCC    3660
```

```
GCTCACACAG GAGGTTACGA TCCCAGCCCT GCATTACGCG GGACCTTTCG ACAACTTGGA   3720

GCGGCTCTCA CGATACCTAC ACATCGGCCA GACGCAGCCG GCTCCGGGAC AGTGGCTCCT   3780

GACACTTCCC ACATTCGACC CCACGCGCCC GGCCTGCGTC CCAGCCGGCG GCCACGAACC   3840

CCCGTTGCAC AGACAGGTGG TGTTCTCCAG CTTTTTGGAG GCCCAGATCC GATTAGCGTT   3900

GTCCGTAGCG GGCCCCGTGC CTGGACGGGG TCTGCCCGGA ACACCGCAGA TCCGAAGGGG   3960

CGTGGAGGCT GCCGCTTGTT TCCTCCACCA GTGGGACGAG ATATCTCGCC TCCTTCCAGA   4020

GGTACTGGAC ACCTTTTTCC ACAACGCGCC CCTTCCCGCA GAGTCTTCCT CCAATGCTTT   4080

CCTGGCCATG TGCGTATTGA CGCACCTTGT CTACCTAGCT GGGCGCGCCG TCTTGGGCCC   4140

ACGGGAGCCG GAGCACGCCG CCCCGGACGC GTACCCAAGG GAGGTGGCGC TGGCCCCGCG   4200

CGACCTGACC TACCTTCTAC TGGCCATGTG GCCATCTTGG ATCTCGGCAA TTTTGAAACA   4260

GCCTTCGCAC GCGGAGGCGG CGCACGCATG TCTTGTCACG CTGCCAACAA TGCTCAAGGC   4320

TGTGCCGTAC CTCACGCTGG AAGCCTCAGC TGGACCACTG CCGGCGGACA TGCGCCACTT   4380

CGCCACGCCA GAAGCGCGTC TGTTTTTCCC CGCGCGATGG CACCACGTCA ACGTGCAGGA   4440

GAAACTGTGG CTGCGTAATG ATTTTATGTC GCTGTGTCAC CGTTCCCCGG GGCGCGCGCG   4500

CATAGCCGTC TTGGTGTGGG CCGTCACTTG CCTAGATCCT GAGGTAATAA GGCAGCTGTG   4560

GTCCACCTTG CGGCCCCTTA CTGCGGATGA ATCCGACACG GCTTCTGGAC TGCTGCGGGT   4620

GCTAGTAGAA ATGGAGTTTG GTCCGCCGCC CAAGACGCCG CGGCGGGAGG CGGTGGCGCC   4680

CGGCGCAACA CTGCCACCGT ACCCCTACGG CCTTGCCACC GGCGAGCGCC TGGTCGGCCA   4740

GGCGCAGGAA CGCTCTGGCG GCGCTGGCAA GATGCCGGTG TCCGGGTTTG AGATAGTTTT   4800

AGGCGCACTG CTGTTCCGCG CCCCCCTACG CATTTTCAGC ACCGCATCAA CCCACAGGAT   4860

CTCAGATTTC GAGGGCGGTT TCCAGATACT GACTCCTCTC CTGGACTGTT GCCCAGATCG   4920

CGAGCCATTC GCCTCCCTGG CCGCCGCACC ACGAAGGACG GTGCCACTGG GAGACCCGTG   4980

CGCCAACATT CACACCCCCG AAGAGATACA GATCTTTGCG CGTCAAGCCG CCTGGCTTCA   5040

ATATACCTTC GCAAATTACC AGATCCCCAG CACCGACAAC CCGATACCGA TCGTTGTGCT   5100

AAACGCTAAC AATAACCTTG AAAACAGCTA CATCCCTCGC GATCGCAAAG CGGACCCGCT   5160

ACGACCATTC TATGTAGTCC CTCTGAAGCC GCAGGGTAGA TGGCCTGAAA TAATGACCAC   5220

AGCAACAACC CCCTGCCGCC TACCGACATC GCCAGAAGAG GCGGGATCAC AGTTCGCCAG   5280

ACTCCTTCAG AGCCAGGTGA GCGCCACATG GTCTGACATC TTCTCCAGGG TTCCCGAGCG   5340

CCTCGCTCCC AATGCGCCTC AGAAGAGTTC CAGACAATG TCAGAAATCC ACGAGGTCGC   5400

CGCCACGCCG CCACTCACAA TCACCCCAAA TAAACCGACC GGAACCCCTC ACGTCTCCCC   5460

GGAGGCTGAT CCAATAACAG AACGCAAACG CGGACAGCAG CCGAAGATTG TCGCGGACAA   5520

CATGCCTAGT CGTATTCTCC CGTCGCTACC GACCCCGAAA CCCAGAGAGC CTAGAATCAC   5580

GCTACCCCAC GCACTGCCCG TTATATCACC CCCAGCACAT CGCCCGTCGC CTATACCGCA   5640

TCTGCCAGCA CCGCAGGTAA CGGAGCCCAA AGGGGTTCTC CAAAGCAAAC GTGGAACTCT   5700

CGTGCTGCGG CCCGCCGCGG TCATTGACCC ACGGAAGCCC GTCTCGGCAC CGATCACGCG   5760

ATATGAGAGG ACGGCGCTCC AGCCCCCCG GACTGAGGGC GAAGGCCGGC GCCCTCCCGA   5820

CACGCAACCC GTCACTTTAA CCTTTCGTCT CCCACCTACC GCACCCACTC CCGCAACTGC   5880

AGCCCTAGAA ACCAAAACAA CTCCCCCATC CACGCCCCCA CACGCCATAG ACATTAGCCC   5940

ACCACAGACA CCTCCCATGT CCACCTCACC TCACGCGAGA GACACAAGCC CCCCCGCAGA   6000
```

-continued

```
AAAGCGGGCC GCACCCGTCA TTCGAGTAAT GGCGCCCACG CAACCGTCGG GAGAGGCAAG   6060

AGTCAAGCGA GTGGAGATCG AACAGGGCCT TTCCACACGC AATGAAGCCC CTCCCCTTGA   6120

ACGCTCGAAT CACGCCGTGC CCGCCGTTAC CCCAAGGCGC ACCGTAGCCC GCGAAATCAG   6180

GATCCCGCCG GAGATAAAGG CGGGTTGGGA CACTGCACCG GACATTCCTC TGCCCCACAG   6240

CTCCCCGGAG TCATCCCCAC CGACTTCCCC CCAGCCTATC CGCGTGGATG ATAAATCGCC   6300

TCTTCCCAAC CTCGTAGAGA GATACGCGCG GGGTTTCCTG GACACGCCCT CTGTAGAGGT   6360

GATGTCCCTG GAAAATCAGG ACATCGCCGT GGACCCCGGA CTGCTAACCC GCCGGATTCC   6420

ATCCGTGGTG CCCATGCCCC ATCCAATTAT GTGGTCACCC ATAGTACCCA TCAGTTTACA   6480

AAACACAGAC ATAGACACTG CAAAGATAAC ACTGATTAGT TTTATTAGAC GCATCAAACA   6540

AAAAGTGGCC GCCCTATCGG CGTCCCTGGC GGAGACGGTT GACAGAATAA AGAAGTGGTA   6600

CTTGTGACTC CACGGTTGTC CAATCGTTGC CTATTTCTTT TTGCCAGAGG GGGGTTTCCT   6660

CGCGTCGGCC ACCGCGGGGG CGGCCGTTTC CGTCGTGGAT GAGAGGGTTG TGAGAATGTC   6720

TGACGCCGGC GACAATGAAT GGGGACCAGA GGACAGGGTG GTTATACTGC TTCCCGAGAC   6780

CCCCAGTGAG TCCTGGCCCC CGGGCGTGGT GCCGGATGCA GGGCCTGGCC TCGAAGGCAC   6840

GGTGAACGTC CCCGCGTCGT AAGCCGACGC CGCGGAAACT CGGTCAGCGC GCTCGCGCGG   6900

TTTCTGATCC CTAAGGGTCT GCAGATGATC CCGCCTTTGA ATTCCACCCA TCCTCCTCAG   6960

ATAGGCCTCA TAATAATGAT GGGCAATTAA GAACACGAGA TAGTGTCTCT TTTGCACGAG   7020

GTATTCGGCC TGCGACATAT TTCCCTGATC CAGGGTATTC ATGCGAGCCA CCAGGGGATG   7080

GTGAGCGTAG TCATGATCCA GTCGCTCCTG GATCACGGGG TCTCTCACCT TAAAGTTGGA   7140

CATCTTCCAC ACAGGCGGGC GAAATAGCCT CAGGAGGAAC ACTTCCCGCA ACAGAACTCC   7200

AGCAGCTGTG AGGTGAGCTG AAGCAGTCCG CGCACGTCAC GGTGCTTTAA TAGGGCAGCC   7260

TCGCAGTCGG GCGTCCCAAG GCAAGGCACT ACAAAACTGA CAGTTTGATC TAGGTCTCGA   7320

ATGGCAAGGG CCGCGTTGTT AGCTAGAACA GCCCTGATTA CGACGCGTGC TAGGGTCCCG   7380

CGTCCGGTAA TATCGCACAG GGGATACACC CTCATATGTT CGCTGCCACA GTAAGAACAG   7440

TAGATCCTCC CCGTGGTCGC ACAGATGGTG AACTGCTTCT CTTTCCTGTC CCTGCTGAAA   7500

AACACGTTGG TGGGAGGAAA ATTGACAGTA TGAAACTTGC CCCTGCCAAA GTTAAGACAG   7560

TGTCCACACT CCATGCACAC AACCGCCCGA GCGCAACGCG CCCGCTTGGC AAGGGCCGCG   7620

CGGGCCACGC GAGAACAGAT GACGGGTATG GACACGCAGG GGGAGAGAAC ATTGTATGCC   7680

AGAAGCCTCC TGCCAAGGTT CCGCACGAGA CCAGGTCCCT CCTGCTCGCA GGCGGGCAGC   7740

ACTACGTGGC GGGACTTAAT AAGGCTCAAA AAACACAGTG ACCCAAGCAT GGCGTCGAAC   7800

GGGTTACCGC AGGGAACCGT AGGGGCGACG CGCTCCAAGG CCTCCCGGAG GCCGGTATCT   7860

GCCGCCCCTA TCCCGAGCCC GTTACCGTCT TCGGTCGCAG CCACACCGCG ACGGGTGTGC   7920

GAGGGCACCT CCAGGAGGGG ACGACGCGGC AACGGCCCAT GCCACTTCTT CCTTAGCCAG   7980

GGTAGCGACG GTGGGGCTT CGAACAGCAG GTCACTAACG GAAAGCGAGA GCAAAGCGCC   8040

AACAGCTTGC AGAGTTGGGC ACAGGCCTTG GAAAATGGAA GCGACAGGTA TTTTGCCCAT   8100

ACGTGGCGCG GTATCGCCCT AGCATGGTCG GCGGCCTGGG CACGGACAG CGTCACCACA   8160

ACCCATACGT GGGCGCCAAG CAGCTGCTGC GCCGCACAAA TCTGCGCCTG TTTGGCGACG   8220

GTGTCTGAGC CAGCGCGCAA CACGGCGATC GCCTGCGCCA GCGACGGGCG GTCCAACAGG   8280

TGCCTGGCCC AGGAGGGCAT GTTTCCCTGG AAACCCCGCT CCCCGAATAT GACAAAAGCC   8340

ACATATTCCT CCACTGGCAC GCCATTCTCG CCCTCGAACA CGCGGTGGGC CGTCAGCTGG   8400
```

-continued

```
GCCTCATCCA AACCAAACCA AGACACAAGA AAGCGATCCC AGCGCTGATC CAGGGCCATG    8460

ACCTTCTCAC CAGCGCGACC GCACGGCCTA AGCTCCACTG AAAGGCGCCC AGAATCCGCA    8520

CCGTCCTACC CCCCTGGCCC GCCCAATATA CCGCTGTGAC GTCTGATGTA CAGGCCCGCG    8580

CGTCGCGGCC GTTGGTGGGA AAACCGGCAC CACCCTGTGC GGCCGAATCC GCCACGGGGG    8640

CTGCCAGACA GTACACTGTC TCCAGCAGCG ACTTCAGTCT CTTGTGACTT TTGGGCGTCA    8700

CCACCAAAAA TTGCAAAACC TGCCTGTAGT CCGTGAAGTA GGTACGGCAT ATTACCATGG    8760

AGTTGTACAC GCCCAGGTTC TTTGAGAACA CCAGGCTCGC CTTGAACTTT GTAAAGTCAT    8820

CCTGCCCCAG CACGACAGAC GTATTTTTGG CAAGGTATAC GTCCGACTCC ACGGGAAGGA    8880

CGTGCCCAAA CTGGGACACG GCGTCGCTTG GTCGGCACAA AAAGCACTTC AGGGTTGTGG    8940

AAAGGCCATT ATTCGATATA ACAAAGCAGG GAGAGAACGG GTAGTGCATC TCCTCCAGGA    9000

GGTGCGCCCA AAACTTATAC ACAAACTCTA AGTGGTACAC GCAACCGTGC TGCATTCTAA    9060

CCGTACATAT GGCGGTAGCA CCGCCCTTAG CATAAACTGG GGCCCCGTCG ATGCACCGTT    9120

CCAAATCCAG GGACTGACCA GACTGTCCCA AGTATGAGGA TACCACCCGA CACAGTTCGT    9180

CCACTACACG CTTACCAACG ACACTCATGG CGACAGCGGG GTGGGGCTGG CAAGGCCCCC    9240

AAAGCGCGAC ACCCGCAGTC AATCAGGGCC GTGCCCGCGC CTCGGAGAAT ACGGCGTCCG    9300

TGCTCACGAT CTTGCGCAGG ACCTGCCTTA CCGTGTCCAC CTTGCTCTCC AACACCAGAG    9360

TATGATCGCA GGCTGCAGGC TGTGCCCGCT GGACGAGAAA GGTTTTTAAA TACTGACAGT    9420

AGTTGATGGC GTTCAATCTA CAATAGATCG TGGGAAATAA AATTTGCATG TCACGAGGCA    9480

GAAGCTGGTC AGACGCGTAC TCCATGTTGG GTTCCACGGG GAGGGAACA CACGCCCAA     9540

GACACGACGG CGCACATAGG GAGCGGAGCA AACAATTGAT TCAAATATTT GACTCCGCAG    9600

CGAGCCGGTT TGCAGAGTGG TCACCTGCCC TGCTCCACAC CCACCCCCGC GTCTCTTCCA    9660

ACTCTCAACT CACGATCCAG GGAAACCACC GTCCAGTGGC CATGTTTGTT CCCTGGCAAC    9720

TCGGTACAAT TACCCGTCAC CGAGATGAGC TCCAAAAACT ACTGGCAGCC TCCCTGCTCC    9780

CGGAGCACCC GGAGGAGAGC CTCGGTAACC CCATAATGAC ACAGATTCAC CAGTCGCTCC    9840

AACCATCTTC CCCCTGCAGG GTCTGTCAGC TCCTATTTTC TCTGGTCCGC GATTCGTCCA    9900

CCCCCATGGG TTTCTTCGAG GACTATGCCT GCCTCTGCTT CTTCTGTCTA TACGCCCCAC    9960

ACTGCTGGAC CTCGACCATG GCGGCAGCGG CAGACCTGTG CGAGATCATG CATCTGCACT   10020

TTCCAGAAGA GGAGGCGACA TACGGGCTAT TCGGACCGGG TCGCCTTATG GGTATCGACT   10080

TGCAGCTGCA CTTCTTTGTT CAAAAGTGCT TTAAGACCAC CGCCGCCGAA AAAATACTGG   10140

GAATATCCAA CCTGCAATTT TTAAAATCAG AATTCATCCG GGGCATGCTC ACAGGCACCA   10200

TCACCTGCAA CTTCTGCTTC AAAACGTCCT GGCCCAGGAC AGACAAGGAG GAGGCCACCG   10260

GCCCCACCCC ATGCTGCCAG ATTACAGACA CCACCACCGC ACCCGCGAGC GGCATACCGG   10320

AACTAGCCCG GGCCACATTC TGCGGCGCAA GTCGCCCCAC AAAGCCCAGC CTACTTCCCG   10380

CGCTAATAGA TATCTGGTCC ACGAGCTCAG AGCTCCTTGA CGAGCCGCGC CCTCGACTGA   10440

TCGCAAGCGA CATGAGTGAA CTCAAATCCG TGGTCGCATC CCACGATCCG TTCTTCTCTC   10500

CCCCGCTTCA GGCAGACACC TCACAGGGTC CATGTCTGAT GCACCCAACC CTGGGGCTAC   10560

GATACAAAAA CGGGACTGCA TCCGTCTGCC TCCTCTGCGA GTGCCTTGCG GCACACCCAG   10620

AGGCACCCAA GGCGCTGCAG ACCCTTCAGT GCGAGGTAAT GGGCCATATA GAAAACAACG   10680

TAAAGCTGGT AGACAGAATT GCCTTTGTGT TGGACAACCC ATTCGCCATG CCATATGTAT   10740
```

-continued

```
CAGATCCGCT ACTTAGAGAG CTGATCCGGG GCTGTACCCC ACAGGAAATT CACAAGCACC   10800
TGTTCTGCGA CCCGCTGTGC GCCCTCAATG CTAAGGTGGT GTCAGAGGAC GTACTATTCC   10860
GCCTGCCCAG GGAGCAGGAG TATAAAAAGC TCAGGGCATC CGCGGCCGCC GGACAGCTCC   10920
TCGATGCCAA CACCCTGTTC GACTGCGAGG TCGTGCAGAC TTTGGTCTTT CTCTTTAAGG   10980
GTCTCCAAAA CGCCAGGGTG GGGAAAACCA CCTCACTAGA CATTATTCGG GAGCTAACCG   11040
CACAACTAAA AAGACACCGC CTAGACCTGG CCCACCCCTC ACAGACGTCA CACTTGTACG   11100
CTTGAGCTGG TCCCGGGCCT TCGCACCCCA TCCACCGATG CCGAAATCAG TGTCCAGCCA   11160
CATCAGCTTG GCGACCTCAA CCGGTCGCAG TGGACCGCGA GACATCAGAA GATGCTTGTC   11220
ATCCCGCCTG CGGTCGGTCC CGCCCGGGGC GCGAAGCGCC AGCGTCAGCA GCAAGCACAG   11280
AAACGGCCTT CGCAAGTTTA TCTCAGACAA GGTATTTTTT AGCATCCTAT CGCACAGACA   11340
CGAGCTAGGA GTGGACTTTC TCCGTGAGAT GGAGACCCCG ATATGCACCT CCAAAACAGT   11400
AATGCTGCCC CTAGACCTGT CTACCGTCGC ACCCGGCCGC TGCGTCTCCC TCTCTCCGTT   11460
TGGACACTCC TCAAACATGG GGTTCCAGTG CGCTCTGTGC CCATCCACAG AAAATCCCAC   11520
CGTTGCCCAA GGCTCCCGGC CTCAGACAAT GGTGGGCGAT GCGCTCAAAA AAAATAACGA   11580
GCTATGCTCG GTAGCGCTGG CCTTTTATCA CCACGCAGAC AAAGTGATCC AACACAAGAC   11640
GTTTTACCTA TCACTCCTCA GTCACTCCAT GGATGTGGTT CGGCAGAGCT TCCTGCAGCC   11700
TGGTCTACTG TACGCTAACC TGGTCCTAAA AACCTTTGGG CACGATCCCC TACCCATCTT   11760
CACTACCAAC AACGGCATGC TAACAATGTG CATCCTTTTT AAAACCCGGG CACTACATCT   11820
GGGAGAAACT GCGCTTAGGC TGCTTATGGA TAACCTCCCC AACTACAAGA TATCGGCGGA   11880
CTGCTGCAGA CAGTCCTACG TGGTCAAGTT TGTCCCAACG CACCCGGACA CCGCAAGCAT   11940
TGCAGTGCAG GTACACACCA TATGCGAAGC GGTTGCGGCG CTAGACTGCA CCGACGAGAT   12000
GCGGGATGAC ATTCAAAAGG GAACCGCACT TGTCAACGCC CTATAACCTC ACATGTAGCC   12060
TGTCACCCCA GCTCCTATTG CAACTGACCA TGTTCAGGTG GTAATAAAGT CATTAAACGA   12120
CAAAGTGATT CTTTTAATCT GTTTATTGTT TTTGAACATG TGGCACACGC TGCAATGTAC   12180
TGCCATGAAA GGTGGTTCTA TATCCACCAC TTGGCGTCTG CCGAAGTCAG TGCCACAATT   12240
TCATTAACAA ACAAGGTCAA TACATTGTGA GGGAGTGTTT TTTGCCATGG TACCATTCGT   12300
GTGGTTTGGG AGAGCGGACG CCATTTGCGT GCAAAATGTG CTTTGCTGGA GGCCAACTTC   12360
CGTCGCGCTG GTTGATGCGC GGCACATTGT GTCAACCAGG GCACCCTCCC CCACCGAGTG   12420
CTTTAATGCG GAGAGGAATG GTGGCCTGGT TGACACCGCG TGCCGGCCAT CTGAACTGTG   12480
ACTGTGTTAT GAGCCACGGG TATGCCCTCG ATACGCCTGC TCTTCAGCAT TGTATGTGTT   12540
TAATGTTGTG CTTGGTGCAA CCGTGATTGT GTTTTTGTAT TTTATTTTAC TGACACTCTT   12600
TGGGAGGGCA CGCTAGCTTC AGTGCGCGCC CGTTGCAACT CGTGTCCTGA ATGCTACGGG   12660
GCCACGCTGG CCACTCGGGG GACAACACT AATCGCCAAC AGACAAACGA GTGGTGGTAT   12720
CGCCCCAAGC CTCCAGCGCC ACCCATTTAG TAACACATCC GGGACATGAA CTGCCACAAA   12780
CACCGTTAAG CCTCTATCCA TGCATTGGGA TTGGAGTGAG GAGGGAGGAG GGCACCAGGT   12840
TCCCGGGGAG GAGGGCACCA GGTTCCCGGG GAGGAGGGCA CCAGGTTCCC GGGGAGGAGG   12900
GCACCAGGTT CCCGGGGAGG AGGGCACCAG GTTCCCGGGG AGGAGGGCAC CAGGTTCCCG   12960
GGGAGGAGGG CACCAGGTTC CGGGGAGGA GGGCACCAGG TTCCCGGGGA GGAGGGCACC   13020
AGGTTCCCGG GGAGGAGGGC ACCAGGTTCC CGGGGAGGAG GCACCAGGT TCCCGGGGAG   13080
GAGGGCACCA GGTTCCCGGG GAGGAGGGCA CCAGGTTCCC GGGGAGGAGG CTGGGGTGCG   13140
```

-continued

```
CCGCGCCGGG TTCCTGGGGT GCGCCGCGCC GGGTTCCTGG GGTGCGCCGC GCCGGGTTCC    13200

TGGGGTGCGC CGCGCCGGGT TCCTGGGGTG CGCCGCGCCG GGTTCCTGGG GTGCGCCGCG    13260

CCGGGTTCCT GGGGTGCGCC GCGCCGGGTT CCTGGGGTGC GGGGTGCGGG GGACCGCGCC    13320

GGGGTACTGC AGGGTTCGCA GGGTTCGGGG GTACTACCTG GTTTCCTGGG GTGTGCCAGG    13380

ACGGGTTCCT GGGGTGCCAC CGCTCCTCGA TACGTGTAAA TCCAAGAGAT CCGTCCTCCG    13440

TGCCGCCGCG CGCGTAATGC GCGAGGGGGG TCGGTCTCCC CTCTTCTTTA TAGCGTTTCC    13500

TGCGAAGGGG GCGTAACCGT AGGACAAACT GCTTATGTAG GGGTTAGCCA CCCATTTCCC    13560

GGGGCCGCGC CAGAGGTGAG CGTGGACCTA GCATCCCGCT CCCATTTACC GAAACCACCC    13620

AGAGGCGAGA TTCCAGGGCC GTGACTCACT AGCTCCCCTC CCATCGAACA ACCACGCTTG    13680

GCTAACACGG CTGGAGTGGC GGTGGGCGGG GCCCCTATAA TCCTGGCCCC CATCTACTGA    13740

AACGACCCAG TAGAAAAATC CCAACCCCAT GACTCATCAG GCCCTATTAT ATAGAATATC    13800

CCAGTAGAGT GACCCAGCTG GTTTCCATAA ATGGATATAC TTCCGGAAAA CGAAGGAGGG    13860

TTGAATACAG TTGGGGGTAG TCCGCTGGTA TTCCCAGCTG AGGTTGCCTT ATTTGGTAAT    13920

GCTTCCGGAA ATACCACCTG AGTACCCCAT TGGTTTATAC CTTGTTTAAT TGTAGAATTA    13980

CAGCTGGATT TACCCAGCCG GGTTTACGCA GCTGCGTATA CCCAGCTGTG TTTACGCAGC    14040

GGGGTTTACG CAGCTGGGTA GACCCAGCTG GGTATACCTA CTGGAATAGG GGCTGCGATG    14100

ACTCAGCTGC GCTAGGATTA AAGGATTATA TATATATA TAGGAAAAAT CAAAACAAAA    14160

CTCTAATCGC TGATTGGTTC CCGCTCTGGG CCAATCAGCT TGGGAGTTCT AGGGATAGGG    14220

GCCAATGGGA GGCCTCCGAA TTTGATTGAC GGCTGGGGCG TCCAATGGAA TGGCGCGGTC    14280

GCCTAGCTCG AACGGGATTG GTCGGCCGGA TGGGCCAATG GCGGCTCGGA AAACTTTGAT    14340

TGACGGGCCG GCGGACCAAT GGGAGCGGGG CAGAGGATTA TGGGGGATTA GCAAATTCAA    14400

GATGGCGGCG CCCATGAAAT GGCCAAAAAT TATAATTTTT CGAGTCGCTC ACGGTCCCAC    14460

CTAGCGGCGT GACCTGGAGG TGACCCCGTG CACCCGGGCG CTCTGAATTT TTCTGCGCAT    14520

GCGCGACTCC TCATCTACAT AATTTATGCA CATAAAAGGA TTAGCGCATG CAAATTAGTC    14580

AGATAGCAGG GCCATCCACA CTTTATGTTG GCCGCGTGCC AGGCGCCGGC GTGGGCGCCG    14640

CGCGCGTGCT CTCTCAGTCG CGCCTAGCTG CTTCCAACAG ACAAAAGCGG GGCGTTAGTG    14700

AGGGAGTGCG CGCGCTGCGC TGACTTGGCC GATTTCCAGT GCATGCTTTG TCACCCCAGC    14760

GCGAGAATGG AATTTTCATT ATTGAGCAAT TTGGGCACCC TGGGCACGAT AACCATACAT    14820

GGATACACGG GTTCCAAATA TGCAAAGTAG ACACTAAGGT ACCATTTGGC ATATTTGGAC    14880

GTCCTGGGCA GGTTAGCTAC CCACCAGAAT ATATGGGACT CTGGGCAGGA TAGCCACCCA    14940

CAATTGTTTT GCGCCCCTCT TTGGCCAGGG GACCAAGGTC GTATGGTTCG CGCTACACTA    15000

AGCCCGAACG TTCAGCTTTG CGTGCTTTCG ACGTCCAGGG GGCTGGCACA CGGGCCGTGA    15060

GCGCCAGCAA CATGGGATCA TGGTAGTAAG ATACAGCATA AATCCCCGTC CGGTGGCGCT    15120

CAACGCCAAT ATGCGCGGCT GCGTGGTATC TCATCGGTGG GCACGCGTAC GGTGGTCTCA    15180

TGGGTATTGG ACTTGTAGGC GAGGGGAGGC GCATACGACA AAAATTGCCG CCGTGAAGGT    15240

CGGGAACCCG CCCGCGCTTC CGCAAGGCAC GGGGCCGCAT CGGACACAGG CTAAGCATTA    15300

AGGATCATAA CACCGCCCTA GAAATGTTTA AGCTGTGACC AAAGCGAACC TCGCATGAGG    15360

CATACGCGAG CGTGGAGGTA GGATTCCCAA GGCTATTGAG AGACGGTGGG TGAAATGATG    15420

AAGAACACAC AGAACAATAA CGGGCGACTA GATAAAAAGA CTCGCTCAAC AGCCCGAAAA    15480
```

-continued

```
CCATCAGCCC GACCGCCGAT GGATTAGGTG CTGCTGGACA AGTCTTTCTA AACCCGCGCA   15540
GGGTTTGTGT CGATCCAGAC GCTTACGAAC GCCCGCTTTA AAAACACTAT TCATAATTAA   15600
CAGAAGTTGA CACCAGCCCG CAGTTACCCA ACCTTCTATT TTTTTGGAGT GTTGACAAGT   15660
TTCCATCGCC CGTTTGGCGT TTCCCGCATG GTGTCAAATT AGTGACGCAC CCTCCCCCCG   15720
TCACTATGGG TTTACCCTGA TTTAGTAAGT AAAACTGCCG CCCCCGCCCA CTCATTTTTT   15780
TACCCTGTTA TTTGCTGTAT TTACATCTAC GGACCCCCTT TTGGTGAGAT GCCGTGGTT    15840
CTAAATAACG TTGTGGTTTT CGGACCCTTT CAGGGACCAA ATCTTTTACG TGTTGCCAAG   15900
GTAGCATTTG CTGGACCCGC ATAGGTTTTT GTGGCACCAG GTTATGGTCT TATGAGCGGG   15960
CTTGACCGGC AAGTTCCAGG CATCCTAAGT GCTTGATGTA GACCCTTAGG GCACCAGGGA   16020
CTACCTAGGT CAAACTCCCC CTTAGTCATG ACGCCGTGCC CACGAGGTTT GAGAGGCGTA   16080
GACATCCGTG TCGACTGCTG GACGGAGGTA GTATAATCAG CTAGGCCTCA GTATTCTATG   16140
TAACAAATGA ATGCCCTAGA GTACTGCGGT TTAGCTAGTT ATACTGCCCG GTTCCACCAG   16200
GCGGCGTTGT GGCCACGGGC GGTTCGTCGC TTGGACCTGG AGGGGTGTCA CATTCTGTGA   16260
CCGCGACGTT GACGTTAGAC ACACGTCGCT GCCGTCCTCA GAATGTGATA GCCCATCACA   16320
GGCATTGTAG CTGTTGCGTT GGTTGGGAGT TTGGGGACCA AATTTCTATA ATTGGTGTCA   16380
CCGCGGCAGC TCTAGCCCTG GAAGATCTGG AAGCTTGCTT CAATGGCTCA GATCGACCCG   16440
GACTACAGTT AGCGAAGTAG ACCCATTATA ATCTTAATCT TAAATCTGGT TGACGGACTT   16500
TCGCGCCGGG AACACGCAGG TGGCAGCGGA TGTGTTTTGC CCAAACACGA GGGTTGCAGG   16560
AAACAGGTGC TGCCGGGGAT TATGTACAGC TTACACCCAG TTTCCTGTAA TCGCCCGCAT   16620
CCGGCCGTCC TGGGCAGCAC CGCACCCTGC GTAAACAACC GCGTACTTTT TCCTCCTCCC   16680
CCCACCCCCA CATCCTTCCT CCCACCCTGC CAGTCCAACC CGCTTCCTGT TTTATTCGCC   16740
TTCAAACAGA AGCACGCATT CTAATGATTC TTACAAAACT TGTTAGTGTT TATTAAATCA   16800
GATACATACA TTCTACGGAC CAAAAATTAG CAACAGCTTG TTATCTATGG TGTATGGCGA   16860
TAGTGTTGGG AGTGTGATGG GCCGGAAAGG TGAAGGCCCA TTAGGGTTTG CACTTGGCGC   16920
TGTAGGTCTA CTCTTGACAA AGATCTAAGC ATTGACATTA GGGCATCCAC GTCAGTGGGA   16980
CCCAGTAGGT CTAAGTTTTC CATACAGTAC ACCCAGTGTA AGATGTCTGT GGTGTGCTGC   17040
GAGACCCTAT AGTGTCCTTG CTTAAAAATA TCAAAGACCT AATATCCCTC GCACACAGCT   17100
CCCCGTCTAC GTGGAGAACA GTGAGCTGAT AAGGGCTGAA ATAACTCATT GTGCCCGCTA   17160
GGTGGCGCTC TAAAAAACGC GGGTCTAAGT GAAGCAGGTC GCGCAAGAGG TCTCTGCGAC   17220
CTGCACGAAA CAGACATTCC GCTAACAGGG GAAACGTTAA CCTGCCCTCC TCCTTTAAAG   17280
CTCTAAGAGC TCCAATTAAT TGGGCCAGTG TGGGTTGAGG TATGAACACG TTTAGGAGGA   17340
ACAATACCAC TTCCCTGTCA TCCGTGCCCA GTTTCCGCGC CACCTCACAG AGAACCTCGT   17400
AAGTGGCCAT GGTGCCGGCT TGTATATGTG AAGGCACCGA TGTGGAAAAA CAAAGGAAAA   17460
TTTATTTTTC CGCCCTAAAC AAAATCACAA GCTTAATAGC TGTCCAGAAT GCGCAGATCA   17520
AAGTCCGAAA CAGATGTTAG GATCTGTTCC ACTGCCGCCT GTAGAACGGA AACATCGCAT   17580
CCCAATATGC TTGCCAGCTG AGGAACTACC CCACCCGAGT GGGTATCCTG CGGAATGACG   17640
TTGGCAGGAA CCAACAGCGC ACAGCCTGCA GCGCTGATAA TAGAGGCGGG CAATGAGCCA   17700
GTCTTTGGGT CAACTAAGGC TTTTGTAATC AGGGTGTTGA CCTCGTGGTG CCAAAAGTCC   17760
AGGTGTTGGG AGCCCCCCAG CAATTTAAGT AACAAGAAGG AAGTGACGTC CGTCGCTAAG   17820
ACTGCCTCTG TTCGCCACGC CAACTTCTCA AGGAGTTCTT TCTCCTGGTC TATAAGTTCT   17880
```

-continued

```
TGGCGGGAAA AGGAGTCTGC CGCGGCATAG CAAAGTGAAC TGGTAGAAAT AGGCGTGAGG    17940

CTTCTGAGCT TACTGGCCAC TAACAGGCAG GCGCTCCCTG TCTTTTGAAA GTGTTCTTTG    18000

GACACCTGCT TTATAAGTAG GAGTCTGTCC AAAAGATTAA GGGCCAACGC GACCACGTTA    18060

GGTTCTAGGT TGTATTCCTG GCAAACTGAA AACATCCATG TGCCCAGTAA CTTACGCATA    18120

TGCGAAGTAA GAGATTGTTG AAAGGTCCCA AATACAGAGT CAGAAGTTAA AAAGCGCGGC    18180

TCAATTTCAA GAATATTGTA AAAGATCCGA TCCTCACATA GCGTGGGATC CAGAAGTCCC    18240

GAGGGCGGGT TATTGGCAGT TGCCATATAG AGTGGCGAGC GTATGTGGCC TACCTGTAGA    18300

GCCTGGAGTT TCAGGGTGCT CTGTCAGGTT CTCCCATCGA CGACGCTGGG CCGCGAGAGT    18360

ACGCTAGCCG TTGTCCGTGT GTTCAGTTGA GGTAGATGGG TCGTGAGAAC ACTGCCCCCC    18420

ACACACACCA GCACCCATGG CGCCAAATGC AAGTGCGGAG CGGCGACGGT GGCTTCTAGG    18480

GAGGAAAAAG GGGGAGAGGT GTGGCTTTTA TGTCATTTCC TGTGGAGAGT CCCCAGGACC    18540

TTGGTTTTCC CCTGGCTGGG TTAATGGCAG GGGCTTTTTA AACTTAACTA TGGAAGATTG    18600

TAGGTTTCCT GCCAGGGGGT GACTAGCTTC CCAGGCTAGG CGGGCCATTT GTACTTTCTT    18660

ACTTGTGTCT TTGTTCTGAC AATACACATA TACACAATAA GTTATGGGCG ACTGGTCTGG    18720

TCCAGGGTGG GGCAAGCAGG ACACGGGGCC TGCCTTTACT CCTCCAAACT GGAAGGCCTG    18780

AGATAATTTT TTAAGTCCGT ATGGGTCATT GCCCCAAAAA ATCACTGCAA ACTTCCATTG    18840

ACACTTTGGA TCTCGTCTTC CATCCTTTCC CAAAAAGCGT CTATAAAAGA TGTGTTGTGG    18900

CCTAGCTTTC GCAGGACAAT CATCTATCTG TCTGTAAGGG ACCGGTGGTT GTTGGTATCT    18960

TGGATGTGGC TTTTTTGGGT GGGTAACTGG AACGCGCCTC ATACGAACTC CAGGTCTGTG    19020

GGGTGGTGAT GTTCTGAGTA CATAGCGGTA TTCGCGAGAT GGGCCAGGTT GTGGGTCATC    19080

GTCTGGTGTA TTATCTCCTG GTGGGCTACT GGCAATTTGT TCATGTGTGC TAACAACAGG    19140

GTAATCCACT TCCATTTCGT CCTCGGATGA CGACCCGTGC AAGATTATGG GCTCTTCCAC    19200

CGTCTCCTGC TCCTGCTGTT CCACCCCCTG CTGCTCCTGC TCTTCCACCT CCTCTAACTC    19260

CTGCTGCTCC TGCTCTTCCA CCTCCTCTAA CTCCTGCTCT CCTGCTCTT CCACCTCCTC    19320

TAACTCCTGC TCTTCCTGCT CTTCCACCTC CTCTAACTCC TGCTCCTCCT GCTCCTCCTG    19380

CTCCTGCTCT TGCTCCTCCA CCTCCTCTAA TTCCTGCTCT TCCTGCTCCT GCTCTTGCTC    19440

TTCCACCTCC TGCTCTTGCT CTTCCACCTC CTGCTCCTCT AACTCCTGCT CCTGCTCCTC    19500

TAACTCCTGC TCCTGCTCCT CTAACTCCTG CTCCTGCTCC TCTAACTCCT GCTCCTGCTC    19560

CTCTAACTCC TGCTCCTGCT CCTCTAACTC CTGCTCCTGC TCCTCTAACT CCTGCTCCTG    19620

CTCCTCTAAC TCCTGCTCCT GCTCCTCTAA CTCCTGCTCC TGATCCTCTA ACTCCTGCTC    19680

CTGCTCCTCT AACTCCTGCT CCTGCTCCTC CTGCTGCTCC TGCTCCTCCT GCTGCTCCTG    19740

TTCATCCTGC TGCTGCTGCT CATCCTGCTG CTGCTGCTCA TCCTGCTGCT GCTGCTCATC    19800

CTGCTGCTGC TGCTCATCCT GCTGCTGCTG CTCATCCTGC TGCTGCTCAT CCTGCTGCTC    19860

CTGCTCATCC TGCTGCTCCT GCTCATCCTG CTGCTCCTGC TCATCCTGCT GCTGCTCATC    19920

CTGCTGCTGC TCATCCTGCT GCTGCTCATC CTGCTGCTGC TCATCCTGCT GCTGCTCATC    19980

CTGCTGCTGC TCATCCTGCT GCTGCTCATC CTGCTGCTGC TCATCCTGCT GCTGCTCATC    20040

CTGCTGCTGC TCATCCTGCT GCTGCTCATC CTGCTGCTGC TCATCCTGCT GCTGCTCATC    20100

CTGCTGCTGC TCATCCTGCT GCTGCTCATC CTGCTGCTGC TCATCCTGCT GCTGCTCATC    20160

CTGCTGCTGC TCATCCTGCT GCTGCTCATC CTGCTGCTGC TCATCCTGCT GCTGTGGCTC    20220
```

```
CCGCTGCTGT GGCTCCCGCT GCTGTGGCTC CCGCTGCTGT GGCTCCCGCT GCTGTGGCTC   20280

CCGCTGCTGT GGCTCCCGCT GCTGTGGCTC CCGCTGCTGG GGCTCCCGCT GCTGTGGCTC   20340

CCGCTGCTGT GGCTCCTGCT GCTGTGGCTC CTGCTGCTGT GGCTCCTGCT GCTGTGGCTC   20400

CTGCTGCTGT GGCTCCTGCT GCTGTGGCTC CTGCTGCTGT GGCTCCTGCT GCTGTGGCTC   20460

CTGCTGCTGT GGCTCCTGCT GTTGTGGCTC CTGCTGTTGT GGCTCCTGCA GGGGCTCCTG   20520

CTGCTGTGGC TCCTGCTGTT GTGGCTCCTG CAGGGGCTCC TGCTGCTGTG GCTCCTGCTG   20580

CTGTGGCTCC TGCTGTTGTG GCTCCTGCAG GGGCTCCTGC TGCTGTGGCT CCTGCTGCTG   20640

TGGCTCCTGC TGTTGTGGCT CCTGCTGCTG TTGTGAACTT GGATGCTCA ACGTTTTGTT   20700

TCCATCGCCC CCGTCCTCCT CGTCCTCCTT CTTGTCCTCC TCCTCGTCAT CCTCCTCGTC   20760

CTCATTGTCC TCATCATCGT CATCCTCCTC GTCCTCCTCC TCCTCGTCCT CCTCCTCGTC   20820

CTCCTCCTCG TCCTCCTCCT CGTCATCCTC CTCGTCATCC TCCTCGTCAT CCTCCTCGTC   20880

ATCCTCCTCG TCATCCTCCT CGTCATCCTC CTCGTCATCC TCCTCGTCAT CCTCCTCGTC   20940

ATCCTCCTCG TCATCCTCCT CGTCATCCTC CTCGTCCTCC TCATCTGTCT CCTGCTCCTC   21000

CTCATCATCC TTATTGTCAT TGTCATCCTT GTCAACCTGA CTTTCCTTGC TAATCTCGTT   21060

GTCCCCATTA TCCTCGCCAG CCTGATTATT TTCGGAACAT TCTTTTTCAT TCTTGGATGC   21120

TTCTTCTGCA ATCTCCGCAA GGAGCACCAA CATGGCTGTG TCATCACCCC AGGATCCCTC   21180

AGACGGGGAT GATGATCCTA TGGAGATGGG AGATGTAGGC GGTTGGCGTG GCGGAGTATC   21240

GCCATCGCTG GATGATCCCA CGTAGATCGG GGACTCTGTG GCCCATGGGG GGTACACACT   21300

ACGGTTGGCG AAGTCACATC TAGGGGGAGA GACTGGGGGC GACTGACATA TTGGGTTTAG   21360

TGTAGAGGGA CCTTGGGGGG ACGATAGCCT TCTTTTTCTC AGGCTACGCA GGGTAGACGG   21420

AGCTAAAGAG TCTGGTGACG ACTTGGAGGG AGGCTCGGGT GGAGGAGTCG TGGGTGAGTG   21480

TGGAGGTGTA GTCTGCTGCG AGGGTGGCGG ACGCATAGGT GTTGAAGAGT CTGGCCTTCC   21540

TGTAGGACTT GAAAGCGGTG GCCTTTGAGA AGACTCTGGA GACTGCGTGG GTGGCAATGC   21600

AGGAGATGGA GAATGAGTAT CCGTGGTCCC CGGAGACACA GGATGGGATG GAGGGATTGG   21660

GGAGGAAGAC GTGGTTACGG GGGGTAAGAG TGCCGGTGGA GGTAAAGGTG TTGCGGGAGC   21720

GGGTGAAGGA ATGGGAGCCA CCGGTAAAGT AGGACTAGAC ACAAATGCTG GCAGCCCGGA   21780

TGTGAACACT GTGGGACTTC CAGGTATAGG CAAGGTGTGG GGTCCACATT CCCGGCCGTC   21840

GATGGAGTCG CGCGACATGCT TCCTTCGCGG TTGTAGATGT AGGTCATCGC CAAGGTCACA   21900

TCTTTCCGGA GACCTGTTTC GTTTCCTACA ACTTCCTCTC GTTAAGGGCG CGCCGGTGCT   21960

CCGTCCCGAC CTCAGGCGCA TTCCCGGGGG CGCCATCCTC GGGAAATCTG GTCTGACAAC   22020

CAAAGTAAAA TTATGGAGGC GGTGGCAGTA TATTCACATT ATGCAATACC CGTAGTGACC   22080

ACAAGGGGGA GCTCTCAGAC AATTAAGCGG TTACACACAG TAGCAGGCTG CAGTACCGCC   22140

CATGGCCACA GGATGTAGAT CGCAGACACT GAAACGCTGA AACACAGCAT TAAGCTGCAA   22200

TACCGCCGAT GGCCACCAGA TGGCACGCGC CGCCAGCAAA TTTAAGTCCT GGTGGCTCAC   22260

CTGCCAGGTA AACAAGGTTA AAGTGGGTTT GCTGGCCTTG CGTTGCCATG GATGCTACCT   22320

AGGCAAGTCC AGATATATAA TCCGGGCGTG AGAAACAGAA ACGGCCAATA ACCCATGTTT   22380

TTCGAAAACC ACCACACACC TTAACACAAA TCATGTACAC CTGGTATTAC TATTTCCCAC   22440

ACATCTTATA GCATTTCAAA GATAAGGGTG CCTTACGGGC CGCCCGAAAC AAGTGGGCGG   22500

GCGCTACTCA CTGTTTATAA GTCAGCCGGA CCAAGCTGCT GCTCTTGGGG ACGTGACTGC   22560

TTCGTGGCGC AGCTGCCTCC AAATGATACA CACATTTTTT GATTGTCCCG GGCGCCGCGT   22620
```

-continued

```
AGTGGAGGGC GGAGTTATAT CAAGCTACTT TCTGATTGGT GCCCCAGGCA GGACTGCCAT  22680
AAAAACTGAA GAAGGCGTGT CTGCTTTGCA GAATTTACCC CCCACTGTGC TCCCGGTTGC  22740
TGGCACCGGT TCAGTGGTCC GACCTGTCGT CTGTGCTCCC CCGTGGACGA CGCCGAGTGC  22800
CTCTCGGGGG TCCATGTCTA GCCTCTTCAT TTCATTACCT TGGGTGGCGT TCATCTGGCT  22860
AGCCCTCCTT GGCGCGGTTG GGGGTGCCCG CGTTCAGGGG CCCATGCGGG GCTCTGCTGC  22920
CCTCACCTGC GCCATCACGC CCCGTGCTGA CATAGTTAGC GTTACCTGGC AAAAAAGGCA  22980
GCTCCCCGGT CCCGTAAACG TCGCCACGTA CAGCCATTCA TATGGGGTGG TGGTTCAGAC  23040
CCAGTACCGC CACAAGGCAA ATATAACCTG TCCTGGGCTT TGGAACTCTA CCCTTGTTAT  23100
CCATAACCTT GCAGTGGATG ATGAGGGCTG TTACCTGTGT ATCTTTAACT CATTTGGTGG  23160
CCGGCAGGTG TCATGCACAG CCTGCCTGGA AGTGACATCT CCCCCTACTG GACACGTGCA  23220
GGTAAATAGC ACAGAAGACG CAGACACCGT CACCTGTTTG GCAACTGGTC GCCCACCCCC  23280
CAATGTCACC TGGGCCGCAC CCTGGAACAA CGCCTCTTCT ACCCAGGAGC AGTTCACTGA  23340
CAGTGATGGT CTTACAGTTG CGTGGAGGAC CGTGAGGCTG CCGCGTGGGG ATAATACCAC  23400
CCCAAGTGAG GGAATATGTC TCATCACCTG GGGAAATGAG AGCATATCAA TCCCGGCTTC  23460
TATTCAAGGC CCCTTGGCCC ATGACCTTCC CGCGGCCCAG GGAACTCTTG CCGGGGTTGC  23520
CATTACTCTG GTGGGCCTAT TTGGGATATT CGCATTACAT CATTGCCGCC GCAAGCAGGG  23580
CGGTGCATCA CCTACTTCAG ATGACATGGA CCCCCTATCC ACCCAGTGAC TAGATGGACA  23640
CCCCGTGAAC CGTCGTGCTT ACCCACCCCC TTCTGATTCT GACAGACAAC ACTACTATGT  23700
CCCAAAGACT GTTTTTTACA GCCCGATGGC CCTTCAGGCC TCCTTGAGTG TCTAGCTGGT  23760
CCCGTGGTCA TTGTGTGGTT TGGCAGTCAC TTCCCCATTT TGGTGTCGCG TTTTGGGTTT  23820
TGCCCTGCCC CCAGCCAACG TGGATCATAT TCTTTCCCGT CAGGGGAGTG ACAAGCTATA  23880
GGACAGAAAG GTCACCTGGC CCAAACGGAG GATCCTAGGT GGGTGTGCAT TTATTAGACG  23940
TTGGTGTGTT GAAGGACGGA TCAGGCGGGG AGGAGGGGGT GGGGGAGACT TACTGCAGCA  24000
CTAGGTTAGG TTGAAAGCCG GGGTAAAAGG CGTGGCTAAA CAACACCTAT ACTACTTGTT  24060
ATTGTAGGCC ATGGCGGCCG AGGATTTCCT AACCATCTTC TTAGATGATG ATGAATCCTG  24120
GAATGAAACT CTAAATATGA GCGGATATGA CTACTCTGGA AACTTCAGCC TAGAAGTGAG  24180
CGTGTGTGAG ATGACCACCG TGGTGCCTTA CACGTGGAAC GTTGGAATAC TCTCTCTGAT  24240
TTTCCTCATA AATGTTCTTG GAAATGGATT GGTCACCTAC ATTTTTTGCA AGCACCGATC  24300
GCGGGCAGGA GCGATAGATA TACTGCTCCT GGGTATCTGC CTAAACTCGC TGTGTCTTAG  24360
CATATCTCTA TTGGCAGAAG TGTTGATGTT TTTGTTTCCC AATATCATCT CCACAGGCTT  24420
GTGCAGACTT GAAATTTTTT TTTACTATTT ATATGTCTAC TTGGATATCT TCAGTGTTGT  24480
GTGCGTCAGT CTAGTGAGGT ACCTCCTGGT GGCATATTCT ACGCGTTCCT GGCCCAAGAA  24540
GCAGTCCCTC GGATGGGTAC TGACATCCGC TGCACTGTTA ATTGCATTGG TGCTGTCGGG  24600
GGATGCCTGT CGACACAGGA GCAGGGTGGT CGACCCGGTC AGCAAGCAGG CCATGTGTTA  24660
TGAGAACGCG GGAAACATGA CTGCAGACTG GCGACTGCAT GTCAGAACCG TGTCAGTTAC  24720
TGCAGGTTTC CTGTTACCCC TGGCCCTCCT TATTCTGTTT TATGCTCTCA CCTGGTGTGT  24780
GGTGAGGAGG ACAAAGCTGC AAGCCAGGCG GAAGGTAAGG GGGGTGATTG TTGCTGTGGT  24840
GCTGCTGTTT TTTGTGTTTT GCTTCCCTTA CCACGTACTA AATCTACTGG ACACTCTGCT  24900
AAGGCGACGC TGGATCCGGG ACAGCTGCTA TACGCGGGGG TTGATAAACG TGGGTCTGGC  24960
```

| | |
|---|---|
| AGTAACCTCG TTACTGCAGG CACTGTACAG CGCCGTGGTT CCCCTGATAT ACTCCTGCCT | 25020 |
| GGGATCCCTC TTTAGGCAGA GGATGTACGG TCTCTTCCAA AGCCTCAGGC AGTCTTTCAT | 25080 |
| GTCCGGCGCC ACCACGTAGC CCGCGGATGT CTACGTGCCC TTCCCCCTTA ATTTAATCTA | 25140 |
| GCCTCCCGTT CCCATGATGC AGAGAGGCGA ATTTGGTTTG TACACAGATG TGACTATGTA | 25200 |
| TTTGTTTTAT TATGCGATTA AATGAGGGGT CTGATCCCAA AAGCAATGTT TAGTGGTGGT | 25260 |
| CGTTGATCTT CTTGACGCTC CATAGGTAGA TTGACTGGAA CGCCATGGCC CACGGGACA | 25320 |
| TGGACAGGGG TGTTAGGTCT GGTGGAACAT GCTGCCACTG CCACGGATGG AACATCAGAG | 25380 |
| ATGGGTCTAT GATCAGGGCA GCGTGTCGCC CGTCACTGGA TGTAAGTCCG GCCACCGTGG | 25440 |
| AGTTGCCTGT GGGGTTTCTG GGATAGTGTC TGGCTGGCAG GGTCTCATCC GCGGCATTTC | 25500 |
| CATGGTAGGT GAGGGTTATC TCGCCTCGCT GTCTCAGTAT GTACTCGAGG GCGTCCTGCT | 25560 |
| CGTACCGGAC CCCCAGGTAC TCTCCCTGGG CCCAGCTGGG CAGCACCGTC CCCCGCAACA | 25620 |
| CTCGGAGGAA AACGCTCTTA GTGTTCTGAG GGATCTGTAT GTTTAGCCAG TGGCTGTCAT | 25680 |
| ACAGCTTGGA CACGTTGGTC TCCAGGTTTA CCGCCCAGCG CTGGGGTGGT GTGGGTCCGT | 25740 |
| ACGTGTATGG TGAGGATTCC GACCGGCCCA CTACACCCAG GGCCACCAGC AGCTGGAAGC | 25800 |
| CCACCTCGCC ACAGCAGATG GAGAATGTGT CGGGTCTGTT TAGAAACTCT GTCAGGGTGG | 25860 |
| AGGCACAGGT AGGGTCGTTA CACAGCGCCA GGACCCATCC CCTGGCGCTG GCGTAGCTGG | 25920 |
| CCTGGCAGCC TGTTCTGAGA CATGTAATCA GACCAGAGAA CCCCGACAAG GACTGTCCTC | 25980 |
| GTTTAAGCTC TTCCACAGTC ACCGTGGCCA CCTCAAAGCC CGTGTTCTGC AACGCGGCCA | 26040 |
| TGAGCGCGTA CGGGGCACTG CTCCCAGGCA GCACCAACGC GGCCACACGG CGCGGGGAGG | 26100 |
| TGGGGCACGA AAACAGGCGC AGCTGACTCC CAAGGCACAT GGCCCTTAGG CTGCCCAGGT | 26160 |
| GATGCTCCAG ACGACCCAGG TCCTTCCTGT GCATGTCCTC CAGTGGGTGC AGGGGAGGCG | 26220 |
| TCACCAGGTT CCACATTTCG TCAGAAAAGG AGGTCCATGA GACTTGCAAG GAAGTCAGGG | 26280 |
| TCTCTTGAAA CACAACTGTC TCGTTCTGCA AAACCGTGAC GTTGTTGCCT TGTCCCTCGG | 26340 |
| GGCCAACGGT GCCCAGTGGG TGTGCCACGC AGCGGTAGTC CCTGGCCGCC CGCAGCACCT | 26400 |
| CTGACAAGTG TACCTGGGGC ACCTCAACCA GTGCCCCAGG GGTCTCTGAA ACCATAAGTT | 26460 |
| CGAGCGGGTT AGGGTGGGCG GGTAGTGAGA GCTGCAGTCC CCTGCAGCCG GCCAGGGCCA | 26520 |
| TCTCGATTGC AGATGGGAGA AGCCCTCCGT CCCCTATGTC GTGCCCAGAT ACAATGAGCC | 26580 |
| TCTTGGACAT CAGGTACTTA ACAAGCATGA ACAGGCTGGC GACCGTGGAC GGGTTCAGAG | 26640 |
| GGGGTATTGG GTGCCTGGAT GCCAGGAAGT TGTGCTCGAA GGTGGACCCG GCTATGAGAC | 26700 |
| AGCTCTGATT CACGGCCAGG TATACCAGGG CGTTGCCTTC GACCTTTACG TCCGGGGTGA | 26760 |
| CCCTGTATCT GGATCCCTTG ACCTCGGCCC AGCTGGTAAA CACCACCGAG TTGAAGGGAA | 26820 |
| GGACCTCCAC CGTTTCTTGC TGTTGTGTGA TGCGCACATG GCGCTCCGAA AGCGTCGGAG | 26880 |
| AGCTGGCAGC CGAGGAGATG GACAGTGCCA CTCCCAGCTC CCGGCAGAAT TCCTTGCAGG | 26940 |
| CGAAGAGGCA CTCCTGTAGG AGGCCGGCTT GGTGGTCCTC TGGACTCCAC GCCACGGCGC | 27000 |
| CAGTTAGCAC TACGTCCTGG AGCTTGGACA CGGGACTGAA CATGAGGTTG GTGAGAGCCT | 27060 |
| CGGTGATGGC ATAGGTGGCC CCGGTGGATA CATTAGTAGC CATCTTGTAG GCCTGCTCCC | 27120 |
| CCATGGCCAT TGCCTGACCC CTCCACGCTG GCACTGGAAG CAGCTCCTGG GGCAGGGCCT | 27180 |
| TCACCCAGGT CTCGAAGTCC TTGTGTAGGA GGTTGGCCAT GGACGGAGTG ATGGCCTCCA | 27240 |
| CCGTGTCGGG CACTCTGGGC GCCACCCTCT CGGCCAGCAT GGACGAGTGC AGCACCAGGT | 27300 |
| GGTAGTCTGA AACCGGTATG TCCAGGGGTC CCACGCCAGC CTGTTGGGCG ATGAGGCCGT | 27360 |

-continued

```
TGGAGCATCG GTCCATGTGT CGCGTAAAGA ACTCCTTGCT GCCAACCGTC GAGTGGCGAA   27420

GTAACTGGTG GATTGTGGAG CCGGTGGCAA AAAGGCCCCA GTCAACATCC TCGGGGTGCC   27480

CCGAGACGCG GACACCATCG GACAGCGCCA GCCAGGGGGA CGGGGGGGTG GACGACGGCT   27540

GGTCTACAGA GAAGACCCTC GTGGTCTCCC CGGTCAGGTC GTCTACTATT CTGATGCCTG   27600

GGTGCTCCGA GGTCCTCCCG AGGACCGTTA CCTGGCACGC GCACAGGCGC GCGGCGCGCT   27660

GCAGTACCTC CAACGGGGTC TCGCCCAGAT CCCCAGGCAC CGCGCCCGAC TCTGCCACCA   27720

CCGCAAACAC CAGGGAGCAA TACACGTTGA GAAAGTGCTC TGCCACCGCC GCCTTCACGG   27780

CATCCGGACC GGCCGCGGGA TCCGCAGGCA GGTGGGTGCG CACCTCGTCG GGTAGCTTGG   27840

AGACAAACAG CTCCAGGCCG GTCCGCGGCG CCAGCGCCTG CAGGTGCCTC ACCACCGGGG   27900

CCGGGTCATG CGATCTGTTT AGTCCGGAGA AGATAGGGCC CTTGGCAAGC CGCTGGACCA   27960

GCTTCAGGGT CTCCAAGATG CGCACCGCAT TGTCGGAGCT GTCGCGATAG AGGTTAGGGT   28020

AGGTGTCCGG TCCATCCGTG GGCTCAAACC TGCCCAGACA CACCACTGTC TGCTGGGGA    28080

TCATCCTTCT CAGGGAGATG CATTCTTTGG AAGTAGTGGT AGAGATGGAG CAGACTGCCA   28140

GGGCGTTGCC AGGAGTGGTG GCGATGGTGC GCACCGTTTT TAAGAAACCC CCCAGGGTGG   28200

GGACTCCCGC TCCCTGCAGC ATCTCGGCCT GCTGTACGCC CTTGGCGAAT ATGCGACGGA   28260

ATCGGCTGTG CGCACGGGGT CCCAGGGCCG GTTCGGTGGC ATACAGGCCG GTGAGGGCCC   28320

CCTGTGTCTG TCCGCCTGGA AACAGGGTGC TGTGAAACAG CAGGTTGCCA AGGCCGCGAA   28380

TACCCCTCTG CACGCTGCTG TGGACGTGGG TGTACGCTCC GTGGATCCCG AACGCCTGTC   28440

TGGCACAGTT CCAGGGCCAC CGTTCCATGG TGCATCTTCC CGGTATCACA AAGTACCTGG   28500

CCACGTTATA ATTGTCCCCG GTTGAAGCCT GCACCGCCAG CGGTAGCAGG TCTGCCCCCA   28560

GGGATATCAT AACAGCCTGC ATAATGACAT CATCTTCAAT GTGTGGCCTA GCCACGGGCT   28620

GGGGACCCTC GGGCACTTCC AACCCCTCGT ACGGTACCAG GTCGGTATTT TGTGTAAATG   28680

CCCTGATAAA CTGAGGTGGG TGTGGTTCTA GCAGGGTCTG TGTGATTTTG GACACCAGGT   28740

GCCTGCCCAC TTCCACTCTA GCCCACTCCT GCAATCCTAG CTCTTGCAGC AGAACTGCAA   28800

GCTCTGTTGA CAATGTTGTG GGCCGGTGGT GCATGTTTGG CCCGTAGCCA AAGGATACAA   28860

CACGCTCGCT CCCCCGTGGC ACAGACCGCC TGATGACATG GGGATATCCA AGGAGCGGTG   28920

ACAGCACAGC GAGCACCGTC TGTATTTCCA CATCCCGTCT CTCTCGCTCC TCCCTCGAAG   28980

TGGGAGGTCT TCGGAAAGTT ATCCATAGCA GATAGTAGCC TCCGGTGCCA CCGGGTACGA   29040

GAGTGAGTGT GCCCGTACGG CTTGTATAAA AGTTCACAAA AGCTTCCTCA TCCGCGGTGA   29100

GATCACTCTC CAACCACAGC CCAGTGACGT CGTAGGCCAT GCCTAGAGGG CGCACCGCCC   29160

CCGGGGACAC CCTCTGTAGT CAGGCTGCCG AGAAACCCGC GAGATCTCTG GGGAGTAGGA   29220

AGAAACTTAG AATCCCCAAA TATGTCGCAG TCACAGGTTG TCGGGCAGAG TCTGTTTCCG   29280

CTTTCATGGG ATCCACAGTT ACTTGTAGCC ATGTCACTAA CCTCAAATAC TCAAAAAAG    29340

CTATCGATGG AAAAATGCTG TGGTCCTAGG TTAGTCCGTG GGAAACAAAA CTTCCTCATA   29400

CACTTCATCT GCAGGCTGAA ATGGTGGCGG ATCCAGACTC CTTACACCAC AGTTGCTCAC   29460

ATTAGAGATA CCTGATTGGT TAATACAAGC GGACGCACGC GTTGGTGGAG GCGTGTTGTC   29520

GCCCAAGATA CTAGCATAGG TGACTGTGCG TTCGCTATGT AGTTGCTGCA TTTCAAGTTG   29580

GGTCGTTACT TCTGTGTTGC AAACCCTTAC TGGAGATAAT GCCATGTCTG TTGTGGAACT   29640

TAAAATACGC GAGTGTATAA CATTTCTAGA TGGTAGAGGT GGTAAACGGC GAGCTAAATG   29700
```

-continued

```
ATTAACATCG GACATATCC TGCCTGCATG AGCATGTGGT GTGTCGTGTG GTGTATATAT   29760

TGGTAATCTT GTTGTTACAT TGTTGAACGA CACAAGTCTG CTCTCTCGGT AGAGATAACC   29820

CACCAGTACG GCTTGGCCAG TACCTAATAA GAAAAAATAA AATCGTTAAT CTCTGTTTTT   29880

ATGTGGCGCT GGTGTTCCAA TTATAAATAA AAACACAACT CACTTAATAT CACAATTACA   29940

CAAATCAGTC CTGAAGTAAC ACCTGTAGTC CAACCGTCAG TGTAGAGCAG GACTAACTTA   30000

ACACAGCATC CAGCACATGT CCATGCTAAG GAAATAAACC AAAGTTATGT TTCGGTTTGC   30060

TTTATGACCA GGGAGCTGCT ACCCAGGTAC AAAAAATCCT TACCCAAAAA TAGAAACAGG   30120

AAGCCACCAG AGAGTGAAGC TTTGTGAAAG CTTTGCCAGC AGAAGAAACA ATATAATAAA   30180

AAGCCACAGC CTGCTAGTAA TGTTATACTC CCTGTAAATA AAAAATATGG ACAGTAATAA   30240

TTTATGACAC CCAATAAGTA TGTGGAAAAA ATGTAATGTA AACCACTATA CTGGTAAAAA   30300

CATACCTTCG TTATTGGTGT CTTGTTCGCG CTTTATAAAC AGTATCCCTA TTGTTGTGGT   30360

TAGTGTAACC AACACTCCTC CTTGTAAAAG TAAAAATGAC ATAAGCCCCT TAGTTGATCC   30420

AATCCAATGT CGTTTCATTG TTATAAACAA GCCGGTCATA CCTGTAATAA AGTTATTCAT   30480

TACAAAATGT TATAATAGTA TTGGTAATGT TTAGTTAAGA TAATGTAAAC TTCACAGTAG   30540

TCATATACCA ATATGTATGC AGCTTATGCA TCCTGCGATG ATTACAGAAA GGCATGAATG   30600

GGAAACGCAA AAAAAGGCCG GTGTTGCCTT GAGTATACCT GTAGTAAAAA ATAAATAATA   30660

TTGTTGGTTG CAATGCTTAG GTGCAAGCAG ACATAATTGC ATAGCAGTAA AAACCAGACT   30720

TACCACCACA TATTGCAAAC ACACATGCAG CGAGCTTGAG ACAAGGCCCA TTATCTGTTG   30780

CAAAGATATG TATAAAAAAA ACAAGCAACA ATGTCCATAA TGGCAAAAAA AACTGGCAAT   30840

GTGTCCAGTT GTTGTAAATC TGCAATCCCA TTGAGAATAT AAGTACCAAC ACCATAACAA   30900

TGCACAGTAA TCCGCTATCA ATAGTGCATT TAACGACTCT TAATGTTCCA CCAAGTGATA   30960

GAATGGCTGA AAAACACATA CAGGGGAATT ACGTTTTTTT AAAAAATTGG AAATATTAGA   31020

TACATAATTT TTATTTAATA AAAAACCTTT AGTAAAACTT ACCAGTAATT ATAGACAATA   31080

AACTTATAAT ACAAACACAA ACAGTACTCA AAGTACTTTG AGTAGAGAAA CTCCAACTGG   31140

CAAAGGCAAT ACATCCTAAA ACAAAAGACA AATACACGAG ACATTTAAAC AATGTATACT   31200

TAGAAAGAAA TAAGTTAAAC ATTTAAAAAA TGTAACTTAC CAACAATTAT AGATGGTCCA   31260

ATGGGAGGGG AAGCTTGAAA ACGTTGTTTT TTTGACTGCA CATATATGTT GTTATTGTAC   31320

AAAAAAGTTG GTAGTAAACA CTTATGTTAC TGAGCAAAAA TATGGTGTTT TGTAAATTTA   31380

TAGTTAAAAG ACAAAACATA ATAGACAAAC ACCCACAACA TGTTATAAGT GCTGCAAACC   31440

AAGTACCCCA CAGGTATTTT TTGTAATTCA TTGTAGACAA AAAGCCCAAG GCCCAAAAAT   31500

GAAGTGGACA AAAGAAATAT GTAATTAAGT GTAGTTGGAC AAGGAATTAT ATAGCTGGAT   31560

GAGTTAGTTT TGCACAGAAC CAGACATCCT ATTTTTGTTT GGAAACCTAA AATCCGGATG   31620

AAGGGCTTAT AAAATGGCAC AGCTGCAAAA AGCTGATAAT GTAACACTGC ATCCTGGTGT   31680

TTTTGATTGT AGCGGAAAAA TGTAATAAAT TTTACAGACA GTTTTGCCTA CTGAGAACAT   31740

GTTGAAAAAA AGGCACTAAG GGCTTTTTTG CCAAAGGAAA AATGCCCCCG TGGGGTTAGG   31800

GGAAAGGGGG GATGGGGTGA TGGGGAATG GTGGGAAAGG GGGGATGGGG TGATGGGGA    31860

ATGGTGGGAA AGGGGTGATG GGGTGATGGG GGAATGGGGG GAAAGGGGGA ATGGGGGGAA   31920

AGGGGGAATG GGGGGAAAGG GGGAATGGGG GGAAAGGGGG GATGGGGGGA AAGGGGGAAT   31980

GGGGGGAAAG GGGGAATGGG GGGAAAGGGG GGATGGGGGG AAAGGGGGAA TGGGGGGAAA   32040

GGGGGGATGG GGGGAAACGG GGGATGGGGG GAAAGGGGGG ATGGGGGGGA AAGGGGGGAT   32100
```

```
GGGGGGGAAA GGGGGGATGG GGGGGAAAGG GGGGATGGGG GGGAAAGGGG GGATGGGGAA    32160

GGGGGGGGGG AGGGGGAAGG GGGTGAAGGG GGAAGGGGGG AGGCGAA                  32207
```

UNIQUE ASSOCIATED KAPOSI'S SARCOMA VIRUS SEQUENCES AND USES THEREOF

This application is a continuation-in-part application of U.S. Ser. No. 08/592,963, filed Jan. 29, 1996, now abandoned, PCT International Application No. PCT/US95/15138, filed Nov. 21, 1995, and PCT/US95/10194, filed Aug. 11, 1995, claiming priority of U.S. Ser. No. 08/420,235, filed Apr. 11, 1995 now U.S. Pat. No. 5,801,042, and of U.S. Ser. No. 08/343,101, filed Nov. 21, 1994, now U.S. Pat. No. 5,630,754, which is a continuation-in-part of U.S. Ser. No. 08/292,365, filed Aug. 18, 1994, now abandoned, which is hereby incorporated by reference.

The invention disclosed herein was made with Government support under a co-operative agreement CCU210852 from the Centers for Disease Control and Prevention, and under National Institutes of Health, National Cancer Institute award CA67391 of the Department of Health and Human Services. Accordingly, the U.S. Government has certain rights in this invention.

Throughout this application, various publications may be referenced by Arabic numerals in brackets. Full citations for these publications may be found at the end of the Detailed Description of the Invention. The disclosures of all publications cited herein are in their entirety hereby incorporated by reference into this application to more fully describe the state of the art to which this invention pertains.

BACKGROUND OF THE INVENTION

Kaposi's sarcoma-associated herpesvirus (KSHV) is a new human herpesvirus (HHV8) believed to cause Kaposi's sarcoma (KS) [1,2].

Kaposi's sarcoma is the most common neoplasm occurring in persons with acquired immunodeficiency syndrome (AIDS). Approximately 15–20% of AIDS patients develop this neoplasm which rarely occurs in immunocompetent individuals. Epidemiologic evidence suggests that AIDS-associated KS (AIDS-KS) has an infectious etiology. Gay and bisexual AIDS patients are approximately twenty times more likely than hemophiliac AIDS patients to develop KS, and KS may be associated with specific sexual practices among gay men with AIDS. KS is uncommon among adult AIDS patients infected through heterosexual or parenteral HIV transmission, or among pediatric AIDS patients infected through vertical HIV transmission. Agents previously suspected of causing KS include cytomegalovirus, hepatitis B virus, human papillomavirus, Epstein-Barr virus (EBV), human herpesvirus 6, human immunodeficiency virus (HIV), and Mycoplasma penetrans. Non-infectious environmental agents, such as nitrite inhalants, also have been proposed to play a role in KS tumorigenesis. Extensive investigations, however, have not demonstrated an etiologic association between any of these agents and AIDS-KS.

SUMMARY OF THE INVENTION

This invention provides an isolated nucleic acid molecule which encodes Kaposi's Sarcoma-Associated Herpesvirus (KSHV) polypeptides. This invention provides an isolated polypeptide molecule of KSHV. This invention provides an antibody specific to the polypeptide. Antisense and triplex oligonucleotide molecules are also provided. This invention provides a vaccine for Kaposi's Sarcoma (KS). This invention provides methods of vaccination, prophylaxis, diagnosis and treatment of a subject with KS and of detecting expression of a DNA virus associated with Kaposi's sarcoma in a cell.

BRIEF DESCRIPTION OF THE FIGURES

FIGS. 2A–2D (FIG. 2A) Sequence of terminal repeat unit (TR) demonstrating its high G+C content (SEQ ID NO:16). Sequences highly similar to conserved herpesvirus pac1 sites are underlined with less similar sites to specific pac1 and pac2 sequences italicized. (FIG. 2B) Southern blot of DNA from BC-1 (lane 1), BCP-1 (lane 2) and a KS lesion (lane 3) digested with NdeII which cuts once in the TR sequence and probed with a plasmid containing the TR sequence. The intense hybridization band at 0.8 kb represents multiple copies of the NdeII-digested single unit TR (FIG. 2C). A schematic representation (FIG. 2C) of genome structures of KSHV in BCP-1 and BC-1 cell lines consistent with the data presented in (FIG. 2B) and (FIG. 2D). TaqI (T) sites flank the TR regions and Nde II (N) sites are within the TRs. Lower case tr refers to the deleted truncated TR unit at the left end of the unique region. DR represents the duplicated region of the LUR buried within the TR. (FIG. 2D) Southern blot hybridization with TR probe of DNA from BC-1 (lane 1), BCP-1 (lane 2), a KS lesion (lane 3), and HBL-6 (lane 4) digested with Taq I, which does not cut in the TR. Taq I-digested DNA from both BC-1 (lane 1) and HBL-6 (lane 4) show similar TR hybridization patterns suggesting identical insertion of a unique sequence into the TR region, which sequencing studies demonstrate is a duplicated portion of the LUR (see Experimental Details Section). BCP-1 TR hybridization (lane 2) shows laddering consistent with a virus population having variable TR region lengths within this cell line due to lytic replication. The absence of TR laddering in KS lesion DNA (lane 3) suggests that a clonal virus population is present in the tumor.

FIGS. 3A–3C CLUSTAL W alignments of KSHV-encoded polypeptide sequences to corresponding human cell signaling pathway polypeptide sequences. FIG. 3A. Two KSHV MIP-like polypeptides (vMIP-I and vMIP-II) are compared to human MIP-1α, MIP-1β and RANTES (amino acid identity to vMIP-I indicated by black reverse shading, to vMIP-II alone by gray reverse shading, and the C—C dimer motif is italicized). Both KSHV MIP genes encode 19 residue N-terminus hydrophobic secretory leader sequences which are relatively poorly conserved (vMIP-I also has a second C—C dimer in the hydrophobic leader sequence without similarity to the chemokine dicysteine motif). Potential O-linked glycosylation sites for vMIP-I (gapped positions 22 and 27) are not present in vMIP-II, which has only one predicted potential serine glycosylation site (position 51) not found in vMIP-I. FIG. 3B. Alignment of the KSHV vIL-6 to human IL-6. FIGS. 3C-1-A–3C-1-B and 3C-2-A–3C-2-B. Alignment of the KSHV vIRF polypeptide to human ICSBP and ISGF3 with the putative ICS-binding typtophans (W) for ICSBP and ISGF3 in italics.

FIGS. 4A–4F Northern hybridization of total RNA extracted from BCP-1 and BC-1 cells with or without 48 hour incubation with TPA and control P3HR1 cells after TPA incubation. All four genes (FIG. 4A, vMIP-I; FIG. 4B, vMIP-II; FIG. 4C, vIL-6; FIG. 4D, vIRF) are TPA inducible but constitutive, noninduced expression of vIL-6 (FIG. 4C) and vIRF (FIG. 4D) is also evident for BCP-1 and BC-1 and of vMIP-I for BCP-1 (FIG. 4A). Representative hybridizations to a human β-actin probe (FIGS. 4E–4F) demonstrate comparable loading of RNA for cell preparations.

FIG. 5B. Anti-huIL-6 monoclonal antibodies do not cross-react with cell-associated or recombinant vIL-6 preparations.

(FIG. 7C) Cytoplasmic localization of vIL-6 in spindle-shaped cells from an AIDS-KS lesion. Of eight KS lesions, only one had readily identifiable vIL-6 staining of a subpopulation of cells. In contrast, the majority of pelleted lymphoma cells from a nonAIDS, EBV-negative PEL have intense vIL-6 staining (FIG. 7E). No immunostaining is present in control angiosarcoma (FIG. 7D) or multiple myeloma tissues (FIG. 7F).

FIG. 8A. CD34 (red) and vIL-6 colocalize (blue) in a KS spindle cell (arrow). Purple coloration is due to overlapping chromagen staining (100×). FIG. 8B. CD45 common leukocyte antigen staining (blue, arrow) on vIL-6 (red) expressing Kaposi's sarcoma cells (100×). FIG. 8C. Low power magnification (20×) demonstrating numerous vIL-6 producing hematopoietic cells (red) in a lymph node from a patient with KS. Arrows only indicate the most prominently staining cells; nuclei counterstained with hematoxylin. FIG. 8D. Colocalization of CD20 (brown, arrows) with vIL-6 (red) in an AIDS-KS patient's lymph node (100×).

DETAILED DESCRIPTION OF THE INVENTION

Definitions

Figure 1A:
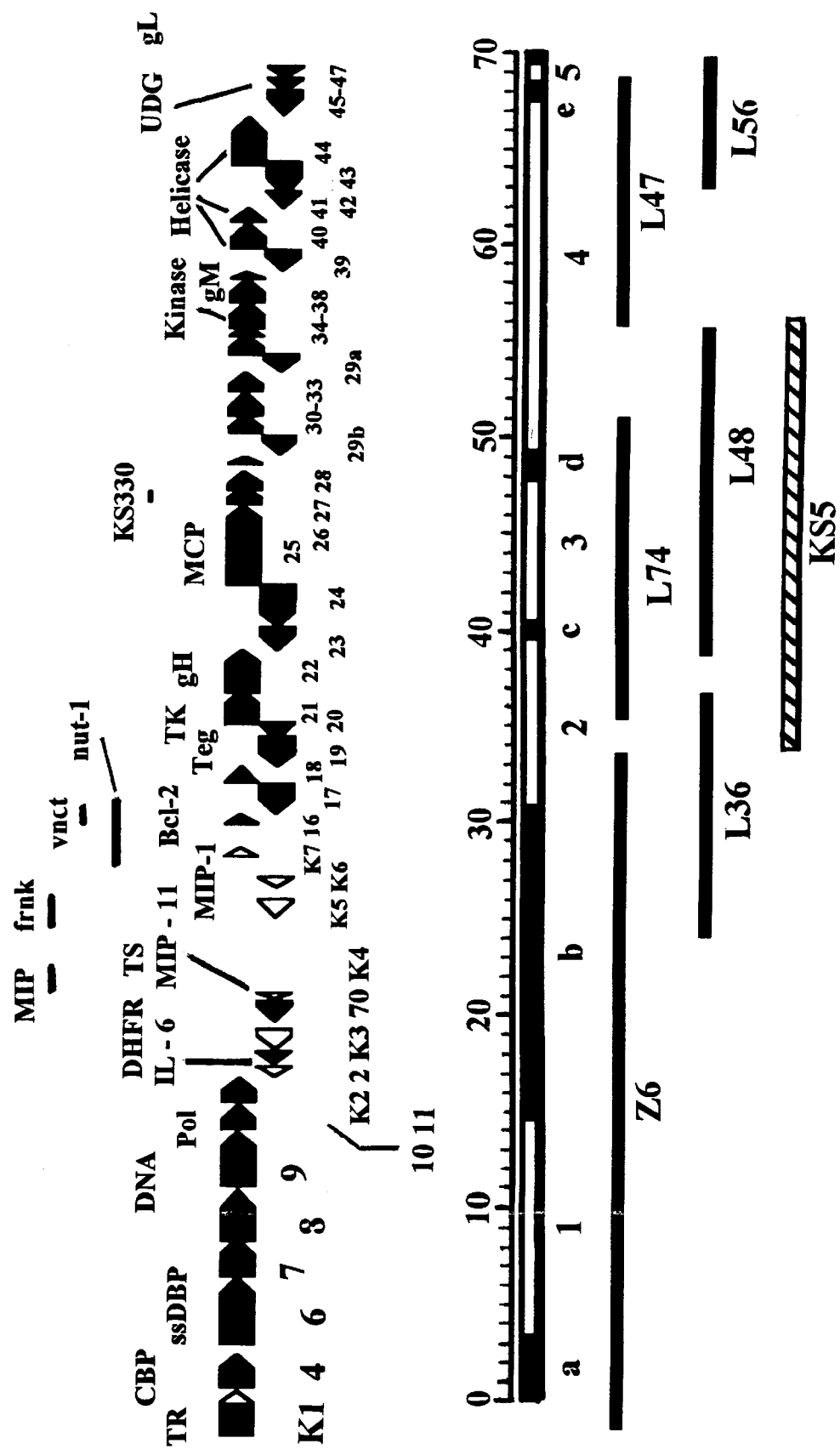
FIGS. 1A and 1B Annotated long unique region (LUR) and terminal repeat (TR) of the KSHV genome. The orientation of identified ORFs in the LUR are denoted by the direction of arrows, with ORFs similar to HVS in dark blue and dis-similar ORFs in light blue. Seven blocks (numbered) of conserved herpesvirus genes with nonconserved interblock regions (lettered) are shown under the kilobase marker; the block numbering scheme differs from the original description by Chee (Chee et al., 1990, *Curr. Topics Microbiol. Immunol.* 154, 125–169). The overlapping cosmid (Z prefix) and lambda (L prefix) clones used to map the KSHV genome are compared to the KS5 lambda phage clone from a KS lesion and shown below. Features and putative coding regions not specifically designated are shown above the ORF map. Repeat regions are shown as white lines (frnk, vnct, waka/jwka, zppa, moi, mdsk). Putative coding regions and other features (see Experimental Details Section I) not designated as ORFs are shown as solid lines.

The following standard abbreviations are used throughout the specification to indicate specific nucleotides:

C=cytosine

A=adenosine

T=thymidine

G=guanosine

The term "nucleic acid", as used herein, refers to either DNA or RNA, including complementary DNA (cDNA), genomic DNA and messenger RNA (mRNA). As used herein, "genomic" means both coding and non-coding regions of the isolated nucleic acid molecule. "Nucleic acid sequence" refers to a single- or double-stranded polymer of deoxyribonucleotide or ribonucleotide bases read from the 5' to the 3' end. It includes both self-replicating plasmids, infectious polymers of DNA or RNA and nonfunctional DNA or RNA.

The term "polypeptide", as used herein, refers to either the full length gene product encoded by the nucleic acid, or portions thereof. Thus, "polypeptide" includes not only the full-length protein, but also partial-length fragments, including peptides less than fifty amino acid residues in length.

The term "SSC" refers to a citrate-saline solution of 0.15 M sodium chloride and 20 mM sodium citrate. Solutions are often expressed as multiples or fractions of this concentration. For example, 6×SSC refers to a solution having a sodium chloride and sodium citrate concentration of 6 times this amount or 0.9 M sodium chloride and 120 mM sodium citrate. 0.2×SSC refers to a solution 0.2 times the SSC concentration or 0.03 M sodium chloride and 4 mM sodium citrate.

The phrase "selectively hybridizing to" and the phrase "specific hybridization" describe a nucleic acid probe that hybridizes, duplexes or binds only to a particular target DNA or RNA sequence when the target sequences are present in a preparation of total cellular DNA or RNA. By selectively hybridizing it is meant that a probe binds to a given target in a manner that is detectable in a different manner from non-target sequence under high stringency conditions of hybridization.

"Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al. (1989) *Molecular Cloning: A Laboratory Manual* (2nd ed.), Cold Spring Harbor Laboratory, Vols. 1–3 or Ausubel, F., et al. (1987) *Current Protocols in Molecular Biology*, New York.

The phrase "nucleic acid molecule encoding" refers to a nucleic acid molecule which directs the expression of a specific polypeptide. The nucleic acid sequences include both the DNA strand sequence that is transcribed into RNA, the complementary DNA strand, and the RNA sequence that is translated into protein. The nucleic acid molecule includes both the full length nucleic acid sequence as well as non-full length sequences. It being further understood that the sequence includes the degenerate codons of the native sequence or sequences which may be introduced to provide codon preference in a specific host cell.

A nucleic acid probe is "specific" for a target organism of interest if it includes a nucleotide sequence which when detected is determinative of the presence of the organism in the presence of a heterogeneous population of proteins and other biologics. A specific nucleic acid probe is targeted to that portion of the sequence which is determinative of the organism and will not hybridize to other sequences, especially those of the host, where a pathogen is being detected.

The phrase "expression cassette", refers to nucleotide sequences which are capable of affecting expression of a structural gene in hosts compatible with such sequences. Such cassettes include at least promoters and optionally, transcription termination signals. Additional factors necessary or helpful in effecting expression may also be used as described herein.

The term "operably linked" as used herein refers to linkage of a promoter upstream from a DNA sequence such that the promoter mediates transcription of the DNA sequence.

The term "vector", refers to viral expression systems, autonomous self-replicating circular DNA (plasmids), and includes both expression and nonexpression plasmids. Where a recombinant microorganism or cell culture is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or is incorporated within the host's genome.

The term "plasmid" refers to an autonomous circular DNA molecule capable of replication in a cell, and includes both the expression and nonexpression types. Where a recombinant microorganism or cell culture is described as hosting an "expression plasmid", this includes latent viral DNA integrated into the host chromosome(s). Where a plasmid is being maintained by a host cell, the plasmid is either being stably replicated by the cells during mitosis as an autonomous structure or is incorporated within the host's genome.

The phrase "recombinant protein" or "recombinantly produced protein" refers to a polypeptide produced using non-native cells. The cells produce the protein because they have been genetically altered by the introduction of the appropriate nucleic acid sequence.

The following terms are used to describe the sequence relationships between two or more nucleic acid molecules: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence.

Optimal alignment of sequences in a comparison window may be conducted by the algorithm of Smith and Waterman (1981) *Adv. Appl. Math.* 2:482, by the algorithm of Needleman and Wunsch (1970) *J. Mol. Biol.* 48:443, by the search-for-similarity method of Pearson and Lipman (1988) *Proc. Natl. Acad. Sci.* 85:2444, or by computerized implementations of these algorithms (GAP, BESTFIT, FASTA, and TFASTA in GCG, the Wisconsin Genetics Software Package Release 8.0, Genetics Computer Group, 575 Science Dr., Madison, Wis.).

As applied to polypeptides, the terms "substantial identity" or "substantial sequence identity" mean that two peptide sequences, when optimally aligned, such as by the programs GAP or BESTFIT using default gap which share at least 90 percent sequence identity, preferably at least 95 percent sequence identity, more preferably at least 99 percent sequence identity or more.

"Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties, such as charge or polarity, are not likely to effect the properties of a protein. Examples include glutamine for asparagine or glutamic acid for aspartic acid.

The phrase "substantially purified" or "isolated" when referring to a herpesvirus polypeptide, means a chemical composition which is essentially free of other cellular components. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. Generally, a substantially purified or isolated protein will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

The phrase "specifically binds to an antibody" or "specifically immunoreactive with", when referring to a polypeptide, refers to a binding reaction which is determinative of the presence of the KSHV polypeptide of the invention in the presence of a heterogeneous population of polypeptides and other biologics including viruses other than KSHV. Thus, under designated immunoassay conditions, the specified antibodies bind to the KSHV antigen and do not bind in a significant amount to other antigens present in the sample.

"Specific binding" to an antibody under such conditions may require an antibody that is selected for its specificity for a particular antigen. For example, antibodies raised to KSHV antigens described herein can be selected to obtain antibodies specifically immunoreactive with KSHV polypeptides and not with other polypeptides.

"Biological sample" as used herein refers to any sample obtained from a living organism or from an organism that has died. Examples of biological samples include body fluids and tissue specimens.

It will be readily understood by those skilled in the art and it is intended here, that when reference is made to particular sequence listings, such reference includes sequences which substantially correspond to the listing and it's complement, including allowances for minor sequencing errors, single base changes, deletions, substitutions and the like, such that any such sequence variation corresponds to the nucleic acid sequence of the pathogenic organism or disease marker to which the relevant sequence listing relates.

I. Nucleic Acid Molecule from KSHV

This invention provides an isolated nucleic acid molecule which encodes a Kaposi's sarcoma-associated herpesvirus (KSHV) polypeptide.

In one embodiment, the isolated nucleic acid molecule which encodes a KSHV polypeptide has the nucleotide sequence as set forth in GenBank Accession Number U75698 and the start and stop codons set forth in Table 1. In another embodiment, the isolated nucleic acid molecule which encodes a KSHV polypeptide has the amino acid sequence defined by the translation of the nucleotide sequence set forth in GenBank Accession Number U75698 and the start and stop codons set forth in Table 1.

In one embodiment, the isolated nucleic acid molecule for a KSHV polypeptide has the 5' untranslated sequence as set forth in GenBank Accession Number U75698 upstream of the ATG start codon. In another embodiment, the isolated nucleic acid molecule for a KSHV polypeptide has the 3' untranslated sequence as set forth in GenBank Accession Number U75698 downstream of the stop codon.

In one embodiment the isolated nucleic acid molecule is genomic DNA. In another embodiment the isolated nucleic acid molecule is cDNA. In another embodiment RNA is derived from the isolated nucleic acid molecule or is capable of hybridizing with the isolated nucleic acid molecule.

Further, the nucleic acid molecule above may be associated with lymphoproliferative diseases including, but not limited to: Hodgkin's disease, non-Hodgkin's lymphoma, lymphatic leukemia, lymphosarcoma, splenomegaly, reticular cell sarcoma, Sezary's syndrome, mycosis fungoides, central nervous system lymphoma, AIDS related central nervous system lymphoma, post-transplant lymphoproliferative disorders, and Burkitt's lymphoma. A lymphoproliferative disorder is characterized as being the uncontrolled clonal or polyclonal expansion of lymphocytes involving lymph nodes, lymphoid tissue and other organs.

A. Isolation and Propagation of KSHV

KSHV can be propagated in vitro. For example, techniques for growing herpesviruses have been described by Ablashi et al. in *Virology* 184, 545–552. Briefly, PHA stimulated cord blood mononuclear cells, macrophage, neuronal, or glial cell lines are cocultivated with cerebrospinal fluid, plasma, peripheral blood leukocytes, or tissue extracts containing viral infected cells or purified virus. The recipient cells are treated with 5 µg/ml polybrene for 2 hours at 37° C. prior to infection. Infected cells are observed by demonstrating morphological changes, as well as being viral antigen positive.

For KSHV isolation, the virus is either harvested directly from cell culture fluid by centrifugation, or the infected cells are harvested, homogenized or lysed and the virus is separated from cellular debris and purified by standard methods of isopycnic sucrose density gradient centrifugation.

One skilled in the art may isolate and propagate KSHV employing the following protocol. Long-term establishment of a B lymphoid cell line infected with KSHV (e.g., RCC-1, HBL-6 or BCBL-1) is accomplished using body-cavity based lymphomas and standard techniques (Glick, 1980, *Fundamentals of Human Lymphoid Culture*, Marcel Dekker, New York; Knowles et al., 1989, *Blood* 73, 792–798; Metcalf, 1984, *Clonal Culture of Hematopoeitic Cells: Techniques and Applications*, Elsevier, N.Y.).

Fresh lymphoma tissue containing viable infected cells is filtered to form a single cell suspension. The cells are separated by Ficoll-Plaque centrifugation and lymphocyte layer is removed. The lymphocytes are then placed at >1×10$^6$ cells/ml into standard lymphocyte tissue culture medium, such as RPMI 1640 supplemented with 10% fetal calf serum. Immortalized lymphocytes containing KSHV are indefinitely grown in the culture media while non-immortalized cells die during course of prolonged cultivation.

Further, KSHV may be propagated in a new cell line by removing media supernatant containing the virus from a continuously-infected cell line at a concentration of >1×10$^6$ cells/ml The media is centrifuged at 2000×g for 10 minutes and filtered through a 0.45µ filter to remove cells. The media is applied in a 1:1 volume with cells growing at >1×10$^6$ cells/ml for 48 hours. The cells are washed, pelleted and placed in fresh culture medium, then tested for KSHV after 14 days.

KSHV may be isolated from a cell line in the following manner. An infected cell line is lysed using standard methods, such as hyposmotic shock or Dounce homogenization or using repeated cycles of freezing and thawing in a small volume (<3 ml), and pelleted at 2000×g for 10 minutes. The supernatant is removed and centrifuged again at 10,000×g for 15 minutes to remove nuclei and organelles. The resulting low-speed, cell-free supernatant is filtered through a 0.45µ filter and centrifuged at 100,000×g for 1 hour to pellet the virus. The virus can then be washed and re-pelleted. The DNA is extracted from the viral pellet by standard techniques (e.g., phenol/chloroform) and tested for the presence of KSHV by Southern blotting and/or PCR using the specific probes described above.

For banding whole virion, the low-speed cell-free supernatant is adjusted to contain 7% PEG-8000. The PEG-supernatant is spun at 10,000×g for 30 min. The supernatant is poured off and the pellet collected and resuspended in a small volume (1–2 ml) of virus buffer (VB, 0.1 M NaCl, 0.01 M Tris, pH 7.5). The virion are isolated by centrifugation at 25,000 rpm in a 10–50% sucrose gradient made with VB. One ml fractions of the gradient are obtained by standard techniques (e.g., using a fractionator) and each fraction is tested by dot blotting using specific hybridizing probes to determine the gradient fraction containing the purified virus (preparation of the fraction is needed in order to detect the presence of the virus, i.e., standard DNA extraction).

The method for isolating the KSHV genome is based on Pellicer et al., 1978, *Cell* 14, 133–141 and Gibson and Roizmann, 1972, *J. Virol.* 10, 1044–52.

A final method for isolating the KSHV genome is clamped homogeneous electric field (CHEF) gel electrophoresis. Agarose plugs are prepared by resuspending cells infected with KSHV in 1% LMP agarose (Biorad) and 0.9% NaCl at 42° C. to a final concentration of 2.5×10$^7$ cells/ml. Solidified agarose plugs are transferred into lysis buffer (0.5M EDTA pH 8.0, 1% sarcosyl, proteinase K at 1 mg/ml final concentration) and incubated for 24 hours. Approximately $10^7$ cells are loaded in each lane. Gels are run at a gradient of 6.0 V/cm with a run time of 28 h on a CHEF Mapper XA pulsed field gel electrophoresis apparatus (Biorad), Southern blotted and hybridized to KS631Bam, KS330Bam and an EBV terminal repeat sequence.

To make a new cell line infected with KSHV, already-infected cells are co-cultivated with a Raji cell line separated by a $0.45\mu$ filter. Approximately, $1-2\times10^6$ already-infected BCBL-1 and $2\times10^6$ Raji cells are co-cultivated for 2–20 days in supplemented RPMI alone or with 20 ng/ml 12-O-tetradecanoyl phorbol-13-acetate (TPA). After 2–20 days co-cultivation, Raji cells are removed, washed and placed in supplemented RPMI 1640 media. A Raji culture co-cultivated with BCBL-1 in 20 ng/ml TPA for 2 days survived and has been kept in continuous suspension culture for >10 weeks. This cell line, designated RCC-1 (Raji Co-Culture, No.1) remains PCR positive for the KSHV sequence after multiple passages. RCC-1 cells periodically undergo rapid cytolysis suggestive of lytic reproduction of KSHV. Thus, RCC-1 is a Raji cell line newly-infected with KSHV. RCC-1 and RCC-$1_{2F5}$ were deposited on Oct. 19, 1994 under ATCC Accession No. CRL 11734 and CRL 11735, respectively, pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. HBL-6 was deposited (as BHL-6) on Nov. 18, 1994 under ATCC Accession No. CRL 11762 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A.

B. Hybridization Probes of KSHV

This invention provides a nucleic acid molecule of at least 14 nucleotides capable of specifically hybridizing with the isolated nucleic acid molecule as set forth in GenBank Accession Numbers U75698, U75699, U75700.

In one embodiment the nucleic acid molecule set forth in GenBank Accession Number U75698 comprises the long unique region (LUR) encoding KSHV polypeptides. In another embodiment the nucleic acid molecule set forth in GenBank Accession Number U75699 comprises the prototypical terminal repeat (TR). In another embodiment the nucleic acid molecule set forth in GenBank Accession Number U75700 comprises the incomplete terminal repeat (ITR).

In one embodiment the molecule is 8 to 36 nucleotides. In another embodiment the molecule is 12 to 25 nucleotides. In another embodiment the molecule is 14 nucleotides.

In one embodiment the molecule is DNA. In another embodiment the molecule is RNA.

In one embodiment the TR molecule contains cis-active elements required for DNA replication and packaging. In another embodiment the TR molecule is contained in a gene-cloning vector. In another embodiment the TR molecule is contained in a gene-therapy vector. In another embodiment the gene-therapy vector is expressed in lymphoid cells. In another embodiment, the TR comprises a molecular marker for determining the clonality of a tumor. In another embodiment, the marker provides a defining feature of the natural history of a tumor in a diagnostic assay.

This invention provides a B-lymphotrophic DNA vector comprising a plasmid or other self-replicable DNA molecule containing the 801 bp KSHV TR or a portion thereof.

High stringency hybridization conditions are selected at about 5° C. lower than the thermal melting point ($T_m$) for the specific sequence at a defined ionic strength and pH. The $T_m$ is the temperature (under defined ionic strength and pH) at which 50% of the salt concentration is at least about 0.02 molar at pH 7 and the temperature is at least about 60° C. As other factors may significantly affect the stringency of hybridization, including, among others, base composition and size of the complementary strands, the presence of organic solvents, i.e. salt or formamide concentration, and the extent of base mismatching, the combination of parameters is more important than the absolute measure of any one. For example, high stringency may be attained by overnight hybridization at about 68° C. in a 6×SSC solution, washing at room temperature with 6×SSC solution, followed by washing at about 68° C. in a 0.6×SSC solution. Hybridization with moderate stringency may be attained for example by: 1) filter pre-hybridizing and hybridizing with a solution of 3×SSC, 50% formamide, 0.1M Tris buffer at pH 7.5, 5×Denhardt's solution; 2.) pre-hybridization at 37° C. for 4 hours; 3) hybridization at 37° C. with amount of labeled probe equal to 3,000,000 cpm total for 16 hours; 4) wash in ×SSC and 0.1% SDS solution; 5) wash 4× for 1 minute each at room temperature in 4×SSC at 60° C. for 30 minutes each; and 6) dry and expose to film.

Nucleic acid probe technology is well known to those skilled in the art who readily appreciate that such probes may vary greatly in length and may be labeled with a detectable label, such as a radioisotope or fluorescent dye, to facilitate detection of the probe. DNA probe molecules may be produced by insertion of a DNA molecule having the full-length or a fragment of the isolated nucleic acid molecule of the DNA virus into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the full length or a fragment of the isolated nucleic acid molecule of the DNA virus downstream of a bacteriophage promoter such as T3, T7 or SP6. Large amounts of RNA probe may be produced by incubating the labeled nucleotides with a linearized isolated nucleic acid molecule of the DNA virus or its fragment where it contains an upstream promoter in the presence of the appropriate RNA polymerase.

As defined herein nucleic acid probes may be DNA or RNA fragments. DNA fragments can be prepared, for example, by digesting plasmid DNA, or by use of PCR, or synthesized by either the phosphoramidite method described by Beaucage and Carruthers, 1981, *Tetrahedron Lett.* 22, 1859–1862 or by the triester method according to Matteucci et al., 1981, *Am. Chem. Soc.* 103:3185. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid. It is also understood that when a specific sequence is identified for use a nucleic probe, a subsequence of the listed sequence which is 25 base pairs (bp) or more in length is also encompassed for use as a probe.

The nucleic acid molecules of the subject invention also include molecules coding for polypeptide analogs, fragments or derivatives of antigenic polypeptides which differ from naturally-occurring forms in terms of the identity or location of one or more amino acid residues (deletion analogs containing less than all of the residues specified for the polypeptide, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

C. Polypeptides of KSHV and Antibodies (Ab's) Thereto

This invention provides an isolated KSHV polypeptide, one from the list as set forth in Table 1 and below.

This invention provides the isolated KSHV polypeptide comprising viral macrophage inflammatory protein III (vMIP-III). In one embodiment, vMIP-III comprises an orphan cytokine. In another embodiment, vMIP-III is encoded by nucleotides 22,529–22,185. In another embodiment, vMIP-III comprises an anti-inflammatory drug. In a preferred embodiment, the drug is useful in treatment of an autoimmune disorder. In the most preferred embodiment, the drug is useful in treatment of rheumatoid arthritis.

This invention provides the isolated KSHV polypeptide comprising dihydrofolate reductase (DHFR) encoded by ORF 2. In one embodiment, DHFR participates in KSHV nucleotide synthesis. In another embodiment, DHFR comprises an enzyme essential for viral replication, inhibition of which prevents virus production. In another embodiment, DHFR comprises a subunit vaccine. In another embodiment, DHFR comprises an antigen for immunologic assays.

In another embodiment, DHFR has the amino acid sequence as set forth in SEQ ID NO:1.

In another embodiment, KSHV DHFR is inhibited by a sulfa drug known to inhibit bacterial DHFR. In a preferred embodiment, KSHV DHFR is inhibited by methotrexate or a derivative thereof known to inhibit mammalian DHFR. In another embodiment, the sulfa drug, methotrexate or a derivative thereof is selective among the human herpesviruses for inhibition of KSHV.

This invention provides the isolated KSHV polypeptide comprising thymidylate synthase (TS) encoded by ORF 70. In one embodiment, TS participates in KSHV nucleotide metabolism. In another embodiment, TS comprises an enzyme essential for viral replication, inhibition of which prevents virus production. In another embodiment, TS comprises a subunit vaccine. In another embodiment, TS comprises an antigen for immunologic assays.

This invention provides the isolated KSHV polypeptide comprising DNA polymerase encoded by ORF 9. In one embodiment, DNA polymerase comprises an enzyme essential for viral replication, inhibition of which prevents virus production. In another embodiment, DNA polymerase comprises a subunit vaccine. In another embodiment, DNA polymerase comprises an antigen for immunologic assays.

This invention provides the isolated KSHV polypeptide comprising alkaline exonuclease encoded by ORF 37. In one embodiment, alkaline exonuclease packages KSHV DNA into the virus particle. In another embodiment, alkaline exonuclease comprises an enzyme essential for viral replication, inhibition of which prevents virus production. In another embodiment, alkaline exonuclease comprises a subunit vaccine. In another embodiment, alkaline exonuclease comprises an antigen for immunologic assays.

This invention provides the isolated KSHV polypeptide comprising helicase-primase, subunits 1, 2 and 3 encoded by ORFs 40, 41 and 44, respectively. In one embodiment, helicase-primase comprises an enzyme activity essential for viral DNA replication. In another embodiment, helicase-primase is inhibited by nucleotide analogs. In another embodiment, helicase-primase is inhibited by known antiviral drugs. In another embodiment, inhibition of helicase-primase prevents KSHV replication.

This invention provides the isolated KSHV polypeptide comprising uracil DNA glycosylase (UDG) encoded by ORF 46. In one embodiment, uracil DNA glycosylase comprises an enzyme essential for KSHV DNA repair during DNA replication. In another embodiment, uracil DNA glycosylase is inhibited by known antiviral drugs. In another embodiment, uracil DNA glycosylase comprises a subunit vaccine. In another embodiment, uracil DNA glycosylase comprises an antigen for immunologic assays.

This invention provides the isolated KSHV polypeptide comprising single-stranded DNA binding protein (SSBP) encoded by ORF 06. In one embodiment, SSBP comprises an enzyme essential for KSHV DNA replication. In another embodiment, SSBP is inhibited by known antiviral drugs. In another embodiment, SSBP increases the processivity of polymerase reactions such as in the conventional PCR method for DNA amplification.

This invention provides the isolated KSHV polypeptide comprising viral protein kinase encoded by ORF 36. In another embodiment, viral protein kinase comprises an antigen for immunologic assays. In another embodiment, viral protein kinase comprises a subunit vaccine.

This invention provides the isolated KSHV polypeptide comprising lytic cycle transactivator protein (LCTP) encoded by ORF 50. In one embodiment, LCTP is required for activation of productive infection from the latent state. In another embodiment, LCTP is inhibited by known antiviral drugs. In another embodiment, prevention of LCTP expression maintains the virus in a latent state unable to replicate.

This invention provides the isolated KSHV polypeptide comprising ribonucleotide reductase, a two-subunit enzyme in which the small and large subunits are encoded by ORF 60 and ORF 61, respectively. In another embodiment, ribonucleotide reductase catalyzes conversion of ribonucleotides into deoxyribonucleotides for DNA replication. In another embodiment, ribonucleotide reductase is inhibited by known antiviral drugs in terminally differentiated cells not expressing cellular ribonucleotide reductase. In another embodiment, ribonucleotide reductase comprises an antigen for immunologic assays. In another embodiment, ribonucleotide reductase comprises a subunit vaccine. In another embodiment, ribonucleotide reductase comprises a transforming agent for establishment of immortalized cell lines.

This invention provides the isolated KSHV polypeptide comprising the protein encoded by ORF K1.

This invention provides the isolated KSHV polypeptide comprising complement-binding protein (v-CBP; CCP) encoded by ORF 4.

This invention provides the isolated KSHV polypeptide comprising transport protein encoded by ORF 7.

This invention provides the isolated KSHV polypeptide comprising glycoprotein B encoded by ORF 8.

This invention provides the isolated KSHV polypeptide comprising the protein encoded by ORF 10.

This invention provides the isolated KSHV polypeptide comprising the protein encoded by ORF 11.

This invention provides the isolated KSHV polypeptide comprising viral interleukin 6 (vIL-6) encoded by ORF K2.

In one embodiment, antibodies selectively recognizing vIL-6 allow differentiation among lymphomas.

This invention provides the isolated KSHV polypeptide comprising BHV4-IE1 I encoded by ORF K3.

This invention provides the isolated KSHV polypeptide comprising vMIP-II encoded by ORF K4. In one embodiment, vMIP-II comprises an anti-inflammatory drug. In a preferred embodiment, the drug is useful in treatment of an autoimmune disorder. In the most preferred embodiment, the drug is useful in treatment of rheumatoid arthritis.

This invention provides the isolated KSHV polypeptide comprising BHV4-IE1 II encoded by ORF K5.

This invention provides the isolated KSHV polypeptide comprising vMIP-I encoded by ORF K6 In one embodiment, vMIP-I comprises an anti-inflammatory drug. In a preferred embodiment, the drug is useful in treatment of an autoimmune disorder. In the most preferred embodiment, the drug is useful in treatment of rheumatoid arthritis.

This invention provides the isolated KSHV polypeptide comprising the protein encoded by ORF K7.

This invention provides the isolated KSHV polypeptide comprising Bcl-2 encoded by ORF 16.

This invention provides the isolated KSHV polypeptide comprising capsid protein I encoded by ORF 17.

This invention provides the isolated KSHV polypeptide comprising the protein encoded by ORF 18.

This invention provides the isolated KSHV polypeptide comprising tegument protein I encoded by ORF 19.

This invention provides the isolated KSHV polypeptide comprising the protein encoded by ORF 20.

This invention provides the isolated KSHV polypeptide comprising thymidine kinase encoded by ORF 21.

This invention provides the isolated KSHV polypeptide comprising glycoprotein H encoded by ORF 22.

In one embodiment, the isolated KSHV polypeptide comprises the protein encoded by ORF 23.

This invention provides the isolated KSHV polypeptide comprising the protein encoded by ORF 24.

This invention provides the isolated KSHV polypeptide comprising major capsid protein encoded by ORF 25.

This invention provides the isolated KSHV polypeptide comprising capsid protein II encoded by ORF 26.

This invention provides the isolated KSHV polypeptide comprising the protein encoded by ORF 27.

This invention provides the isolated KSHV polypeptide comprising the protein encoded by ORF 28.

This invention provides the isolated KSHV polypeptide comprising packaging protein II encoded by ORF 29b.

This invention provides the isolated KSHV polypeptide comprising the protein encoded by ORF 30.

This invention provides the isolated KSHV polypeptide comprising the protein encoded by ORF 31.

This invention provides the isolated KSHV polypeptide comprising the protein encoded by ORF 32.

This invention provides the isolated KSHV polypeptide comprising the protein encoded by ORF 33.

This invention provides the isolated KSHV polypeptide comprising packaging protein I encoded by ORF 29a.

This invention provides the isolated KSHV polypeptide comprising the protein encoded by ORF 34.

This invention provides the isolated KSHV polypeptide comprising the protein encoded by ORF 35.

This invention provides the isolated KSHV polypeptide comprising the protein encoded by ORF 38.

This invention provides the isolated KSHV polypeptide comprising glycoprotein M encoded by ORF 39.

This invention provides the isolated KSHV polypeptide comprising the protein encoded by ORF 42.

This invention provides the isolated KSHV polypeptide comprising capsid protein III encoded by ORF 43.

This invention provides the isolated KSHV polypeptide comprising virion assembly protein encoded by ORF 45.

This invention provides the isolated KSHV polypeptide comprising glycoprotein L encoded by ORF 47.

This invention provides the isolated KSHV polypeptide comprising the protein encoded by ORF 48.

This invention provides the isolated KSHV polypeptide comprising the protein encoded by ORF 49.

This invention provides the isolated KSHV polypeptide comprising the protein encoded by ORF K8.

This invention provides the isolated KSHV polypeptide comprising the protein encoded by ORF 52.

This invention provides the isolated KSHV polypeptide comprising the protein encoded by ORF 53.

This invention provides the isolated KSHV polypeptide comprising dUTPase encoded by ORF 54.

This invention provides the isolated KSHV polypeptide comprising the protein encoded by ORF 55.

This invention provides the isolated KSHV polypeptide comprising DNA replication protein I encoded by ORF 56.

This invention provides the isolated KSHV polypeptide comprising immediate early protein II (IEP-II) encoded by ORF 57.

This invention provides the isolated KSHV polypeptide comprising viral interferon regulatory factor 1 (vIRF1; ICSBP) encoded by ORF K9. In one embodiment, vIRF1 is a transforming polypeptide.

This invention provides the isolated KSHV polypeptide comprising the protein encoded by ORF K10.

This invention provides the isolated KSHV polypeptide comprising the protein encoded by ORF K11.

This invention provides the isolated KSHV polypeptide comprising phosphoprotein encoded by ORF 58.

This invention provides the isolated KSHV polypeptide comprising DNA replication protein II encoded by ORF 59.

This invention provides the isolated KSHV polypeptide comprising assembly/DNA maturation protein encoded by ORF 62.

This invention provides the isolated KSHV polypeptide comprising tegument protein II encoded by ORF 63.

This invention provides the isolated KSHV polypeptide comprising tegument protein III encoded by ORF 64.

This invention provides the isolated KSHV polypeptide comprising capsid protein IV encoded by ORF 65.

This invention provides the isolated KSHV polypeptide comprising the protein encoded by ORF 66.

This invention provides the isolated KSHV polypeptide comprising tegument protein IV encoded by ORF 67.

This invention provides the isolated KSHV polypeptide comprising glycoprotein encoded by ORF 68.

This invention provides the isolated KSHV polypeptide comprising the protein encoded by ORF 69.

This invention provides the isolated KSHV polypeptide comprising Kaposin encoded by ORF K12.

This invention provides the isolated KSHV polypeptide comprising the protein encoded by ORF K13.

This invention provides the isolated KSHV polypeptide comprising cyclin D encoded by ORF 72.

This invention provides the isolated KSHV polypeptide comprising immediate-early protein (IEP) encoded by ORF 73.

This invention provides the isolated KSHV polypeptide comprising OX-2 encoded by ORF K14.

This invention provides the isolated KSHV polypeptide comprising G-protein coupled receptor encoded by ORF 74.

This invention provides the isolated KSHV polypeptide comprising tegument protein/FGARAT encoded by ORF 75.

This invention provides the isolated KSHV polypeptide comprising the protein encoded by ORF K15.

This invention provides the isolated KSHV polypeptide comprising viral interferon regulatory factor 2 (vIRF2) encoded by nucleotides 88,910–88,410.

This invention provides the isolated KSHV polypeptide comprising viral interferon regulatory factor 3 (vIRF3) encoded by nucleotides 90,541–89,600.

This invention provides the isolated KSHV polypeptide comprising viral interferon regulatory factor 4 (vIRF4) encoded by nucleotides 94,127–93,636.

This invention provides the isolated KSHV polypeptide comprising a precursor of secreted glycoprotein X (gX) encoded by nucleotides 90,173–90,643.

This invention provides the isolated KSHV polypeptide comprising protein T1.1 (nut-1) encoded by nucleotides 28,661–29,741.

Further, the isolated polypeptide may be linked to a second polypeptide to form a fusion protein by linking the isolated nucleic acid molecule to a second nucleic acid molecule and expression in a suitable host cell. In one embodiment the second nucleic acid molecule encodes beta-galactosidase. Other nucleic acid molecules which are used to form a fusion protein are known to those skilled in the art.

This invention provides an antibody which specifically binds to the polypeptide encoded by the isolated nucleic acid molecule. In one embodiment the antibody is a monoclonal antibody. In another embodiment the antibody recognizes an epitope of the KSHV polypeptide. In another embodiment the antibody is a polyclonal antibody. In another embodiment the antibody recognizes more than one epitope of the KSHV polypeptide. In another embodiment the antibody is an anti-idiotypic antibody.

An antibody, polypeptide or isolated nucleic acid molecule may be labeled with a detectable marker including, but not limited to: a radioactive label, or a colorimetric, a luminescent, or a fluorescent marker, or gold. Radioactive labels include, but are not limited to: $^{3}H$, $^{14}C$, $^{32}P$, $^{33}P$; $^{35}S$, $^{36}Cl$, $^{51}Cr$, $^{57}Co$, $^{59}Co$, $^{59}Fe$, $^{90}Y$, $^{125}I$, $^{131}I$, and $^{86}Re$. Fluorescent markers include, but are not limited to: fluorescein, rhodamine and auramine. Colorimetric markers include, but are not limited to: biotin, and digoxigenin. Methods of producing the polyclonal or monoclonal antibody are known to those of ordinary skill in the art.

Further, the antibody, polypeptide or nucleic acid molecule may be detected by a second antibody which may be linked to an enzyme, such as alkaline phosphatase or horseradish peroxidase. Other enzymes which may be employed are well known to one of ordinary skill in the art.

This invention provides a method of producing a polypeptide encoded by the isolated nucleic acid molecule, which comprises growing a host-vector system under suitable conditions permitting production of the polypeptide and recovering the polypeptide so produced. Suitable host cells include bacteria, yeast, filamentous fungal, plant, insect and mammalian cells. Host-vector systems for producing and recovering a polypeptide are well known to those skilled in the art and include, but are not limited to, *E. coli* and pMAL (New England Biolabs), the Sf9 insect cell-baculovirus expression system, and mammalian cells (such as HeLa, COS, NIH 3T3 and HEK293) transfected with a mammalian expression vector by Lipofectin (Gibco-BRL) or calcium phosphate precipitation or other methods to achieve vector entry into the cell. Those of skill in the art are. knowledgeable in the numerous expression systems available for expression of KSHV polypeptide.

This invention provides a method to select specific regions on the polypeptide encoded by the isolated nucleic acid molecule of the DNA virus to generate antibodies. Amino acid sequences may be analyzed by methods well known to those skilled in the art to determine whether they produce hydrophobic or hydrophilic regions in the polypeptides which they build. In the case of a cell membrane polypeptide, hydrophobic regions are well known to form the part of the polypeptide that is inserted into the lipid bilayer of the cell membrane, while hydrophilic regions are located on the cell surface, in an aqueous environment. Usually, the hydrophilic regions will be more immunogenic than the hydrophobic regions. Therefore the hydrophilic amino acid sequences may be selected and used to generate antibodies specific to polypeptide encoded by the isolated nucleic acid molecule encoding the DNA virus. The selected peptides may be prepared using commercially available machines. As an alternative, nucleic acid may be cloned and expressed and the resulting polypeptide recovered and used as an immunogen.

Polyclonal antibodies against the polypeptide may be produced by immunizing animals using a selected KSHV polypeptide. Monoclonal antibodies are prepared using hybridoma technology by fusing antibody producing B cells from immunized animals with myeloma cells and selecting the resulting hybridoma cell line producing the desired antibody, as described further below.

II. Immunoassays

The antibodies raised against KSHV polypeptide antigens may be detectably labeled, utilizing conventional labelling techniques well-known to the art, as described above.

In addition, enzymes may be used as labels. Suitable enzymes include alkaline phosphatase, beta-galactosidase, glucose-6-phosphate dehydrogenase, maleate dehydrogenase and peroxidase. Two principal types of enzyme immunoassay are the enzyme-linked immunosorbent assay (ELISA), and the homogeneous enzyme immunoassay, also known as enzyme-multiplied immunoassay (EMIT, Syva Corporation, Palo Alto, Calif.). In the ELISA system, separation may be achieved, for example, by the use of antibodies coupled to a solid phase. The EMIT system depends on deactivation of the enzyme in the tracer-antibody complex; activity is thus measured without the need for a separation step.

Additionally, chemiluminescent compounds may be used as labels. Typical chemiluminescent compounds include luminol, isoluminol, aromatic acridinium esters, imidazoles, acridinium salts, and oxalate esters. Similarly, bioluminescent compounds may be utilized for labelling, the bioluminescent compounds including luciferin, luciferase, and aequorin.

A description of a radioimmunoassay (RIA) may be found in: *Laboratory Techniques in Biochemistry and Molecular Biology* (1978) North Holland Publishing Company, New York, with particular reference to the chapter entitled "An Introduction to Radioimmune Assay and Related Techniques" by T. Chard. A description of general immunometric assays of various types can be found in the following U.S. Pat. Nos. 4,376,110 (David et al.) or 4,098,876 (Piasio).

A. Assays for KSHV Polypeptide Antigens

One can use immunoassays to detect the virus, its components, or antibodies thereto. A general overview of the applicable technology is in Harlow and Lane (1988) *Antibodies, A Laboratory Manual*, Cold Spring Harbor Publication, New York.

In one embodiment, antibodies to KSHV polypeptide antigens can be used. In brief, to produce antibodies, the polypeptide being targeted is expressed and purified. The product is injected into a mammal capable of producing antibodies. Either polyclonal or monoclonal antibodies (including recombinant antibodies) specific for the gene product can be used in various immunoassays. Such assays include competitive immunoassays, radioimmunoassays, Western blots, ELISA, indirect immunofluorescent assays and the like. For competitive immunoassays, see Harlow and Lane at pages 567–573 and 584–589.

Monoclonal antibodies or recombinant antibodies may be obtained by techniques familiar to those skilled in the art. Briefly, spleen cells or other lymphocytes from an animal immunized with a desired antigen are immortalized, commonly by fusion with a myeloma cell (see, Kohler and Milstein, 1976, Eur. J. Immunol. 6, 511–519). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Newer techniques using recombinant phage antibody expression systems can also be used to generate monoclonal antibodies. See, for example: McCafferty et al. (1990) Nature 348, 552; Hoogenboom et al. (1991) Nuc. Acids Res. 19, 4133; and Marks et al. (1991) J. Mol Biol. 222, 581–597.

Methods for characterizing naturally processed peptides bound to MHC (major histocompatibility complex) I molecules can be used. See Falk et al., 1991, Nature 351; 290 and PCT publication No. WO 92/21033 published Nov. 26, 1992. Typically, these methods involve isolation of MHC class I molecules by immunoprecipitation or affinity chromatography from an appropriate cell or cell line. Other methods involve direct amino acid sequencing of the more abundant peptides in various HPLC fractions by known automatic sequencing of peptides eluted from Class I molecules of the B cell type (Jardetzkey et al., 1991, Nature 353, 326), and of the human MHC class I molecule, HLA-A2.1 type by mass spectrometry (Hunt et al., 1991, Eur. J. Immunol. 21, 2963–2970). See also, Rötzschke and Falk, 1991, Immunol. Today 12, 447, for a general review of the characterization of naturally processed peptides in MHC class I. Further, Marloes et al., 1991, Eur. J. Immunol. 21, 2963–2970, describe how class I binding motifs can be applied to the identification of potential viral immunogenic peptides in vitro.

The polypeptides described herein produced by recombinant technology may be purified by standard techniques well known to those of skill in the art. Recombinantly produced viral polypeptides can be directly expressed or expressed as a fusion protein.

The protein is then purified by a combination of cell lysis (e.g., sonication) and affinity chromatography. For fusion products, subsequent digestion of the fusion protein with an appropriate proteolytic enzyme releases the desired peptide.

The polypeptides may be purified to substantial purity by standard techniques well known in the art, including selective precipitation with such substances as ammonium sulfate, column chromatography, immunopurification methods, and others. See, for instance, Scopes, 1982, *Protein Purification: Principles and Practice*, Springer-Verlag, New York.

B. Assays for Antibodies Specifically Binding to KSHV Polypeptides

Antibodies reactive with polypeptide antigens of KSHV can also be measured by a variety of immunoassay methods that are similar to the procedures described above for measurement of antigens. For a review of immunological and immunoassay procedures applicable to the measurement of antibodies by immunoassay techniques, see *Basic and Clinical Immunology*, 7th Edition, Stites and Terr, Eds., and Harlow and Lane, 1988, *Antibodies, A Laboratory Manual*, Cold Spring Harbor, N.Y.

In brief, immunoassays to measure antibodies reactive with polypeptide antigens of KSHV can be either competitive or noncompetitive binding assays. In competitive binding assays, the sample analyte competes with a labeled analyte for specific binding sites on a capture agent bound to a solid surface. Preferably the capture agent is a purified recombinant human herpesvirus polypeptide produced as described above. Other sources of human herpesvirus polypeptides, including isolated or partially purified naturally occurring polypeptide, may also be used.

Noncompetitive assays are typically sandwich assays, in which the sample analyte is bound between two analyte-specific binding reagents. One of the binding agents is used as a capture agent and is bound to a solid surface. The second binding agent is labeled and is used to measure or detect the resultant complex by visual or instrument means. A number of combinations of capture agent and labeled binding agent can be used. A variety of different immunoassay. formats, separation techniques and labels can also be used similar to those described above for the measurement of KSHV polypeptide antigens.

Hemagglutination Inhibition (HI) and Complement Fixation (CF) are two laboratory tests that can be used to detect infection with human herpesvirus by testing for the presence of antibodies against the virus or antigens of the virus.

Serological methods can also be useful when one wishes to detect antibody to a specific viral variant. For example, one may wish to see how well a vaccine recipient has responded to a new preparation by assay of patient sera.

IIA. Vector, Cell Line and Transgenic Mammal

This invention provides a replicable vector containing the isolated nucleic acid molecule encoding a KSHV polypeptide. The vector includes, but is not limited to: a plasmid, cosmid, λ phage or yeast artificial chromosome (YAC) which contains the isolated nucleic acid molecule.

To obtain the vector, for example, insert and vector DNA can both be exposed to a restriction enzyme to create complementary ends on both molecules which base pair with each other and are then ligated together with DNA ligase. Alternatively, linkers can be ligated to the insert DNA which correspond to a restriction site in the vector DNA, which is then digested with the restriction enzyme which cuts at that site. Other means are available and well-known to those skilled in the art.

This invention provides a host cell containing the vector. Suitable host cells include, but are not limited to, bacteria (such as *E. coli*), yeast, fungi, plant, insect and mammalian cells. Suitable animal cells include, but are not limited to Vero cells, HeLa cells, Cos cells, CV1 cells and various primary mammalian cells.

This invention provides a transgenic nonhuman mammal which comprises the isolated nucleic acid molecule introduced into the mammal at an embryonic stage. Methods of producing a transgenic nonhuman mammal are known to those skilled in the art.

III. Diagnostic Assays for KS

This invention embraces diagnostic test kits for detecting the presence of KSHV in biological samples, such as skin samples or samples of other affected tissue, comprising a container containing a nucleic acid sequence specific for a KSHV polypeptide and instructional material for performing the test. A container containing nucleic acid primers to any one of such sequences is optionally included.

This invention further embraces diagnostic test kits for detecting the presence of KSHV in biological samples, such as serum or solid tissue samples, comprising a container containing antibodies to a KSHV polypeptide, and instructional material for performing the test. Alternatively, inactivated viral particles or polypeptides derived from the human herpesvirus may be used in a diagnostic test kit to detect antibodies specific for a KSHV polypeptide.

A. Nucleic Acid Assays

This invention provides a method of diagnosing Kaposi's sarcoma in a subject which comprises: (a) obtaining a nucleic acid molecule from a tumor lesion or a suitable bodily fluid of the subject; (b) contacting the nucleic acid molecule with a labeled nucleic acid molecule of at least 15 nucleotides capable of specifically hybridizing with the isolated nucleic acid molecule of KSHV under hybridizing conditions; and (c) determining the presence of the nucleic acid molecule hybridized, the presence of which is indicative of Kaposi's sarcoma in the subject, thereby diagnosing Kaposi's sarcoma in the subject.

In one embodiment the nucleic acid molecule from the tumor lesion is amplified before step (b). In another embodiment the polymerase chain reaction (PCR) is employed to amplify the nucleic acid molecule. Methods of amplifying nucleic acid molecules are known to those skilled in the art.

A person of ordinary skill in the art will be able to obtain appropriate nucleic acid sample for diagnosing Kaposi's sarcoma in the subject. The DNA sample obtained by the above described method may be cleaved by restriction enzyme before analysis, a technique well-known in the art.

In the above described methods, a size fractionation may be employed which is effected by a polyacrylamide gel. In one embodiment, the size fractionation is effected by an agarose gel. Further, transferring the nucleic acid fragments into a solid matrix may be employed before a hybridization step. One example of such solid matrix is nitrocellulose paper.

This invention provides a method of detecting expression of a KSHV gene in a cell which comprises obtaining mRNA from the cell, contacting the mRNA with a labeled nucleic acid molecule of KSHV under hybridizing conditions, determining the presence of mRNA hybridized to the molecule, thereby detecting expression of the KSHV gene. In one embodiment cDNA is prepared from the mRNA obtained from the cell and used to detect KSHV expression.

Accepted means for conducting hybridization assays are known and general overviews of the technology can be had from a review of: *Nucleic Acid Hybridization: A Practical Approach* (1985). Hames and Higgins, Eds., IRL Press; *Hybridization of Nucleic Acids Immobilized on Solid Supports*, Meinkoth and Wahl; *Analytical Biochemistry* (1984) 238, 267–284 and Innis et al., *PCR Protocols* (1990) Academic Press, San Diego.

Target-specific probes may be used in the nucleic acid hybridization diagnostic assays for KS. The probes are specific for or complementary to the target of interest. For precise allelic differentiations, the probes should be about 14 nucleotides long and preferably about 20–30 nucleotides. For more general detection of KSHV, nucleic acid probes are about 50 to 1000 nucleotides, most preferably about 200 to 400 nucleotides.

A specific nucleic acid probe can be RNA, DNA, oligonucleotide, or their analogs. The probes may be single or double stranded nucleic acid molecules. The probes of the invention may be synthesized enzymatically, using methods well known in the art (e.g., nick translation, primer extension, reverse transcription, the polymerase chain reaction, and others) or chemically (e.g., by methods described by Beaucage and Carruthers or Matteucci et al., supra).

The probe must be of sufficient length to be able to form a stable duplex with its target nucleic acid in the sample, i.e., at least about 14 nucleotides, and may be longer (e.g., at least about 50 or 100 bases in length). Often the probe will be more than about 100 bases in length. For example, when probe is prepared by nick-translation of DNA in the presence of labeled nucleotides the average probe length may be about 100–600 bases.

For discussions of nucleic acid probe design and annealing conditions see, for example, Ausubel et al., supra; Berger and Kimmel, Eds., *Methods in Enzymology* Vol. 152, (1987) Academic Press, New York; or *Hybridization with Nucleic Acid Probes*, pp. 495–524, (1993) Elsevier, Amsterdam.

Usually, at least a part of the probe will have considerable sequence identity with the target nucleic acid. Although the extent of the sequence identity required for specific hybridization will depend on the length of the probe and the hybridization conditions, the probe will usually have at least 70% identity to the target nucleic acid, more usually at least 80% identity, still more usually at least 90% identity and most usually at least 95% or 100% identity.

The following stringent hybridization and washing conditions will be adequate to distinguish a specific probe (e.g., a fluorescently labeled nucleic acid probe) from a probe that is not specific: incubation of the probe with the sample for 12 hours at 37° C. in a solution containing denatured probe, 50% formamide, 2×SSC, and 0.1% (w/v) dextran sulfate, followed by washing in 1×SSC at 70° C. for 5 minutes; 2×SSC at 37° C. for 5 minutes; 0.2×SSC at room temperature for 5 minutes, and $H_2O$ at room temperature for 5 minutes. Those of skill are aware that it will often be advantageous in nucleic acid hybridizations (i.e., in situ, Southern, or Northern) to include detergents (e.g., sodium dodecyl sulfate), chelating agents (e.g., EDTA) or other reagents (e.g., buffers, Denhardt's solution, dextran sulfate) in the hybridization or wash solutions. To evaluate specificity, probes can be tested on host cells containing KSHV and compared with the results from cells containing non-KSHV virus.

It will be apparent to those of ordinary skill in the art that a convenient method for determining whether a probe is specific for a KSHV nucleic acid molecule utilizes a Southern blot (or Dot blot) using DNA prepared from the virus. Briefly, to identify a target-specific probe, DNA is isolated from the virus. Test DNA, either viral or cellular, is transferred to a solid (e.g., charged nylon) matrix. The probes are labeled by conventional methods. Following denaturation and/or prehybridization steps known in the art, the probe is hybridized to the immobilized DNAs under stringent conditions, such as defined above.

It is further appreciated that in determining probe specificity and in utilizing the method of this invention to detect KSHV, a certain amount of background signal is typical and can easily be distinguished by one of skill from a specific signal. Two-fold signal over background is acceptable.

A preferred method for detecting the KSHV polypeptide is the use of PCR and/or dot blot hybridization. Other methods to test for the presence or absence of KSHV for detection or prognosis, or risk assessment for KS includes Southern transfers, solution hybridization or non-radioactive detection systems, all of which are well known to those of skill in the art. Hybridization is carried out using probes. Visualization of the hybridized portions allows the qualitative determination of the presence or absence of the causal agent.

Similarly, a Northern transfer or reverse transcriptase PCR may be used for the detection of KSHV messenger RNA in a sample. These procedures are also well known in the art. See Sambrook et al. (1989) *Molecular Cloning: A Laboratory Manual* (2nd ed.), Cold Spring Harbor Laboratory, Vols. 1–3.

An alternative means for determining the presence of the human herpesvirus is in situ hybridization, or more recently, in situ polymerase chain reaction. In situ PCR is described in Neuvo et al. (1993) Intracellular localization of PCR-amplified hepatitis C DNA, in *American Journal of Surgical Pathology* 17(7), 683–690; Bagasra et al. (1992) Detection of HIV-1 provirus in mononuclear cells by in situ PCR, in *New England Journal of Medicine* 326(21),1385–1391; and Heniford et al. (1993) Variation in cellular EGF receptor mRNA expression demonstrated by in situ reverse transcriptase polymerase chain reaction, in *Nucleic Acids Research* 21, 3159–3166. In situ hybridization assays are well known and are generally described in *Methods Enzymol*. Vol. 152, (1987) Berger and Kimmel, Eds., Academic Press, New York. In an in situ hybridization, cells are fixed to a solid support, typically a glass slide. The cells are then contacted with a hybridization solution at a moderate temperature to permit annealing of target-specific probes that are labeled. The probes are preferably labeled with radio-isotopes or fluorescent reporters.

The above-described probes are also useful for in situ hybridization or in order to locate tissues which express the gene, or for other hybridization assays for the presence of the gene or its mRNA in various biological tissues. In situ hybridization is a sensitive localization method which is not dependent on expression of polypeptide antigens or native versus denatured conditions.

Synthetic oligonucleotide (oligo) probes and riboprobes made from KSHV phagemids or plasmids are also provided. Successful hybridization conditions in tissue sections is readily transferable from one probe to another. Commercially-synthesized oligonucleotide probes are prepared using the nucleotide sequence of the identified gene. These probes are chosen for length (45–65 mers), high G-C content (50–70%) and are screened for uniqueness against other viral sequences in GenBank.

Oligos are 3' end-labeled with [$\alpha$-$^{35}$S]dATP to specific activities in the range of $1\times10^{10}$ dpm/$\mu$g using terminal deoxynucleotidyl transferase. Unincorporated labeled nucleotides are removed from the oligo probe by centrifugation through a Sephadex G-25 column or by elution from a Waters Sep Pak C-18 column.

KS tissue embedded in OCT compound and snap frozen in freezing isopentane cooled with dry ice is cut at 6 $\mu$m intervals and thawed onto 3-aminopropyltriethoxysilane treated slides and allowed to air dry. The slides are then fixed in 4% freshly prepared paraformaldehyde and rinsed in water. Formalin-fixed, paraffin embedded KS tissues cut at 6 $\mu$m and baked onto glass slides can also be used. These sections are then deparaffinized in xylenes and rehydrated through graded alcohols. Prehybridization in 20 mM Tris pH 7.5, 0.02% Denhardt's solution, 10% dextran sulfate for 30 min at 37° C. is followed by hybridization overnight in a solution of 50% formamide (v/v), 10% dextran sulfate (w/v), 20 mM sodium phosphate (pH 7.4), 3×SSC, 1×Denhardt's solution, 100 $\mu$g/ml salmon sperm DNA, 125 $\mu$g/ml yeast tRNA and the oligo probe ($10^6$ cpm/ml) at 42° C. overnight. The slides are washed twice with 3×SSC and twice with 1×SSC for 15 minutes each at room temperature and visualized by autoradiography. Briefly, sections are dehydrated through graded alcohols containing 0.3M ammonium acetate, and air dried. The slides are dipped in Kodak NTB2 emulsion, exposed for days to weeks, developed, and counterstained with hematoxylin and eosin (H&E).

Alternative immunohistochemical protocols may be employed which are well known to those skilled in the art.

B. Immunologic Assays

This invention provides a method of diagnosing Kaposi's sarcoma in a subject, which comprises (a) obtaining a suitable bodily fluid sample from the subject, (b) contacting the suitable bodily fluid of the subject to a support having already bound thereto an antibody recognizing the KSHV polypeptide, so as to bind the antibody to a specific KSHV polypeptide antigen, (c) removing unbound bodily fluid from the support, and (d) determining the level of the antibody bound by the antigen, thereby diagnosing Kaposi's sarcoma.

This invention provides a method of diagnosing Kaposi's sarcoma in a subject, which comprises (a) obtaining a suitable bodily fluid sample from the subject, (b) contacting the suitable bodily fluid of the subject to a support having already bound thereto the KSHV polypeptide antigen, so as to bind the antigen to a specific Kaposi's sarcoma antibody, (c) removing unbound bodily fluid from the support, and (d) determining the level of the antigen bound by the Kaposi's sarcoma antibody, thereby diagnosing Kaposi's sarcoma.

The suitable bodily fluid sample is any bodily fluid sample which would contain Kaposi's sarcoma antibody, antigen or fragments thereof. A suitable bodily fluid includes, but is not limited to: serum, plasma, cerebrospinal fluid, lymphocytes, urine, transudates, or exudates. In the preferred embodiment, the suitable bodily fluid sample is serum or plasma. In addition, the sample may be cells from bone marrow, or a supernatant from a cell culture. Methods of obtaining a suitable bodily fluid sample from a subject are known to those skilled in the art. Methods of determining the level of antibody or antigen include, but are not limited to: ELISA, IFA, and Western blotting. Other methods are known to those skilled in the art. Further, a subject infected with KSHV may be diagnosed as infected with the above-described methods.

The detection of KSHV and the detection of virus-associated KS are essentially identical processes. The basic principle is to detect the virus using specific ligands that bind to the virus but not to other polypeptides or nucleic acids in a normal human cell or its environs. The ligands can be nucleic acid molecules, polypeptides or antibodies. The ligands can be naturally-occurring or genetically or physically modified, such as nucleic acids with non-natural nucleotide bases or antibody derivatives, i.e., Fab or chimeric antibodies. Serological tests for detection of antibodies to the virus present in subject sera may also be performed by using the KSHV polypeptide as an antigen, as described herein.

Samples can be taken from patients with KS or from patients at risk for KS, such as AIDS patients. Typically the samples are taken from blood (cells, serum and/or plasma) or from solid tissue samples such as skin lesions. The most accurate diagnosis for KS will occur if elevated titers of the virus are detected in the blood or in involved lesions. KS may also be indicated if antibodies to the virus are detected and if other diagnostic factors for KS are present.

See Immunoassays above for more details on the immunoreagents of the invention for use in diagnostic assays for KS.

IV. Treatment of Human Herpesvirus-Induced KS

This invention provides a method for treating a subject with Kaposi's sarcoma (KS) comprising administering to the subject having KS a pharmaceutically effective amount of an antiviral agent in a pharmaceutically acceptable carrier, wherein the agent is effective to treat the subject with KSHV.

Further, this invention provides a method of prophylaxis or treatment for Kaposi's sarcoma (KS) by administering to a patient at risk for KS, an antibody that binds to KSHV in a pharmaceutically acceptable carrier.

This invention provides a method of treating a subject with Kaposi's sarcoma comprising administering to the subject an effective amount of an antisense molecule capable of hybridizing to the isolated DNA molecule of KSHV under conditions such that the antisense molecule selectively enters a KS tumor cell of the subject, so as to treat the subject.

A. Nucleic Acid Therapeutics

This invention provides an antisense molecule capable of hybridizing to the isolated nucleic acid molecule of KSHV. In one embodiment the antisense molecule is DNA. In another embodiment the antisense molecule is RNA. In another embodiment, the antisense molecule is a nucleic acid derivative (e.g., DNA or RNA with a protein backbone).

The present invention extends to the preparation of antisense nucleic acids and ribozymes that may be used to interfere with the expression of a polypeptide either by masking the mRNA with an antisense nucleic acid or cleaving it with a ribozyme, respectively.

This invention provides inhibitory nucleic acid therapeutics which can inhibit the activity of herpesviruses in patients with KS by binding to the isolated nucleic acid molecule of KSHV. Inhibitory nucleic acids may be single-stranded nucleic acids, which can specifically bind to a complementary nucleic acid sequence. By binding to the appropriate target sequence, an RNA—RNA, a DNA—DNA, or RNA-DNA duplex or triplex is formed. These nucleic acids are often termed "antisense" because they are usually complementary to the sense or coding strand of the gene, although recently approaches for use of "sense" nucleic acids have also been developed. The term "inhibitory nucleic acids" as used herein, refers to both "sense" and "antisense" nucleic acids.

By binding to the target nucleic acid, the inhibitory nucleic acid can inhibit the function of the target nucleic acid. This could, for example, be a result of blocking DNA transcription, processing or poly(A) addition to mRNA, DNA replication, translation, or promoting inhibitory mechanisms of the cells, such as promoting RNA degradation. Inhibitory nucleic acid methods therefore encompass a number of different approaches to altering expression of herpesvirus genes. These different types of inhibitory nucleic acid technology are described in Helene and Toulme (1990) *Biochim. Biophys. Acta.* 1049, 99–125, which is referred to hereinafter as "Helene and Toulme."

In brief, inhibitory nucleic acid therapy approaches can be classified into those that target DNA sequences, those that target RNA sequences (including pre-mRNA and mRNA), those that target proteins (sense strand approaches), and those that cause cleavage or chemical modification of the target nucleic acids.

Approaches targeting DNA fall into several categories. Nucleic acids can be designed to bind to the major groove of the duplex DNA to form a triple helical or "triplex" structure. Alternatively, inhibitory nucleic acids are designed to bind to regions of single stranded DNA resulting from the opening of the duplex DNA during replication or transcription.

More commonly, inhibitory nucleic acids are designed to bind to mRNA or mRNA precursors. Inhibitory nucleic acids are used to prevent maturation of pre-mRNA. Inhibitory nucleic acids may be designed to interfere with RNA processing, splicing or translation.

The inhibitory nucleic acids can be targeted to mRNA. In this approach, the inhibitory nucleic acids are designed to specifically block translation of the encoded protein. Using this approach, the inhibitory nucleic acid can be used to selectively suppress certain cellular functions by inhibition of translation of mRNA encoding critical proteins. For example, an inhibitory nucleic acid complementary to regions of c-myc mRNA inhibits c-myc protein expression in a human promyelocytic leukemia cell line, HL60, which overexpresses the c-myc proto-oncogene. See Wickstrom et al. (1988) *PNAS* 85, 1028–1032 and Harel-Bellan et al. (1988) *Exp. Med.* 168, 2309–2318. As described in Helene and Toulme, inhibitory nucleic acids targeting mRNA have been shown to work by several different mechanisms to inhibit translation of the encoded protein(s).

The inhibitory nucleic acids introduced into the cell can also encompass the "sense" strand of the gene or mRNA to trap or compete for the enzymes or binding proteins involved in mRNA translation, as described in Helene and Toulme.

Lastly, the inhibitory nucleic acids can be used to induce chemical inactivation or cleavage of the target genes or mRNA. Chemical inactivation can occur by the induction of crosslinks between the inhibitory nucleic acid and the target nucleic acid within the cell. Other chemical modifications of the target nucleic acids induced by appropriately derivatized inhibitory nucleic acids may also be used.

Cleavage, and therefore inactivation, of the target nucleic acids may be effected by attaching a substituent to the inhibitory nucleic acid which can be activated to induce cleavage reactions. The substituent can be one that affects either chemical, or enzymatic cleavage. Alternatively, cleavage can be induced by the use of ribozymes or catalytic RNA. In this approach, the inhibitory nucleic acids would comprise either naturally occurring RNA (ribozymes) or synthetic nucleic acids with catalytic activity.

The targeting of inhibitory nucleic acids to specific cells of the immune system by conjugation with targeting moieties binding receptors on the surface of these cells can be used for all of the above forms of inhibitory nucleic acid therapy. This invention encompasses all of the forms of inhibitory nucleic acid therapy as described above and as described in Helene and Toulme.

An example of an antiherpes virus inhibitory nucleic acid is ISIS 2922 (ISIS Pharmaceuticals) which has activity against CMV (see *Biotechnology News* 14:5).

A problem associated with inhibitory nucleic acid therapy is the effective delivery of the inhibitory nucleic acid to the target cell in vivo and the subsequent internalization of the inhibitory nucleic acid by that cell. This can be accomplished by linking the inhibitory nucleic acid to a targeting moiety to form a conjugate that binds to a specific receptor on the surface of the target infected cell, and which is internalized after binding.

B. Antiviral Agents

The use of combinations of antiviral drugs and sequential treatments are useful for treatment of herpesvirus infections and will also be useful for the treatment of herpesvirus-induced KS. For example, Snoeck et al. (1992) *Eur. J. Clin. Micro. Infect. Dis.* 11, 1144–1155, found additive or synergistic effects against CMV when combining antiherpes drugs (e.g., combinations of zidovudine [3'-azido-3'- deoxythymidine, AZT] with HPMPC, ganciclovir, foscarnet or acyclovir or of HPMPC with other antivirals). Similarly, in treatment of cytomegalovirus retinitis, induction with ganciclovir followed by maintenance with foscarnet has been suggested as a way to maximize efficacy while minimizing the adverse side effects of either treatment alone. An anti-herpetic composition that contains acyclovir and, e.g., 2-acetylpyridine-5-((2-pyridylamino)thiocarbonyl)-thiocarbonohydrazone is described in U.S. Pat. No. 5,175,165 (assigned to Burroughs Wellcome Co.). Combinations of TS-inhibitors and viral TK-inhibitors in antiherpetic medicines are disclosed in U.S. Pat. No. 5,137,724, assigned to Stichting Rega VZW. A synergistic inhibitory effect on EBV replication using certain ratios of combinations of HPMPC with AZT was reported by Lin et al. (1991) *Antimicrob Agents Chemother* 35:2440–3.

U.S. Pat. Nos. 5,164,395 and 5,021,437 (Blumenkopf; Burroughs Wellcome) describe the use of a ribonucleotide reductase inhibitor (an acetylpyridine derivative) for treatment of herpes infections, including the use of the acetylpyridine derivative in combination with acyclovir. U.S. Pat. No. 5,137,724 (Balzari et al. (1990) *Mol. Pharm.* 37,402–7) describes the use of thymidylate synthase inhibitors (e.g., 5-fluoro-uracil and 5-fluro-2'-deoxyuridine) in combination with compounds having viral thymidine kinase inhibiting activity.

With the discovery of a disease causal agent for KS now identified, effective therapeutic or prophylactic protocols to alleviate or prevent the symptoms of herpes virus-associated KS can be formulated. Due to the viral nature of the disease, antiviral agents have application here for treatment, such as interferons, nucleoside analogues, ribavirin, amantadine, and pyrophosphate analogues of phosphonoacetic acid (foscarnet) (reviewed in Gorbach et al., 1992, *Infectious Disease* Ch.35, 289, W. B. Saunders, Philadelphia, Pa.) and the like. Immunological therapy will also be effective in many cases to manage and alleviate symptoms caused by the disease agents described here. Antiviral agents include agents or compositions that directly bind to viral products and interfere with disease progress; and, excludes agents that do not impact directly on viral multiplication or viral titer. Antiviral agents do not include immunoregulatory agents that do not directly affect viral titer or bind to viral products. Antiviral agents are effective if they inactivate the virus, otherwise inhibit its infectivity or multiplication, or alleviate the symptoms of KS.

The antiherpesvirus agents that will be useful for treating virus-induced KS can be grouped into broad classes based on their presumed modes of action. These classes include agents that act (1) by inhibition of viral DNA polymerase, (2) by targeting other viral enzymes and proteins, (3) by miscellaneous or incompletely understood mechanisms, or (4) by binding a target nucleic acid (i.e., inhibitory nucleic acid therapeutics, supra). Antiviral agents may also be used in combination (i.e., together or sequentially) to achieve synergistic or additive effects or other benefits.

Although it is convenient to group antiviral agents by their supposed mechanism of action, the applicants do not intend to be bound by any particular mechanism of antiviral action. Moreover, it will be understood by those of skill that an agent may act on more than one target in a virus or virus-infected cell or through more than one mechanism.

i) Inhibitors of DNA Polymerase

Many antiherpesvirus agents in clinical use or in development today are nucleoside analogs believed to act through inhibition of viral DNA replication, especially through inhibition of viral DNA polymerase. These nucleoside analogs act as alternative substrates for the viral DNA polymerase or as competitive inhibitors of DNA polymerase substrates. Usually these agents are preferentially phosphorylated by viral thymidine kinase (TK), if one is present, and/or have higher affinity for viral DNA polymerase than for the cellular DNA polymerases, resulting in selective antiviral activity. Where a nucleoside analogue is incorporated into the viral DNA, viral activity or reproduction may be affected in a variety of ways. For example, the analogue may act as a chain terminator, cause increased lability (e.g., susceptibility to breakage) of analogue-containing DNA, and/or impair the ability of the substituted DNA to act as template for transcription or replication (see, e.g., Balzarini et al., supra).

It will be known to one of skill that, like many drugs, many of the agents useful for treatment of herpes virus infections are modified (i.e., "activated") by the host, host cell, or virus-infected host cell metabolic enzymes. For example, acyclovir is triphosphorylated to its active form, with the first phosphorylation being carried out by the herpes virus thymidine kinase, when present. Other examples are the reported conversion of the compound HOE 602 to ganciclovir in a three-step metabolic pathway (Winkler et al., 1990, *Antiviral Research* 14, 61–74) and the phosphorylation of ganciclovir to its active form by, e.g., a CMV nucleotide kinase. It will be apparent to one of skill that the specific metabolic capabilities of a virus can affect the sensitivity of that virus to specific drugs, and is one factor in the choice of an antiviral drug. The mechanism of action of certain anti-herpesvirus agents is discussed in De Clercq (1993, *Antimicrobial Chemotherapy* 32, Suppl. A, 121–132) and in other references cited supra and infra.

Anti-herpesvirus medications suitable for treating viral induced KS include, but are not limited to, nucleoside analogs including acyclic nucleoside phosphonate analogs (e.g., phosphonyl-methoxyalkylpurines and -pyrimidines), and cyclic nucleoside analogs. These include drugs such as: vidarabine (9-β-D-arabinofuranosyladenine; adenine arabinoside, ara-A, Vira-A, Parke-Davis); 1-β-D-arabinofuranosyluracil (ara-U); 1-β-D-arabinofuranosyl-cytosine (ara-C); HPMPC [(S)-1-[3-hydroxy-2-(phosphonylmethoxy)propyl]cytosine (e.g., GS504, Gilead Science)] and its cyclic form (cHPMPC); HPMPA [(S)-9-(3-hydroxy-2-phosphonylmethoxypropyl) adenine] and its cyclic form (cHPMPA); (S)-HPMPDAP [(S)-9-(3-hydroxy-2-phosphonylmethoxypropyl)-2,6-diaminopurine]; PMEDAP [9-(2-phosphonyl-methoxyethyl)-2,6-diaminopurine]; HOE 602 [2-amino-9-(1,3-bis (isopropoxy)-2-propoxymethyl)purine]; PMEA [9-(2-phosphonylmethoxyethyl)adenine]; bromovinyl-deoxyuridine (Burns and Sandford, 1990, *J. Infect. Dis.* 162:634–7); 1-β-D-arabinofuranosyl-E-5-(2-bromovinyl)-uridine or -2'-deoxyuridine; BVaraU (1-β-D-arabinofuranosyl-E-5-(2-bromovinyl)-uracil, brovavir, Bristol-Myers Squibb, Yamsa Shoyu); BVDU [(E)-5-(2-bromovinyl)-2'-deoxyuridine, brivudin, e.g., Helpin] and its carbocyclic analogue (in which the sugar moiety is replaced by a cyclopentane ring); IVDU [(E)-5-(2-iodovinyl)-2'-deoxyuridine] and its carbocyclic analogue, C-IVDU (Balzarini et al., supra); and 5-mercutithio analogs of 2'-deoxyuridine (Holliday and Williams, 1992, *Antimicrob. Agents Chemother.* 36, 1935); acyclovir [9-([2-hydroxyethoxy]methyl)guanine; e.g., Zovirax (Burroughs Wellcome)]; penciclovir (9-[4-hydroxy-2-(hydroxymethyl) butyl]-guanine); ganciclovir [(9-[1,3-dihydroxy-2 propoxymethyl]-guanine) e.g., Cymevene, Cytovene (Syntex), DHPG (Stals et al., 1993, *Antimicrobial Agents Chemother.* 37, 218–223; isopropylether derivatives of ganciclovir (see, e.g., Winkelmann et al., 1988, *Drug Res.* 38, 1545–1548); cygalovir; famciclovir [2-amino-9-(4-acetoxy-3-(acetoxymethyl)but-1-yl)purine (Smithkline Beecham)]; valacyclovir (Burroughs Wellcome); desciclovir [(2-amino-9-(2-ethoxymethyl)purine)] and 2-amino-9-(2-hydroxyethoxymethyl)-9H-purine, prodrugs of acyclovir]; CDG (carbocyclic 2'-deoxyguanosine); and purine nucleosides with the pentafuranosyl ring replaced by a cyclobutane ring (e.g., cyclobut-A [(+−)-9-[1β, 2α, 3β)-2,3-bis (hydroxymethyl)-1-cyclobutyl]adenine], cyclobut-G [(+−)-9-[1β,2α,3β)-2,3-bis(hydroxymethyl)-1-cyclobutyl] guanine], BHCG [(R)-(1α,2β,1α)-9-(2,3-bis (hydroxymethyl)cyclobutyl]guanine], and an active isomer of racemic BHCG, SQ 34,514 [1R-1α,2β,3α)-2-amino-9-[2,3-bis(hydroxymethyl)cyclobutyl]-6H-purin-6-one (see, Braitman et al., 1991, *Antimicrob. Agents and Chemotherapy* 35, 1464–1468). Certain of these antiherpesviral agents are discussed in Gorach et al., 1992, *Infectious Disease* Ch.35, 289, W. B. Saunders, Philadelphia; Saunders et al., 1990, *J. Acquir. Immune Defic. Syndr.* 3, 571; Yamanaka et al., 1991, *Mol. Pharmacol.* 40, 446; and Greenspan et al., 1990, *J. Acquir. Immune Defic. Syndr.* 3, 571.

Triciribine and triciribine monophosphate are potent inhibitors against herpes viruses. (Ickes et al., 1994, Antiviral Research 23, Seventh International Conf. on Antiviral Research, Abstract No. 122, Supp. 1.), HIV-1 and HIV-2 (Kucera et al., 1993, *AIDS Res. Human Retroviruses* 9, 307–314) and are additional nucleoside analogs that may be used to treat KS. An exemplary protocol for these agents is an intravenous injection of about 0.35 mg/meter$^2$ (0.7 mg/kg) once weekly or every other week for at least two doses, preferably up to about four to eight weeks.

Acyclovir and ganciclovir are of interest because of their accepted use in clinical settings. Acyclovir, an acyclic analogue of guanine, is phosphorylated by a herpesvirus thymidine kinase and undergoes further phosphorylation to be incorporated as a chain. terminator by the viral DNA polymerase during viral replication. It has therapeutic activity against a broad range of herpesviruses, Herpes simplex Types 1 and 2, Varicella-Zoster, Cytomegalovirus, and Epstein-Barr Virus, and is used to treat disease such as herpes encephalitis, neonatal herpesvirus infections, chickenpox in immunocompromised hosts, herpes zoster recurrences, CMV retinitis, EBV infections, chronic fatigue syndrome, and hairy leukoplakia in AIDS patients. Exemplary intravenous dosages or oral dosages are 250 mg/kg/m$^2$ body surface area, every 8 hours for 7 days, or maintenance doses of 200–400 mg IV or orally twice a day to suppress recurrence. Ganciclovir has been shown to be more active than acyclovir against some herpesviruses. See, e.g., Oren and Soble, 1991, *Clinical Infectious Diseases* 14, 741–6. Treatment protocols for ganciclovir are 5 mg/kg twice a day IV or 2.5 mg/kg three times a day for 10–14 days. Maintenance doses are 5–6 mg/kg for 5–7 days.

Also of interest is HPMPC. HPMPC is reported to be more, active than either acyclovir or ganciclovir in the chemotherapy and prophylaxis of various HSV-1, HSV-2, TK-HSV, VZV or CMV infections in animal models (De Clercq, supra).

Nucleoside analogs such as BVaraU are potent inhibitors of HSV-1, EBV, and VZV that have greater activity than acyclovir in animal models of encephalitis. FIAC (fluroidoarbinosyl cytosine) and its related fluroethyl and iodo compounds (e.g., FEAU, FIAU) have potent selective activity against herpesviruses, and HPMPA ((S)-1-([3-hydroxy-2-phosphorylmethoxy]propyl)adenine) has been demonstrated to be more potent against HSV and CMV than acyclovir or ganciclovir and are of choice in advanced cases of KS. Cladribine (2-chlorodeoxyadenosine) is another nucleoside analogue known as a highly specific antilymphocyte agent (i.e., a immunosuppressive drug).

Other useful antiviral agents include: 5-thien-2-yl-2'-deoxyuridine derivatives, e.g., BTDU [5-5(5-bromothien-2-yl)-2'-deoxyuridine] and CTDU [b-(5-chlorothien-2-yl)-2'-deoxyuridine]; and OXT-A [9-(2-deoxy-2-hydroxymethyl-β-D-erythro-oxetanosyl)adenine] and OXT-G [9-(2-deoxy-2-hydroxymethyl-β-D-erythro-oxetanosyl)guanine]. Although OXT-G is believed to act by inhibiting viral DNA synthesis its mechanism of action has not yet been elucidated. These and other compounds are described in Andrei et al., 1992, *Eur. J. Clin. Microbiol. Infect. Dis.* 11, 143–51. Additional antiviral purine derivatives useful in treating herpesvirus infections are disclosed in U.S. Pat. No. 5,108, 994 (assigned to Beecham Group P.L.C.). 6-Methoxypurine arabinoside (ara-M; Burroughs Wellcome) is a potent inhibitor of varicella-zoster virus, and will be useful for treatment of KS.

Certain thymidine analogs [e.g., idoxuridine (5-ido-2'-deoxyuridine)] and triflurothymidine) have antiherpes viral activity, but due to their systemic toxicity, are largely used for topical herpesviral infections, including HSV stromal keratitis and uveitis, and are not preferred here unless other options are ruled out.

Other useful antiviral agents that have demonstrated antiherpes viral activity include foscarnet sodium (trisodium phosphonoformate, PFA, Foscavir (Astra)) and phosphonoacetic acid (PAA). Foscarnet is an inorganic pyrophosphate analogue that acts by competitively blocking the pyrophosphate-binding site of DNA polymerase. These agents which block DNA polymerase directly without processing by viral thymidine kinase. Foscarnet is reported to be less toxic than PAA.

ii) Other Antivirals

Although applicants do not intend to be bound by a particular mechanism of antiviral action, the antiherpesvirus agents described above are believed to act through inhibition of viral DNA polymerase. However, viral replication requires not only the replication of the viral nucleic acid but also the production of viral proteins and other essential components. Accordingly, the present invention contemplates treatment of KS by the inhibition of viral proliferation by targeting viral proteins other than DNA polymerase (e.g., by inhibition of their synthesis or activity, or destruction of viral proteins after their synthesis). For example, administration of agents that inhibit a viral serine protease, e.g., such as one important in development of the viral capsid will be useful in treatment of viral induced KS.

Other viral enzyme targets include: OMP decarboxylase inhibitors (a target of, e.g., parazofurin), CTP synthetase inhibitors (targets of, e.g., cyclopentenylcytosine), IMP dehydrogenase, ribonucleotide reductase (a target of, e.g., carboxyl-containing N-alkyldipeptides as described in U.S. Pat. No. 5,110,799 (Tolman et al., Merck)), thymidine kinase (a target of, e.g., 1-[2-(hydroxymethyl) cycloalkylmethyl]-5-substituted-uracils and -guanines as described in, e.g., U.S. Pat. Nos. 4,863,927 and 4,782,062 (Tolman et al ., Merck) as well as other enzymes. It will be apparent to one of ordinary skill in the art that there are additional viral proteins, both characterized and as yet to be discovered, that can serve as target for antiviral agents. Kutapressin is a liver derivative available from Schwarz Parma of Milwaukee, Wis. in an injectable form of 25 mg/ml. The recommended dosage for herpesviruses is from 200 to 25 mg/ml per day for an average adult of 150 pounds.

Poly(I) Poly($C_{12}U$), an accepted antiviral drug known as Ampligen from HEM Pharmaceuticals of Rockville, Md. has been shown to inhibit herpesviruses and is another antiviral agent suitable for treating KS. Intravenous injection is the preferred route of administration. Dosages from about 100 to 600 mg/$m^2$ are administered two to three times weekly to adults averaging 150 pounds. It is best to administer at least 200 mg/$m^2$ per week.

Other antiviral agents reported to show activity against herpes viruses (e.g., varicella zoster and herpes simplex) and will be useful for the treatment of herpesvirus-induced KS include mappicine ketone (SmithKline Beecham); Compounds A,79296 and A,73209 (Abbott) for varicella zoster, and Compound 882C87 (Burroughs Wellcome) (see, *The Pink Sheet* 55(20) May 17, 1993).

Interferon is known inhibit replication of herpes viruses. See Oren and Soble, supra. Interferon has known toxicity problems and it is expected that second generation derivatives will soon be available that will retain interferon's antiviral properties but have reduced side affects.

It is also contemplated that herpes virus-induced KS may be treated by administering a herpesvirus reactivating agent to induce reactivation of the latent virus. Preferably the reactivation is combined with simultaneous or sequential administration of an anti-herpesvirus agent. Controlled reactivation over a short period of time or reactivation in the presence of an antiviral agent is believed to minimize the adverse effects of certain herpesvirus infections (e.g., as discussed in PCT Application WO 93/04683). Reactivating agents include agents such as estrogen, phorbol esters, forskolin and β-adrenergic blocking agents.

Agents useful for treatment of herpesvirus infections and for treatment of herpesvirus-induced KS are described in numerous U.S. Patents. For example, ganciclovir is an example of a antiviral guanine acyclic nucleotide of the type described in U.S. Pat. Nos. 4,355,032 and 4,603,219.

Acyclovir is an example of a class of antiviral purine derivatives, including 9-(2-hydroxyethylmethyl)adenine, of the type described in U.S. Pat. Nos. 4,287,188, 4,294,831 and 4,199,574.

Brivudin is an example of an antiviral deoxyuridine derivative of the type described in U.S. Pat. No. 4,424,211.

Vidarabine is an example of an antiviral purine nucleoside of the type described in British Pat. 1,159,290.

Brovavir is an example of an antiviral deoxyuridine derivative of the type described in U.S. Pat. Nos. 4,542,210 and 4,386,076.

BHCG is an example of an antiviral carbocyclic nucleoside analogue of the type described in U.S. Pat. Nos. 5,153,352, 5,034,394 and 5,126,345.

HPMPC is an example of an antiviral phosphonyl methoxyalkyl derivative with of the type described in U.S. Pat. No. 5,142,051.

CDG (Carbocyclic 2'-deoxyguanosine) is an example of an antiviral carbocyclic nucleoside analogue of the type described in U.S. Pat. Nos. 4,543,255, 4,855,466, and 4,894,458.

Foscarnet is described in U.S. Pat. No. 4,339,445.

Trifluridine and its corresponding ribonucleoside is described in U.S. Pat. No. 3,201,387.

U.S. Pat. No. 5,321,030 (Kaddurah-Daouk et al.; Amira) describes the use of creatine analogs as antiheroes viral agents. U.S. Pat. No. 5,306,722 (Kim et al.; Bristol-Meyers Squibb) describes thymidine kinase inhibitors useful for treating HSV infections and for inhibiting herpes thymidine kinase. Other antiherpesvirus compositions are described in U.S. Pat. Nos. 5,286,649 and 5,098,708 (Konishi et al., Bristol-Meyers Squibb) and U.S. Pat. No. 5,175,165 (Blumenkopf et al.; Burroughs Wellcome). U.S. Pat. No. 4,880,820 (Ashton et al., Merck) describes the antiherpes virus agent (S)-9-(2,3-dihydroxy-1-propoxymethyl)guanine.

U.S. Pat. No. 4,708,935 (Suhadolnik et al., Research Corporation) describes a 3'-deoxyadenosine compound effective in inhibiting HSV and EBV. U.S. Pat. No. 4,386,076 (Machida et al., Yamasa Shoyu Kabushiki Kaisha describes use of (E)-5-(2-halogenovinyl)-arabinofuranosyluracil as an antiherpesvirus agent. U.S. Pat. No. 4,340,599 (Lieb et al., Bayer Aktiengesellschaft) describes phosphonohydroxyacetic acid derivatives useful as antiherpes agents. U.S. Pat. Nos. 4,093,715 and 4,093,716 (Lin et al., Research Corporation) describe 5'-amino-5'-deoxythymidine and 5-iodo-5'-amino-2',5'-dideoxycytidine as potent inhibitors of herpes simplex virus. U.S. Pat. No. 4,069,382 (Baker et al., Parke, Davis & Company) describes 9-(5-O-Acyl-beta-D-arabinofuranosyl)adenine compounds useful as antiviral agents. U.S. Pat. No. 3,927,216 (Witkowski et al.) describes the use of 1,2,4-triazole-3-carboxamide and 1,2,4-triazole-3-thiocarboxamide for inhibiting herpes virus infections. U.S. Pat. No. 5,179,093 (Afonso et al., Schering) describes quinoline-2,4-dione derivatives active against herpes simplex virus 1 and 2, cytomegalovirus and Epstein Barr virus.

iii) Administration

The subjects to be treated or whose tissue may be used herein may be a mammal, or more specifically a human, horse, pig, rabbit, dog, monkey, or rodent. In the preferred embodiment the subject is a human.

The compositions are administered in a manner compatible with the dosage formulation, and in a therapeutically effective amount. Precise amounts of active ingredient required to be administered depend on the judgment of the practitioner and are peculiar to each subject.

Suitable regimes for initial administration and booster shots are also variable, but are typified by an initial administration followed by repeated doses at one or more hour intervals by a subsequent injection or other administration.

As used herein administration means a method of administering to a subject. Such methods are well known to those skilled in the art and include, but are not limited to, administration topically, parenterally, orally, intravenously, intramuscularly, subcutaneously or by aerosol. Administration of the agent may be effected continuously or intermittently such that the therapeutic agent in the patient is effective to treat a subject with Kaposi's sarcoma or a subject infected with a DNA virus associated with Kaposi's sarcoma.

The antiviral compositions for treating herpesvirus-induced KS are preferably administered to human patients via oral, intravenous or parenteral administrations and other systemic forms. Those of skill in the art will understand appropriate administration protocol for the individual compositions to be employed by the physician.

The pharmaceutical formulations or compositions of this invention may be in the dosage form of solid, semi-solid, or liquid such as, e.g., suspensions, aerosols or the like. Preferably the compositions are administered in unit dosage forms suitable for single administration of precise dosage amounts. The compositions may also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solution, dextrose solution, and Hank's solution. In addition, the pharmaceutical composition or formulation may also include other carriers, adjuvants; or nontoxic, nontherapeutic, nonimmunogenic stabilizers and the like. Effective amounts of such diluent or carrier are those amounts which are effective to obtain a pharmaceutically acceptable formulation in terms of solubility of components, or biological activity, etc.

V. Immunological Approaches to Therapy

Having identified a primary causal agent of KS in humans as a novel human herpesvirus, there are immunosuppressive therapies that can modulate the immunologic dysfunction that arises from the presence of viral-infected tissue. In particular, agents that block the immunological attack of the viral-infected cells will ameliorate the symptoms of KS and/or reduce disease progression. Such therapies include antibodies that prevent immune system targeting of viral-infected cells. Such agents include antibodies which bind to cytokines that otherwise upregulate the immune system in response to viral infection.

The antibody may be administered to a patient either singly or in a cocktail containing two or more antibodies, other therapeutic agents, compositions, or the like, including, but not limited to, immunosuppressive agents, potentiators and side-effect relieving agents. Of particular interest are immunosuppressive agents useful in suppressing allergic reactions of a host. Immunosuppressive agents of interest include prednisone, prednisolone, DECADRON (Merck, Sharp & Dohme, West Point, Pa.), cyclophosphamide, cyclosporine, 6-mercaptopurine, methotrexate, azathioprine and i.v. gamma globulin or their combination. Potentiators of interest include monensin, ammonium chloride and chloroquine. All of these agents are administered in generally accepted efficacious dose ranges such as those disclosed in the *Physician Desk Reference*, 41st Ed. (1987), Publisher Edward R. Barnhart, N.J.

Immune globulin from persons previously infected with human herpesviruses or related viruses can be obtained using standard techniques. Appropriate titers of antibodies are known for this therapy and are readily applied to the treatment of KS. Immune globulin can be administered via parenteral injection or by intrathecal shunt. In brief, immune globulin preparations may be obtained from individual donors who are screened for antibodies to the KS-associated human herpesvirus, and plasmas from high-titered donors are pooled. Alternatively, plasmas from donors are pooled and then tested for antibodies to the human herpesvirus of the invention; high-titered pools are then selected for use in KS patients.

Antibodies may be formulated into an injectable preparation. Parenteral formulations are known and are suitable for use in the invention, preferably for i.m. or i.v. administration. The formulations containing therapeutically effective amounts of antibodies or immunotoxins are either sterile liquid solutions, liquid suspensions or lyophilized versions and optionally contain stabilizers or excipients. Lyophilized compositions are reconstituted with suitable diluents, e.g., water for injection, saline, 0.3% glycine and the like, at a level of about from 0.01 mg/kg of host body weight to 10 mg/kg where appropriate. Typically, the pharmaceutical compositions containing the antibodies or immunotoxins will be administered in a therapeutically effective dose in a range of from about 0.01 mg/kg to about 5 mg/kg of the treated mammal. A preferred therapeutically effective dose of the pharmaceutical composition containing antibody or immunotoxin will be in a range of from about 0.01 mg/kg to about 0.5 mg/kg body weight of the treated mammal administered over several days to two weeks by daily intravenous infusion, each given over a one hour period, in a sequential patient dose-escalation regimen.

Antibody may be administered systemically by injection i.m., subcutaneously or intraperitoneally or directly into KS lesions. The dose will be dependent upon the properties of the antibody or immunotoxin employed, e.g., its activity and biological half-life, the concentration of antibody in the formulation, the site and rate of dosage, the clinical tolerance of the patient involved, the disease afflicting the patient and the like as is well within the skill of the physician.

The antibody of the present invention may be administered in solution. The pH of the solution should be in the range of pH 5 to 9.5, preferably pH 6.5 to 7.5. The antibody or derivatives thereof should be in a solution having a suitable pharmaceutically acceptable buffer such as phosphate, tris (hydroxymethyl) aminomethane-HCl or citrate and the like. Buffer concentrations should be in the range of 1 to 100 mM. The solution of antibody may also contain a salt, such as sodium chloride or potassium chloride in a concentration of 50 to 150 mM. An effective amount of a stabilizing agent such as an albumin, a globulin, a gelatin, a protamine or a salt of protamine may also be included and may be added to a solution containing antibody or immunotoxin or to the composition from which the solution is prepared.

Systemic administration of antibody is made daily, generally by intramuscular injection, although intravascular infusion is acceptable. Administration may also be intranasal or by other nonparenteral routes. Antibody or immunotoxin may also be administered via microspheres, liposomes or other microparticulate delivery systems placed in certain tissues including blood.

In therapeutic applications, the dosages of compounds used in accordance with the invention vary depending on the class of compound and the condition being treated. The age, weight, and clinical condition of the recipient patient; and the experience and judgment of the clinician or practitioner administering the therapy are among the factors affecting the selected dosage. For example, the dosage of an immunoglobulin can range from about 0.1 milligram per kilogram of body weight per day to about 10 mg/kg per day for polyclonal antibodies and about 5% to about 20% of that amount for monoclonal antibodies. In such a case, the immunoglobulin can be administered once daily as an intravenous infusion. Preferably, the dosage is repeated daily until either a therapeutic result is achieved or until side effects warrant discontinuation of therapy. Generally, the dose should be sufficient to treat or ameliorate symptoms or signs of KS without producing unacceptable toxicity to the patient.

An effective amount of the compound is that which provides either subjective relief of a symptom(s) or an objectively identifiable improvement as noted by the clinician or other qualified observer. The dosing range varies with the compound used, the route of administration and the potency of the particular compound.

VI. Vaccines and Prophylaxis for KS

This invention provides substances suitable for use as vaccines for the prevention of KS and methods for administering them. The vaccines are directed against KSHV and most preferably comprise antigens obtained from KSHV. In one embodiment, the vaccine contains attenuated KSHV. In another embodiment, the vaccine contains killed KSHV. In another embodiment, the vaccine contains a nucleic acid vector encoding a KSHV polypeptide. In another embodiment, the vaccine is a subunit vaccine containing a KSHV polypeptide.

This invention provides a recombinant KSHV virus with a gene encoding a KSHV polypeptide deleted from the genome. The recombinant virus is useful as an attenuated vaccine to prevent KSHV infection.

This invention provides a method of vaccinating a subject against Kaposi's sarcoma, comprising administering to the subject an effective amount of the peptide or polypeptide encoded by the isolated DNA molecule, and a suitable acceptable carrier, thereby vaccinating the subject. In one embodiment naked DNA is administered to the subject in an effective amount to vaccinate the subject against Kaposi's sarcoma.

This invention provides a method of immunizing a subject against disease caused by KSHV which comprises administering to the subject an effective immunizing dose of an isolated herpesvirus subunit vaccine.

A. Vaccines

The vaccine can be made using synthetic peptide or recombinantly-produced polypeptide described above as antigen. Typically, a vaccine will include from about 1 to 50 micrograms of antigen. More preferably, the amount of polypeptide is from about 15 to about 45 micrograms. Typically, the vaccine is formulated so that a dose includes about 0.5 milliliters. The vaccine may be administered by any route known in the art. Preferably, the route is parenteral. More preferably, it is subcutaneous or intramuscular.

There are a number of strategies for amplifying an antigen's effectiveness, particularly as related to the art of vaccines. For example, cyclization or circularization of a peptide can increase the peptide's antigenic and immunogenic potency. See U.S. Pat. No. 5,001,049. More conventionally, an antigen can be conjugated to a suitable carrier, usually a protein molecule. This procedure has several facets. It can allow multiple copies of an antigen, such as a peptide, to be conjugated to a single larger carrier molecule. Additionally, the carrier may possess properties which facilitate transport, binding, absorption or transfer of the antigen.

For parenteral administration, such as subcutaneous injection, examples of suitable carriers are the tetanus toxoid, the diphtheria toxoid, serum albumin and lamprey, or keyhole limpet, hemocyanin because they provide the resultant conjugate with minimum genetic restriction. Conjugates including these universal carriers can function as T cell clone activators in individuals having very different gene sets.

The conjugation between a peptide and a carrier can be accomplished using one of the methods known in the art. Specifically, the conjugation can use bifunctional cross-linkers as binding agents as detailed, for example, by Means and Feeney, "A recent review of protein modification techniques," *Bioconjugate Chem.* 1, 2–12 (1990).

Vaccines against a number of the Herpesviruses have been successfully developed. Vaccines against Varicella-Zoster Virus using a live attenuated Oka strain is effective in preventing herpes zoster in the elderly, and in preventing chickenpox in both immunocompromised and normal children (Hardy, I., et al., 1990, *Inf. Dis. Clin. N. Amer.* 4, 159; Hardy, I. et al., 1991, *New Engl. J. Med.* 325, 1545; Levin, M. J. et al., 1992, *J. Inf. Dis.* 166, 253; Gershon, A. A., 1992, *J. Inf. Des.* 166(Suppl), 563. Vaccines against Herpes simplex Types 1 and 2 are also commercially available with some success in protection against primary disease, but have been less successful in preventing the establishment of latent infection in sensory ganglia (Roizman, B., 1991, *Rev. Inf. Disease* 13(Suppl. 11), S892; Skinner, G. R. et al., 1992, *Med. Microbiol. Immunol.* 180, 305).

Vaccines against KSHV can be made from the KSHV envelope glycoproteins. These polypeptides can be purified and used for vaccination (Lasky, L. A., 1990, *J. Med. Virol.* 31, 59). MHC-binding peptides from cells infected with the human herpesvirus can be identified for vaccine candidates per the methodology of Marloes, et al., 1991, *Eur. J. Immunol.* 21, 2963–2970.

The KSHV antigen may be combined or mixed with various solutions and other compounds as is known in the art. For example, it may be administered in water, saline or buffered vehicles with or without various adjuvants or immunodiluting agents. Examples of such adjuvants or agents include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, Corynebacterium parvum (Propionibacterium acnes), Bordetella pertussis, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich. Other suitable adjuvants are Amphigen (oil-in-water), Alhydrogel (aluminum hydroxide), or a mixture of Amphigen and Alhydrogel. Only aluminum is approved for human use.

The proportion of antigen and adjuvant can be varied over a broad range so long as both are present in effective amounts. For example, aluminum hydroxide can be present in an amount of about 0.5% of the vaccine mixture ($Al_2O_3$ basis) On a per-dose basis, the amount of the antigen can range from about 0.1 $\mu$g to about 100 $\mu$g protein per patient. A preferable range is from about 1 $\mu$g to about 50 $\mu$g per dose. A more preferred range is about 15 $\mu$g to about 45 $\mu$g. A suitable dose size is about 0.5 ml. Accordingly, a dose for intramuscular injection, for example, would comprise 0.5 ml containing 45 $\mu$g of antigen in admixture with 0.5% aluminum hydroxide. After formulation, the vaccine may be incorporated into a sterile container which is then sealed and stored at a low temperature, for example 4° C., or it may be freeze-dried. Lyophilization permits long-term storage in a stabilized form.

The vaccines may be administered by any conventional method for the administration of vaccines including oral and parenteral (e.g., subcutaneous or intramuscular) injection. Intramuscular administration is preferred. The treatment may consist of a single dose of vaccine or a plurality of doses over a period of time. It is preferred that the dose be given to a human patient within the first 8 months of life. The antigen of the invention can be combined with appropriate doses of compounds including influenza antigens, such as influenza type A antigens. Also, the antigen could be a component of a recombinant vaccine which could be adaptable for oral administration.

Vaccines of the invention may be combined with other vaccines for other diseases to produce multivalent vaccines. A pharmaceutically effective amount of the antigen can be employed with a pharmaceutically acceptable carrier such as a protein or diluent useful for the vaccination of mammals, particularly humans. Other vaccines may be prepared according to methods well-known to those skilled in the art.

Those of skill will readily recognize that it is only necessary to expose a mammal to appropriate epitopes in order to elicit effective immunoprotection. The epitopes are typically segments of amino acids which are a small portion of the whole protein. Using recombinant genetics, it is routine to alter a natural protein's primary structure to create derivatives embracing epitopes that are identical to or substantially the same as (immunologically equivalent to) the naturally occurring epitopes. Such derivatives may include peptide fragments, amino acid substitutions, amino acid deletions and amino acid additions of the amino acid sequence for the viral polypeptides from the human herpesvirus. For example, it is known in the protein art that certain amino acid residues can be substituted with amino acids of similar size and polarity without an undue effect upon the biological activity of the protein. The human herpesvirus polypeptides have significant tertiary structure and the epitopes are usually conformational. Thus, modifications should generally preserve conformation to produce a protective immune response.

B. Antibody Prophylaxis

Therapeutic, intravenous, polyclonal or monoclonal antibodies can been used as a mode of passive immunotherapy of herpesviral diseases including perinatal varicella and CMV. Immune globulin from persons previously infected with the human herpesvirus and bearing a suitably high titer of antibodies against the virus can be given in combination with antiviral agents (e.g. ganciclovir), or in combination with other modes of immunotherapy that are currently being evaluated for the treatment of KS, which are targeted to modulating the immune response (i.e. treatment with copolymer-1, antiidiotypic monoclonal antibodies, T cell "vaccination"). Antibodies to human herpesvirus can be administered to the patient as described herein. Antibodies specific for an epitope expressed on cells infected with the human herpesvirus are preferred and can be obtained as described above.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or. ferric hydroxides, and such organic bases as isopropylamine, trimethylamine, 2-ethylamino ethanol, histidine, procaine, and the like.

C. Monitoring Therapeutic Efficacy

This invention provides a method for monitoring the therapeutic efficacy of treatment for Kaposi's sarcoma which comprises: (a) determining in a first sample from a subject with Kaposi's sarcoma the presence of the isolated nucleic acid molecule; (b) administering to the subject a therapeutic amount of an agent such that the agent is contacted to the cell in a sample; (c) determining after a suitable period of time the amount of the isolated nucleic acid molecule in the second sample from the treated subject; and (d) comparing the amount of isolated nucleic acid molecule determined in the first sample with the amount determined in the second sample, a difference indicating the effectiveness of the agent, thereby monitoring the therapeutic efficacy of treatment for Kaposi's sarcoma. As defined herein "amount" is viral load or copy number. Methods of determining viral load or copy number are known to those skilled in the art.

VII. Screening Assays for Pharmaceuticals for Alleviating the Symptoms of KS

Since an agent involved in the causation or progression of KS has been identified and described, assays directed to identifying potential pharmaceutical agents that inhibit the biological activity of the agent are possible. KS drug screening assays which determine whether or not a drug has activity against the virus described herein are contemplated in this invention. Such assays comprise incubating a compound to be evaluated for use in KS treatment with cells which express the KS associated human herpesvirus polypeptides or peptides and determining therefrom the effect of the compound on the activity of such agent. In vitro assays in which the virus is maintained in suitable cell culture are preferred, though in vivo animal models would also be effective.

Compounds with activity against the agent of interest or peptides from such agent can be screened in in vitro as well as in vivo assay systems. In vitro assays include infecting peripheral blood leukocytes or susceptible T cell lines such as MT-4 with the agent of interest in the presence of varying concentrations of compounds targeted against viral replication, including nucleoside analogs, chain terminators, antisense oligonucleotides and random polypeptides (Asada et al., 1989, *J. Clin. Microbiol.* 27, 2204; Kikuta et al., 1989, *Lancet* Oct. 7, 861). Infected cultures and their supernatants can be assayed for the total amount of virus including the presence of the viral genome by quantitative PCR, by dot blot assays or by using immunologic methods. For example, a culture of susceptible cells could be infected with KSHV in the presence of various concentrations of drug, fixed on slides after a period of days, and examined for viral antigen by indirect immunofluorescence with monoclonal antibodies to viral polypeptides (Kikuta et al., supra). Alternatively, chemically adhered MT-4 cell monolayers can be used for an infectious agent assay using indirect immunofluorescent antibody staining to search for focus reduction (Higashi et al., 1989, *J. Clin. Micro.* 27, 2204).

As an alternative to whole cell in vitro assays, purified KSHV enzymes isolated from a host cell or produced by recombinant techniques can be used as targets for rational drug design to determine the effect of the potential drug on enzyme activity. KSHV enzymes amenable to this approach include, but are not limited to, dihydrofolate reductase (DHFR), thymidylate synthase (TS), thymidine kinase or DNA polymerase. A measure of enzyme activity indicates effect on the agent itself.

Drug screens using herpes viral products are known and have been previously described in EP 0514830 (herpes proteases) and WO 94/04920 ($U_L13$ gene product).

This invention provides an assay for screening anti-KS chemotherapeutics. Infected cells can be incubated in the presence of a chemical agent that is a potential chemotherapeutic against KS (e.g., acyclo-guanosine). The level of virus in the cells is then determined after several days by immunofluorescence assay for antigens, Southern blotting for viral genome DNA or Northern blotting for mRNA and compared to control cells. This assay can quickly screen large numbers of chemical compounds that may be useful against KS.

Further, this invention provides an assay system that is employed to identify drugs or other molecules capable of binding to the nucleic acid molecule or proteins, either in the cytoplasm or in the nucleus, thereby inhibiting or potentiating transcriptional activity. Such assay would be useful in the development of drugs that would be specific against particular cellular activity, or that would potentiate such activity, in time or in level of activity.

This invention provides a method of screening for a KSHV-selective antiviral drug in vivo comprising: (a) expression of KSHV DHFR or KSHV TS in a bacterial auxotroph (nutritional mutant); (b) measuring bacterial growth rate in the absence and presence of the drug; and (c) comparing the rates so measured so as to identify the drug that inhibits KSHV DHFR or KSHV TS in vivo.

Methods well known to those skilled in the art allow selection or production of a suitable bacterial auxotroph and measurement of bacterial growth.

The following reviews of antifolate compounds are provided to more fully describe the state of the art, particularly as it pertains to inhibitors of dihydrofolate reductase and thymidylate synthase: (a) Unger, 1996, Current concepts of treatment in medical oncology: new anticancer drugs, *Journal of Cancer Research & Clinical Oncology* 122, 189–198; (b) Jackson, 1995, Toxicity prediction from metabolic pathway modelling, *Toxicology* 102, 197–205; (c) Schultz, 1995, Newer antifolates in cancer therapy, *Progress in Drug Research* 44, 129–157; (d) van der Wilt and Peters, 1994, New targets for pyrimidine antimetabolites in the treatment of solid tumours 1: Thymidylate synthase, *Pharm World Sci* 16, 167; (e) Fleisher, 1993, Antifolate analogs: mechanism of action, analytical methodology, and clinical efficacy, *Therapeutic Drug Monitoring* 15, 521–526; (f) Eggott et al., 1993, Antifolates in rheumatoid arthritis: a hypothetical mechanism of action, *Clinical & Experimental Rheumatology* 11 Suppl 8, S101–S105; (g) Huennekens et al., 1992, Membrane transport of folate compounds, *Journal of Nutritional Science & Vitaminology* Spec No, 52–57; (h) Fleming and Schilsky, 1992, Antifolates: the next generation, *Seminars in Oncology* 19, 707–719; and (i) Bertino et al., 1992, Enzymes of the thymidylate cycle as targets for chemotherapeutic agents: mechanisms of resistance, *Mount Sinai Journal of Medicine* 59, 391–395.

This invention provides a method of determining the health of a subject with AIDS comprising: (a) measuring the plasma concentration of vMIP-I, vMIP-II or vMIP-III; and (b) comparing the measured value to a standard curve relating AIDS clinical course to the is measured value so as to determine the health of the subject.

VIII. Treatment of HIV

This invention provides a method of inhibiting HIV replication, comprising administering to the subject or treating cells of a subject with an effective amount of a polypeptide which is encoded by a nucleic acid molecule, so as to inhibit replication of HIV. In one embodiment, the polypeptide is one from the list provided in Table 1.

This invention is further illustrated in the Experimental Details Sections which follow. These sections are set forth to aid in understanding the invention but is not intended to, and should not be construed to, limit in any way the invention as set forth in the claims which follow thereafter.

EXPERIMENTAL DETAILS SECTION I

NUCLEOTIDE SEQUENCE OF THE KAPOSI'S SARCOMA-ASSOCIATED HERPESVIRUS

The genome of the Kaposi's sarcoma-associated herpesvirus (KSHV or HHV8) was mapped with cosmid and phage genomic libraries from the BC-1 cell line. Its nucleotide sequence was determined except for a 3 kb region at the right end of the genome that was refractory to cloning. The BC-1 KSHV genome consists of a 140.5 kb long unique coding region (LUR) flanked by multiple G+C rich 801 bp terminal repeat sequences. A genomic duplication that apparently arose in the. parental tumor is present in this cell culture-derived strain. At least 81 open reading frames (ORFs), including 66 with similarity to herpesvirus saimiri ORFs, and 5 internal repeat regions are present in the LUR. The virus encodes genes similar to complement-binding proteins, three cytokines (two macrophage inflammatory proteins and interleukin-6), dihydrofolate reductase, bcl-2, interferon regulatory factor, IL-8 receptor, NCAM-like adhesin, and a D-type cyclin, as well as viral structural and metabolic proteins. Terminal repeat analysis of virus DNA from a KS lesion suggests a monoclonal expansion of KSHV in the KS tumor. The complete genome sequence is set forth in Genbank Accession Numbers U75698 (LUR), U75699 (TR) and U75700 (ITR).

Kaposi's sarcoma is a vascular tumor of mixed cellular composition (Tappero et al., 1993, *J. Am. Acad. Dermatol.* 28, 371–395). The histology and relatively benign course in persons without severe immunosuppression has led to suggestions that KS tumor cell proliferation is cytokine induced (Ensoli et al., 1992, *Immunol. Rev.* 127, 147–155). Epidemiologic studies indicate the tumor is under strict immunologic control and is likely to be caused by a sexually transmitted infectious agent other than HIV (Peterman et al., 1993, *AIDS* 7, 605–611). KS-associated herpesvirus (KSHV) was discovered in an AIDS-KS lesion by representational difference analysis (RDA) and shown to be present in almost all AIDS-KS lesions (Chang et al., 1994, *Science* 265, 1865–1869). These. findings have been confirmed and extended to nearly all KS lesions examined from the various epidemiologic classes of KS (Boshoff et al., 1995, *Lancet* 345, 1043–1044; Dupin et al., 1995, *Lancet* 345, 761–762; Moore and Chang, 1995, *New Eng. J. Med.* 332, 1181–1185; Schalling et al., 1995, *Nature Med.* 1, 707–708; Chang et al., 1996, *Arch. Int. Med.* 156, 202–204). KSHV is the eighth presumed human herpesvirus (HHV8) identified to date.

The virus was initially identified from two herpesvirus DNA fragments, KS330Bam and KS631Bam (Chang et al., 1994, *Science* 265, 1865–1869). Subsequent sequencing of a 21 kb AIDS-KS genomic library fragment (KS5) hybridizing to KS330Bam demonstrated that KSHV is a gammaherpesvirus related to herpesvirus saimiri (HVS) belonging to the genus Rhadinovirus (Moore et al., 1996, *J. Virol.* 70, 549–558). Colinear similarity (synteny) of genes in this region is maintained between KSHV and HVS, as well as Epstein-Barr virus (EBV) and equine herpesvirus 2 (EHV2). A 12 kb region (L54 and SGL-1) containing the KS631Bam sequence includes cyclin D and IL-8Ra genes unique to rhadinoviruses.

KSHV is not readily transmitted to uninfected cell lines (Moore et al., 1996, *J. Virol.* 70, 549–558), but it is present in a rare B cell primary effusion (body cavity-based) lymphoma (PEL) frequently associated with KS (Cesarman et al., 1995, *New Eng. J. Med.* 332, 1186–1191). BC-1 is a PEL cell line containing a high KSHV genome copy number and is coinfected with EBV (Cesarman et al., 1995, *Blood* 86, 2708–2714). The KSHV genome form in BC-1 and its parental tumor comigrates with 270 kb linear markers on pulsed field gel electrophoresis (PFGE) (Moore et al., 1996, *J. Virol.* 70, 549–558). However, the genome size based on encapsidated DNA from an EBV-negative cell line (Renne et al., 1996, *Nature Med.* 2, 342–346) is estimated to be 165 kb (Moore et al., 1996, *J. Virol.* 70, 549–558). Estimates from KS lesions indicate a genome size larger than that of EBV (172 kb) (Decker et al., 1996, *J. Exp. Med.* 184, 283–288).

To determine the genomic sequence of KSHV and identify novel virus genes, contiguous overlapping virus DNA inserts from BC-1 genomic libraries were mapped. With the exception of a small, unclonable repeat region at its right end, the genome was sequenced to high redundancy allowing definition of the viral genome structure and identification of genes that may play a role in KSHV-related pathogenesis.

MATERIALS AND METHODS

Library generation and screening. BC-1, HBL-6 and BCP-1 cells were maintained in RPMI 1640 with 20% fetal calf serum (Moore et al., 1996, *J. Virol.* 70, 549–558; Cesarman et al., 1995, *Blood* 86, 2708–2714; Gao et al., 1996, *Nature Med.* 2, 925–928). DNA from BC-1 cells was commercially cloned (Sambrook et al., 1989, *Molecular Cloning: A laboratory manual*, Cold Spring Harbor Press, Salem, Mass.) into either Lambda FIX II or S-Cos1 vectors (Stratagene, La Jolla, Calif.). Phage and cosmid libraries were screened by standard methods (Benton et al., 1977, *Science* 196, 180–182; Hanahan and Meselson, 1983, *Methods Enzymol.* 100, 333–342).

Initial library screening was performed using the KS330Bam and KS631Bam RDA fragments (Chang et al., 1994, *Science* 265, 1865–1869). Overlapping clones were sequentially identified using probes synthesized from the ends of previously identified clones (FIG. 1) (Feinberg and Vogelstein, 1983, *Anal. Biochem.* 132, 6; Melton et al., 1984, *Nucl. Acids Res.* 12, 7035–7056). The map was considered circularly permuted by the presence of multiple, identical TR units in cosmids Z2 and Z6. Each candidate phage or cosmid was confirmed by tertiary screening.

Shotgun Sequencing and Sequence Verification

Lambda and cosmid DNA was purified by standard methods (Sambrook et al., 1989, *Molecular Cloning: A laboratory manual*, Cold Spring Harbor Press, Salem, Mass.). Shotgun sequencing (Deininger, 1983, *Anal. Biochem.* 129, 216–223; Bankier et al., 1987, *Meth. Enzymol.* 155, 51–93) was performed on sonicated DNA. A 1–4 kb fraction was subcloned into M13mp19 (New England Biolabs, Inc., Beverly, Mass.) and propagated in XL1-Blue cells (Stratagene, La Jolla, Calif.) (Sambrook et al., 1989, *Molecular Cloning: A laboratory manual*, Cold Spring Harbor Press, Salem, Mass.) M13 phages were positively screened using insert DNA from the phage or cosmid, and negatively screened with vector arm DNA or adjacent genome inserts.

Automated dideoxy cycle sequencing was performed with M13 (−21) CS+ or FS dye primer kits (Perkin-Elmer, Branchburg N.J.) on ABI 373A or 377 sequenators (ABI, Foster City, Calif.). Approximately 300 M13 sequences were typically required to achieve initial coverage for each 10 kb of insert sequence. Minimum sequence fidelity standards were defined as complete bidirectional coverage with at least 4 overlapping sequences at any given site. For regions with sequence gaps, ambiguities or frameshifts that did not meet these criteria, primer walking was done with custom primers (Perkin-Elmer) and dye terminator chemistry (FS or Ready Reaction kits, Perkin-Elmer). An unsequenced 3 kb region adjacent to the right end TR sequence in the Z2 cosmid insert could not be cloned into M13 or Bluescript despite repeated efforts.

Sequence Assembly and Open Reading Frame Analysis

Sequence data were edited using Factura (ABI, Foster City, Calif.) and assembled into contiguous sequences using electropherograms with AutoAssembler (ABI, Foster City, Calif.) and into larger assemblies with AssemblyLIGN (IBI-Kodak, Rochester N.Y.). Base positions not clearly resolved by multiple sequencing attempts (less than 10 bases in total) were assigned the majority base pair designation. The entire sequence (in 1–5 kb fragments) and all predicted open reading frames (ORFs) were analyzed using BLASTX, BLASTP and BLASTN (Altschul et al., 1990, *J. Mol. Biol.* 215, 403–410). The sequence was further analyzed using MOTIFS (Moore et al., 1996, *J. Virol.* 70, 549–558), REPEAT and BESTFIT (GCG), and MacVector (IBI, New Haven, Conn.).

ORF Assignment and Nomenclature

All ORFs with similarities to HVS were identified. These and other potential ORFs having >100 amino acids were found using MacVector. ORFs not similar to HVS ORFs were included in the map (FIG. 1) based on similarity to other known genes, optimum initiation codon context (Kozak, 1987, *Nucl. Acids Res.* 15, 8125–8148), size and position. Conservative selections were made to minimize spurious assignments; this underestimates the number of true reading frames. KSHV ORF nomenclature is based on HVS similarities; KSHV ORFs not similar to HVS genes are numbered in consecutive order with a K prefix. ORFs with sequence but not positional similarity to HVS ORFs were assigned the HVS ORF number (e.g., ORF 2). As new ORFs are identified, it is suggested that they be designated by decimal notation. The standard map orientation (FIG. 1) of the KSHV genome is the same as for HVS (Albrecht et al., 1992, *J. Virol.* 66, 5047–5058) and EHV2 (Telford et al., 1995, *J. Mol. Biol.* 249, 520–528), and reversed relative to the EBV standard map (Baer et al., 1984, *Nature* 310, 207–211).

RESULTS

Genomic Mapping and Sequence Characteristics

Figure 1B:
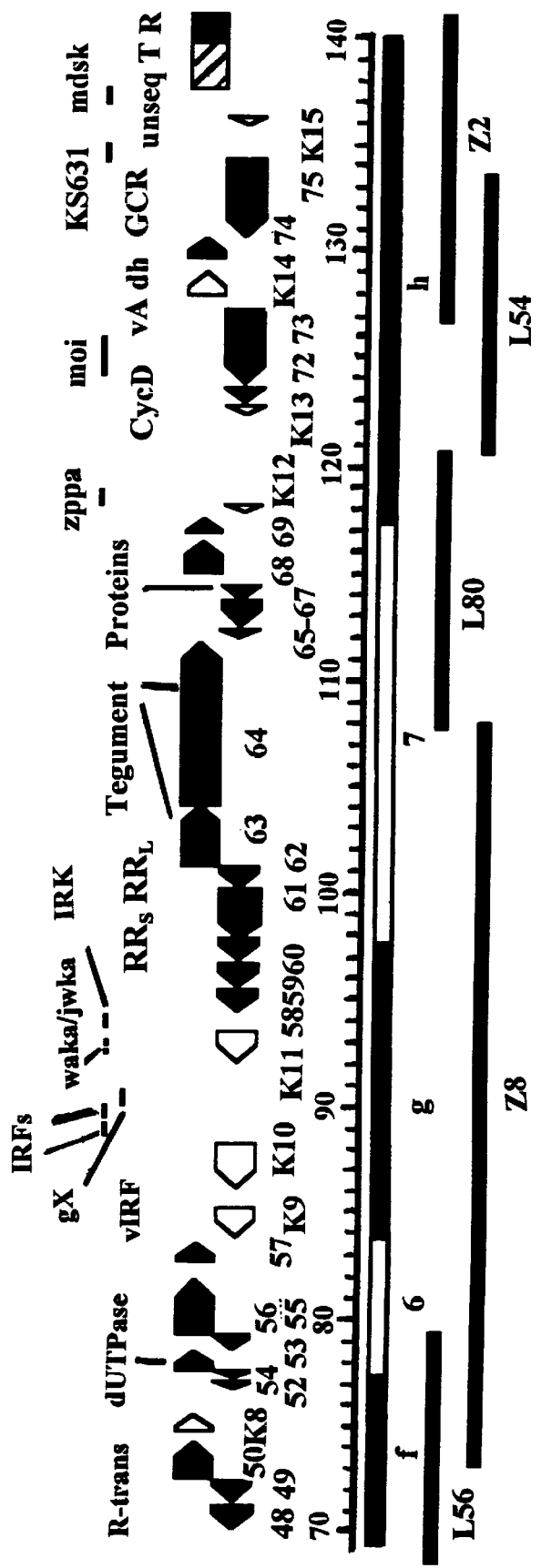

Complete genome mapping was achieved with 7 lambda and 3 cosmid clones (FIG. 1). The structure of the BC-1 KSHV genome is similar to HVS in having a long unique region (LUR) flanked by TR units. The ~140.5 kb LUR sequence has 53.5% G+C content and includes all identified KSHV ORFs. TR regions consist of multiple 801 bp direct repeat units having 84.5% G+C content (FIG. 2A) with potential packaging and cleavage sites. Minor sequence variations are present among repeat units. The first TR unit at the left (Z6) TR junction (205 bp) is deleted and truncated in BC-1 compared to the prototypical TR unit.

The genome sequence abutting the right terminal repeat region is incomplete due to a 3 kb region in the Z2 cosmid insert that could not be cloned into sequencing vectors. Partial sequence information from primer walking indicates that this region contains stretches of 16 bp A+G rich imperfect direct repeats interspersed with at least one stretch of 16 bp C+T rich imperfect direct repeats. These may form a larger inverted repeat that could have contributed to our difficulty in subcloning this region. Greater than 12-fold average sequence redundancy was achieved for the entire LUR with complete bidirectional coverage by at least 4 overlapping reads except in the unclonable region.

Figure 2B:
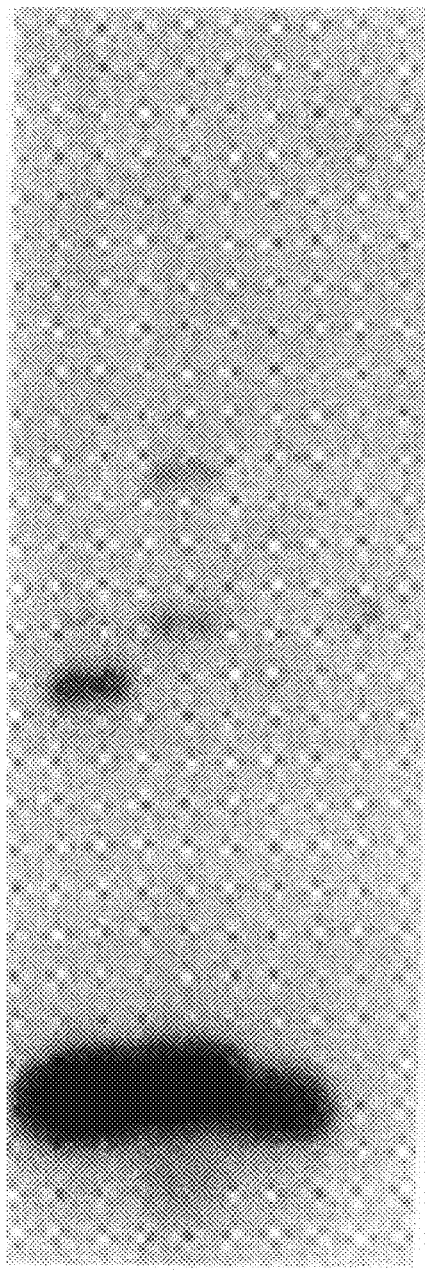
Figure 2C:
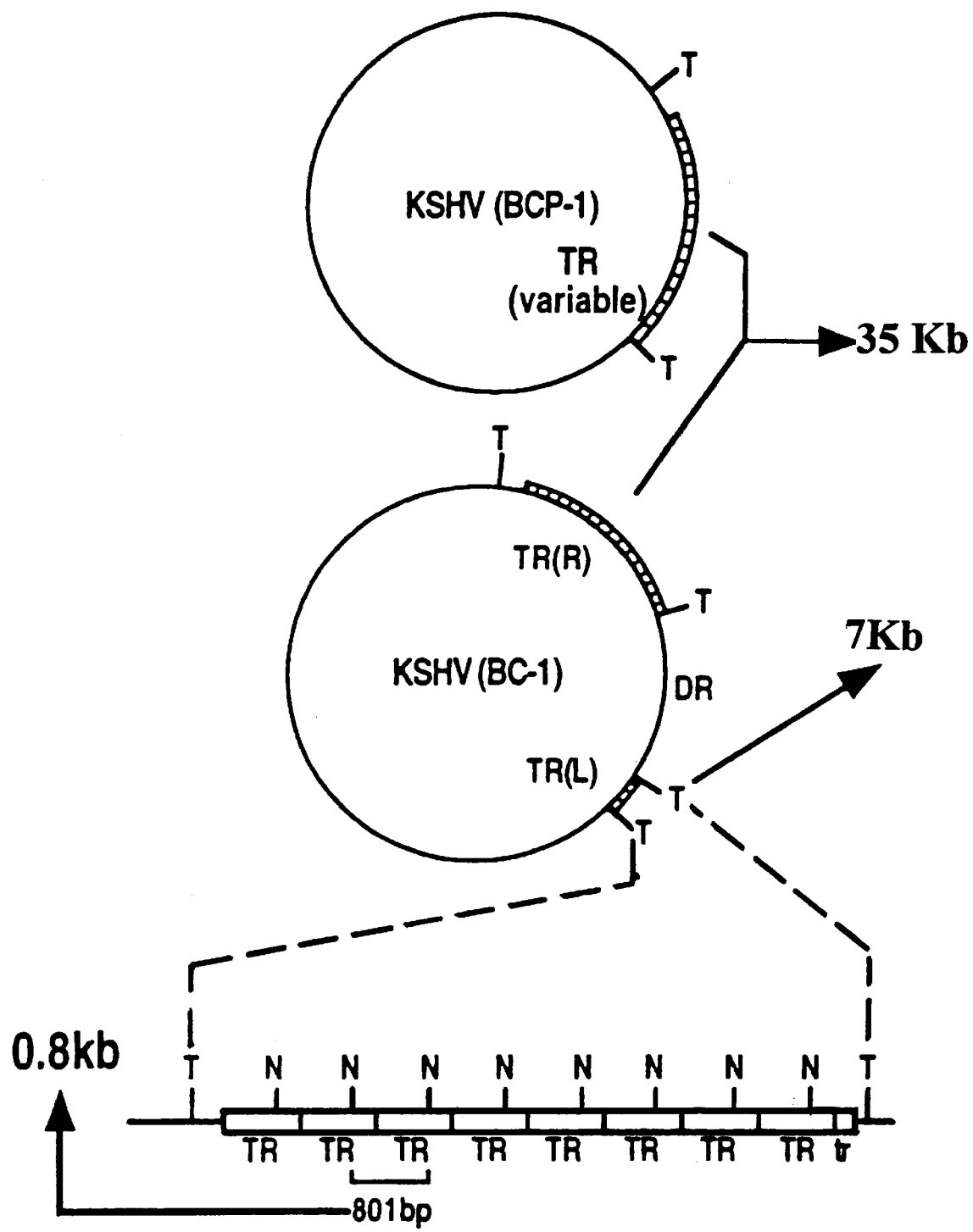
Figure 2D:
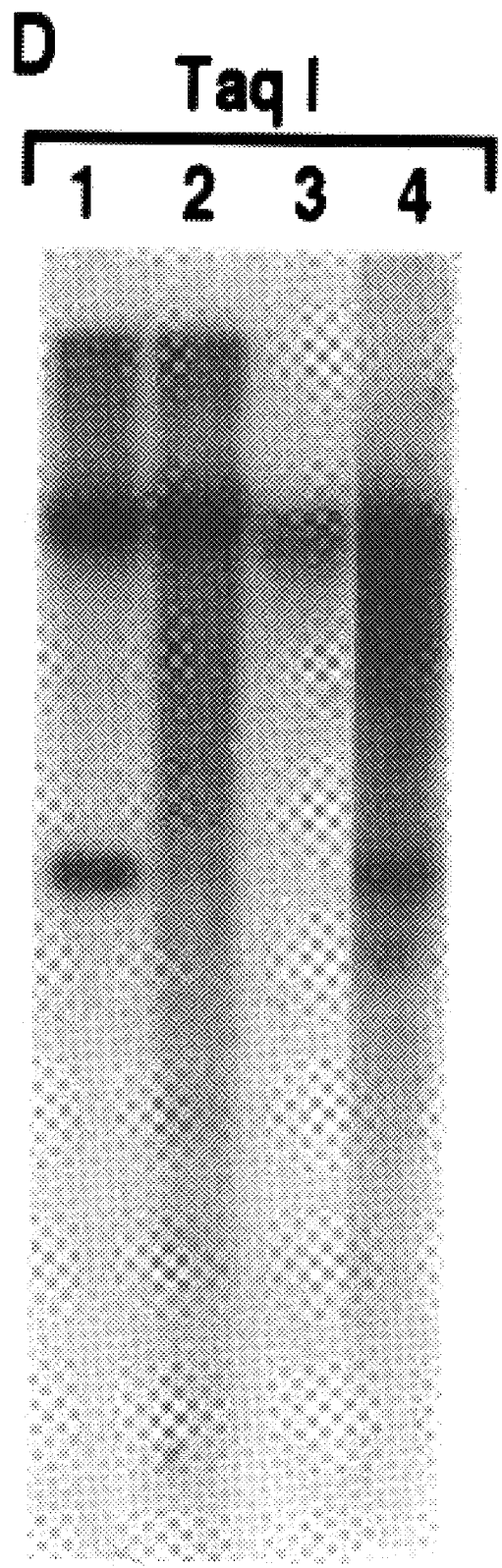
Figure 4B:
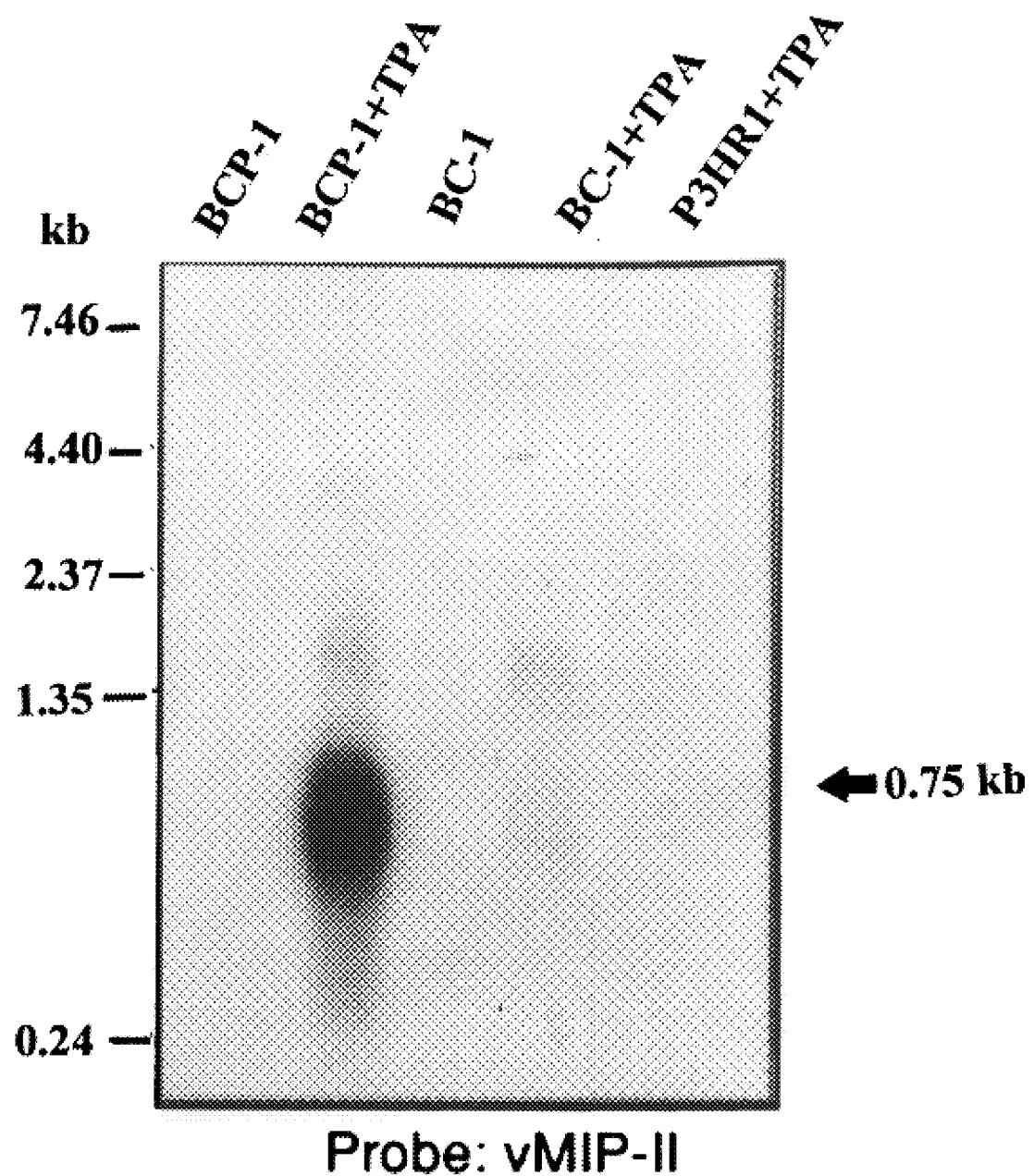
Figure 4C:
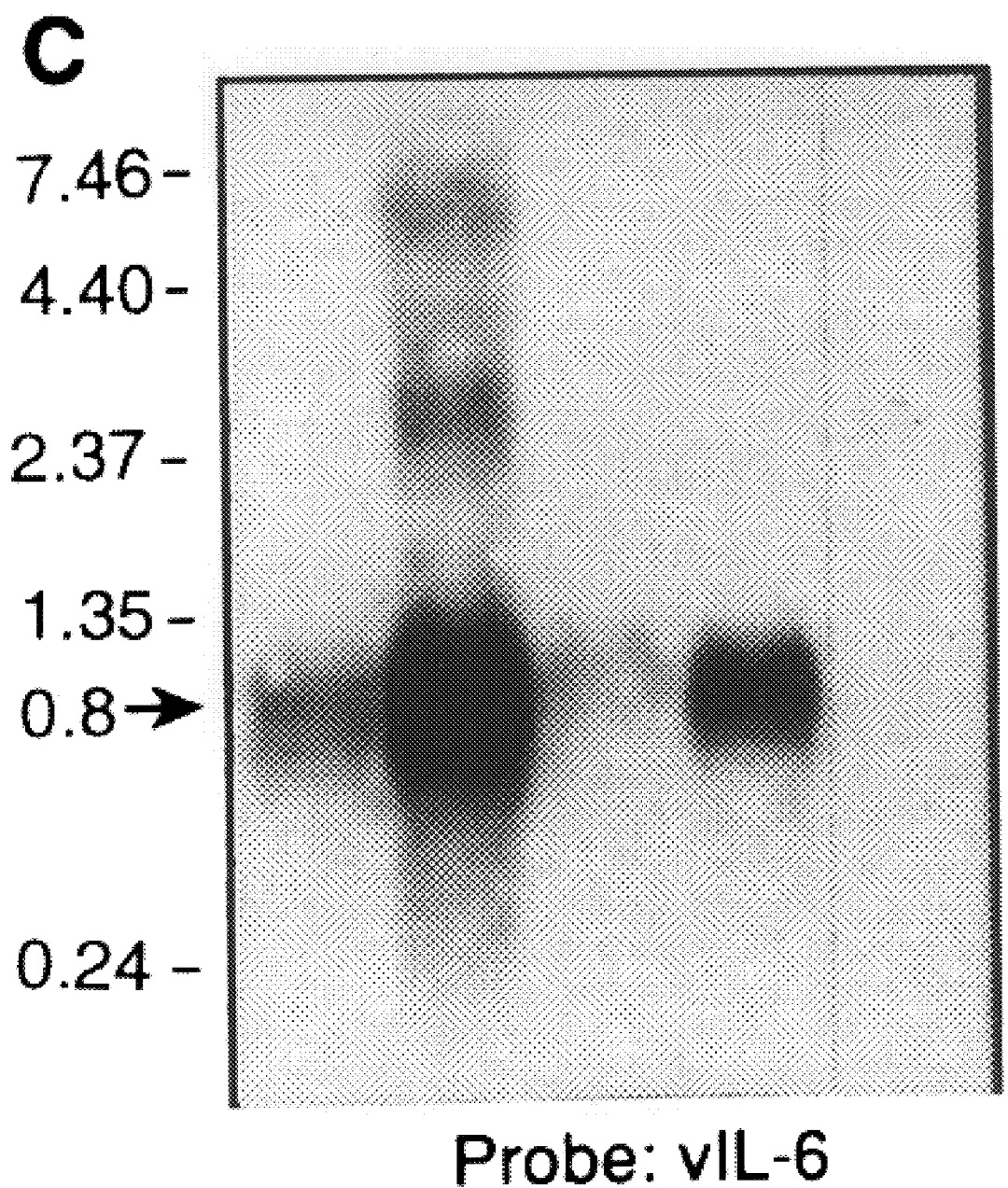
Figure 4D:
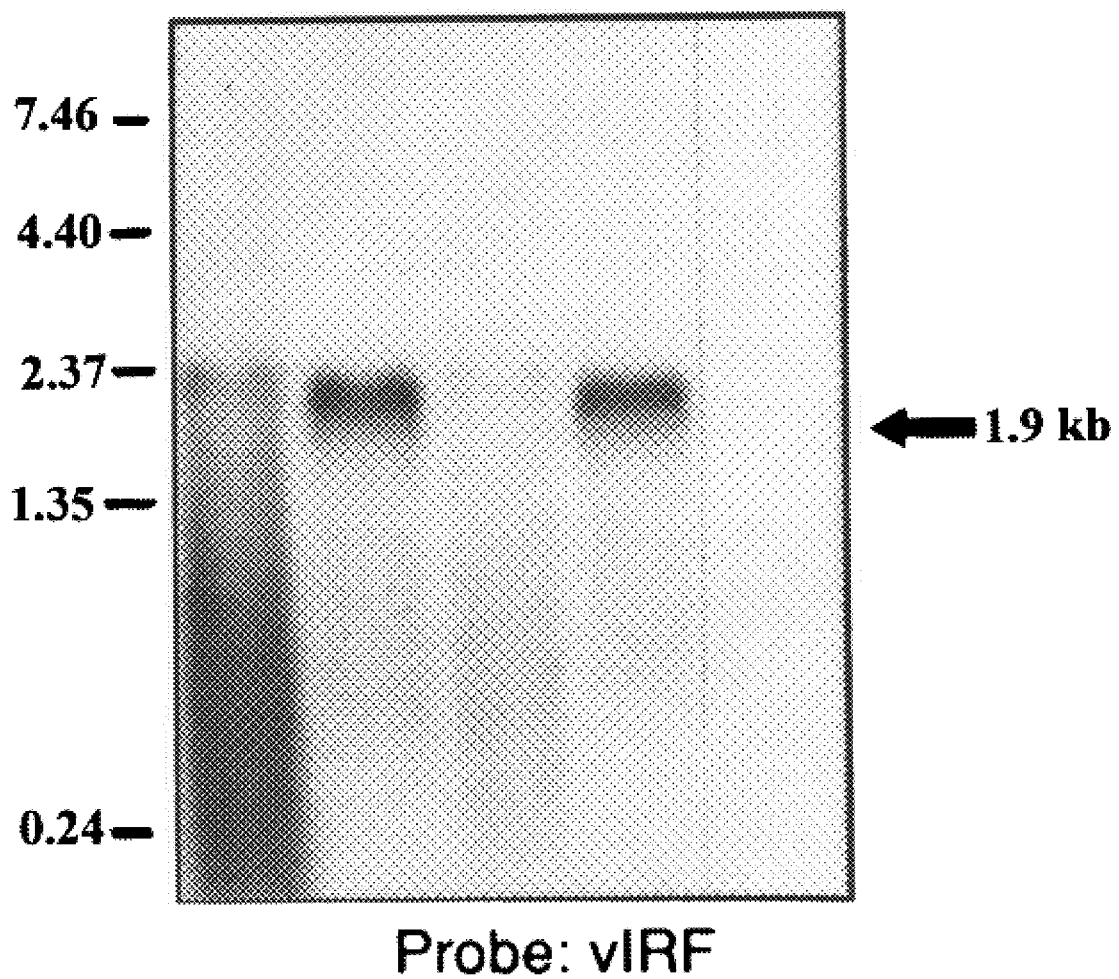
Figure 4E:
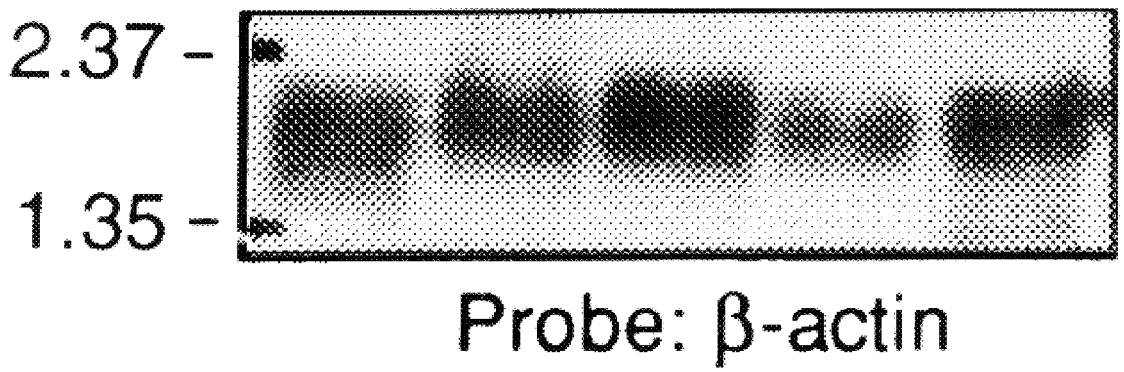
Figure 4F:
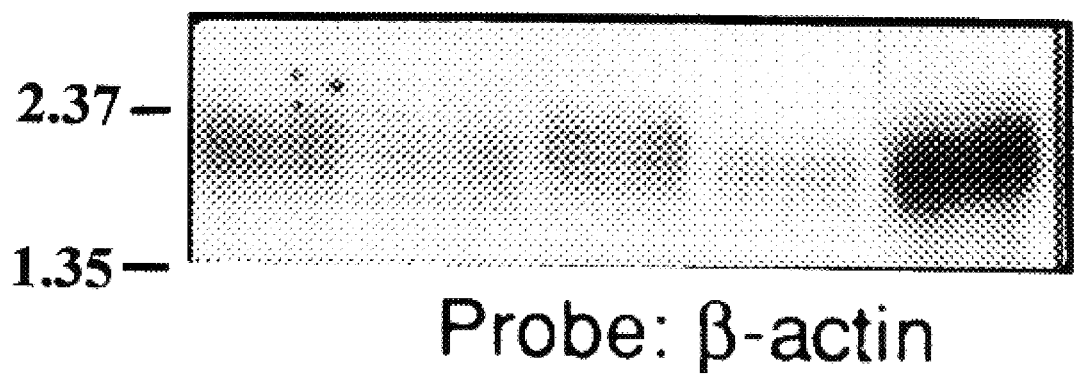

The BC-1 TR region was examined by Southern blotting since sequencing of the entire region is not possible due to its repeat structure. BC-1, BCP-1 (an EBV-negative, KSHV infected cell line) and KS lesion DNAs have an intense ~800 bp signal consistent with the unit length repeat sequence when digested with enzymes that cut once in the TR and hybridized to a TR probe (FIGS. 2B and 2C). Digestion with enzymes that do not cut in the TR indicates that the BC-1 strain contains a unique region buried in the TR, flanked by ~7 kb and ~35 kb TR sequences (FIGS. 2C and 2D). An identical pattern occurs in HBL-6, a cell line independently derived from the same tumor as BC-1, suggesting that this duplication was present in the parental tumor (FIGS. 2C and 2D). The restriction pattern with Not I, which also cuts only once within the TR but rarely within the LUR, suggests that the buried region is at least 33 kb. Partial sequencing of this region demonstrates that it is a precise genomic duplication of the region beginning at ORF K8. The LUR is 140 kb including the right end unsequenced gap (<3 kb). The estimated KSHV genomic size in BC-1 and HBL-6 (including the duplicated region) is approximately 210 kb.

Based on the EBV replication model used in clonality studies (Raab-Traub and Flynn, 1986, Cell 47, 883–889), the polymorphic BCP-1 laddering pattern may reflect lytic virus replication and superinfection (FIG. 2C). The EBV laddering pattern occurs when TR units are deleted or duplicated during lytic. replication and is a stochastic process for each infected cell (Raab-Traub and Flynn, 1986, Cell 47, 883–889). No laddering is present for BC-1 which is under tight latent KSHV replication control (Moore et al., 1996, J. Virol. 70, 549–558). KS lesion DNA also shows a single hybridizing band suggesting that virus in KS tumor cells may be of monoclonal origin.

Features and Coding Regions of the KSHV LUR

The KSHV genome shares the 7 block (B) organization (B1–B7, FIG. 1) of other herpesviruses (Chee et al., 1990, Curr. Topics Microbiol. Immunol. 154, 125–169), with subfamily specific or unique ORFs present between blocks (interblock regions (IB) a–h, FIG. 1). ORF analysis indicates that only 79% of the sequenced 137.5 kb LUR encodes 81 identifiable ORFs which is likely to be due to a conservative assignment of ORF positions. The overall LUR CpG dinucleotide observed/expected (O/E) ratio is 0.75 consistent with a moderate loss of methylated cytosines, but there is marked regional variation. The lowest CpG O/E ratios (<0.67) occur in IBa (bp 1–3200), in B5 (68,602–69,405) and IBh (117,352–137,507). The highest O/E ratios (>0.88) extend from B2 to B3 (30,701–47,849), in IBe (67,301–68,600), and in B6 (77,251–83,600). Comparison to the KS5 sequence (Moore et al., 1996, J. Virol. 70, 549–558) shows a high sequence conservation between these two strains with only 21 point mutations over the comparable 20.7 kb region (0.1%). A frameshift within BC-1 ORF 28 (position 49,004) compared to KS5 ORF 28 was not resolvable despite repeated sequencing of KS5 and PCR products amplified from BC-1. Two additional frameshifts in noncoding regions (bp 47,862 and 49,338) are also present compared to the KS5 sequence.

Several repeat regions are present in the LUR (FIG. 1). A 143 bp sequence is repeated within ORF K11 at positions 92,678–92,820 and 92,852–92,994 (waka/jwka). Complex repeats are present in other regions of the genome: 20 and 30 bp repeats in the region from 24,285–24,902 (frnk), a 13 bp repeat between bases 29,775 and 29,942 (vnct), two separate 23 bp repeat stretches between bases 118,123 and 118,697 (zppa), and 15 different 11–16 bp repeats throughout the region from 124,527 to 126,276 (moi). A complex A–G rich repeat region (mdsk) begins at 137,099 and extends into the unsequenced gap.

Conserved ORFs with similar genes found in other herpesviruses are listed in Table 1, along with their polarity, map positions, sizes, relatedness to HVS and EBV ORFs, and putative functions. Conserved ORFs coding for viral structural proteins and enzymes include genes involved in viral DNA replication (e.g., DNA polymerase (ORF 9)), nucleotide synthesis (e.g., dihydrofolate reductase (DHFR, ORF 2), thymidylate synthase (TS, ORF 70)), regulators of gene expression (R transactivator (LCTP, ORF50)) and 5 conserved herpesvirus structural capsid and 5 glycoprotein genes.

Several genes that are similar to HVS ORFs also have unique features. ORF 45 has sequence similarity to nuclear and transcription factors (chick nucleolin and yeast SIR3) and has an extended acidic domain typical for transactivator proteins between amino acids 90 and 115. ORF73 also has an extended acidic domain separated into two regions by a glutamine-rich sequence encoded by the moi repeat. The first region consists almost exclusively of aspartic and glutamic acid residue repeats while the second glutamic acid rich region has a repeated leucine heptad motif suggestive of a leucine zipper structure. ORF 75, a putative tegument protein, has a high level of similarity to the purine biosynthetic enzyme of E. coli and D. melanogaster N-formylglycinamide ribotide amidotransferase (FGARAT).

ORFs K3 and K5 are not similar to HVS genes but are similar to the major immediate early bovine herpesvirus type 4 (BHV4) gene IE1 (12 and 13% identity respectively) (van Santen, 1991, J. Virol. 65, 5211–5224). These genes have no significant similarity to the herpes simplex virus I (HSV1) a0 (which is similar to BHV4 IE1), but encode proteins sharing with the HSV1 ICP0 protein a cysteine-rich region which may form a zinc finger motif (van Santen, 1991, J. Virol. 65, 5211–5224). The protein encoded by ORF K5 has a region similar to the nuclear localization site present in the late form of the BHV4 protein. ORF K8 has a purine binding motif (GLLVTGKS) in the C-terminus of the protein which is similar to a motif present in the KSHV TK (ORF21) (Moore et al., 1996, J. Virol. 70, 549–558).

No KSHV genes with similarity to HVS ORFs 1, 3, 5, 12, 13, 14, 15, 51 and 71 were identified in the KSHV LUR sequence. HVS ORF 1 codes for a transforming protein, responsible for HVS-induced in vitro lymphocyte transformation (Akari et al., 1996, Virology 218, 382–388) and has poor sequence conservation among HVS strains (Jung and Desrosiers, 1991, J. Virol. 65, 6953–6960; Jung and Desrosiers, 1995, Molec. Cellular Biol. 15, 6506–6512). Functional KSHV genes similar to this gene may be present but were not identifiable by sequence comparison. Likewise, no KSHV genes similar to EBV latency and transformation-associated proteins (EBNA-1, EBNA-2, EBNA-LP, LMP-1, LMP-2 or gp350/220) were found despite some similarity to repeat sequences present in these genes. KSHV also does not have a gene similar to the BZLF1 EBV transactivator gene.

Several sequences were not given ORF assignments although they have characteristics of expressed genes. The sequence between bp 90,173 and 90,643 is similar to the precursor of secreted glycoprotein X (gX), encoded by a number of alphaherpesviruses (pseudorabies, EHV1), and which does not form part of the virion structure. Like the cognate gene in EHV1, the KSHV form lacks the highly-acidic carboxy terminus of the pseudorabies gene.

Two polyadenylated transcripts expressed at high copy number in BCBL-1 are present at positions 28,661–29,741 (T1.1) in IBb and 118,130–117,436 (T0.7) in IBh. T0.7 encodes a 60 residue polypeptide (ORF K12, also called Kaposin) and T1.1 (also referred to as nut-1) has been speculated to be a U RNA-like transcript.

Cell Cycle Regulation and Cell Signaling Proteins

A number of ORFs which are either unique to KSHV or shared only with other gammaherpesviruses encode genes similar to oncoproteins and cell signaling proteins. ORF 16, similar to EBV BHRF1 and HVS ORF16, encodes a functional Bcl-2-like protein which can inhibit Bax-mediated apoptosis. ORF 72 encodes a functional cyclin D gene, also found in HVS (Nicholas et al., 1992, Nature 355, 362–365), that can substitute for human cyclin D in phosphorylating the retinoblastoma tumor suppressor protein.

KSHV encodes a functionally-active IL-6 (ORF K2) and two macrophage inflammatory proteins (MIPs) (ORFs K4 and K6) which are not found in other human herpesviruses. The vIL-6 has 62% amino acid similarity to the human IL-6 and can substitute for human IL-6 in preventing mouse myeloma cell apoptosis. Both MIP-like proteins have conserved C—C dimer signatures characteristic of β-chemokines and near sequence identity to human MIP-1α in their N-terminus regions. vMIP-I (QRF K6) can inhibit CCR-5 dependent HIV-1 replication. An open reading frame spanning nucleotide numbers (bp) 22,529–22,185 (vMIP-III) has low conservation with MIP 1β (BLASTX poisson p=0.0015) but retains the C—C dimer motif. ORF K9 (vIRF1) encodes a 449 residue protein with similarity to the family of interferon regulatory factors (IRF) (David, 1995, *Pharmac. Ther.* 65, 149–161). It has 13.4% amino acid identity to human interferon consensus sequence binding protein and partial conservation of the IRF DNA-binding domain. Three additional open reading frames at bp 88,910–88,410 (vIRF2), bp 90,541–89,600 (vIRF3) and bp 94,127–93,636 (vIRF4) also have low similarity to IRF-like proteins (p>0.35). No conserved interferon consensus sequences were found in this region of the genome.

Other genes encoding signal transduction polypeptides, which are also found in other herpesviruses, include a complement-binding protein (v-CBP, ORF 4), a neural cell adhesion molecule (NCAM)-like protein (v-adh, ORF K14) and an IL8 receptor (ORF 74). Genes similar to ORFs 4 and 74 are present in other rhadinoviruses and ORF 4 is similar to variola B19L and D12L proteins. ORF K14 (v-adh) is similar to the rat and human OX-2 membrane antigens, various NCAMs and the poliovirus receptor-related protein PRR1. OX-2 is in turn similar to ORF U85 of human herpesviruses 6 and 7 but there is no significant similarity between the KSHV and betaherpesvirus OX-2/NCAM ORFs. Like other immunoglobulin family adhesion proteins, v-adh has V-like, C-like, transmembrane and cytoplasmic domains, and an RGD binding site for fibronectin at residues 268–270. The vIL-8R has a seven transmembrane spanning domain structure characteristic of G-protein coupled chemoattractant receptors which includes the EBV-induced EBI1 protein (Birkenbach et al., 1993, *J. Virol.* 67, 2209–2220).

DISCUSSION

The full-length sequence of the KSHV genome in BC-1 cells provides the opportunity to investigate molecular mechanisms of KSHV-associated pathogenesis. The KSHV genome has standard features of rhadinovirus genomes including a single unique coding region flanked by high G+C terminal repeat regions which are the presumed sites for genome circularization. In addition to having 66 conserved herpesvirus genes involved in herpesvirus replication and structure, KSHV is unique in encoding a number of proteins mimicking cell cycle regulatory and signaling proteins.

Our estimated size of the BC-1 derived genome (210 kb including the duplicated portion) is consistent with that found using encapsidated virion DNA (Zhong et al., 1996, *Proc. Natl. Acad. Sci. USA* 93, 6641–6646). Genomic rearrangements are common in cultured herpesviruses (Baer et al., 1984, *Nature* 310, 207–211; Cha et al., 1996, *J. Virol.* 70, 78–83). However, the genomic duplication present in the BC-1 KSHV probably did not arise during tissue culture passage. TR hybridization studies indicate that this insertion of a duplicated LUR fragment into the BC-1 TR is also present in KSHV from the independently derived HBL-6 cell line (Gaidano et al., 1996, *Leukemia* 10, 1237–40).

Despite this genomic rearrangement, the KSHV genome is well conserved within coding regions. There is less than 0.1% base pair variation between the BC-1 and the 21 kb KS5 fragment isolated from a KS lesion. Higher levels of variation may be present in strains from other geographic regions or other disease conditions. Within the LUR, synteny to HVS is lost at ORFs 2 and 70 but there is concordance in all other regions conserved with HVS. Several conserved genes, such as thymidine kinase (TK) (Cesarman et al., 1995, *Blood* 86, 2708–2714), TS and DHFR (which is present in HVS, see Albrecht et al., 1992, *J. Virol.* 66, 5047–5058, but not human herpesviruses), encode proteins that are appropriate targets for existing drugs.

Molecular mimicry by KSHV of cell cycle regulatory and signaling proteins is a prominent feature of the virus. The KSHV genome has genes similar to cellular complement-binding proteins (ORF 4), cytokines (ORFs K2, K4 and K6), a bcl-2 protein (ORF 16), a cytokine transduction pathway protein (K9), an IL-8R-like protein (ORF74) and a D-type cyclin (ORF72). Additional regions coding for proteins with some similarity to MIP and IRF-like proteins are also present in the KSHV genome. There is a striking parallel between the KSHV genes that are similar to cellular genes and the cellular genes known to be induced by EBV infection. Cellular cyclin D, CD21/CR2, bcl-2, an IL-8R-like protein (EBI1), IL-6 and adhesion molecules are upregulated by EBV infection (Birkenbach et al., 1993, *J. Virol.* 67, 2209–2220; Palmero et al., 1993, *Oncogene* 8, 1049–1054; Finke et al., 1992, *Blood* 80, 459–469; Finke et al., 1994, *Leukemia & Lymphoma* 12, 413–419; Jones et al., 1995, *J. Exper. Med.* 182, 1213–1221). This suggests that KSHV modifies the same signaling and regulation pathways that EBV modifies after infection, but does so by introducing exogenous genes from its own genome.

Cellular defense against virus infection commonly involves cell cycle shutdown, apoptosis (for review, see Shen and Shenk, 1995, *Curr. Opin. Genet. Devel.* 5, 105–111) and elaboration of cell-mediated immunity (CMI). The KSHV-encoded v-bcl-2, v-cyclin and v-IL-6 are active in preventing either apoptosis or cell cycle shutdown (Chang et al., 1996, *Nature* 382, 410). At least one of the β-chemokine KSHV gene products, v-MIP-I, prevents CCR5-mediated HIV infection of transfected cells. β-chemokines are not known to be required for successful EBV infection of cells although EBV-infected B cells express higher levels of MIP-1α than normal tonsillar lymphocytes (Harris et al., 1993, 151, 5975–5983). The autocrine dependence of EBV-infected B cells on small and uncharacterized protein factors in addition to IL-6 (Tosato et al., 1990, *J. Virol.* 64, 3033–3041) leads to speculation that β-chemokines may also play a role in the EBV life cycle.

KSHV has not formally been shown to be a transforming virus and genes similar to the major transforming genes of HVS and EBV are not present in the BC-1 strain KSHV. Nonetheless, dysregulation of cell proliferation control caused by the identified KSHV-encoded proto-oncogenes and cytokines may contribute to neoplastic expansion of virus-infected cells. Preliminary studies suggest that subgenomic KSHV fragments can transform NIH 3T3 cells. If KSHV replication, like that of EBV, involves recombination of TR units (Raab-Traub and Flynn, 1986, *Cell* 47, 883–889), a monomorphic TR hybridization pattern present in a KS lesion would indicate a clonal virus population in the tumor. This is consistent with KS being a true neoplastic proliferation arising from single transformed, KS-infected cell rather than KSHV being a "passenger virus". Identification of KSHV genes similar to known oncoproteins and cell proliferation factors in the current study provides evidence that KSHV is likely to be a transforming virus.

EXPERIMENTAL DETAILS SECTION II

MOLECULAR MIMICRY OF HUMAN CYTOKINE AND CYTOKINE RESPONSE PATHWAY GENES BY KSHV

Four virus genes encoding proteins similar to two human macrophage inflammatory protein (MIP) chemokines, an IL-6 and an interferon regulatory factor (IRF or ICSBP) polypeptide are present in the genome of Kaposi's sarcoma-associated herpesvirus (KSHV). Expression of these genes is inducible in infected cell lines by phorbol esters. vIL-6 is functionally active in B9 cell proliferation assays. It is primarily expressed in KSHV-infected hematopoietic cells rather than KS lesions. vMIP-I inhibits replication of CCR5-dependent HIV-1 strains in vitro indicating that it is functional and could contribute to interactions between these two viruses. Mimicry of cell signaling proteins by KSHV may abrogate host cell defenses and contribute to KSHV-associated neoplasia.

Kaposi's sarcoma-associated herpesvirus (KSHV) is a gammaherpesvirus related to Epstein-Barr virus (EBV) and herpesvirus saimiri (HVS). It is present in nearly all KS lesions including the various types of HIV-related and HIV-unrelated KS (Chang et al., 1994, Science 265, 1865–1869; Boshoff et al., 1995, Lancet 345, 1043–1044; Dupin et al., 1995, Lancet 345, 761–762; Schalling et al., 1995, Nature Med. 1, 707–708). Viral DNA preferentially localizes to KS tumors (Boshoff et al., 1995, Nature Med. 1, 1274–1278) and serologic studies show that KSHV is specifically associated with KS. Related lymphoproliferative disorders frequently occurring in patients with KS, such as primary effusion lymphomas (PEL), a rare B cell lymphoma, and some forms of Castleman's disease are also associated with KSHV infection (Cesarman et al., 1995, New Eng. J. Med. 332, 1186–1191; Soulier et al., 1995, Blood 86, 1276–1280). Three KSHV-encoded cytokine-like polypeptides and a polypeptide similar to interferon regulatory factor genes have now been identified. Paradoxically, while cytokine dysregulation has been proposed to cause Kaposi's sarcoma (Ensoli et al., 1994, Nature 371, 674–680; Miles, 1992, Cancer Treatment & Research 63, 129–140), in vitro spindle cell lines used for these studies over the past decade are uniformly uninfected with KSHV (Ambroziak et al., Science 268, 582–583; Lebbé et al., 1995, Lancet 345, 1180).

To identify unique genes in the KSHV genome, genomic sequencing (see METHODS) was performed using Supercos-1 and Lambda FIX II genomic libraries from BC-1, a nonHodgkin's lymphoma cell line stably infected with both KSHV and EBV (Cesarman et al., 1995, Blood 86, 2708–2714). The KSHV DNA fragments KS330Bam and KS631Bam (Chang et al., 1994, Science 265, 1865–1869) were used as hybridization starting points for mapping and bi-directional sequencing. Open reading frame (ORF) analysis (see METHODS) of the Z6 cosmid sequence identified two separate coding regions (ORFs K4 and K6) with sequence similarity to β-chemokines and a third coding region (ORF K2) similar to human interleukin-6 (huIL-6); a fourth coding region (ORF K9) is present in the Z8 cosmid insert sequence with sequence similarity to interferon regulatory factor (IRF) polypeptides (FIGS. 3A–3C). None of these KSHV genes are similar to other known viral genes. Parenthetically, a protein with conserved cysteine motifs similar to β-chemokine motif signatures has recently been reported in the molluscum contagiosum virus (MCV) genome. Neither vMIP-I nor vMIP-II has significant similarity to the MCV protein.

The cellular counterparts to these four viral genes encode polypeptides involved in cell responses to infection. For example, the MIP/RANTES (macrophage inflammatory protein/regulated on activation, normal T cell expressed and secreted) family of 8–10 kDa β-chemoattractant cytokines (chemokines) play an important role in virus infection-mediated inflammation (Cook et al., 1995, Science 269, 1583–1585). β-chemokines are the natural ligand for. CCR5 and can block entry of non-syncytium inducing (NSI), primary lymphocyte and macrophage-tropic HIV-1 strains in vitro by binding to this HIV co-receptor (Cocchi et al., 1995, Science 270, 1811–1815). IL-6, initially described by its effect on B cell differentiation (Hirano et al., 1985, Proc Natl Acad Sci, USA 85, 5490; Kishimoto et al., 1995, Blood 86, 1243–1254), has pleiotropic effects on a wide variety of cells and may play a pathogenic role in multiple myeloma, multicentric Castleman's disease (a KSHV-related disorder), AIDS-KS and EBV-related postransplant lymphoproliferative disease (Klein et al., 1995, Blood 85, 863–872; Hilbert et al., 1995, J Exp Med 182, 243–248; Brandt et al., 1990, Curr Topic Microbiol Immunol 166, 37–41; Leger et al., 1991, Blood 78, 2923–2930; Burger et al., 1994, Annal Hematol 69, 25–31; Tosato et al., 1993, J Clin Invest 91, 2806–2814). IL-6 production is induced by either EBV or CMV infection and is an autocrine factor for EBV-infected lymphoblastoid cells that enhances their tumorigenicity in nude mice (Tosato et al., 1990, J Virol 64, 3033–3041; Scala et al., 1990, J Exp Med 172, 61–68; Almeida et al., 1994, Blood 83, 370–376). Cell lines derived from KS lesions, although not infected with KSHV, also produce and respond to IL-6 (Miles et al., 1990, Proc Natl Acad Sci USA 87, 4068–4072; Yang et al., 1994, J Immunol 152, 943–955). While MIP and IL-6 are secreted cytokines, the IRF family of polypeptides regulate interferon-inducible genes in response to γ- or α-/β-interferon cytokines by binding to specific interferon consensus sequences. (ICS) within interferon-inducible promoter regions. A broad array of cellular responses to interferons is modulated by the repressor or transactivator functions of IRF polypeptides and several members (IRF-1 and IRF-2) have opposing anti-oncogenic and oncogenic activities (Sharf et al., 1995, J Biol Chem 270, 13063–13069; Harada et al., 1993, Science 259, 971–974; Weisz et al., 1994, Internat Immunol 6, 1125–1131; Weisz et al., 1992, J Biol Chem 267, 25589–25596).

The 289 bp ORF K6 (ORF MIP1) gene encodes a 10.5 kDa polypeptide (vMIP-I; MIP1) having 37.9% amino acid identity (71% similarity) to huMIP-1α and slightly lower similarity to other β-chemokines (FIG. 3A). ORF K4 also encodes a predicted 10.5 kDa polypeptide (vMIP-II; vMIP1α-II) with close similarity and amino acid hydrophobicity profile to vMIP-I. The two KSHV-encoded MIP β-chemokines are separated from each other on the KSHV genome by 5.5 kb of intervening sequence containing at least 4 ORFs (see METHODS). Both polypeptides have conserved β-chemokine motifs (FIG. 3A, residues 17–55) which include a characteristic C—C dicysteine dimer (FIG. 3A, residues 36–37), and have near sequence identity to human MIP-1α at residues 56–84. However, the two polypeptides show only 49.0% amino acid identity to each other and are markedly divergent at the nucleotide level indicating that this duplication is not a cloning artifact. The two viral. polypeptides are more closely related to each other phylogenetically than to huMIP-1α, huMIP-1β or huRANTES suggesting that they arose by gene duplication rather than independent acquisition from the host genome (see Sequence alignment in METHODS). The reason for this double gene dosage in the viral genome is unknown.

The KSHV ORF K2 (FIG. 3B) encodes a hypothetical 204 residue, 23.4 kDa IL-6-like polypeptide with a hydrophobic 19 amino acid secretory signaling peptide having 24.8% amino acid identity and 62.2% similarity to the human polypeptide. vIL-6 also has a conserved sequence characteristic for IL-6-like interleukins (amino acids 101–125 of the gapped polypeptide) as well as conserved four cysteines which are present in IL-6 polypeptides (gapped alignment residue positions 72, 78, 101 and 111 in FIG. 3B). IL-6 is a glycosylated cytokine and potential N-linked glycosylation sites in the vIL-6 sequence are present at gapped positions 96 and 107 in FIG. 3C. The 449 residue KSHV vIRF polypeptide encoded by ORF K9 has lower overall amino acid identity (approximately 13%) to its human cellular counterparts than either of the vMIPs or the vIL-6, but has a conserved region derived from the IRF family of polypeptides (FIG. 3C, gapped residues 88–121). This region includes the tryptophan-rich IRF ICS DNA binding domain although only two of four tryptophans thought to be involved in DNA binding are positionally conserved. It is preceded by an 87-residue hydrophilic N-terminus with little apparent IRF similarity. A low degree of amino acid similarity is present at the C-terminus corresponding to the IRF family transactivator/repressor region.

Figure 5A:
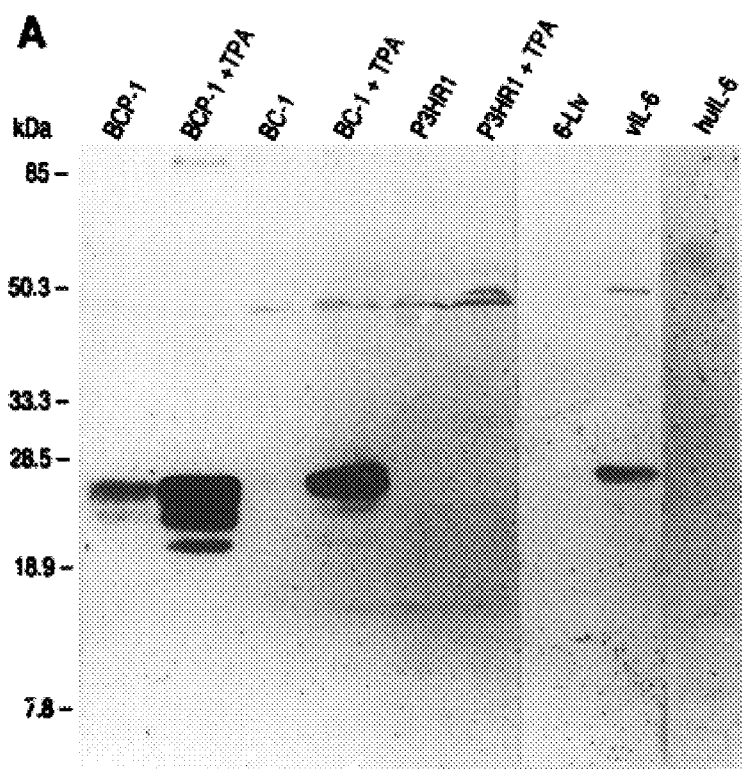
FIGS. 5A–5B FIG. 5A. Immunoblot of rabbit antipeptide antibodies generated from amino acid sequences of vIL-6, THYSPPKFDR (SEQ ID NO:2) and PDVTPDVHDR (SEQ ID NO:3), against cell lysates of BCP-1, BC-1, P3HR1 cell lines with and without TPA induction (lanes 1–6), 1 µg human rIL-6 (lane 7), and concentrated COS7 rvIL-6 and 6-LIv supernatants (lanes 8–9). Anti-vIL-6 antibodies specifically recognize the viral IL-6 polypeptide in both recombinant supernatants and cell lines but not human IL-6. The BCP-1 cell line constitutively expresses low levels of vIL-6 whereas polypeptide expression increases on TPA treatment for both BC-1 (KSHV and EBV coinfected) and BCP-1 (KSHV infection alone) indicating lytic phase expression. Preimmune sera from immunized rabbits did not react on immunoblotting to any of the preparations.
Figure 5B:
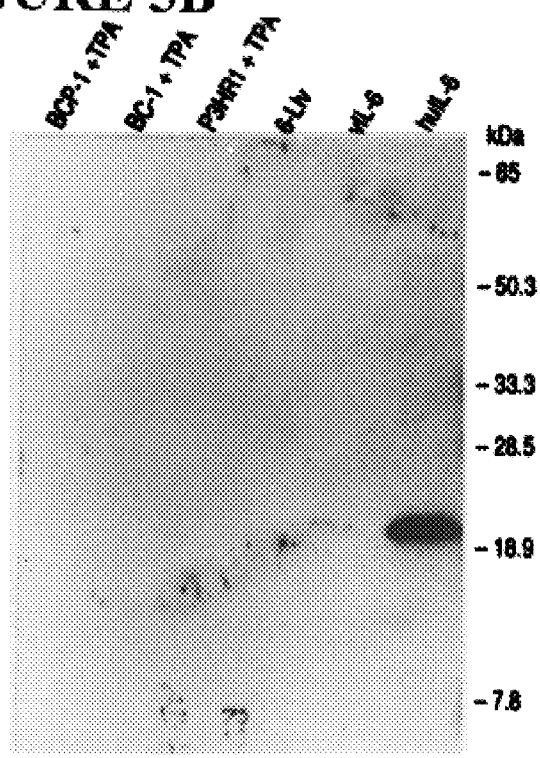
Figure 6:
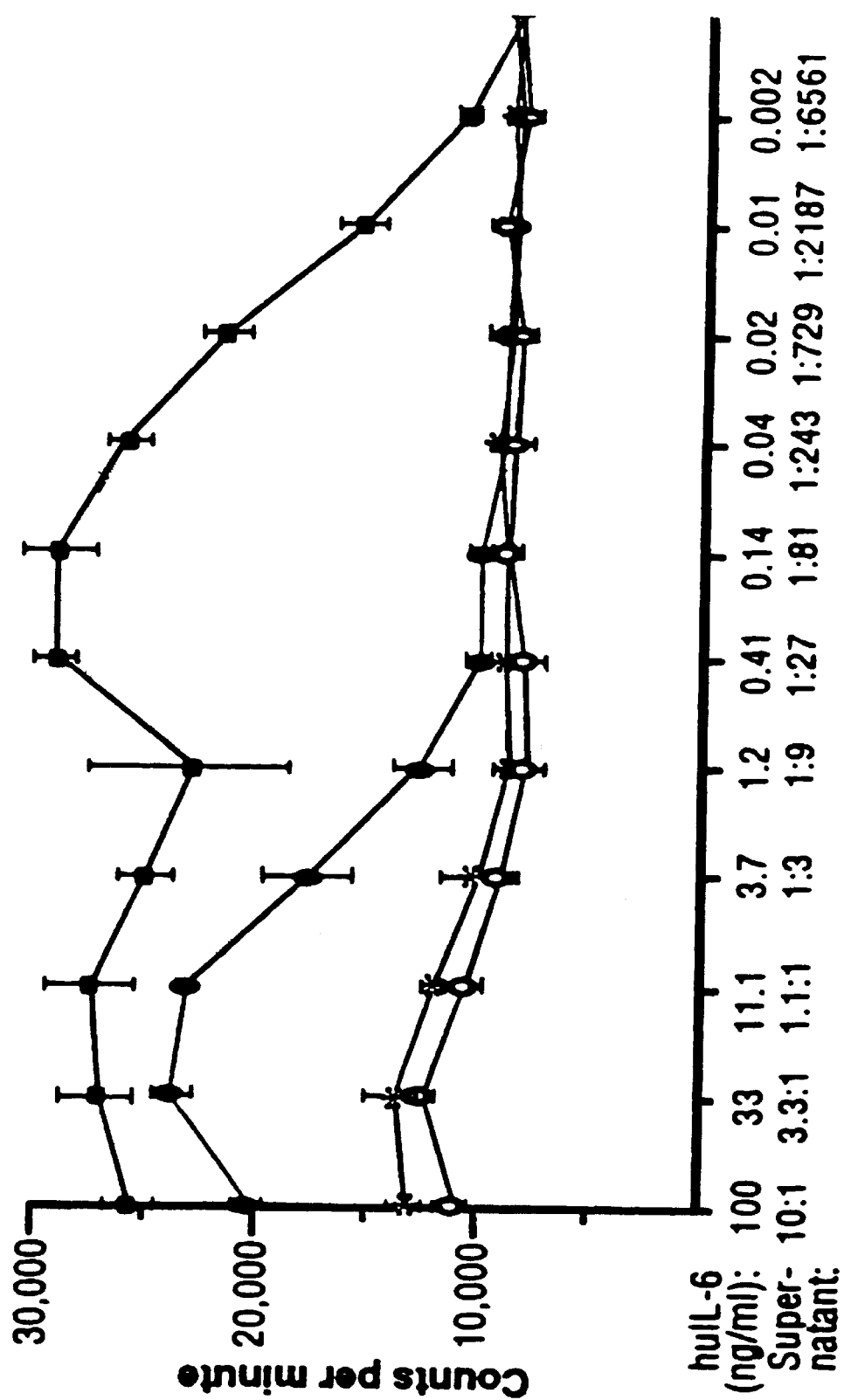
FIG. 6 Dose-response curves for $^3$H-thymidine uptake in IL-6-dependent B9 mouse plasmacytoma cells with serial dilutions of rhuIL-6 (filled squares) and COS7 supernatants of rvIL-6 (filled circles), r6-LIv (open squares) or control LacZ (open circles) pMET7 transfections. Undiluted rvIL-6 supernatants from this transfection lot show similar B9 proliferation activity to huIL-6>0.02 ng/ml whereas the reverse construct (r6-LIv) and the LacZ control show no increased ability to induce B9 proliferation. Concentrated supernatants at greater than 1:1 dilution may have increased activity due to concentration of COS7 conditioning factors.

The four KSHV cell signaling pathway genes show similar patterns of expression in virus-infected lymphocyte cell lines by Northern blotting (see METHODS). Whole RNA was extracted from BCP-1 (a cell line infected with KSHV alone) and BC-1 (EBV and KSHV coinfected, see Cesarman et al., 1995, *Blood* 86, 2708–2714) with or without pretreatment with 20 ng/ml 12-O-tetradecanoylphorbol-13-acetate (TPA, Sigma, St. Louis Mo.) for 48 hours. While constitutive expression of these genes was variable between the two cell lines, expression of all four gene transcripts increased in BCP-1 and BC-1 cells after TPA induction (FIGS. 4A–4D). This pattern is consistent with expression occurring primarily during lytic phase virus replication. Examination of viral terminal repeat sequences of BCP-1 and BC-1 demonstrates that low level of virus lytic replication occurs in BCP-1 but not BC-1 without TPA induction (see METHODS), and both cell lines can be induced to express lytic phase genes by TPA treatment despite repression of DNA replication in BC-1. Lower level latent expression is also likely, particularly for vIL-6 (FIG. 4C) and vIRF (FIG. 4D), since these transcripts are detectable without TPA induction in BC-1 cells which are under tight latency control. To determine if in vitro KS spindle cell cultures retain defective or partial virus sequences that include these genes, DNA was extracted from four KS spindle cell lines (KS-2, KS-10, KS-13 and KS-22) and PCR amplified for vMIP-I, vMIP-II, vIL-6 and vIRF sequences (see METHODS). None of the spindle cell DNA samples were positive for any of the four genes.

vIL-6 was examined in more detail using bioassays and antibody localization studies to determine whether it is functionally conserved. Recombinant vIL-6 (rvIL-6) is specifically recognized by antipeptide antibodies which do not cross-react with huIL-6 (FIGS. 5A–5B) (see METHODS). vIL-6 is produced constitutively in BCP-1 cells and increases markedly after 48 hour TPA induction, consistent with Northern hybridization experiments. The BC-1 cell line coinfected with both KSHV and EBV only shows vIL-6 polypeptide expression after TPA induction (FIG. 5A, lanes 3–4) and control EBV-infected P3HR1 cells are negative for vIL-6 expression (FIG. 5A, lanes 5–6). Multiple high molecular weight bands present after TPA induction (21–25 kDa) may represent precursor forms of the polypeptide. Despite regions of sequence dissimilarity between huIL-6 and vIL-6, the virus interleukin 6 has biologic activity in functional bioassays using the IL-6-dependent mouse plasmacytoma cell line B9 (see METHODS). COS7 supernatants from the forward construct (rvIL-6) support B9 cell proliferation measured by $^3$H-thymidine uptake indicating that vIL-6 can substitute for cellular IL-6 in preventing B9 apoptosis (FIG. 6). vIL-6 supported B9 proliferation is dose dependent with the unconcentrated supernatant from the experiment shown in FIG. 6 having biologic activity equivalent to approximately 20 pg per ml huIL-6.

Figure 7A:
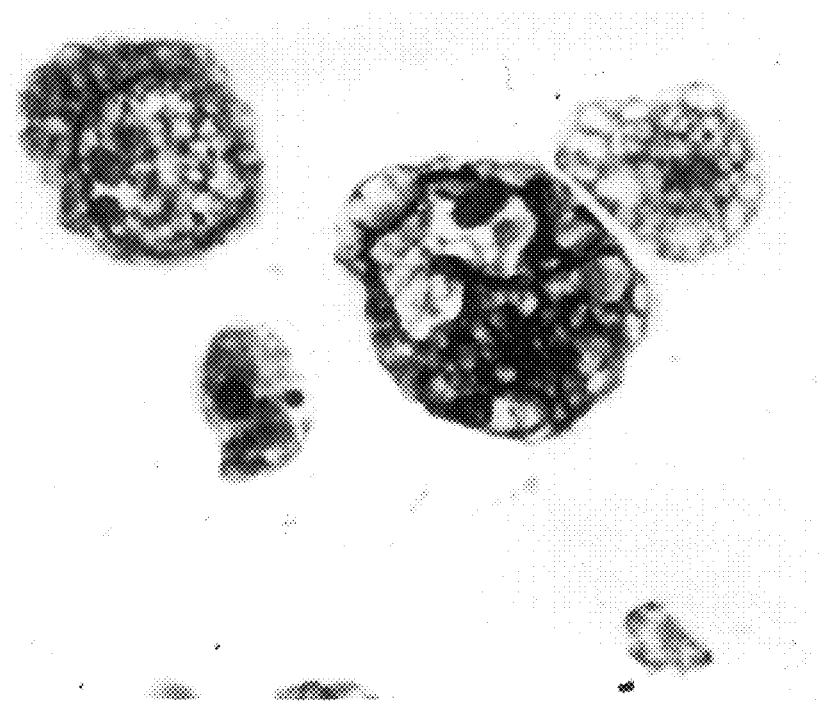
FIGS. 7A–7F Rabbit anti-vIL-6 peptide antibody reactivity localized using goat-antirabbit immunoglobulin-peroxidase conjugate (brown) with hematoxylin counterstaining (blue) at ×100 magnification demonstrates vIL-6 production in both KSHV-infected cell lines and tissues. The KSHV-infected cell line BCP-1 (FIG. 7A), but not the control EBV-infected cell line P3HR1 (FIG. 7B), shows prominent cytoplasmic vIL-6 localization.
Figure 7B:
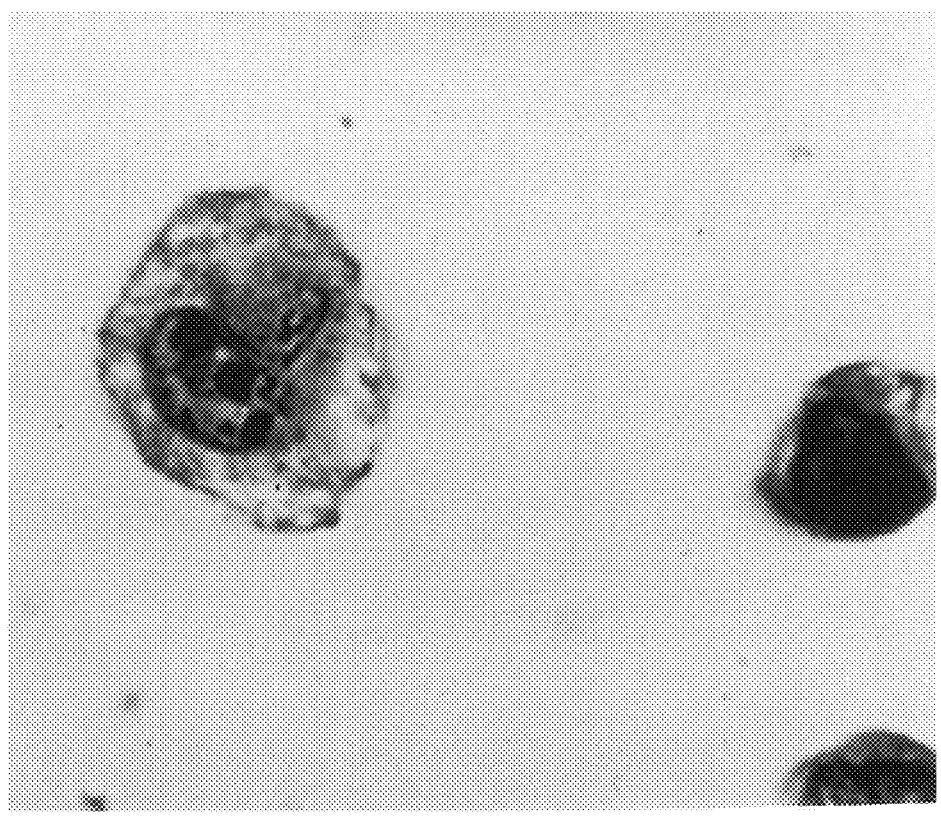
Figure 7C:
Figure 7D:
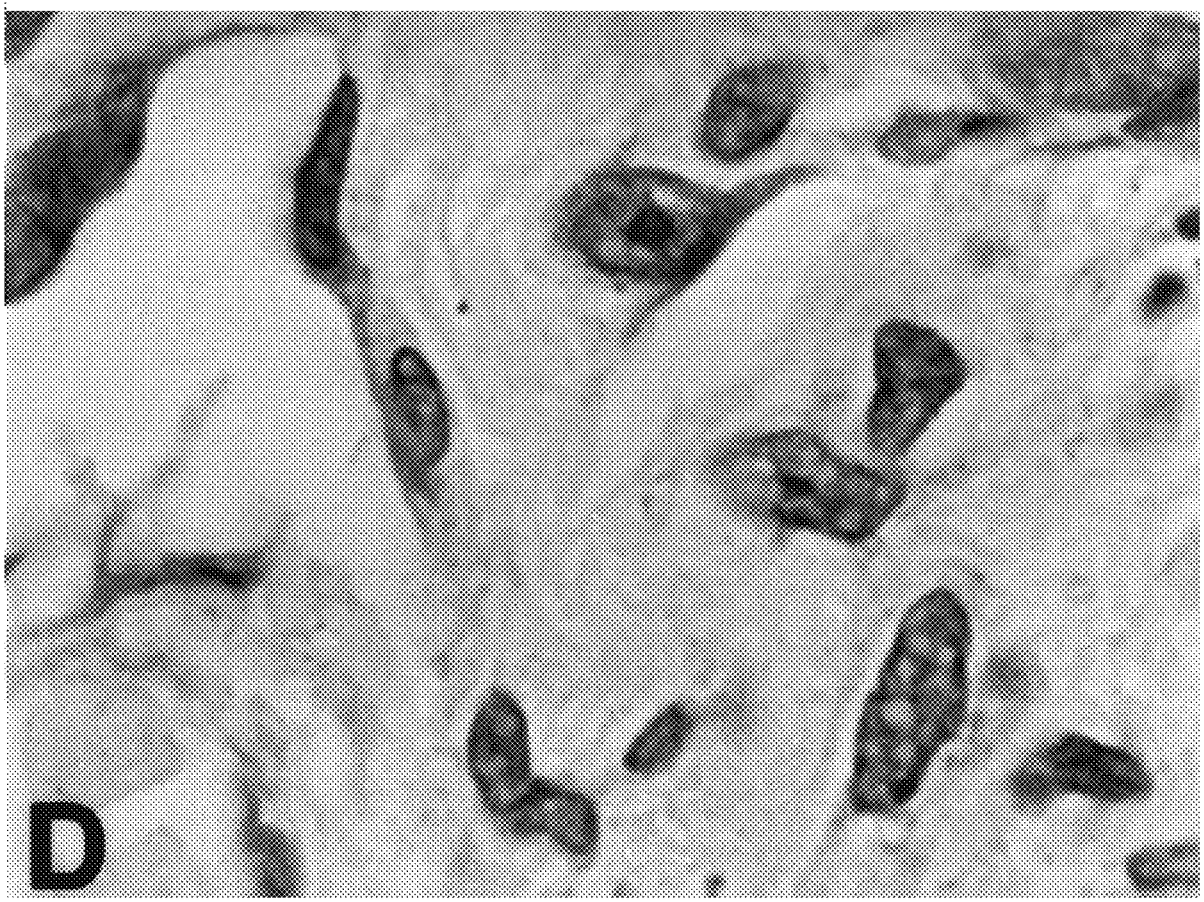
Figure 7E:
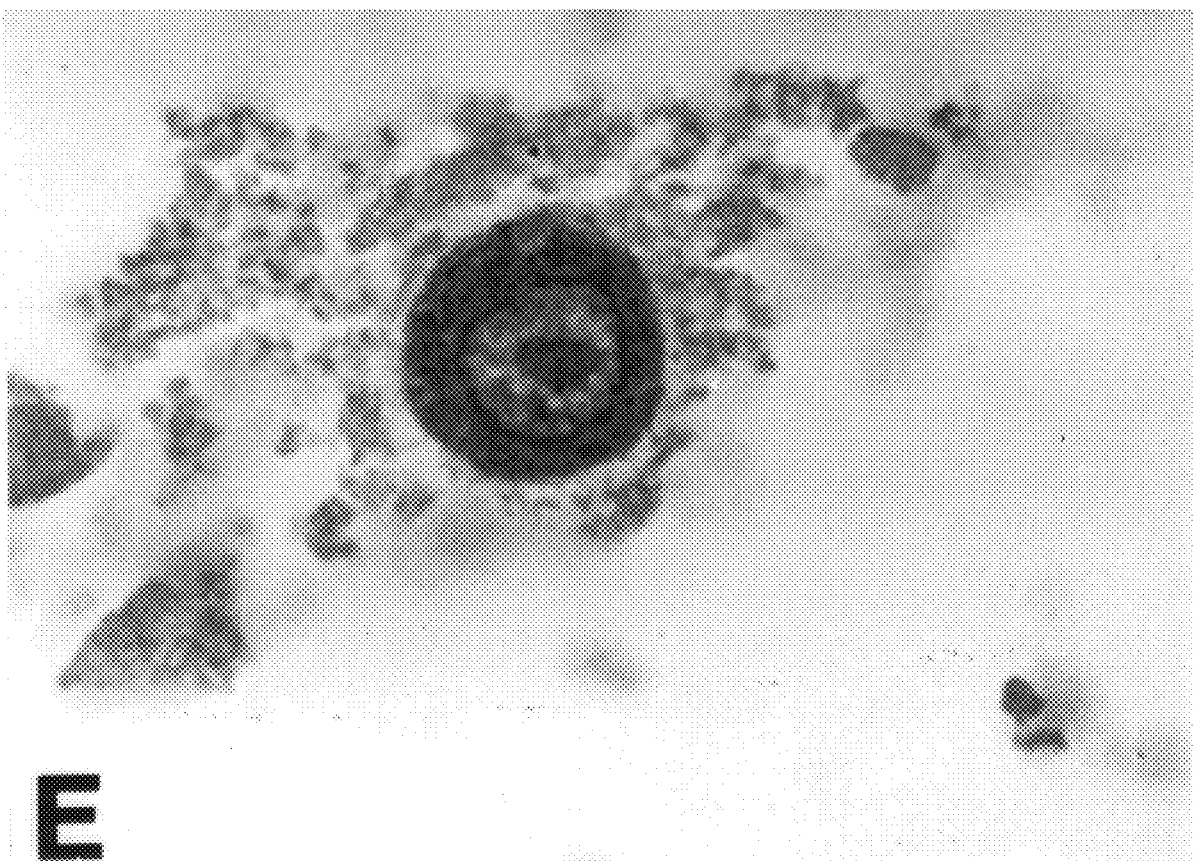
Figure 7F:
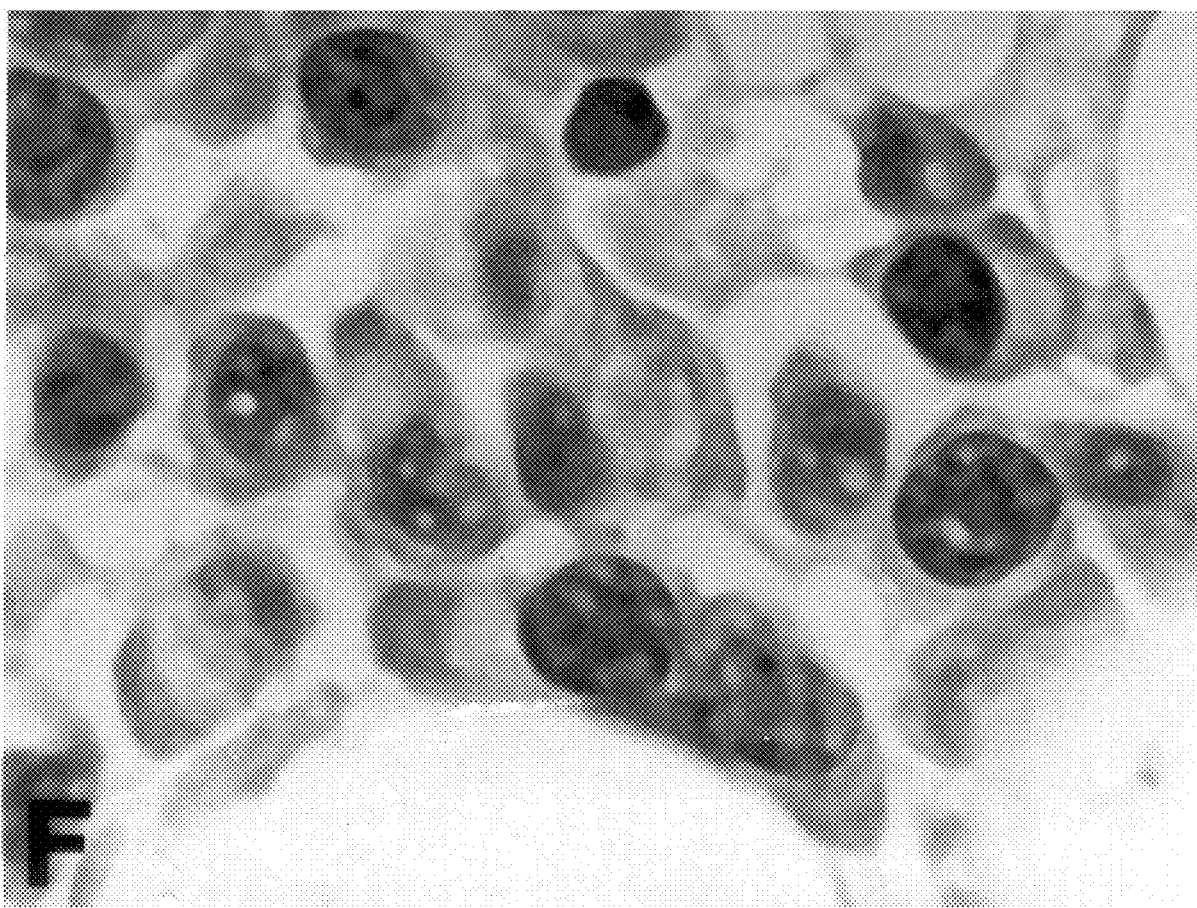
Figure 8A:
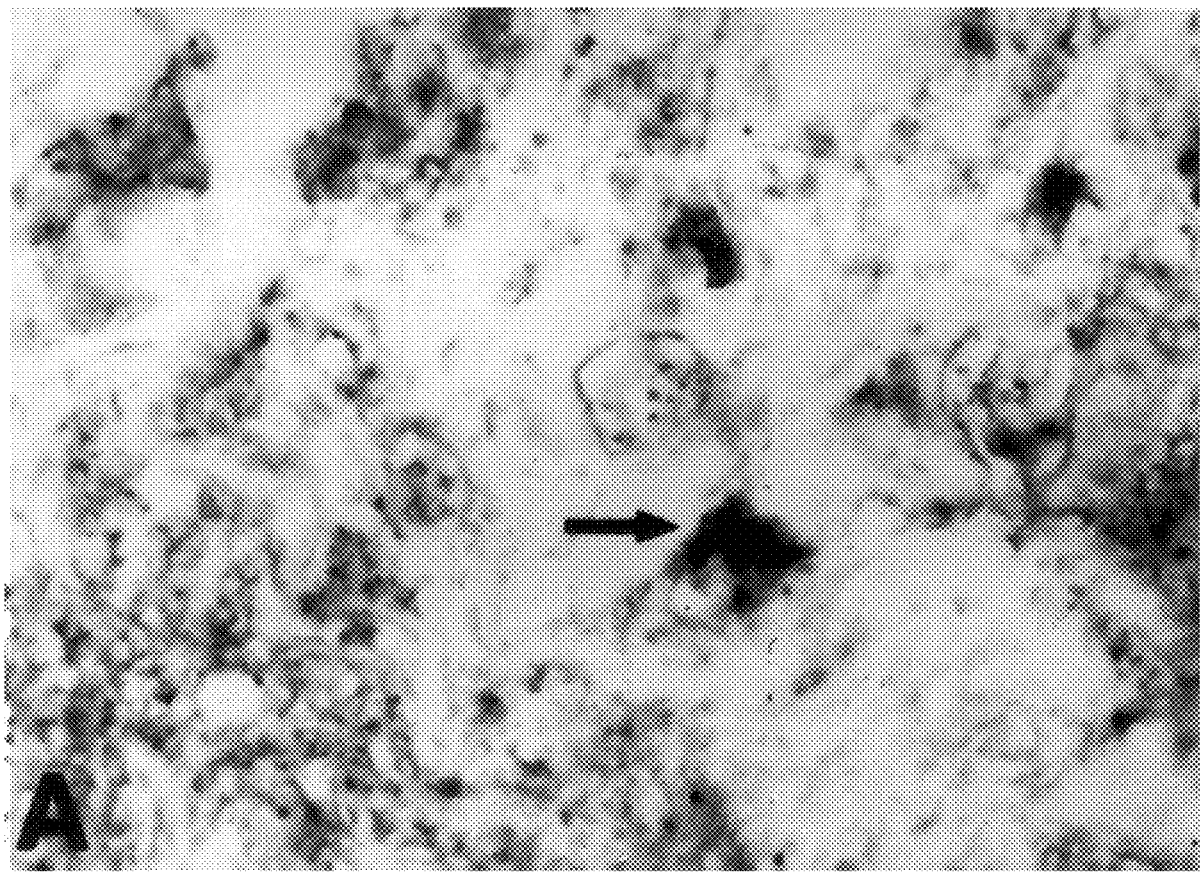
FIGS. 8A–8D Double antibody labeling of anti-vIL-6 and cell surface antigens. Examples of both CD34 and CD20 colocalization with vIL-6 were found in a KS lesion.
Figure 8B:
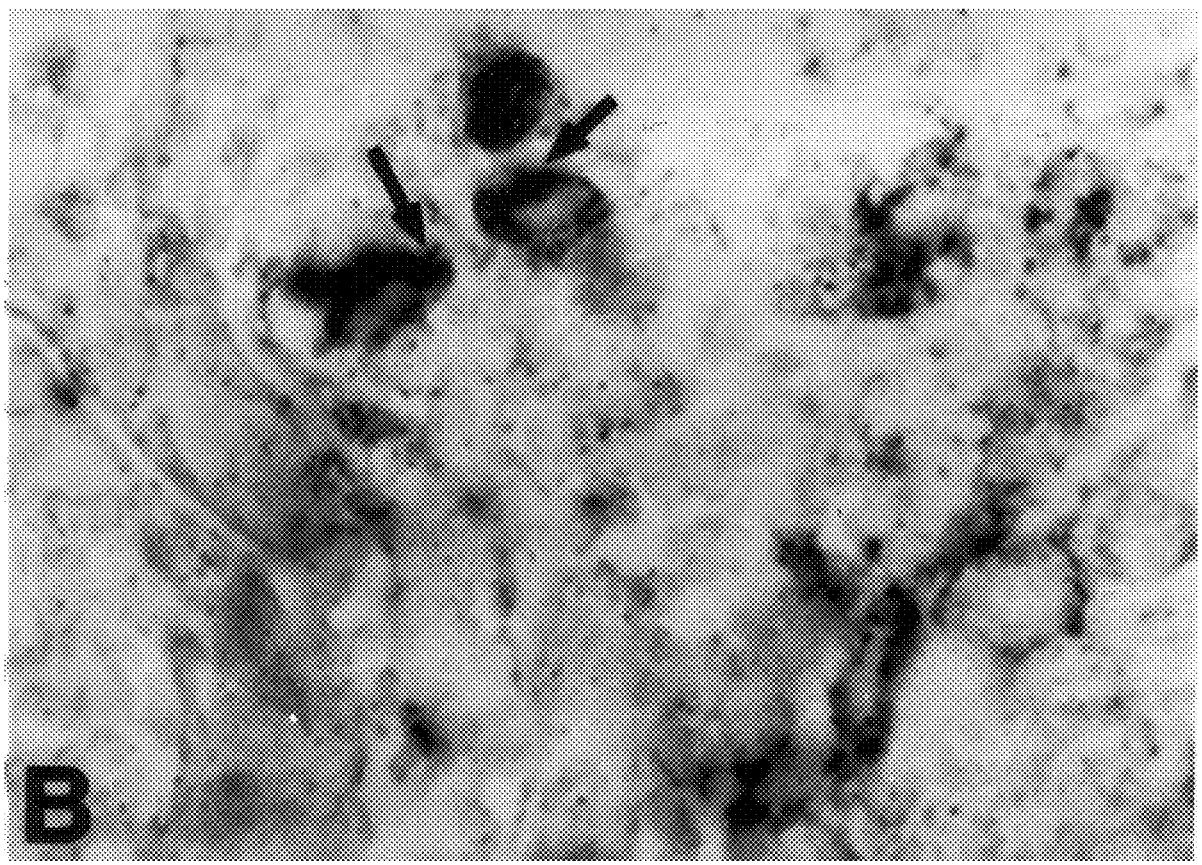

Forty-three percent of noninduced BCP-1 cells (FIG. 7A) have intracellular cytoplasmic vIL-6 immunostaining (see METHODS) suggestive of constitutive virus polypeptide expression in cultured infected cells, whereas no specific immunoreactive staining is present in uninfected control P3HR1 cells (FIG. 7B). vIL-6 production was rarely detected in KS tissues and only one of eight KS lesions examined showed clear, specific vIL-6 immunostaining in less than 2% of cells (FIG. 7C). The specificity of this low positivity rate was confirmed using preimmune sera and neutralization with excess vIL-6 peptides. Rare vIL-6-producing cells in the KS lesion are positive for either CD34, an endothelial cell marker (FIG. 8A), or CD45, a pan-hematopoietic cell marker (FIG. 8B), demonstrating that both endothelial and hematopoietic cells in KS lesions produce vIL6. It is possible that these rare vIL-6 positive cells are entering lytic phase replication which has been shown to occur using the KSHV T1.1 lytic phase RNA probe. In contrast, well over half (65%) of ascitic lymphoma cells pelleted from an HIV-negative PEL are strongly positive for vIL-6 (FIG. 7E) and express the plasma cell marker EMA (Cesarman et al., 1995, *Blood* 86, 2708–2714) indicating that either most PEL cells in vivo are replicating a lytic form of KSHV or that latently infected PEL cells can express high levels of vIL-6. No specific staining occurred with any control tissues examined including normal skin, tonsillar tissue, multiple myeloma or angiosarcoma using either preimmune or post-immune rabbit anti-vIL-6 antibody (FIGS. 7E and 7F).

Figure 8C:
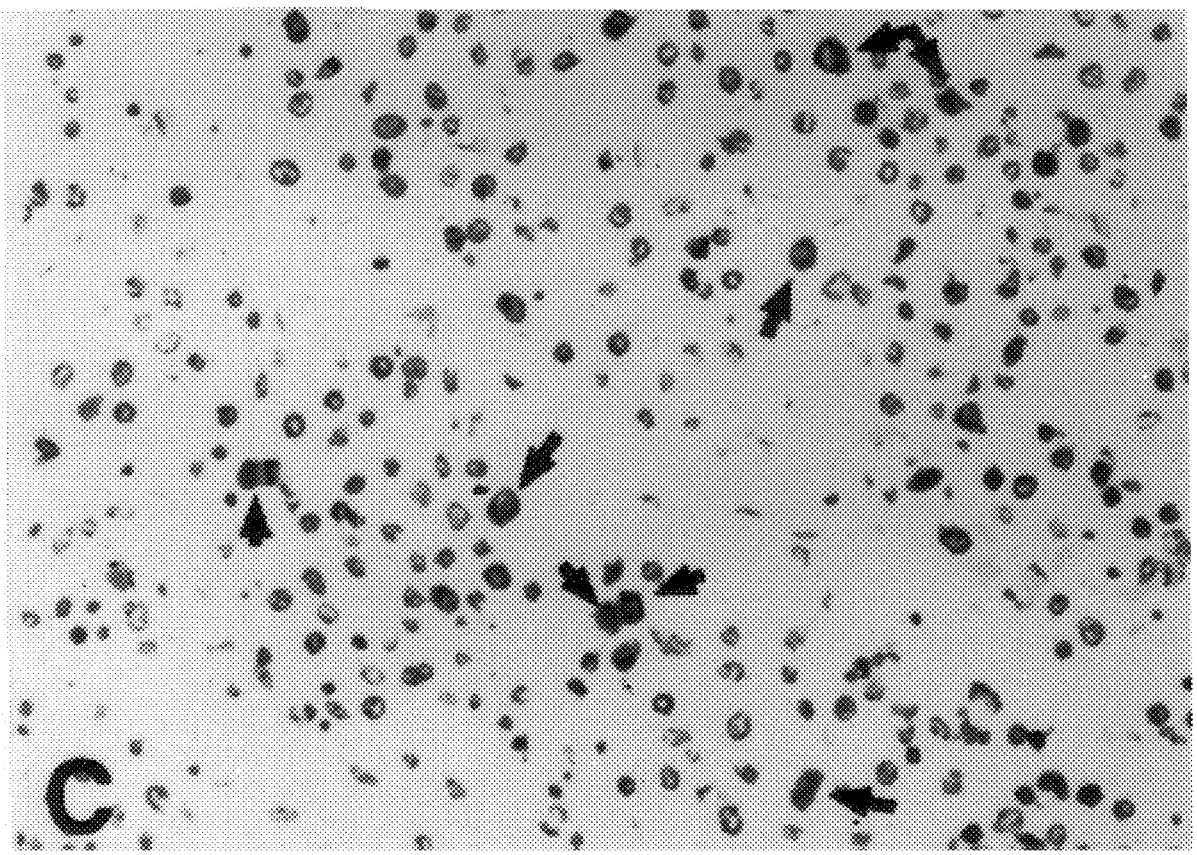
Figure 8D:
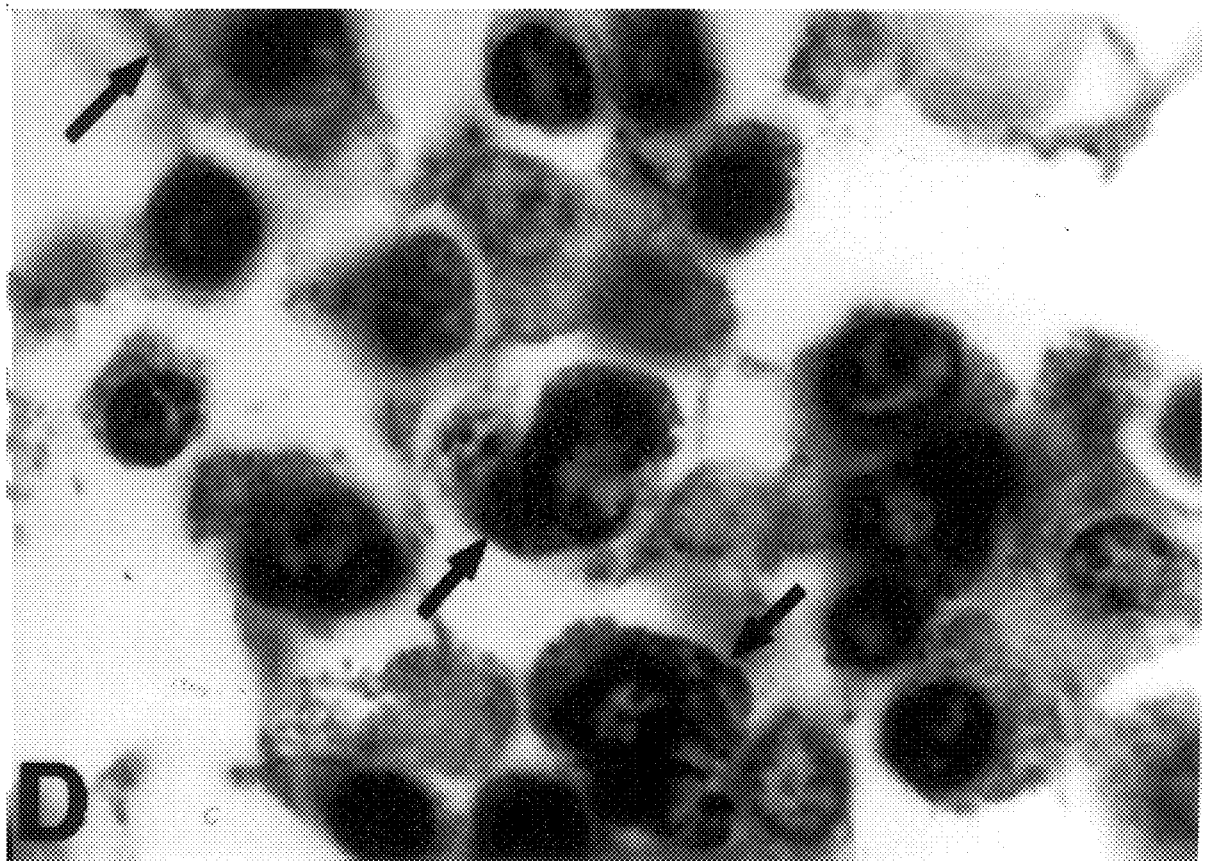

Virus dissemination to nonKS tissues was found by examining a lymph node from a patient with AIDS-KS who did not develop PEL. Numerous vIL-6-staining hematopoietic cells were present in this lymph node (FIG. 8C) which was free of KS microscopically. vIL-6 positive lymph node cells were present in relatively B-cell rich areas and some express CD20 B cell surface antigen (FIG. 8D), but not EMA surface antigen (unlike PEL cells) (Cesarman et al., 1995, *Blood* 86, 2708–2714). No colocalization of vIL-6 positivity with the T cell surface antigen CD3 or the macrophage antigen CD68 was detected, although phagocytosis of vIL-6 immunopositive cells by macrophages was frequently observed.

To investigate whether the vMIP-I can inhibit NSI HIV-1 virus entry, human CD4+ cat kidney cells (CCC/CD4) were transiently transfected with plasmids expressing human CCR5 and vMIP-I or its reverse construct I-PIMv (see CCR5 and vMIP-I cloning in METHODS). These cells were infected with either M23 or SF162 primary NSI HIV-1 isolates which are known to use CCR5 as a co-receptor (Clapham et al., 1992, *J Virol* 66, 3531–3537) or with the HIV-2 variant ROD/B which can infect CD4+ CCC cells without human CCR5. Virus entry and replication was assayed by immunostaining for retroviral antigen production (FIG. 9). vMIP-I cotransfection reduced NSI HIV-1 foci generation to less than half that of the reverse-construct negative control but had no effect on ROD/B HIV-2 replication.

Molecular piracy of host cell genes is a newly recognized feature of some DNA viruses, particularly herpesviruses and poxviruses (Murphy, 1994, *Infect Agents Dis* 3, 137–154; Albrecht et al., 1992, *J Virol* 66, 5047–5058; Gao and Murphy, 1994, *J Biol Chem* 269, 28539–28542; Chee et al., 1990, *Curr Top Microbiol Immunol* 154, 125–169; Massung et al., 1994, *Virol* 201, 215–240). The degree to which KSHV has incorporated cellular genes into its genome is exceptional. In addition to vMIP-I and vMIP-II, vIL-6 and vIRF, KSHV also encodes polypeptides similar to bcl-2 (ORF 16), cyclin D (ORF 72), complement-binding proteins similiar to CD21/CR2 (ORF 4), an NCAM-like adhesion protein (ORF K14), and an IL-8 receptor (ORF 74). EBV also either encodes (BHRF1/bcl-2) or induces (CR-2; cyclin D; IL-6; bcl-2; adhesion molecules and an IL-8R-like EBI1 protein) these same cellular polypeptides (Cleary et al., 1986, *Cell* 47, 19–28; Tosato et al., 1990, *J Virol* 64, 3033–3041; Palmero et al., 1993, *Oncogene* 8, 1049; Larcher et al., 1995, *Eur J Immunol* 25, 1713–1719; Birkenbach et al., 1993, *J Virol* 67, 2209–2220). Thus, both viruses may modify similar host cell signaling and regulatory pathways. EBV appears to effect these changes through induction of cellular gene expression whereas KSHV introduces the polypeptides exogenously from its own genome.

Identification of these virus-encoded cellular-like polypeptides leads to speculation about their. potential roles in protecting against cellular antiviral responses. huIL-6 inhibits γ-interferon-induced, Bax-mediated apoptosis in myeloma cell lines (Lichtenstein et al., 1995, *Cellular Immunology* 162, 248–255) and vIL-6 may play a similar role in infected B cells. KSHV-encoded vIRF, vbcl-2 and v-cyclin may also interfere with host-cell mediated apoptosis induced by virus infection and v-cyclin may prevent G1 cell cycle arrest of infected cells. Interference with interferon-induced MHC antigen presentation and cell-mediated immune response (Holzinger et al., 1993, *Immunol Let* 35, 109–117) by vIRF is also possible. The β-chemokine polypeptides vMIP-I and vMIP-II may have agonist or antagonist signal transduction roles. Their sequence conservation and duplicate gene dosage are indicative of a key role in KSHV replication and survival.

Uncontrolled cell growth from cell-signaling pathway dysregulation is an obvious potential by-product of this virus strategy. Given the paucity of vIL-6 expressing cells in KS lesions, it is unlikely that vIL-6 significantly contributes to KS cell neoplasia. KSHV induction of hu-IL6, however, with subsequent induction of vascular endothelial growth factor-mediated angiogenesis (Holzinger et al., 1993, *Immunol Let* 35, 109–117), is a possibility. vIL-6 could also potentially contribute to the pathogenesis of KSHV-related lymphoproliferative disorders such as PEL or the plasma cell variant of Castleman's disease.

The oncogenic potential of cellular cyclin and bcl-2 overexpression is well-established and these virus-encoded polypeptides may also contribute to KSHV-related neoplasia.

Figure 9:
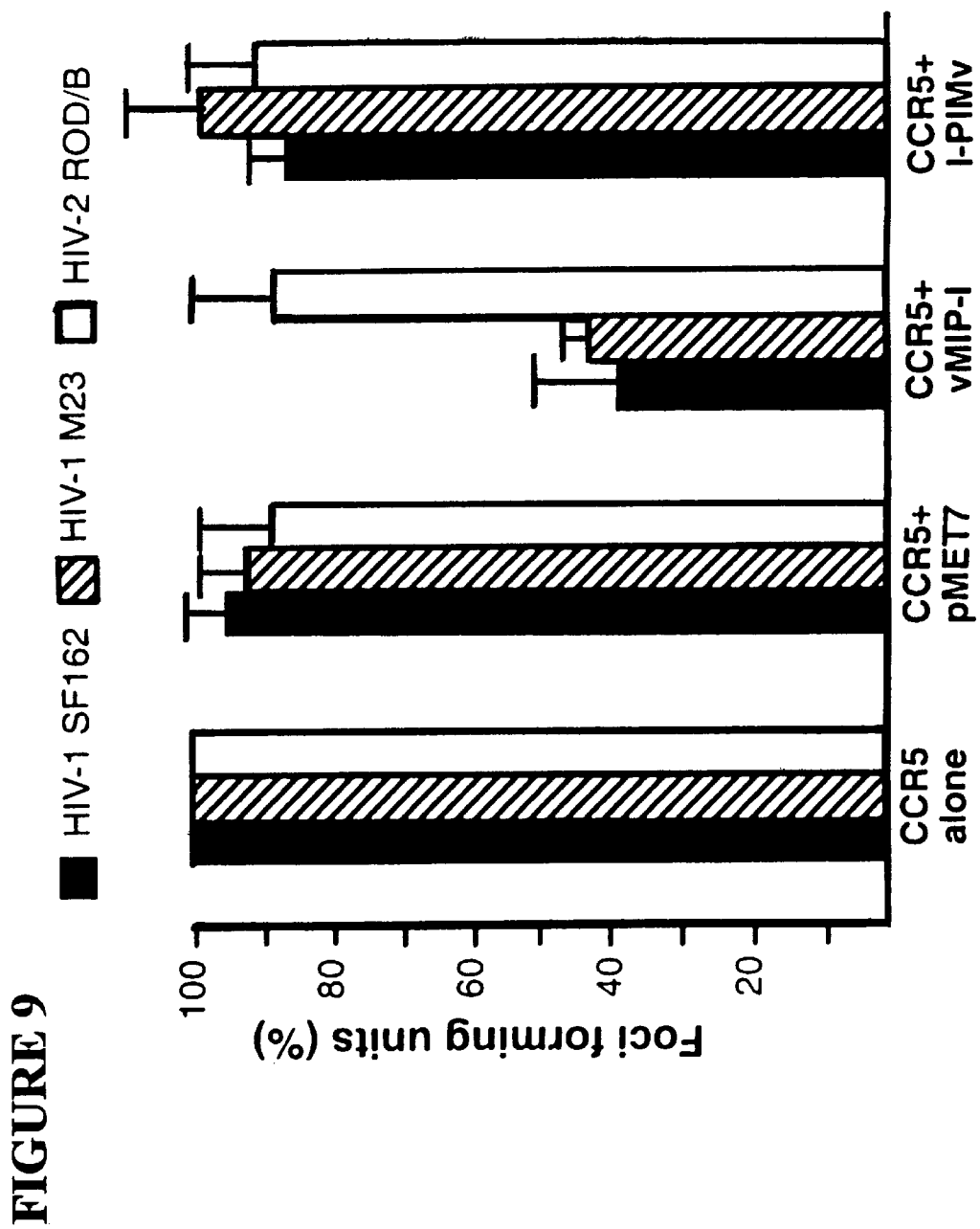
FIG. 9 Quantification of CCC/CD4 cell infection by primary NSI SF162 and M23 HIV-1 strains and HIV-2 strain ROD/B in the presence or absence of vMIP-I. CCC/CD4 cells were transiently cotransfected with CCR5 alone, CCR5 plus empty pMET7 vector, CCR5 plus vMIP-I in pMET7 vector, or CCR5 plus the reverse orientation I-PIMv. The results after 72 hours of incubation with each retrovirus are expressed as a percentage of the foci forming units for cells transfected with CCR5 alone. The forward vMIP-I construct inhibited NSI HIV-1 replication but not HIV-2 replication while the reverse I-PIMv construct had no effect on replication of any of the retroviruses.

KSHV vMIP-I inhibits NSI HIV-1 replication in vitro (FIG. 9). Studies from early in the AIDS epidemic indicate that survival is longer for AIDS-KS patients than for other AIDS patients, and that 93% of US AIDS patients surviving >3 years had KS compared to only 28% of remaining AIDS patients dying within 3 years of diagnosis (Hardy, 1991, *J AIDS* 4, 386–391; Lemp et al., 1990, *J Am Med Assoc* 263, 402–406; Rothenberg et al., 1987, *New Eng J Med* 317, 1297–1302; Jacobson et al., 1993, *Am J Epidemiol* 138, 953–964; Lundgren et al., 1995, *Am J Epidemiol* 141, 652–658). This may be due to KS occurring at relatively high CD4+ counts and high mortality for other AIDS-defining conditions. Recent surveillance data also indicates that the epidemiology of AIDS-KS is changing as the AIDS epidemic progresses (ibid).

METHODS

Genomic Sequencing. Genomic inserts were randomly sheared, cloned into M13mp18, and sequenced to an average of 12-fold redundancy with complete bidirectional sequencing. The descriptive nomenclature of KSHV polypeptides is based on the naming system derived for herpesvirus saimiri (Albrecht et al., 1992, *J Virol* 66, 5047–5058).

Open reading frame (ORF) analysis. Assembled sequence contigs were analyzed using MacVector (IBI-Kodak, Rochester N.Y.) for potential open reading frames greater than 25 amino acid residues and analyzed using BLASTX and BEAUTY-BLASTX (Altschul et al., 1990, *J Mol Biol* 215, 403–410; Worley et al., 1995, *Genome Res* 5, 173–184; http://dot.imgen.bcm.tmc.edu:9331/seq-search/nucleic_acid-search.html). Similar proteins aligned to the four KSHV polypeptides (in italics:) included (name (species, sequence bank accession number, smallest sum Poisson distribution probability score)): (1) vMIP-I: LD78 (MIP-1α) (human, gi 127077, p=9.8xe-22), MIP-1α (Rattus, gi 790633, p=3.3xe-20), MIP-1α (Mus, gi 127079, p=1.7xe-19), MIP-1β (Mus, gi 1346534, p=7.8xe-18); (2) vMIP-II: LD78 (MIP-1a) (human, gi 127077, p=7.1xe-23), MIP-1α (Mus, gi 127079, p=8.9xe-21), MIP-1α (Rattus, gi 790633, p=1.2xe-20), MIP-1β (Mus, gi 1346534, p=3.8xe-20); (3) vIL-6: 26 kDa polypeptide (IL-6) (human, gi 23835, p=7.2xe-17), IL-6 (Macaca, gi 514386, p=1.6xe-16); and (4) vIRF: ICSBP (Gallus, gi662355, p=1.1xe-11), ICSBP (Mus, sp p23611, p=1.0xe-10), lymphoid specific interferon regulatory factor (Mus, gi 972949, p=2.0xe-10), ISGF3 (Mus, gi 1263310, p=8.1xe-10), IRF4 (human, gi 1272477, p=1.0xe-9), ISGF3 (human, sp Q00978, 3.9xe-9), ICSBP (human, sp Q02556, p=2.3xe-8).

Sequence alignment. Amino acid sequences were aligned using CLUSTAL W (Thompson et al., 1994, *Nuc Acids Res* 22, 4673–4680) and compared using PAUP 3.1.1. Both rooted and unrooted bootstrap comparisons produced phylogenetic trees having all 100 bootstrap replicates with viral polypeptides being less divergent from each other than from the human polypeptides.

Northern blotting. Northern blotting was performed using standard conditions with random-labeled probes (Chang et al., 1994, *Science* 265, 1865–1869) derived from PCR products for the following primer sets: vMIP-I: 5'-AGC ATA TAA GGA ACT CGG CGT TAC-3' (SEQ ID NO:4), 5'-GGT AGA TAA ATC CCC CCC CTT TG-3' (SEQ ID NO:5); vMIP-II: 5'-TGC ATC AGC TTC TTC ACC CAG-3' (SEQ ID NO:6), 5'-TGC TGT CTC GGT TAC CAG AAA AG-3' (SEQ ID NO:7); vIL-6: 5'-TCA CGT CGC TCT TTA CTT ATC GTG-3' (SEQ ID NO:8), 5'-CGC CCT TCA GTG AGA CTT CGT AAC-3' (SEQ ID NO:9); vIRF: 5' CTT GCG ATG AAC CAT CCA GG-3' (SEQ ID NO:10), 5'-ACA ACA CCC AAT TCC CCG TC-3' (SEQ ID NO:11) on total cell RNA extracted with RNAzol according to manufacturer's instructions (TelTest Inc, Friendswood Tex.) and 10 μg of total RNA was loaded in each lane. BCP-1, BC-1 and P3HR1 were maintained in culture conditions and induced with TPA as previously described (Gao et al., 1996, *New Eng J Med* 335, 233–241). PCR amplification for these viral genes was performed using the vMIP-I, vMIP-II, vIL-6, and vIRF primer sets with 35 amplification cycles and compared to dilutions of whole BC-1 DNA as a positive control using PCR conditions previously described (Moore and Chang, 1995, *New Eng J Med* 332, 1181–1185). KS spindle cell line DNA used for these experiments was described in Dictor et al., 1996, *Am J Pathol* 148, 2009–2016. Amplifiability of DNA samples was confirmed using human HLA-DQ alpha and pyruvate dehydrogenase primers.

vIL-6 cloning. vIL-6 was cloned from a 695 bp polymerase chain reaction (PCR) product using the following primer set: 5'-TCA CGT CGC TCT TTA CTT ATC GTG-3'

(SEQ ID NO:12) and 5'-CGC CCT TCA GTG AGA CTT CGT AAC-3' (SEQ ID NO:13), amplified for 35 cycles using the 0.1 μg of BC-1 DNA as a template. PCR product was initially cloned into pCR 2.1 (Invitrogen, San Diego Calif.) and an EcoRV insert was then cloned into the pMET7 expression vector (Takebe et al., 1988, Mol Cell Biol 8, 466–472) and transfected using DEAE-dextran with chloroquine into COS7 cells (CRL-1651, American Type Culture Collection, Rockville Md.). The sequence was also cloned into the pMET7 vector in the reverse orientation (6-LIv) relative to the SRa promoter as a negative control, with orientation and sequence fidelity of both constructs confirmed by bidirectional sequencing using dye-primer chemistry on an ABI 377 sequenator (Applied Biosystems Inc, Foster City Calif.).

15 ml of serum-free COS7 supernatants were concentrated to 1.5 ml by ultrafiltration with a Centriplus 10 filter (Amicon, Beverly Mass.) and 100 μl of supernatant concentrate or 1 μg of rhuIL-6 (R&D Systems, Minneapolis Minn.) was loaded per each lane in Laemmli buffer. For cell lysate immunoblotting, exponential phase cells with and without 20 ng/ml TPA induction for 48 hours were pelleted and 100 μg of whole cell protein solubilized in Laemmli buffer was loaded per lane, electrophoresed on a 15% SDS-polyacrylamide gel and immunoblotted and developed using standard conditions (Gao et al., 1996, New Eng J Med 335, 233–241) with either rabbit antipeptide antibody (1:100–1:1000 dilution) or anti-huIL-6 (1 μg per ml, R&D Systems, Minneapolis Minn.).

Cell line B9. B9 mouse plasmacytoma cell line were maintained in Iscove's Modified Dulbecco's Medium (IMDM) (Gibco, Gaithersburg, Md.), 10% fetal calf serum, 1% penicillin/streptomycin, 1% glutamine, 50 μM β-mercaptoethanol, and 10 ng per ml rhuIL-6 (R&D Systems, Minneapolis, Minn.). $^3$H-thymidine uptake was used to measure B9 proliferation in response to huIL-6 or recombinant supernatants according to standard protocols (R&D Systems, Minneapolis, Minn.). Briefly, serial 1:3 dilutions of huIL-6 or Centriplus 10 concentrated recombinant supernatants were incubated with $2\times10^4$ cells per well in a 96 well plate for 24 hours at 37° C. with 10 μl of thymidine stock solution (50 μl of 1 mCi/ml $^3$H-thymidine in 1 ml IMDM) added to each well during the final four hours of incubation.

Cells were harvested and incorporated $^3$H-thymidine determined using a liquid scintillation counter. Each data point is the average of six determinations with standard deviations shown.

vIL-6 immunostaining. Immunostaining was performed using avidin-biotin complex (ABC) method after deparaffinization of tissues and quenching for 30 minutes with 0.03% $H_2O_2$ in PES. The primary antibody was applied at a dilution of 1:1250 after blocking with 10% normal goat serum, 1% BSA, 0.5% Tween 20. The secondary biotinylated goat anti-rabbit antibody (1:200 in PBS) was applied for 30 minutes at room temperature followed by three 5 minute washes in PBS. Peroxidase-linked ABC (1:100 in PBS) was applied for 30 minutes followed by three 5 minute washes in PBS. A diamino-benzidine (DAB) chromogen detection solution (0.25% DAB, 0.01% $H_2O_2$ in PBS) was applied for 5 minutes. Slides are then washed, counterstained with hematoxylin and coverslipped. Amino ethyl carbazole (AEC) or Vector Red staining was also used allowing better discrimination of double-labeled cells with Fast Blue counterstaining for some surface antigens. For CD68, in which staining might be obscured by vIL-6 cytoplasmic staining, double label immunofluorescence was used. Microwaved tissue sections were blocked with 2% human serum, 1% bovine serum albumin (BSA) in PBS for 30 minutes, incubated overnight with primary antibodies and developed with fluorescein-conjugated goat anti-rabbit IgG (1:100, Sigma) for vIL-6 localization and rhodamine-conjugated horse anti-mouse IgG (1:100, Sigma) for CD68 localization for 30 minutes. After washing, secondary antibody incubation was repeated twice with washing for 15 minutes each to amplify staining. For the remaining membrane antigens, slides were developed first for vIL-6 and then then secondly with the cellular antigen, as well as the reverse localization (cellular antigen antibody first, anti-vIL-6 second) to achieve optimal visualization and discrimination of both antigens. In each case, the first antibody was developed using AEC (Sigma) with blocking solution pre-incubation (1% BSA, 10% normal horse serum, 0.5% Tween 20 for 30 minutes) and development per manufacturer's instructions. The second antibody was developed using the ABC-alkaline phosphatase technique with Fast Blue chromagen. Both microwaving and trypsinization resulted in poorer localization and specificity of vIL-6 immunolocalization. In cases where this was required for optimal localization of membrane antigen, these techniques were applied after vIL-6 AEC localization. Vector-Red (Vector, Burlingame, Calif.) staining was used as an alternative stain to AEC to achieve optimal discrimination and was performed per manufacturer's protocol using the ABC-alkaline phosphatase technique. Cell antigen antibodies examined included CD68 (1:800, from clone Kim 6), epithelial membrane antigen (EMA, 1:500, Dako, Carpinteria, Calif.), CD3 (1:200, Dako), CD20, (1:200, Dako), OPD4 (1:100, Dako), CD34 (1:15, Dako), CD45 (1:400, from clone 9.4), L26 (1:100, Immunotech, Westbrook, Me.) and Leu22 (1:100, Becton-Dickinson, San Jose, Calif.) on tissues prepared according to manufacturer's instructions. Specific vIL-6 colocalization was only found with CD34 and CD45 in KS lesions, EMA in PEL, and CD20 and CD45 in lymph node tissues.

Immunohistochemical vIL-6 localization was performed on exponential phase BCP-1 cells with or without 48 hour TPA incubation after embedding in 1% agar in saline. The percentages of positive cells were determined from cell counts of three random high power microscopic fields per slide. Lower percentages of BCP-1 cells stain positively for vIL-6 after TPA treatment possibly reflecting cell lysis and death from lytic virus replication induction by TPA. Immunostaining of cells and tissues was demonstrated to be specific by neutralization using overnight incubation of antisera with 0.1 μg/ml vIL-6 synthetic peptides at 4° C. and by use of preimmune rabbit antisera run in parallel with the postimmune sera for the tissues or cell preparations. No specific staining was seen after either peptide neutralization or use of preimmune sera.

CCR5 and vMIP-I cloning. CCR5 was cloned into pRc-CMV vector (Invitrogen) and both forward and reverse orientations of the vMIP-I gene were cloned into pMET7 after PCR amplification using the following primer pairs: 5'-AGC ATA TAA GGA ACT CGG CGT TAC-3' (SEQ ID NO:14), 5'-GGT AGA TAA ACT CCC CCC CTT TG-3' (SEQ ID NO:15). CCR5 alone and with the forward construct (vMIP-I), the reverse construct (I-PIMv) and empty pMET7 vector were transfected into CCC/CD4 cells (CCC cat cells stably expressing human CD4, see McKnight et al., 1994, Virol 201, 8–18) using Lipofectamine (Gibco). After 48 hours, media was removed from the transfected cells and 1000 $TCID_{50}$ of SF162, M23 or ROD/B virus culture stock was added. Cells were washed four times after 4 hours of virus incubation and grown in DMEM with 5% FCS for 72 hours before immunostaining for HIV-1 p24 or HIV-2 gp105 as previously described. Each condition was replicated 3–4 times (FIG. 9) with medians and error bars representing the standard deviations expressed as percentages of the CCR5 alone foci.

EXPERIMENTAL DETAILS SECTION III

The following patents are hereby incorporated by reference to more fully describe the invention described herein:

1. Fowlkes, CARBOXY TERMINAL IL-6 MUTEINS, U.S. Pat. No. 5,565,336, ISSUED Oct. 15, 1996;
2. Skelly et al., METHOD OF MAKING CYSTEINE DEPLETED IL-6 MUTEINS, U.S. Pat. No. 5,545,537, ISSUED Aug. 13, 1996;
3. Ulrich, COMPOSITION AND METHOD FOR TREATING INFLAMMATION, U.S. Pat. No. 5,376,368, ISSUED Dec. 27, 1994;
4. Skelly et al., CYSTEINE DEPLETED IL-6 MUTEINS, U.S. Pat. No. 5,359,034, ISSUED Oct. 25, 1994;
5. Williams, ULTRAPURE HUMAN INTERLEUKIN 6, U.S. Pat. No. 5,338,834, ISSUED Aug. 16, 1994;
6. Fowlkes, CARBOXY TERMINAL IL-6 MUTEINS, U.S. Pat. No. 5,338,833, ISSUED Aug. 16, 1994;
7. Ulrich, COMPOSITION AND METHOD FOR TREATING INFLAMMATION, U.S. Pat. No. 5,300,292, ISSUED Apr. 05, 1994;
8. Mikayama et al., MODIFIED HIL-6, U.S. Pat. No. 5,264,209, ISSUED Nov. 23, 1993;
9. Park, HYPERGLYCOSYLATED CYTOKINE CONJUGATES, U.S. Pat. No. 5,217,881, ISSUED Jun. 08, 1993;
10. Goldberg and Faquin, INTERLEUKIN 6 TO STIMULATE ERYTHROPOIETIN PRODUCTION, U.S. Pat. No. 5,188,828, ISSUED Feb. 23, 1993;
11. Miles et al., METHOD TO TREAT KAPOSI'S SARCOMA, U.S. Pat. No. 5,470,824, ISSUED Nov. 28, 1995;
12. Li and Ruben, MACROPHAGE INFLAMMATORY PROTEIN -3 AND -4 [Isolated polynucleotide encoding said polypeptide], U.S. Pat. No. 5,504,003, ISSUED Apr. 02, 1996;
13. Gewirtz, SUPPRESSION OF MEGAKARYOCYTOPOIESIS BY MACROPHAGE INFLAMMATORY PROTEINS [Reducing number of circulating platelets in bloodstream], U.S. Pat. No. 5,306,709, ISSUED Apr. 26, 1994;
14. Fahey et al., METHOD AND AGENTS FOR PROMOTING WOUND HEALING, U.S. Pat. No. 5,145,676, ISSUED Sep. 8, 1992;
15. Rosen et al., POLYNUCLEOTIDE ENCODING MACROPHAGE INFLAMMATORY PROTEIN GAMMA, U.S. Pat. No. 5,556,767, ISSUED Sep. 17, 1996;
16. Chuntharapai et al., ANTIBODIES TO HUMAN IL-8 TYPE A RECEPTOR, U.S. Pat. No. 5,543,503, ISSUED Aug. 06, 1996;
17. Chuntharapai et al., ANTIBODIES TO HUMAN IL-8 TYPE B RECEPTOR [A monoclonal antibody as anti-inflammatory agent treating an inflammatory disorder], U.S. Pat. No. 5,440,021, ISSUED Aug. 08, 1995;
18. Kunkel et al., LABELLED MONOCYTE CHEMOATTRACTANT PROTEIN MATERIAL AND MEDICAL USES THEREOF, U.S. Pat. No. 5,413,778, ISSUED May 9, 1995;
19. Lyle and Kunkel, LABELLED INTERLEUKIN-8 AND MEDICAL USES THEREOF [Radionuclide labeled chemokines, imaging agents], U.S. Pat. No. 5,346,686, ISSUED Sep. 13, 1994;
20. Jones et al., ANTI-CANCER QUINAZOLINE DERIVATIVES, U.S. Pat. No. 4,564,616, ISSUED Jan. 14, 1986;
21. DeGraw et al., ANTIINFLAMMATORY AND ANTINEOPLASTIC 5-DEAZAAMINOPTERINS AND 5,10-DIDEAZAAMINOPTERINS, U.S. Pat. No. 5,536,724, ISSUED Jul. 16, 1996;
22. Mahan et al., IN VIVO SELECTION OF MICROBIAL VIRULENCE GENES [Genetic engineering and expression using auxotrophic or antibiotic sensitive microorganism's chromosome], U.S. Pat. No. 5,434,065, ISSUED Jul. 18, 1995;
23. DeGraw et al., 8,10-DIDEAZATETRAHYDROFOLIC ACID DERIVATIVES [Antitumor agents], U.S. Pat. No. 5,167,963, ISSUED Dec. 1, 1992; and
24. Watanabe, 6,7-DIHYDROPYRROL[3,4-C]PYRIDO[2,3-D] PYRIMIDINE DERIVATIVES [STRUCTURALLY SIMILAR TO THYMIDYLIC ACID], U.S. Pat. No. 4,925,939, ISSUED May 15, 1990.

REFERENCES

1. Chang, Yuan, E. Cesarman, M. S. Pessin, F. Lee, J. Culpepper, D. M. Knowles and Patrick S. Moore (1994) Identification of herpesvirus-like DNA sequences in AIDS-associated Kaposi's sarcoma. *Science* 265, 1865–1869.
2. Moore, Patrick S. and Yuan Chang (1995) Detection of herpesvirus-like DNA sequences in Kaposi's sarcoma in patients with and those without HIV infection. *New Eng J Med* 332, 1181–1185.
3. Cesarman, E., Yuan Chang, Patrick S. Moore, J. W. Said and D. M. Knowles (1995) Kaposi's sarcoma-associated herpesvirus-like DNA sequences are present in AIDS-related body cavity based lymphomas. *New Eng J Med* 332, 1186–1191.
4. Cesarman, E., Patrick S. Moore, P. H. Rao, G. Inghirami, D. M. Knowles and Yuan Chang (1995) In vitro establishment and characterization of two AIDS-related lymphoma cell lines containing Kaposi's-sarcoma associated herpesvirus-like (KSHV) DNA sequences. *Blood* 86, 2708–2714.

TABLE 1

KSHV Genome ORFs and their similarity to genes in other herpesviruses.

| Name | Pol | Start | Stop | Size | HVS % Sim | HVS % Id | EBV Name | EBV % Sim | EBV % Id | Function |
|---|---|---|---|---|---|---|---|---|---|---|
| K1 | + | 105 | 974 | 289 | | | | | | Complement binding protein (v-CBP) |
| ORF*** | + | 1142 | 2794 | 550 | 45.3 | 31.2 | | | | |
| ORF6 | + | 3210 | 6611 | 1133 | 74.1 | 55.2 | BALF2 | 65.6 | 42.1 | ssDNA binding protein (SSBP) |
| ORF7 | + | 6628 | 8715 | 695 | 65.0 | 44.7 | BALF3 | 59.9 | 41.3 | Transport protein |
| ORF8 | + | 8699 | 11,236 | 845 | 72.5 | 54.9 | BALF4 | 62.1 | 42.6 | Glycoprotein B (gB) |
| ORF9 | + | 11,363 | 14,401 | 1012 | 77.6 | 62.1 | BALF5 | 70.9 | 55.6 | DNA polymerase (pol) |
| ORF10 | + | 14,519 | 15,775 | 418 | 50.4 | 26.2 | | | | |
| ORF11 | + | 15,790 | 17,013 | 407 | 49.4 | 28.9 | Raji LF2 | 44.4 | 27.9 | |
| K2 | − | 17,875 | 17,261 | 204 | | | | | | vIL-6 |
| ORF02 | − | 18,553 | 17,921 | 210 | 65.8 | 48.4 | | | | DHPR |
| K3 | − | 19,609 | 18,608 | 333 | | | | | | BHV4-IE1 I |
| ORF70 | − | 21,104 | 20,091 | 337 | 79.5 | 66.4 | | | | Thymidylate synthase (TS) |
| K4 | − | 21,832 | 21,548 | 94 | | | | | | vMIP-II |
| K5 | − | 26,483 | 25,713 | 257 | | | | | | BHV4-IE1 II |
| K6 | − | 27,424 | 27,137 | 95 | | | | | | vMIP-I |
| K7 | + | 28,622 | 29,002 | 126 | | | | | | |
| ORF16 | + | 30,145 | 30,672 | 175 | 50.0 | 26.7 | BHRF1 | 46.3 | 22.8 | Bcl-2 |
| ORF17 | − | 32,482 | 30,821 | 553 | 60.3 | 42.9 | BVRF2 | 58.8 | 34.3 | Capsid protein I |
| ORF18 | + | 32,424 | 33,197 | 257 | 70.6 | 48.4 | | | | |
| ORF19 | − | 34,843 | 33,194 | 549 | 62.8 | 43.8 | BVRF1 | 62.5 | 42.0 | Tegument protein I |
| ORF20 | − | 35,573 | 34,611 | 320 | 59.6 | 42.7 | BXRF1 | 54.7 | 34.6 | |
| ORF21 | + | 35,383 | 37,125 | 580 | 50.9 | 32.5 | BXLF1 | 50.7 | 28.2 | Thymidine kinase (TK) |
| ORF22 | + | 37,113 | 39,305 | 730 | 53.9 | 35.1 | BXLF2 | 48.3 | 26.5 | Glycoprotein H (gH) |
| ORF23 | − | 40,516 | 39,302 | 404 | 57.4 | 33.7 | BTRF1 | 51.0 | 31.0 | |
| ORF24 | − | 42,778 | 40,520 | 752 | 65.8 | 45.6 | BcRF1 | 56.4 | 37.7 | |
| ORF25 | + | 42,777 | 46,907 | 1376 | 80.9 | 65.8 | BcLF1 | 74.8 | 56.8 | Major capsid protein (MCP) |
| ORF26 | + | 46,933 | 47,850 | 305 | 76.8 | 58.3 | BDLF1 | 73.4 | 46.8 | Capsid protein II |
| ORF27 | + | 47,873 | 48,745 | 290 | 49.6 | 29.6 | BDLF2 | 43.3 | 19.6 | |
| ORF28 | + | 48,991 | 49,299 | 102 | 42.2 | 21.7 | BDLF3 | | | |
| ORF29b | − | 50,417 | 49,362 | 351 | 41.8 | 17.0 | BDRF1 | 43.3 | 16.3 | Packaging protein II |
| ORF30 | + | 50,623 | 50,856 | 77 | 52.1 | 31.0 | BDLF3.5 | | | |
| ORF31 | + | 50,763 | 51,437 | 224 | 63.0 | 43.5 | BDLF4 | 58.9 | 36.4 | |
| ORF32 | + | 51,404 | 52,768 | 454 | 51.7 | 30.1 | BGLF1 | 47.0 | 26.6 | |
| ORF33 | + | 52,761 | 53,699 | 312 | 58.6 | 36.4 | BGLF2 | 52.8 | 32.2 | |
| ORF29a | − | 54,676 | 53,738 | 312 | 41.9 | 15.8 | BGRF1 | 57.1 | 40.6 | Packaging protein I |
| ORF34 | + | 54,675 | 55,658 | 327 | 58.9 | 42.7 | BGLF3 | 54.8 | 33.0 | |
| ORF35 | + | 55,639 | 56,091 | 151 | 60.0 | 31.7 | BGLF3.5 | | | |
| ORF36 | + | 55,976 | 57,310 | 444 | 49.4 | 31.1 | BGLF4 | 50.0 | 30.2 | Viral protein kinase |
| ORF37 | + | 57,273 | 58,733 | 486 | 65.9 | 50.4 | BGLF5 | 60.1 | 42.7 | Alkaline exonuclease (AE) |
| ORF38 | + | 58,688 | 58,873 | 61 | 58.6 | 39.7 | BBLF1 | 52.5 | 23.0 | |
| ORF39 | − | 60,175 | 58,976 | 399 | 73.2 | 52.1 | BBRF3 | 65.2 | 43.6 | Glycoprotein M (gM) |
| ORF40 | + | 60,308 | 61,681 | 457 | 51.9 | 28.1 | BBLF2 | 47.1 | 23.3 | Helicase-primase, subunit 1 |
| ORF41 | + | 61,827 | 62,444 | 205 | 53.4 | 29.2 | BBLF3 | | | Helicase-primase, subunit 2 |
| ORF42 | − | 63,272 | 62,436 | 278 | 55.8 | 38.9 | BBRF2 | 52.9 | 33.0 | |
| ORF43 | − | 64,953 | 63,136 | 605 | 74.9 | 60.5 | BBRF1 | 67.6 | 50.1 | Capsid protein III |
| ORF44 | + | 64,892 | 67,258 | 788 | 75.5 | 61.4 | BBLF4 | 67.8 | 51.1 | Helicase-primase, subunit 3 |
| ORF45 | − | 68,576 | 67,353 | 407 | 50.2 | 30.7 | BKRF4 | 48.9 | 26.2 | Virion assembly protein |
| ORF46 | − | 69,404 | 68,637 | 255 | 73.0 | 59.5 | BKRF3 | 69.2 | 54.8 | Uracil DNA glycosylase (UDG) |
| ORF47 | − | 69,915 | 69,412 | 167 | 53.0 | 29.9 | BKRF4 | 53.8 | 24.2 | Glycoprotein L (gL) |
| ORF48 | − | 71,381 | 70,173 | 402 | 47.3 | 24.4 | BRRF2 | 46.1 | 18.8 | |
| ORF49 | − | 72,538 | 71,630 | 302 | 45.4 | 21.2 | BRRF1 | 49.8 | 28.0 | |
| ORF50 | + | 72,734 | 74,629 | 631 | 46.5 | 24.9 | BRLF1 | 41.4 | 19.0 | Transactivator (LCTP) |
| K8 | + | 74,850 | 75,569 | 239 | | | | | | |
| ORF52 | − | 77,197 | 76,802 | 131 | 50.0 | 33.3 | BLRF2 | 54.6 | 36.9 | |
| ORF53 | − | 77,665 | 77,333 | 110 | 59.6 | 36.0 | BLRF1 | 58.1 | 40.9 | |
| ORF54 | + | 77,667 | 78,623 | 318 | 55.0 | 35.5 | BLLF3 | 53.7 | 32.4 | dUTPase |
| ORF55 | − | 79,448 | 78,765 | 227 | 64.4 | 46.4 | BSRF1 | 61.6 | 44.0 | |
| ORF56 | + | 79,436 | 81,967 | 843 | 62.5 | 44.3 | BSLF1 | 56.6 | 35.4 | DNA replication protein I |
| ORF57 | + | 82,717 | 83,544 | 275 | 56.9 | 31.5 | BMLF1 | 45.1 | 22.0 | Immediate-early protein II (IEP-II) |
| K9 | − | 85,209 | 83,860 | 449 | | | | | | vIRF1 (ICSBP) |
| K10 | − | 88,164 | 86,074 | 696 | | | | | | |
| K11 | − | 93,367 | 91,964 | 467 | | | | | | |
| ORF58 | − | 95,544 | 94,471 | 357 | 55.9 | 28.7 | BMRF2 | 50.6 | 25.3 | Phosphoprotein |
| ORF59 | − | 96,739 | 95,549 | 396 | 54.1 | 32.3 | BMRF1 | 50.7 | 28.3 | DNA replication protein II |
| ORF60 | − | 97,787 | 96,870 | 305 | 79.3 | 64.6 | BaRF1 | 74.8 | 57.3 | Ribonucleotide reductase, small |
| ORF61 | − | 100,194 | 97,816 | 792 | 69.4 | 52.4 | BORF2 | 64.1 | 43.6 | Ribonucleotide reductase, large |
| ORF62 | − | 101,194 | 100,199 | 331 | 64.6 | 40.2 | BORF1 | 57.7 | 34.7 | Assembly/DNA maturation |
| ORF63 | + | 101,208 | 103,994 | 927 | 53.1 | 32.1 | BOLF1 | 47.0 | 24.5 | Tegument protein II |
| ORF64 | + | 104,000 | 111,907 | 2635 | 50.1 | 29.7 | BPLF1 | 46.6 | 26.1 | Tegument protein III |
| ORF65 | − | 112,443 | 111,931 | 170 | 60.4 | 40.3 | BFRF3 | 49.4 | 27.8 | Capsid protein IV |
| ORF66 | − | 113,759 | 112,470 | 429 | 58.7 | 34.7 | BFRF2 | 50.0 | 28.0 | |
| ORF67 | − | 114,508 | 113,693 | 271 | 71.8 | 53.0 | BPRF1 | 62.8 | 39.5 | Tegument protein IV |
| ORF68 | + | 114,768 | 116,405 | 545 | 64.7 | 45.4 | BFLF1 | 58.3 | 36.2 | Glycoprotein |
| ORF69 | + | 116,669 | 117,346 | 225 | 71.1 | 53.6 | BFLF2 | 60.7 | 41.7 | |
| K12 | − | 118,101 | 117,919 | 60 | | | | | | Kaposin |

TABLE 1-continued

KSHV Genome ORFs and their similarity to genes in other herpesviruses.

| Name | Pol | Start | Stop | Size | HVS % Sim | HVS % Id | EBV Name | EBV % Sim | EBV % Id | Function |
|---|---|---|---|---|---|---|---|---|---|---|
| K13 | − | 122,710 | 122,291 | 139 | | | | | | |
| ORF72 | − | 123,566 | 122,793 | 257 | 53.0 | 32.5 | | | | Cyclin D |
| ORF73 | − | 127,296 | 123,808 | 1162 | 51.2 | 31.8 | | | | Immediate-early protein (IEP) |
| K14 | + | 127,883 | 128,929 | 348 | | | | | | OX-2 (v-adh) |
| ORF74 | + | 129,371 | 130,399 | 342 | 57.8 | 34.1 | | | | G-protein coupled receptor |
| ORF75 | − | 134,440 | 130,550 | 1296 | 54.8 | 36.3 | BNRF1 | | | Tegument protein/FGARAT |
| K15 | − | 136,279 | 135,977 | 100 | | | | | | |

Legend to Table 1. Name (e.g. K1 or ORF4) refers to the KSHV ORF designation; Pol signifies polarity of the ORF within the KSHV genome; Start refers to the position of the first LUR nucleotide in the start codon; Stop refers to the position of the last LUR nucleotide in the stop codon; Size indicates the number of amino acid residues encoded by the KSHV ORF; HVS%Sim indicates the percent similarity of the indicated KSHV ORF to the corresponding ORF of herpesvirus saimiri; HVS%Id indicates the percent identity of the indicated KSHV ORF to the corresponding ORF of herpesvirus saimiri; EBV Name indicates the EBV ORF designation; EBV%Sim indicates the percent similarity of the indicated KSHV ORF to the named Epstein-Barr virus ORF; EBV%Id indicates the percent identity of the indicated KSHV ORF to the named Epstein-Barr virus ORF. The asterisks in the KSHV Name column indicate comparison of KSHV ORF4 to HVS ORF4a (*) and HVS ORF4b (**). The entire unannotated genomic sequence is deposited in GenBank® under the accession numbers: U75698 (LUR), U75699 (terminal repeat), and U75700 (incomplete terminal repeat). The sequence of the LUR (U75698) is also set forth in its entirety in the Sequence Listing below. Specifically, the sequence of the LUR is set forth in 5' to 3' order in SEQ ID Nos:17–20. More specifically, nucleotides 1–35,100 of the LUR are set forth in SEQ ID NO:17 numbered nucleotides 1–35,100, respectively; nucleotides 35,101–70,200 of the LUR are set forth in SEQ ID NO:18 numbered nucleotides 1–35,100, respectively; nucleotides 70,201–105,300 of the LUR are set forth in SEQ ID NO:19 numbered nucleotides 1–35,100, respectively; and nucleotides 105,301–137,507 of the LUR are set forth in SEQ ID NO:20 numbered nucleotides 1–32,207, respectively.

What is claimed is:

1. An isolated nucleic acid which corresponds to an open reading frame within Kaposi's sarcoma-associated herpesvirus selected from the group of nucleic acids having the following sequences:

a) in SEQ ID NO: 17:
  1) nucleotide number 11,363 to nucleotide number 14,401 (ORF9);
  2) nucleotide number 21,104 to nucleotide number 20,091 (ORF70)
  3) nucleotide number 22,529 to nucleotide number 22,185 (vMIP III);
  4) nucleotide number 27,424 to nucleotide number 27,137 (ORF K6);

b) in SEQ ID NO: 18:
  1) nucleotide number 283 to nucleotide number 2,025 (ORF21);
  2) nucleotide number 20,876 to nucleotide number 22,210 (ORF36);

c) in SEQ ID NO: 19:
  1) nucleotide number 2,534 to nucleotide number 4,429 (ORF50);
  2) nucleotide number 4,650 to nucleotide number 5,369 (ORF K8);

d) in SEQ ID NO: 20:
  1) nucleotide number 12,801 to nucleotide number 12,619 (ORF K12); and
  2) nucleotide number 30,979 to nucleotide number 30,677 (ORF K15).

2. The nucleic acid of claim 1, wherein the nucleic acid is genomic DNA.

3. The nucleic acid of claim 1, wherein the nucleic acid is RNA.

4. The nucleic acid of claim 1, wherein the nucleic acid is cDNA.

5. The nucleic acid of claim 1, wherein the nucleic acid is labeled with a detectable marker.

6. The nucleic acid of claim 5, wherein the detectable marker is a radioactive, a colorimetric, a luminescent, or a fluorescent label.

7. A replicable vector which comprises the nucleic acid of claim 1.

8. A host cell which comprises the vector of claim 7.

9. The host cell of claim 8, wherein the host cell is a eukaryotic cell.

10. The host cell of claim 8, wherein the host cell is a bacterial cell.

11. The vector of claim 7, wherein the vector is a plasmid.

12. The vector of claim 7, wherein the vector is a cosmid.

13. The vector of claim 7, wherein the vector is a λ phage.

14. The vector of claim 7, wherein the vector is a YAC.

15. A nucleic acid probe of at least 14 nucleotides capable of specifically hybridizing with the nucleic acid of claim 1.

* * * * *